(12) United States Patent
Das et al.

(10) Patent No.: US 6,825,355 B2
(45) Date of Patent: Nov. 30, 2004

(54) BENZOTHIAZOLE PROTEIN TROSINE KINASE INHIBITORS

(75) Inventors: Jagabandhu Das, Mercerville, NJ (US); Joel C. Barrish, Holland, PA (US); John Wityak, Robbinsville, NJ (US)

(73) Assignee: Bristol-Myers Squibb Co., Princeton, NJ (US)

(*) Notice: Subject to any disclaimer, the term of this patent is extended or adjusted under 35 U.S.C. 154(b) by 312 days.

(21) Appl. No.: 10/032,609

(22) Filed: Oct. 26, 2001

(65) Prior Publication Data

US 2002/0123484 A1 Sep. 5, 2002

Related U.S. Application Data

(63) Continuation of application No. 09/173,413, filed on Oct. 15, 1998, now abandoned.
(60) Provisional application No. 60/065,042, filed on Nov. 10, 1997.

(51) Int. Cl.$^7$ ............................................. C07D 277/68
(52) U.S. Cl. ........................................ 548/161; 548/164
(58) Field of Search ................................. 548/161, 164

(56) References Cited

U.S. PATENT DOCUMENTS

| | | | |
|---|---|---|---|
| 3,966,706 A | 6/1976 | Ramanathan | |
| 4,317,682 A | 3/1982 | Katsura et al. | |
| 4,970,318 A | 11/1990 | Schnur et al. | |
| 5,036,086 A | 7/1991 | Taguchi et al. | |
| 5,496,816 A | 3/1996 | Blizzard et al. | |

FOREIGN PATENT DOCUMENTS

| | | | |
|---|---|---|---|
| CA | 2174473 | 10/1996 | |
| EP | 343893 | 11/1989 | |
| EP | 535521 | 4/1993 | |
| EP | 638564 | 2/1995 | |
| HU | 205347 | 6/1988 | |
| JP | 50-140442 | * 11/1975 | ................ 514/365 |
| JP | 62-194251 | * 8/1987 | ................ 514/365 |
| JP | 2-306916 | 12/1990 | |
| WO | WO 98/04536 | 2/1998 | |
| WO | WO 98/24805 | 6/1998 | |
| WO | WO99/24404 | 5/1999 | |
| WO | WO99/31073 | 6/1999 | |

OTHER PUBLICATIONS

Couquelet Chemical Abstracts 72:66857c 1972.*
Schnur, R. et al., J. Med. Chem., vol. 34, pp. 1975–1982 (1991).
Rodgers, J. et al., Biorg. & Medicinal Chemistry Letters, vol. 6, No. 24, pp. 2919–2924 (1996).
Pasquino, S. et al., Ann. Chim. vol. 66, Nos. 9–10, pp. 593–598 (1976).
Martani, A. et al., Boll. Chim. Farm., vol. 101, pp. 829–840 (1962).
Weiss, A., et al., Cell, "Signal Transduction by Lymphocyte Antigen Receptors", vol. 76, pp. 263–274 (1994).
Cooper, J. A., et al., Journal of Biological Chemistry, "Phosphorylation Sites in Enolase and Lactate Dehydrogenase Utilized by Tyrosine Protein Kinases in Vivo and in Vitro", vol. 259, No. 12, pp. 7835–7841 (1984).
Bolen,J. B., et al., FASEB Journal, "The Src family of tyrosine protein kinases in hemopoietic signal transduction", vol. 6, pp. 3403–3409 (1992).
Chan, A.C., et al., EMBO Journal, "Activation of ZAP–70 kinase activity by phosphorylation of tyrosine 493 is required for lymphocyte antigen receptor function", vol. 14, pp. 2499–2508, (1995).
Ihle, J. N., Seminars in Immunology, "The Janus protein tyrosine kinases in hematopoietic cytokine", vol. 7, pp. 247–254 (1995).
Iwashima, M., et al., Science, "Sequential Interactions of the TCR with Two Distinct Cytoplasmic Tyrosine Kinases", vol. 263, pp. 1136–1139 (1994).
Schieven, G. L., et al., Journal of Biological Chemistry, "ZAP–70 Tyrosine Kinase, CD45, and T Cell Receptor Involvement in UV– and $H_2O_2$–induced T Cell Signal Transduction", vol. 269, No. 32, pp. 20718–20726 (1994).
Ulrich, A., et al., Cell, "Signal Transduction by Receptors with Tyrosine Kinase Activity", vol. 61, pp. 203–212 (1990).

* cited by examiner

Primary Examiner—Robert Gerstl
(74) Attorney, Agent, or Firm—Ronald Hermenau; Stephen B. Davis

(57) ABSTRACT

Novel benzothiazoles and salts thereof, pharmaceutical compositions containing such compounds, and methods of using such compounds in the treatment of protein tyrosine kinase-associated disorders such as immunologic disorders.

2 Claims, No Drawings

BENZOTHIAZOLE PROTEIN TROSINE KINASE INHIBITORS

This application is a Continuation of Ser. No. 09/173,413 filed Oct. 15, 1998 now abandoned, which claims priority from provisional Ser. No. 60/065,042 filed on Nov. 10, 1997. The entirety of each of these applications is incorporated herein by reference.

FIELD OF THE INVENTION

The present invention relates to benzothiazoles and salts thereof, to methods of using such compounds in treating protein tyrosine kinase-associated disorders such as immunologic disorders, and to pharmaceutical compositions containing such compounds.

BACKGROUND OF THE INVENTION

Protein tyrosine kinases (PTKs) are enzymes which, in conjunction with ATP as a substrate, phosphorylate tyrosine residues in peptides and proteins. These enzymes are key elements in the regulation of cell signaling including cell proliferation and cell differentiation. PTKs comprise, inter alia, receptor tyrosine kinases (RPTKs), including members of the epidermal growth factor kinase family (e.g., HER1 and HER2), platelet derived growth factor (PDGF), and kinases that play a role in angiogenesis (Tie-2 and KDR); and, in addition, non-receptor tyrosine kinases, including members of the Syk, JAK and Src (e.g. src, fyn, lyn, Lck and blk) families (see Bolen, J. B., Rowley, R. B., Spana, C., and Tsygankov, A. Y., "The src family of tyrosine protein kinases in hemopoietic signal transduction", *FASEB J.*, 6, 3403–3409 (1992); Ulhrich, A. and Schlessinger, J., "Signal transduction by receptors with tyrosine kinase activity", *Cell*, 61, 203–212 (1990); and Ihle, J. N., "The Janus protein tyrosine kinases in hematopoetic cytokine signaling", *Sem. Immunol.*, 7, 247–254 (1995)).

Enhanced activity of PTKs has been implicated in a variety of malignant and nonmalignant proliferative diseases. In addition, PTKs play a central role in the regulation of cells of the immune system. PTK inhibitors can thus impact a wide variety of oncologic and immunologic disorders. Such disorders may be ameliorated by selective inhibition of a certain receptor or non-receptor PTK, such as Lck, or due to the homology among PTK classes, by inhibition of more than one PTK by an inhibitor.

A PTK of particular interest is Lck which is found in T cells where it is involved in phosphorylating key protein substrates. It is required for productive antigen receptor signaling and cell activation. In the absence of Lck activity, the T cell receptor (TCR) zeta chain is not phosphorylated, the kinase ZAP-70 is not activated, and $Ca^{2+}$ mobilization essential for T cell activation does not occur (see Weiss, A. and Littman, D. R., "Signal transduction by lymphocyte antigen receptors", *Cell*, 76, 263–274 (1994); Iwashima, M., Irving, B. A., van Oers, N. S. C., Chan, A. C., and Weiss, A., "Sequential interactions of the TCR with two distinct cytoplasmic tyrosine kinases", *Science*, 263, 1136–1139 (1994); and Chan, A. C., Dalton, M., Johnson, R., Kong, G., Wang, T., Thoma, R., and Kurosaki, T., "Activation of ZAP-70 kinase activity by phosphorylation of tyrosine 493 is required for lymphocyte antigen receptor function", *EMBO J.*, 14, 2499–2508 (1995)). Inhibitors of Lck are thus useful in the treatment of T-cell mediated disorders such as chronic diseases with an important T cell component, for example rheumatoid arthritis, multiple sclerosis and lupus, as well as acute diseases where T cells are known to play an essential role, for example acute transplant rejection and delayed-type hypersensitivity (DTH) reactions.

SUMMARY OF THE INVENTION

The present invention provides benzothiazole compounds of the following formula I and salts thereof, for use as protein tyrosine kinase inhibitors:

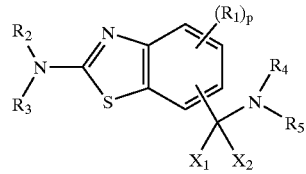

(I)

where
p is 0, 1, 2 or 3;
$X_1$ and $X_2$ are each hydrogen, or together form =O or =S;
each $R_1$ is independently selected from:
  (1) hydrogen or $R_6$, where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more (preferably, one or two) groups $Z_3$;
  (2) —OH or —$OR_6$;
  (3) —SH or —$SR_6$;
  (4) —$C(O)_qH$, —$C(O)_qR_6$, or —O—$C(O)_qR_6$, where q is 1 or 2;
  (5) —$SO_3H$ or —$S(O)_qR_6$;
  (6) halo;
  (7) cyano;
  (8) nitro;
  (9) —$Z_4$—$NR_7R_8$;
  (10) —$Z_4$—$N(R_9)$—$Z_5$—$NR_{10}R_{11}$;
  (11) —$Z_4$—$N(R_{12})$—$Z_5$—$R_6$;
  (12) —$P(O)(OR_6)_2$;
  (13) any two groups $R_1$ may together be alkylene or alkenylene completing a 3- to 8-membered saturated or unsaturated ring together with the carbon atoms to which they are attached, which ring is unsubstituted or substituted with $Z_1$, $Z_2$ and $Z_3$; or
  (14) any two groups $R_1$ may, together with the carbons to which they are attached, form a heterocyclo group, which group is unsubstituted or substituted with $Z_1$, $Z_2$ and $Z_3$;
$R_2$ and $R_3$ are each independently:
  (1) hydrogen or $R_6$;
  (2) —$Z_4$—$R_6$; or
  (3) —$Z_{13}$—$NR_7R_8$;
$R_4$ and $R_5$:
  (1) are each independently hydrogen or $R_6$; or
  (2) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;
$R_7$, $R_8$, $R_9$, $R_{10}$, $R_{11}$ and $R_{12}$:
  (1) are each independently hydrogen or $R_6$;
  (2) $R_7$ and $R_8$ may together be alkylene or alkenylene, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$ is:
(1) cyano;
(2) nitro;
(3) —$NH_2$;
(4) —NHOalkyl;
(5) —OH;
(6) —NHOaryl;
(7) —NHCOOalkyl;
(8) —NHCOOaryl;
(9) —$NHSO_2$alkyl;
(10) —$NHSO_2$aryl;
(11) aryl;
(12) heteroaryl;
(13) —Oalkyl; or
(14) —Oaryl;

$R_{14}$ is:
(1) —$NO_2$;
(2) —COOalkyl; or
3) —COOaryl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —$C(O)_q$H, —$C(O)_qZ_6$, or —O—$C(O)_qZ_6$;
(5) —$SO_3$H or $S(O)_qZ_6$;
(6) halo;
(7) cyano;
(8) nitro;
(9) —$Z_4$—$NZ_7Z_8$;
(10) —$Z_4$—$N(Z_9)$—$Z_5$—$NZ_7Z_8$;
(11) —$Z_4$—$N(Z_{10})$—$Z_5$—$Z_6$;
(12) —$Z_4$—$N(Z_{10})$—$Z_5$—H;
(13) oxo;
(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—$(CH_2)_q$—O—;

$Z_4$ and $Z_5$ are each independently:
(1) a single bond;
(2) —$Z_{11}$—$S(O)_q$—$Z_{12}$—;
(3) —$Z_{11}$—C(O)—$Z_{12}$—;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$—; or
(8) —$Z_{11}$—C(O)—O—$Z_{12}$—;

$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$Z_{11}$ and $Z_{12}$ are each independently:
(1) a single bond;
(2) alkylene;
(3) alkenylene; or
(4) alkynylene;

$Z_{13}$ is:
(1) a single bond;
(2) —$Z_{11}$—$S(O)_q$—$Z_{12}$—;
(3) —$Z_{11}$—C(O)—$Z_{12}$—;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$—;
(8) —$Z_{11}$—C(O)—O—$Z_{12}$—;
(9) —$C(NR_{13})$—;
(10) —$C(CHR_{14})$—; or
(11) —$C(C(R_{14})_2)$—.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a straight chain bridge of 1 to 5 carbon atoms connected by single bonds (e.g., —$(CH_2)_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —$CH_2$—CH=CH—, —$CH_2$—CH=CH—$CH_2$—, —$C(CH_3)_2$CH=CH— and —CH($C_2H_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —CH$_2$—C≡C—, —CH(CH$_3$)—C≡C— and —C≡C—CH(C$_2$H$_5$)CH$_2$—.

The terms "ar" or "aryl" refer to phenyl, naphthyl and biphenyl.

The terms "cycloalkyl" and "cycloalkenyl" refer to cyclic hydrocarbon groups of 3 to 12 carbon atoms.

The terms "halogen" and "halo" refer to fluorine, chlorine, bromine and iodine.

The term "unsaturated ring" includes partially unsaturated and aromatic rings. The terms "heterocycle", "heterocyclic" or "heterocyclo" refer to fully saturated or unsaturated, including aromatic ("heteroaryl") or nonaromatic cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

Where q is 1 or 2, "—C(O)$_q$H" denotes —C(O)—H or —C(O)—OH; "—C(O)$_q$R$_6$" or "—C(O)$_q$Z$_6$" denote, respectively, —C(O)—R$_6$ or —C(O)—OR$_6$, or —C(O)—Z$_6$ or —C(O)—OZ$_6$; "—O—C(O)$_q$R$_6$" or "—O—C(O)$_q$Z$_6$" denote, respectively, —O—C(O)—R$_6$ or —O—C(O)—OR$_6$, or —O—C(O)—Z$_6$ or —O—C(O)—OZ$_6$; and "—S(O)$_q$R$_6$" or "—S(O)$_q$Z$_6$" denote, respectively, —SO—R$_6$ or —SO$_2$—R$_6$, or —SO—Z$_6$ or —SO$_2$—Z$_6$.

Compounds of the formula I may in some cases form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

All stereoisomers of the present compounds, such as those which may exist due to asymmetric carbons on the R substituents of the compound of the formula I, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Throughout the specification, groups and substituents thereof are chosen to provide stable moieties and compounds.

Preferred Compounds

Compounds of the formula I, and salts thereof, wherein one or more, and especially all, of p, $X_1$, $X_2$, $R_1$, $R_2$, $R_3$, $R_4$, and $R_5$ are selected from the following definitions, are preferred compounds of the present invention:

p is 0 or 1;

each $R_1$ is independently selected from hydrogen, halo, alkyl or alkoxy;

$X_1$ and $X_2$ together form =O or =S;

$R_2$ is hydrogen;

$R_3$ is selected from hydrogen, alkyl, —$Z_4$—$R_6$ or —$Z_{13}$—$NR_7R_8$;

$R_4$ is hydrogen; and $R_5$ is selected from aryl groups which are substituted with $Z_1$, $Z_2$ and one or more (such as one or two) groups $Z_3$.

Such compounds where the group —C($X_1$)($X_2$)—N($R_4$)($R_5$) of formula I is bonded at the 6-position of the benzothiazole core are particularly preferred.

Methods of Preparation

The compounds of the formula I may be prepared by methods such as those illustrated in the following Schemes A to C and I to X. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art.

Therefore, one of ordinary skill in the art, upon reading this specification and the documents cited herein, is fully taught how to make the compounds claimed herein.

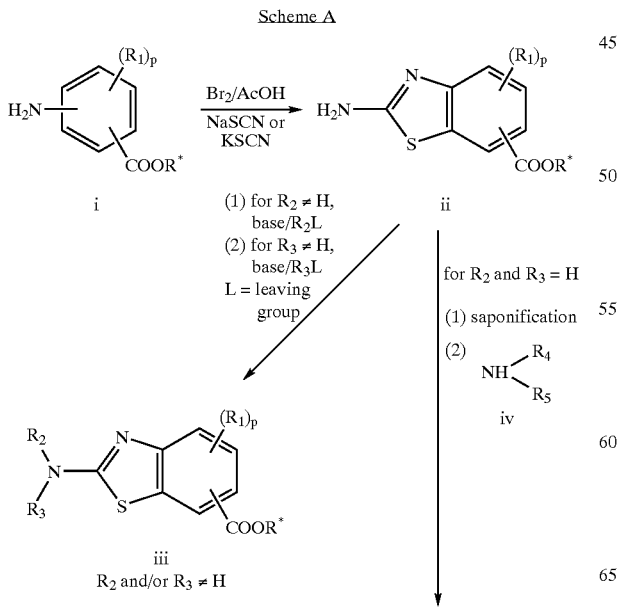

Scheme A

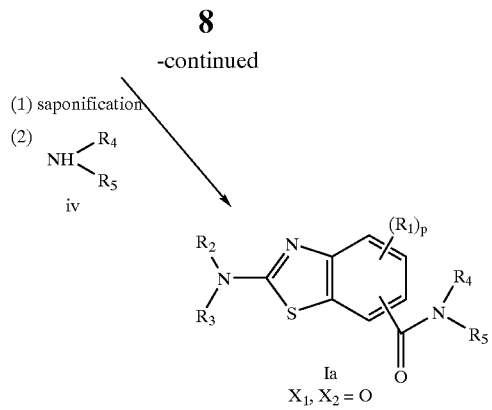

Scheme A illustrates a general method for forming compound Ia, which is a compound of the formula I where $X_1$ and $X_2$ together form =O. As shown in Scheme A, a 2-amino substituted benzothiazolecarboxyate ii may be prepared by reacting an appropriately substituted aminobenzoate i with sodium or potassium thiocyanate and bromine in an acidic solvent such as acetic acid (see U.S. Pat. No. 5,496,816). R* is a carboxyl protecting group such as alkyl or arylalkyl.

Compound Ia where $R_2$ and $R_3$ are hydrogen may be formed by saponification of ii followed by reaction with amine iv by methods known in the art. Alternatively, ii may be reacted with $R_2L$ where L is a leaving group such as halogen (for example, in equimolar portions), optionally followed by reaction with $R_3L$ (for example, in equimolar portions) to form iii. The compound iii may then be saponified and reacted with amine iv to form Ia where $R_2$ and/or $R_3$ are other than hydrogen.

Methods for preparing preferred substituents on the compounds I are illustrated in the following Schemes I to X.

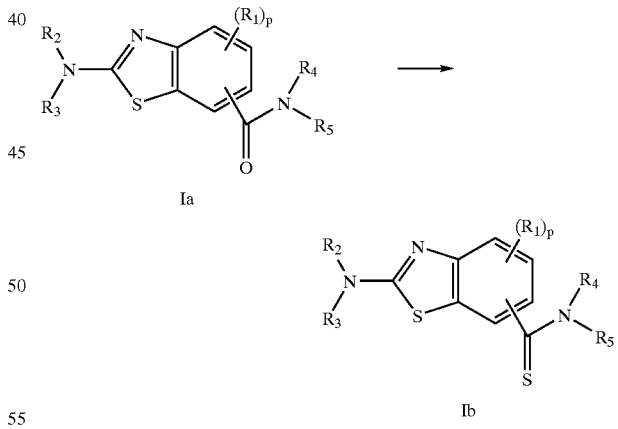

Scheme B illustrates a general method for forming compound Ib, which is a compound of the formula I where $X_1$ and $X_2$ together form =S. As shown in Scheme B, the compound of the formula Ia obtained in Scheme A may be converted into the corresponding thioamide Ib using a reagent such as Lawesson's reagent (2,4-bis(4-methoxyphenyl)-1,3-dithia-2,4-diphosphetane-2,4-disulfide (see *Bull. Soc. Chim. Belg.*, 87, 223 (1978)).

Methods for preparing preferred substituents on the compounds I are illustrated in the following Schemes I to X.

Scheme C

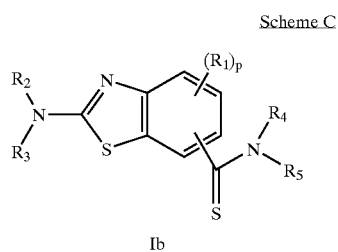
Ib reduction →

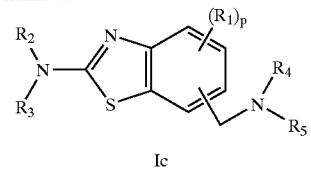
Ic

Scheme C illustrates a general method for forming compound Ic, which is a compound of the formula I where $X_1$ and $X_2$ are each hydrogen. As shown in Scheme C, the compound of the formula Ib obtained in Scheme B may be converted into the corresponding amine Ic by reduction, for example, by reaction with Raney nickel.

Methods for preparing preferred substituents on the compounds I are illustrated in the following Schemes I to X.

Scheme I

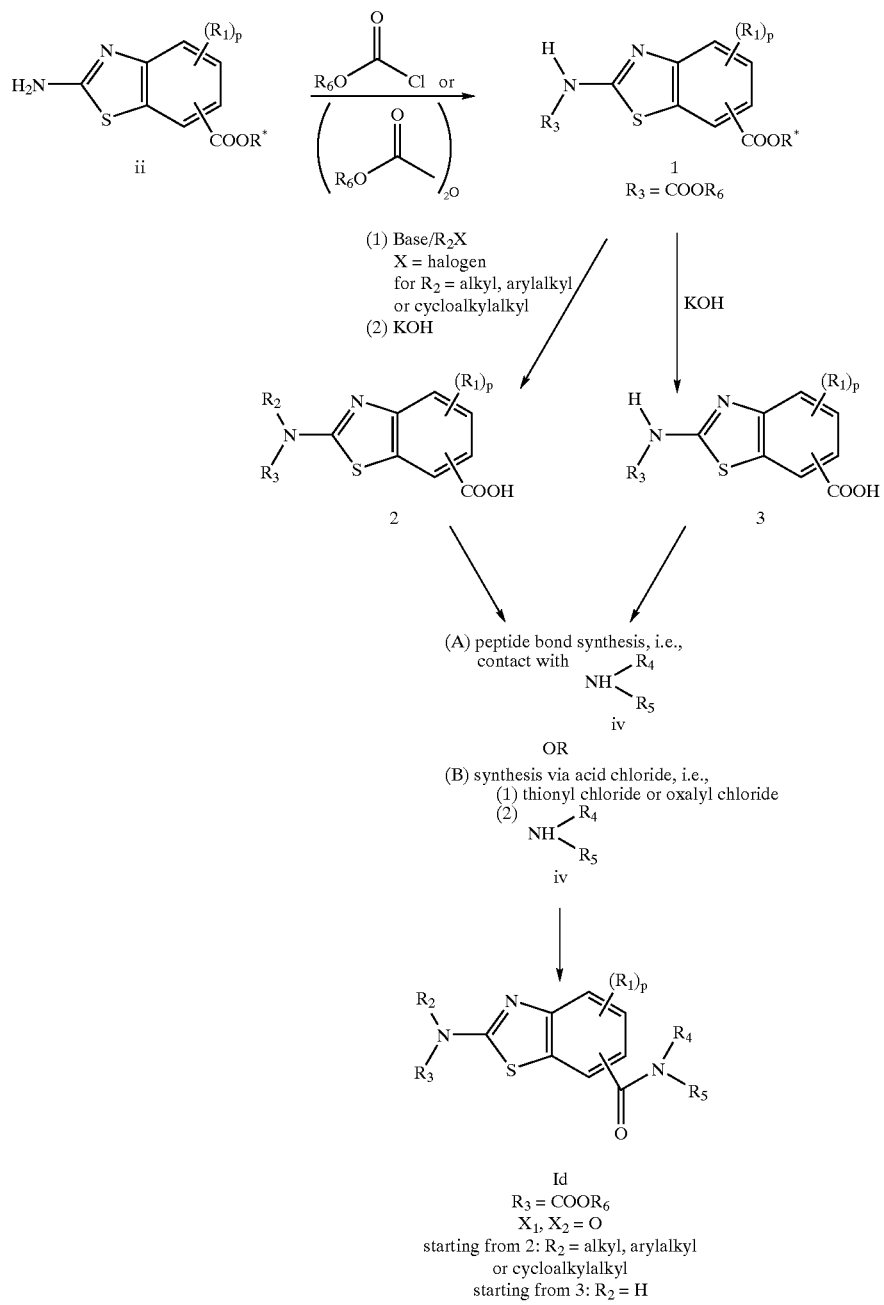

As shown in Scheme I, carboxylate ii can be reacted with a chloroformate or dicarbonate to form 1. Compound 1 can be treated with a base such as sodium hydride, sodium/potassium hexamethyldisilazide, or lithium diisopropylamide (LDA) and an alkylating agent $R_2X$ where X is halogen and $R_2$ is preferably alkyl, arylalkyl, or cycloalkylalkyl, and then saponified with an aqueous base such as potassium hydroxide to give 2. Compound 1 may, alternatively, be simply saponified with an aqueous base such as potassium hydroxide to give 3 where $R_2$ is hydrogen.

Acid 2 may be reacted with an amine iv using reaction conditions well known in the art for peptide bond synthesis (see, for example, Bodanszky and Bodanszky, The Practice of Peptide Chemistry, Springer-Verlag, 1984; Bodanszky, Principles of Peptide Synthesis, Springer-Verlag, 1984) to give the compound Id which a compound of the formula I where $X_1$ and $X_2$ together form =O, $R_3$ is $COOR_6$, and, since 2 is the starting material, $R_2$ is preferably alkyl, arylalkyl or cycloalkylalkyl. For example, reagents which activate the carboxyl group of 2 for reaction with the amine iv include bis-(2-oxo-3-oxazolidinyl)-phosphinic chloride (BOP chloride), benzotriazol-1-yloxy-tris-(dimethylamino)phosphonium hexafluorophosphate (BOP reagent), [O-(7-azabenzotriazol-1-yl)-1,1,3,3-tetramethyluronium] hexafluorophosphate (HATU), and carbodiimides such as dicyclohexylcarbodiimide (DCC) or 3-ethyl-3'-(dimethylamino)propylcarbodiimide (EDCI) either alone or in combination with a hydroxybenztriazole. Alternatively, the activated ester intermediate can be isolated and then treated with the appropriate amine iv in a nonprotic solvent such as tetrahydrofuran (THF) or dimethylformamide (DMF) in the presence of a base, for example, an organic base such as sodium/potassium hexamethyldisilazide, triethylamine, diisopropylethylamine or 1,8-diazabicyclo[5.4.0]undec-7-ene (DBU), or an inorganic base such as sodium, potassium or cesium carbonate or sodium or potassium hydride. Alternatively, the acid halide of 2 may be prepared, for example, by reaction with thionyl chloride or oxalyl chloride, followed by subsequent reaction with amine iv to provide compound Id.

Similar reactions employed above for the conversion of 2 to Id may be used to convert 3 to Id where, in the latter, $R_2$ is hydrogen.

Scheme II

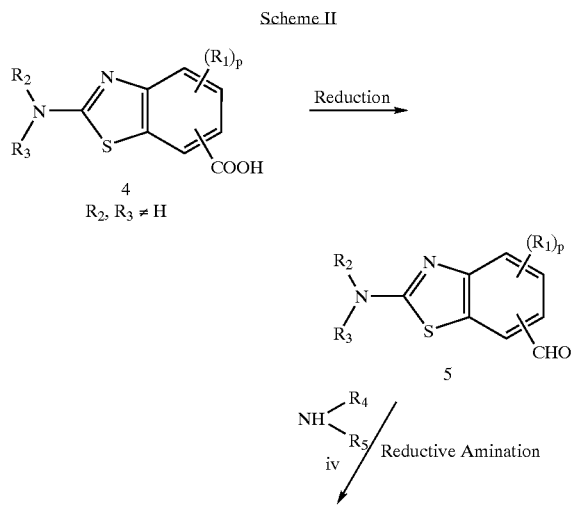

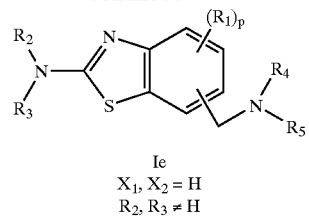

Ie
$X_1, X_2 = H$
$R_2, R_3 \neq H$

As shown in Scheme II, acid 4 where $R_2$ and $R_3$ are not hydrogen and are selected such that the nitrogen to which they are attached is non-basic, is reduced to the aldehyde 5 by methods well know in the art (see March, Advanced Organic Chemistry, Wiley, 1985). For example, the acid 4 may be converted to its corresponding ester followed by reduction with diisobutylaluminum hydride. Alternatively, the acid 4 may be reduced to the corresponding primary alcohol, for example, by treatment with borane/THF, $LiAlH_4$, or via reduction of a mixed anhydride, followed by subsequent oxidation to the aldehyde 5 using Cr(VI) (e.g., pyridinium chlorochromate, "PCC") or under Swern or Moffatt conditions (e.g., $(COCl)_2$/dimethylsulfoxide). The starting acid 4 may be obtained, for example, by saponification of iii.

Reductive amination (see Hudlicky, Reductions in Organic Chemistry, Wiley, 1984) of aldehyde 5 with amine iv in the presence of a reducing agent such as $NaBH_3CN$, $NaBH(OAc)_3$ (Ac=acetyl) or hydrogen and a palladium catalyst produces the amine compound Ie, which is a compound of the formula I where $X_1$ and $X_2$ are each hydrogen and $R_2$ and $R_3$ are each not hydrogen.

Scheme III

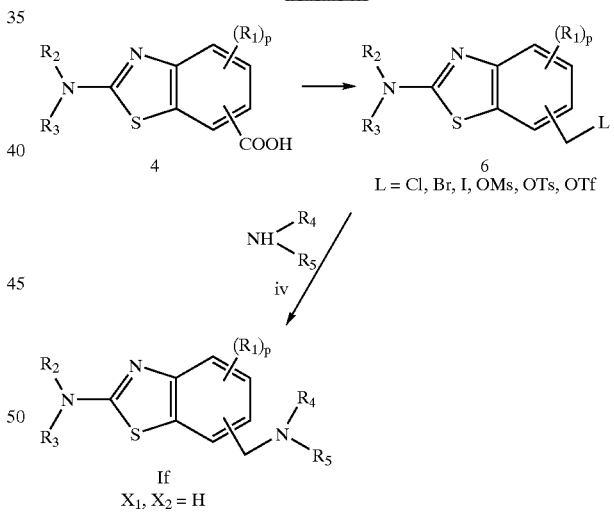

If
$X_1, X_2 = H$

As shown in Scheme III, reduction of the acid 4 to a primary alcohol (for example, by treatment with borane/tetrahydrofuran, $LiAlH_4$, or via reduction of a mixed anhydride), followed by conversion by methods well known in the art (see March, Advanced Organic Chemistry, Wiley, 1985), provides 6 which contains a leaving group such as a halide, tosylate (OTs), mesylate (OMs) or triflate (OTf). The groups $R_2$ and $R_3$ are selected such that the resulting nitrogen to which they are attached is non-basic. Compound 6 can then be converted into compound If, which is a compound of the formula I where $X_1$ and $X_2$ are each hydrogen, by a displacement reaction with amine iv, preferably where amine iv is used in excess.

Scheme IV

Amide/Thioamide

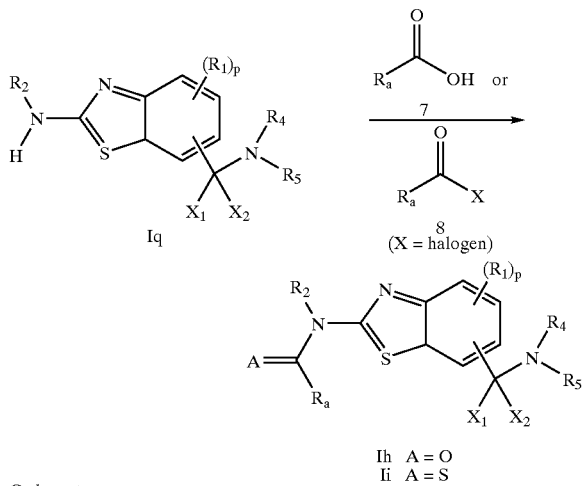

Ih A = O
Ii A = S

Carbamate

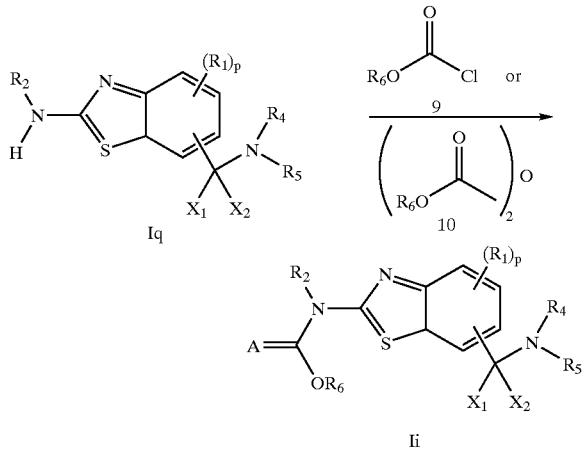

Urea/Thiourea

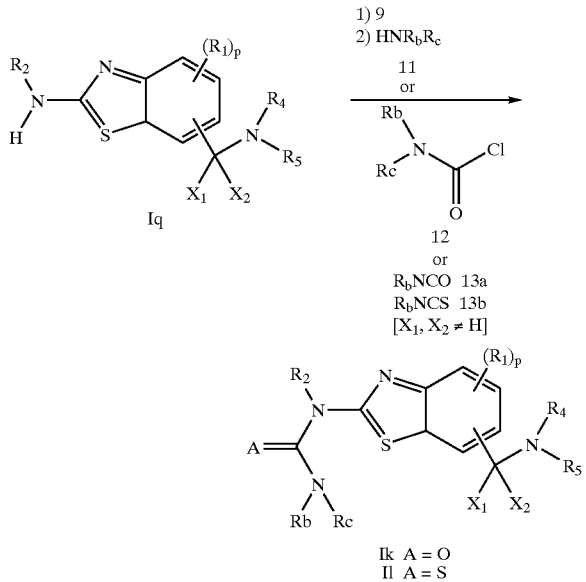

Ik A = O
Il A = S $R_2$ = any group as defined
$R_3$ = acyl or thioacyl

Scheme IV illustrates methods which may be used for the preparation of formula I compounds (that is, Ih, Ii, Ij, Ik and Il) where $R_2$ is any group as defined and $R_3$ is an acyl or thioacyl group, $X_1$ and $X_2$ are not hydrogen, and $R_1$ is not a primary or secondary amine. The starting compound Ig can be prepared by suitable methods described herein.

Amide Ih can be prepared by treatment of amine compound Ig with a carboxylic acid 7 in the presence of reagents which activate the carboxyl group for reaction as described above, for example BOP reagent, HATU, and carbodiimides such as DCC or EDCI either alone or in combination with a hydroxybenztriazole. Alternatively, the acid halide 8 may be reacted with amine compound Ig in the presence of an acid scavenger such as diisopropylethylamine. The corresponding thioamide Ii can be prepared by the treatment of amide Ih (where $X_1,X_2 \neq O$) with Lawesson's reagent as described above.

Carbamate Ij can be prepared by treatment of amine compound Ig with a chloroformate 9 or dicarbonate 10 in the presence of an acid scavenger such as diisopropylethylamine.

The urea Ik may be prepared by treatment of amine compound Ig with either: 1) a chloroformate 9, such as phenylchloroformate, followed by reaction with an amine 11; 2) a carbamoyl chloride 12 in the presence of an acid scavenger such as diisopropylethylamine; or 3) reaction with an isocyanate 13a (where $R_c$ in Ik=H). The corresponding thiourea Il may be prepared by treatment of amine compound Ig with a thioisocyanate 13b.

$R_a$ is selected from those groups included in the definition of $R_6$ such that the group —C(=A)—$R_a$ is an acyl or thioacyl group within the definition of $R_3$. $R_b$ and $R_c$ are selected from those groups included in the definitions of $R_7$ and $R_8$, such that the group —C(=A)—N($R_b$)($R_c$) is an acyl or thioacyl group within the definition of $R_3$.

Scheme V

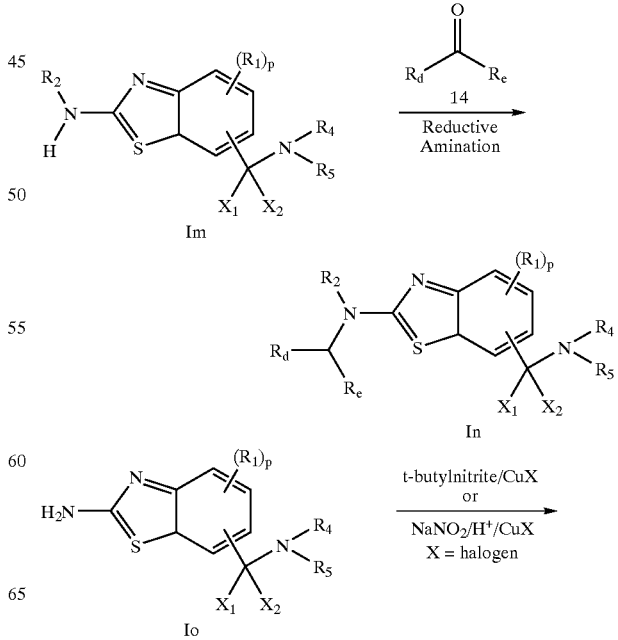

-continued

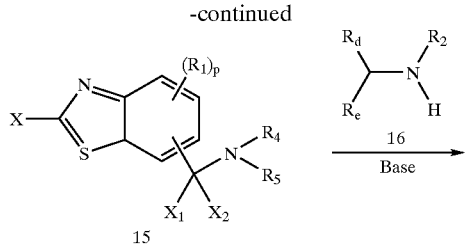

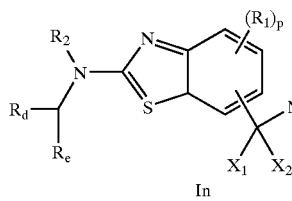

R₂ = any group as defined other than acyl
R₃ = alkyl, cycloalkyl, cycloalkylakyl, cycloalkenylalkyl, aralkyl or saturated heterocycle Scheme V illustrates a method which can be used for the preparation of In, which is a compound of the formula I where R₂ is any group as defined other than acyl, and which is selected such that the nitrogen to which it is attached is basic, R₃ is alkyl, cycloalkyl, cycloalkylalkyl, cycloalkenylalkyl, aralkyl, or saturated heterocycle, and X₁ and X₂ together are oxygen. The starting compounds Im and Io can be prepared by suitable methods described herein.

As shown in Scheme V, amine compound Im is reacted with an aldehyde or ketone 14 under reductive amination conditions described above to give the amine In. Compound In may also be prepared by treatment of an amino benzothiazole Io, where R₂ and R₃ are hydrogen, with t-butyl nitrite or sodium nitrite in the presence of a copper (I) halide to give the halo-substituted benzothiazole 15, followed by displacement with amine 16 in the presence of a base such as sodium or potassium hydride or the like (see Lee et al., *J. Heterocyclic Chemistry*, 22, 1621 (1985)).

R_d and R_e are independently selected from hydrogen, alkyl, aryl, cycloalkyl or cycloalkenyl, or together are alkylene or alkenylene completing a 3- to 8-membered saturated or unsaturated ring, such that the group —CH(R_d)(R_e) is a group within the definition of R₃.

Scheme VI

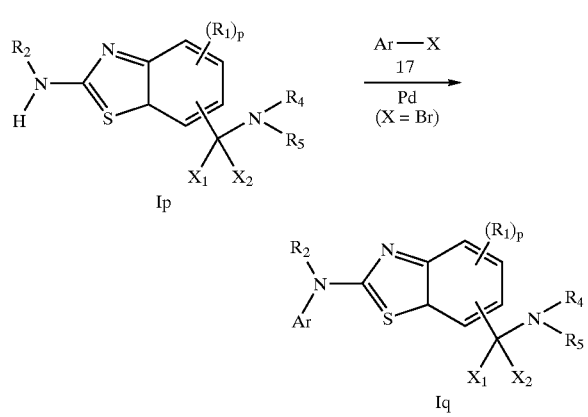

R₂ = any group as defined other than acyl
R₃ = aryl, heteroaryl

As shown in Scheme VI, when R₂ is any group as defined other than acyl, and is selected such that the nitrogen to which it is attached is basic, R₃ is aryl or heteroaryl, and X₁ and X₂ are not hydrogen, amine compound Ip may be reacted with a halophenyl or haloheteroaromatic group 17 in the presence of a palladium (0) catalyst (see *J. Am. Chem. Soc.*, 118, 7215 (1996)) to give amine Iq, where Iq is a compound of the formula I having the particular substituents described in this Scheme. The starting compound Ip can be prepared by suitable methods described herein.

Scheme VII

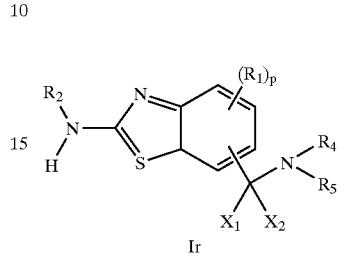
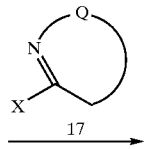

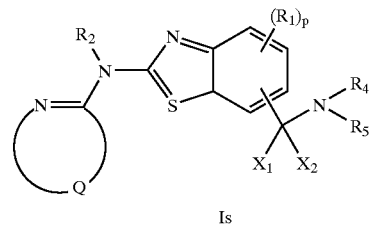

R₂ = any group as defined
R₃ = heteroaryl

As shown in Scheme VII, when R₂ is any group as defined and R₃ is a heteroaromatic group, amine compound Ir may be reacted with a 2-halosubstituted heteroaromatic compound 17 where Q, together with atoms to which is is bonded, forms a 5- or 6-membered monocyclic or 10- to 12-membered bicyclic heteroaromatic group (such as forming 2-chloropyridine or 2-chloropyrimidine) to give the amine Is, where Is is a compound of the formula I having the particular substituents described in this Scheme. The starting compound Ir can be prepared by suitable methods described herein.

Scheme VIII

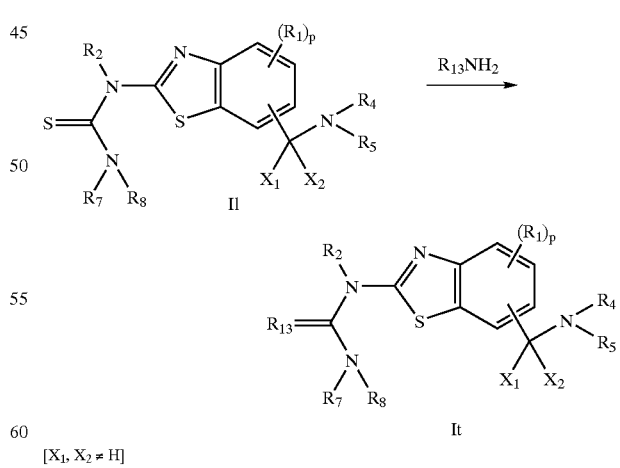

[X₁, X₂ ≠ H]

As shown in Scheme VIII, thiourea compound Il (where X₁ and X₂ are not hydrogen) may be reacted with the appropriate amine in the presence of bis-(2-oxo-3-oxazolidinyl)phosphinic chloride (BOP chloride)

benzotriazol-1-yloxy-tris(dimethylamino)phosphonium hexafluorophosphate (BOP-reagent), [O-(7-azabenzotriazol-1-yl)-1,1,3,3-tetramethyluronium] hexafluorophosphate (HATU) and carbodiimide, such as dicyclohexyl carbodiimide (DCC) or 3-ethyl-3'-(dimethylamino)propyl carbodiimide (EDCI) or diisopropyl carbodiimide (DIC) in the presence of an organic base such as triethylamine, diisopropylethylamine or dimethylaminopyridine in solvents such as dimethylformamide, dichloromethane or tetrahydrofuran to form compound It.

Alternatively, Compound Il can be reacted with the appropriate amine in the presence of a mercury (II) salt such as mercuric chloride to form It, or by other methods known in the literature.

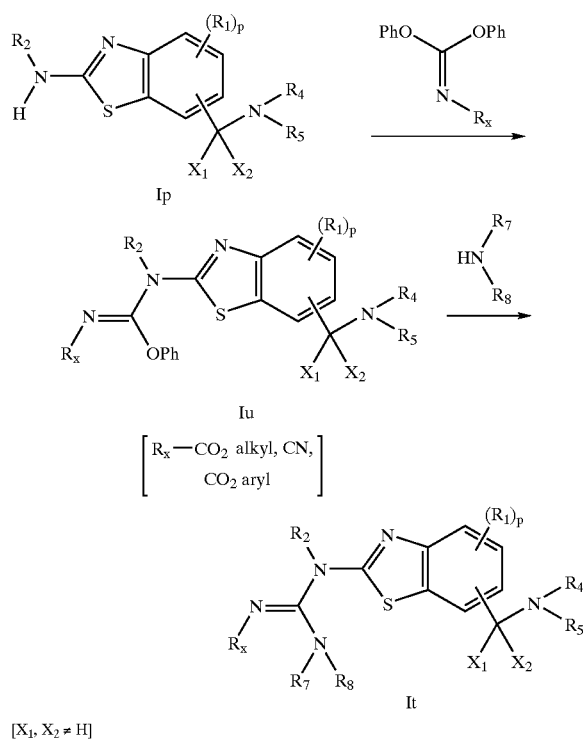

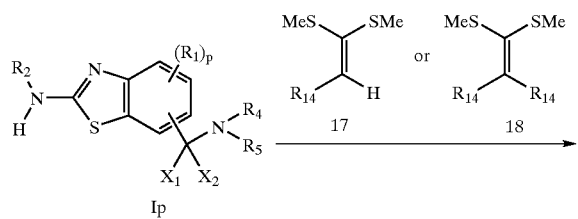

As shown in Scheme IX, amine Ip (where $X_1$ and $X_2$ are not hydrogen) can be reacted with diphenylcyanocarbonimidate either alone or in the presence of a base such as sodium hydride, sodium hexamethyldisilazide or dimethylaminopyridine in acetonitrile or tetrahydrofuran, dimethylformamide at room temperature or elevated temperature to form intermediate compound Iu which can be reacted with an amine ($R_7R_8NH$) to form compound It (where R=cyanide).

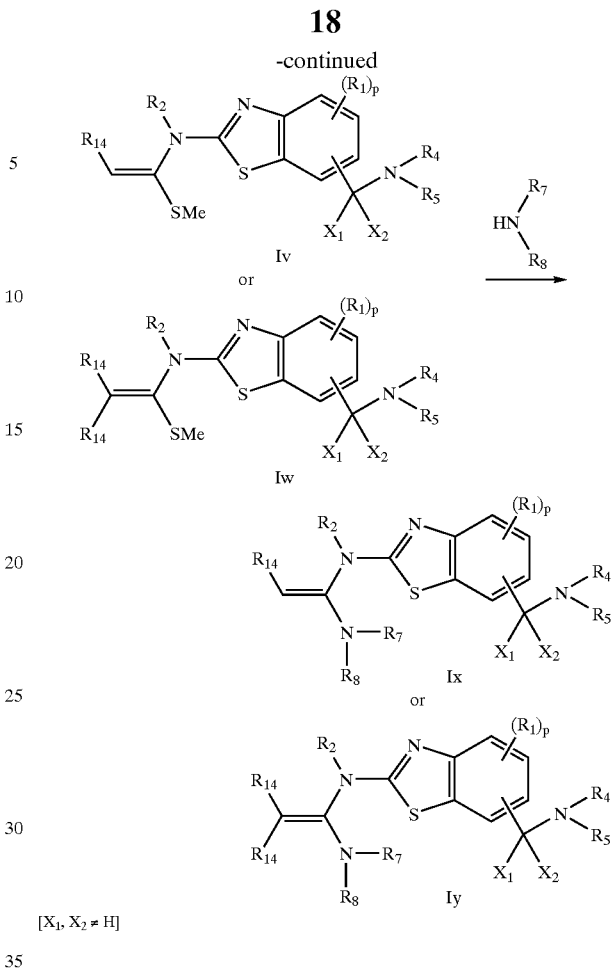

As shown in Scheme X, compound Ip (where $X_1$ and $X_2$ are not hydrogen) can be reacted with 17 or 18 either alone or in the presence of a base such as sodium hydride, sodium hexamethyl disilazide or dimethylaminopyridine in dimethyl formamide or tetrahydrofuran at room temperature or higher to form compounds Iv or Iw respectively which can be reacted with an amine ($R_7R_8NH$) at room temperature or higher to form compounds Ix or Iy respectively.

Utility

The compounds of the present invention inhibit protein tyrosine kinases, especially Lck and, to varying degrees, other Src family kinases such as Fyn, Lyn, Src, Yes, Hck, Fgr and Blk. They are thus useful in the treatment, including prevention and therapy, of protein tyrosine kinase-associated disorders such as immunologic and oncologic disorders. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation.

Compounds of the present invention inhibit T cell activation. The treatment of T cell mediated diseases, including inhibition of T cell activation and proliferation, is a particularly preferred embodiment of the present invention. Compounds which selectively inhibit T cell activation and proliferation are preferred. Compounds of the present invention which block the activation of endothelial cell PTK by oxidative stress, thereby limiting surface expression of adhesion molecules that induce neutrophil binding, and which inhibit PTK necessary for neutrophil activation are useful, for example, in the treatment of ischemia and reperfusion injury.

The present invention thus provides methods for the treatment of protein tyrosine kinase-associated disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compounds of the present invention in treating protein tyrosine kinase-associated disorders is exemplified by, but is not limited to, treating a range of disorders such as: transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis; serum sickness; uticaria; allergic diseases such as respiratory allergies (asthma, hayfever, allergic rhinitis) or skin allergies; scleracierma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides a method for treating the aforementioned disorders such as atopic dermatitis by administration of any compound capable of inhibiting protein tyrosine kinase.

Src-family kinases other than Lck, such as Hck and Fgr, are important in the Fc gamma receptor induced respiratory burst of neutrophils as well as the Fc gamma receptor responses of monocytes and macrophages. The compounds of the present invention inhibit the Fc gamma induced respiratory burst response in neutrophils. The ability to inhibit Fc gamma receptor dependent responses of neutrophils and potentially other cells' responses could result in additional anti-inflammatory activity for the present compounds beyond their effects on T cells. The activity against T cells and potentially other cells is especially of value, for example, in the treatment of inflammatory diseases such as arthritis or inflammatory bowel disease. In particular, the present compounds are of value for the treatment of autoimmune glomerulonephritis and other instances of glomerulonephritis induced by deposition of immune complexes in the kidney that trigger Fc gamma receptor responses leading to kidney damage.

In addition, Src family kinases other than Lck, such as Lyn and Src, are important in the Fc epsilon receptor induced degranulation of mast cells and basophils that plays an important role in asthma, allergic rhinitis, and other allergic disease. Fc epsilon receptors are stimulated by IgE-antigen complexes. The compounds of the present invention inhibit the Fc epsilon induced degranulation responses, including in the basophil cell line RBL that does not express Lck. The ability to inhibit Fc epsilon receptor dependent mast cell and basophil responses could result in additional anti-inflammatory activity for the present compounds beyond their effect on T cells. The activity of the present compounds towards T cells suggests they could be of value for treatment of asthma, allergic rhinitis, atopic dermatitis and other instances of allergic disease. Activity of the present compounds against mast cells and basophil responses could potentially also be of benefit for treatment of these diseases.

The activity of the present compounds towards T cells is of value in the treatment of any of the aforementioned disorders. Furthermore, the potential combined activity towards T cells, neutrophils and other cells may be of additional value in the treatment of any of the aforementioned disorders.

In a particular embodiment, the compounds of the present invention are useful for the treatment of the aforementioned exemplary disorders irrespective of their etiology, for example, for the treatment of transplant rejection, rheumatoid arthritis, multiple sclerosis, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

The present invention also provides pharmaceutical compositions comprising at least one of the compounds of the formula I capable of treating a protein tyrosine kinase-associated disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isbtonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to protein tyrosine kinase-associated disorders.

The compounds of the present invention may be employed alone or in combination with each other and/or other suitable therapeutic agents useful in the treatment of protein tyrosine kinase-associated disorders such as PTK inhibitors other than those of the present invention, antiinflammatories, antiproliferatives, chemotherapeutic agents, and immunosuppressants.

Exemplary such other therapeutic agents include the following cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, steroids such as prednisone or dexamethasone, gold compounds, antiproliferative agents such as methotrexate, FK506 (tacrolimus, Prograf), mycophenolate mofetil, cytotoxic drugs such as azathiprine and cyclophosphamide, TNF-α inhibitors such as tenidap, anti-TNF antibodies or soluble TNF receptor, and rapamycin (sirolimus or Rapamune) or derivatives thereof, and the PTK inhibitors disclosed in the following U.S. patent applications, incorporated herein by reference in their entirety: Ser. No. 09/097,338, filed Jun. 15, 1998, and Ser. No. 09/094,797 filed Jun. 15, 1998. See the following documents and references cited therein: Hollenbaugh, D., Douthwright, J., McDonald, V., and Aruffo, A., "Cleavable CD40Ig fusion proteins and the binding to sgp39", *J. Immunol. Methods* (Netherlands), 188(1), p. 1–7 (Dec. 15, 1995); Hollenbaugh, D., Grosmaire, L. S., Kullas, C. D., Chalupny, N. J., Braesch-Andersen, S., Noelle, R. J., Stamenkovic, I., Ledbetter, J. A., and Aruffo, A., "The human T cell antigen gp39, a member of the TNF gene family, is a ligand for the CD40 receptor: expression of a soluble form of gp39 with B cell co-stimulatory activity", *EMBO J* (England), 11(12), p 4313–4321 (December 1992); and Moreland, L. W. et al., Treatment of rheumatoid arthritis with a recombinant human tumor necrosis factor receptor (p75)-Fc fusion protein, *New England J. of Medicine*, 337 (3), p. 141–147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The following assays can be employed in ascertaining the degree of activity of a compound ("test compound") as a PTK inhibitor. Compounds described in the following Examples have been tested in one or more of these assays, and have shown activity.

Enzyme Assay Using Lck, Fyn, Lyn, Hck, Fgr or Src

The following assay has been carried out using the protein tyrosine kinases Lck, Fyn, Lyn, Hck, Fgr and Src.

The protein tyrosine kinase of interest is incubated in kinase buffer (20 mM MOPS, pH7, 10 mM $MgCl_2$) in the presence of the test compound. The reaction is initiated by the addition of substrates to the final concentration of 1 μM ATP, 3.3 μCi/ml [33P] gamma-ATP, and 0.1 mg/ml acid denatured enolase (prepared as described in Cooper, J. A., Esch, F. S., Taylor, S. S., and Hunter, T., "Phosphorylation sites in enolase and lactate dehydrogenase utilized by tyrosine protein kinases in vivo and in vitro", *J. Biol. Chem.*, 259, 7835–7841 (1984)). The reaction is stopped after 10 minutes by the addition of 10% trichloroacetic acid, 100 mM sodium pyrophosphate followed by 2 mg/ml bovine serum albumin. The labeled enolase protein substrate is precipitated at 4 degrees, harvested onto Packard Unifilter plates and counted in a Topcount scintillation counter to ascertain the protein tyrosine kinase inhibitory activity of the test compound (activity inversely proportional to the amount of labeled enolase protein obtained). The exact concentration of reagents and the amount of label can be varied as needed.

This assay is advantageous as it employs an exogenous substrate (enolase) for more accurate enzyme kinetics, and can be conducted in a 96-well format that is readily automated. In addition, His-tagged protein tyrosine kinases (described below) offer much higher production yields and purity relative to GST-protein tyrosine kinase fusion protein.

The protein tyrosine kinase may be obtained from commercial sources or by recombinant methods described herewith. For the preparation of recombinant Lck, human Lck was prepared as a His-tagged fusion protein using the Life Technologies (Gibco) baculovirus vector pFastBac Hta (commercially available) in insect cells. A cDNA encoding human Lck isolated by PCR (polymerase chain reaction) was inserted into the vector and the protein was expressed using the methods described by the manufacturer. The Lck was purified by affinity chromatography. For the production of Lck in insect cells using baculovirus, see Spana, C., O'Rourke, E. C., Bolen, J. B., and Fargnoli, J., "Analysis of the tyrosine kinase p56lck expressed as a glutathione S-transferase protein in *Spodoptera frugiperda* cells," *Protein expression and purification*, Vol. 4, p. 390–397 (1993). Similar methods may be used for the recombinant production of other Src-family kinases.

Cell Assays (1) Cellular Tyrosine Phosphorylation

Jurkat T cells are incubated with the test compound and then stimulated by the addition of antibody to CD3 (monoclonal antibody G19-4). Cells are lysed after 4 minutes or at another desired time by the addition of a lysis buffer containing NP-40 detergent. Phosphorylation of proteins is detected by anti-phosphotyrosine immunoblotting. Detection of phosphorylation of specific proteins of interest such as ZAP-70 is detected by immunoprecipitation with anti-ZAP-70 antibody followed by anti-phosphotyrosine immunoblotting. Such procedures are described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and $H_2O_2$ induced T cell signal transduction", *J. Biol. Chem.*, 269, 20718–20726 (1994), and the references incorporated therein. The Lck inhibitors inhibit the tyrosine phosphorylation of cellular proteins induced by anti-CD3 antibodies.

For the preparation of G19-4, see Hansen, J. A., Martin, P. J., Beatty, P. G., Clark, E. A., and Ledbetter, J. A., "Human T lymphocyte cell surface molecules defined by the workshop monoclonal antibodies," in *Leukocyte Typing I*, A. Bernard, J. Boumsell, J. Dausett, C. Milstein, and S. Schlossman, eds. (New York: Springer Verlag), p. 195–212 (1984); and Ledbetter, J. A., June, C. H., Rabinovitch, P. S., Grossman, A., Tsu, T. T., and Imboden, J. B., "Signal transduction through CD4 receptors: stimulatory vs. inhibitory activity is regulated by CD4 proximity to the CD3JT cell receptor", *Eur. J. Immunol.*, 18, 525 (1988).

(2) Calcium Assay

Lck inhibitors block calcium mobilization in T cells stimulated with anti-CD3 antibodies. Cells are loaded with the calcium indicator dye indo-1, treated with anti-CD3 antibody such as the monoclonal antibody G19-4, and calcium mobilization is measured using flow cytometry by recording changes in the blue/violet indo-1 ratio as described in Schieven, G. L., Mittler, R. S., Nadler, S. G., Kirihara, J. M., Bolen, J. B., Kanner, S. B., and Ledbetter, J. A., "ZAP-70 tyrosine kinase, CD45 and T cell receptor involvement in UV and $H_2O_2$ induced T cell signal transduction", *J. Biol. Chem.*, 269, 20718–20726 (1994), and the references incorporated therein.

(3) Proliferation Assays

Lck inhibitors inhibit the proliferation of normal human peripheral blood T cells stimulated to grow with anti-CD3 plus anti-CD28 antibodies. A 96 well plate is coated with a monoclonal antibody to CD3 (such as G19-4), the antibody is allowed to bind, and then the plate is washed. The antibody bound to the plate serves to stimulate the cells. Normal human peripheral blood T cells are added to the wells along with test compound plus anti-CD28 antibody to provide co-stimulation. After a desired period of time (e.g., 3 days), the [3H]-thymidine is added to the cells, and after further incubation to allow incorporation of the label into newly synthesized DNA, the cells are harvested and counted in a scintillation counter to measure cell proliferation.

The following Examples illustrate embodiments of the present invention, and are not intended to limit the scope of the claims. Abbreviations employed in the Examples are defined below. Compounds of the Examples are identified by the example and step in which they are prepared (for example, "1A" denotes the title compound of step A of Example 1), or by the example only where the compound is the title compound of the example (for example, "2" denotes the title compound of Example 2).

Abbreviations aq.=aqueous
conc.=concentrated
DMSO=dimethylsulfoxide
EtOAc=ethyl acetate
$Et_2O$=diethyl ether
h=hours
HATU=N-[dimethylamino-1H-1,2,3-triazolo-[4,5-b] pyridin-1-yl methylene]-N-methyl methanaminium hexafluorophosphate N-oxide
MeOH=methanol
MOPS=4-morpholine-propanesulfonic acid
MS=mass spectrometry
Ret Time=retention time
RT=room temperature
satd.=saturated
TFA=trifluoroacetic acid
THF=tetrahydrofuran

EXAMPLE 1

Preparation of [6-[[(2,4,6-Trimethylphenyl)amino]carbon]-2-benzothiazolyl]carbamic acid, 1,1-dimethylethyl ester

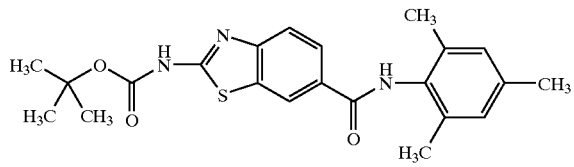

A. Ethyl-2-amino-benzothiazole-6-carboxylate

A solution of ethyl-4-aminobenzoate (35 g, 212 mmol) in glacial acetic acid (300 mL) was added to a stirred solution of sodium thiocyanate (69 g, 848 mmol) in acetic acid (150 mL). The mixture was cooled in an ice-water bath and a solution of bromine (12 mL, 233 mmol) in acetic acid (60 mL) was added dropwise via an addition funnel. The reaction mixture was stirred at 0° C. to RT for 4 h and then poured into water (1.5 L). Saturated sodium carbonate solution was added to neutralize the solution. Precipitated solid was filtered, washed with water and EtOAc, and dried in vacuo to obtain the title compound of this step (31.65 g, 67.2% yield).

B. Ethyl-2-tert-butoxycarbonyloxyamino-benzothiazole-6-carboxylate

A suspension of 1A (10 g, 45 mmol), di-t-butyldicarbonate (11.78 g, 54 mmol) and 4-dimethylaminopyridine (549 mg, 4.5 mmol) in dichloromethane (330 mL) was stirred at RT overnight. Additional di-t-butyldicarbonate (3 g, 13.75 mmol) was added. After 20 h, the mixture was concentrated under reduced pressure and the residue was diluted with a 1:1 mixture of EtOAc and Et$_2$O (200 mL). Solid was filtered and dried in vacuo to obtain the title compound of this step (10.5 g, 72.4% yield).

C. 2-tert-Butoxycarbonyloxyamino-benzothiazole-6-carboxylic acid

A 1 N solution of sodium hydroxide in water (931 mL) was added to a suspension of 1B (10 g, 31.05 mmol) in methanol (170 mL). The mixture was stirred at RT overnight, cooled to 0° C. and acidified with aqueous HCl solution. The precipitated solid was filtered, washed with water and dried under reduced pressure. The solid was suspended in tetrahydrofuran and concentrated under reduced pressure. It was further diluted with toluene and concentrated under reduced pressure to remove water. The solid was collected and dried in vacuo over phosphorus pentoxide to obtain the title acid of this step (8.32 g, 91% yield).

D. [6-[[(2,4,6-Trimethylphenyl)amino]carbonyl]-2-benzothiazolyl]carbamic acid, 1,1-dimethylethyl ester Diisopropylethyl amine (1.83 mL, 10.48 mmol) was added to a stirred suspension of 1C (2.57 g, 8.73 mmol), 2,4,6-trimethylaniline (1.47 mL, 10.48 mmol) and HATU (3.98 g, 10.48 mmol) in dimethylformamide (77.1 mL). The solution was stirred at RT overnight and then diluted with EtOAc (70 mL). The reaction mixture was washed with 2 N aq. HCl solution (80 mL). The aq. layer was extracted with EtOAc (25 mL). The EtOAc extracts were combined, washed with 2 N aq. HCl solution (60 mL), brine, dried (Na$_2$SO$_4$), and concentrated. The crude residue was triturated with a 4:1 mixture of ether and EtOAc (100 mL). Solid was collected and dried in vacuo to obtain the title compound of this Example (2.88 g, 80.1% yield).

MS=412.2 (M$^+$+H).

EXAMPLE 2

Preparation of 2-Amino-N-(2,4,6-trimethylphenyl)-6-benzothiazolecarboxamide, trifluoroacetate (1:1)

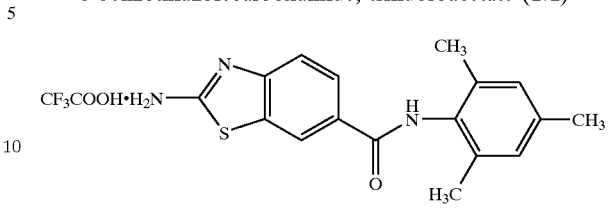

A solution of 1D (77.8 mg, 0.19 mmol) in trifluoroacetic acid (5.3 mL) was stirred at RT for 1.5 h. The solution was concentrated under reduced pressure and the residue was coevaporated with ether. Trituration with ether-hexanes mixture gave the title product (62 mg, 72% yield) as an off-white solid.

MS=311.9 (M$^+$+H).

EXAMPLE 3

Preparation of 2-(Acetylamino)-N-(2,4,6-trimethylphenyl)-6-benzothiazolecarboxamide

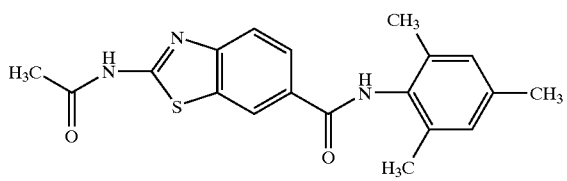

A. Ethyl-2-acetamido-benzothiazole-6-carboxylate

A suspension of 1A (150 mg, 0.67 mmol) and acetic anhydride (0.18 mL, 1.86 mmol) in dichloromethane (19 mL) and pyridine (3.7 mL) was stirred at RT. After 2 h, additional pyridine (3 mL) and 4-dimethylaminopyridine (8.2 mg, 0.067 mmol) were added. The mixture was stirred for 16 h, diluted with dichloromethane (20 mL) and washed with 2 N aq. HCl solution (20 mL, 3×), saturated. aq. KHCO$_3$ solution (20 mL, 2×) and brine. The dichloromethane extract was dried (Na$_2$SO$_4$), filtered and concentrated. The residue was triturated with an ether-hexanes mixture to obtain the title compound of this step (130 mg, 73% yield).

B. 2-Acetamido-benzothiazole-6-carboxylic acid

A 2 M aq. solution of potassium hydroxide (5.7 mL) and ethanol (8 mL) were added to a a solution of 3A (100 mg, 0.38 mmol) in THF (5 mL). The homogenous solution was stirred at RT overnight, cooled to 0° C. and acidified with 6 M aq. HCl solution. Most of the ethanol and THF were removed by distillation under reduced pressure. The precipitated solid was filtered, washed with water and dried in vacuo to obtain the title acid of this step (64 mg, 72% yield) as a white solid.

C. 2-(Acetylamino)-N-(2,4,6-trimethylphenyl)-6-benzothiazolecarboxamide

Analogous to the preparation of 1D except using 3B to give the title compound of this Example as a light yellow solid (21.5%).

MS=354 (M$^+$+H).

EXAMPLE 4

Preparation of 2-(Benzoylamino)-N-(2,4,6-trimethylphenyl)-6-benzothiazolecarboxamide

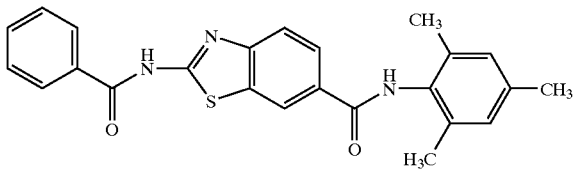

A solution of the free base of 2 (100 mg, 0.32 mmol, obtained by treatment of a solution of the trifluoroacetate salt 2 in dichloromethane with aq. sodium bicarbonate solution) and benzoic anhydride (200 mg, 0.89 mmol) in THF (8.9 mL) and pyridine (1.8 mL) was stirred at RT overnight. Additional benzoic anhydride (200 mg, 0.89 mmol) and 4-dimethylaminopyridine (3.9 mg, 0.032 mmol) were added and the solution was stirred for 2 days. Additional 4-dimethylaminopyridine (3.9 mg, 0.032 mmol) was added and the solution was stirred for an additional 1 h. The mixture was diluted with dichloromethane (40 mL), washed with 1 N aq. HCl solution (15 mL), dried ($Na_2SO_4$), filtered and concentrated. The residue was triturated with ether to obtain a white solid which was suspended in dichloromethane and washed with saturated. aq. $KHCO_3$ solution (3×). The dichloromethane extract was dried ($Na_2SO_4$), filtered and concentrated. Trituration of the crude solid with EtOAc (15 mL) afforded the title compound (49 mg, 37%) as a white solid.

MS=416.1 ($M^+$+H).

EXAMPLE 5

Preparation of 2-[(1-Oxopropyl)amino]-N-(2,4,6-trimethylphenyl)-6-benzothiazolecarboxamide

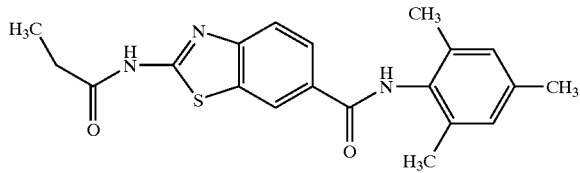

Analogous to the preparation of 4 except using propionic anhydride gave the title compound 5 as a white solid.
MS=367 ($M^+$+H).

EXAMPLE 6

Preparation of 2-[(1-Oxobutyl)amino]-N-2,4,6-trimethylphenyl)-6-benzothiazolecarboxamide

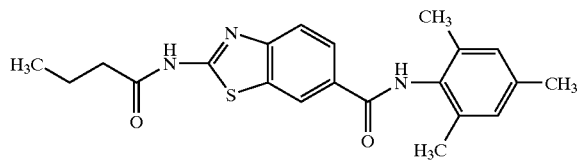

Analogous to the preparation of 4 except using butyric anhydride gave the title compound 6 as a white solid.
MS=382 ($M^+$+H).

EXAMPLE 7

Preparation of 2-[[[(1,1-Dimethylethyl)amino]carbonyl]amino]-N-(2,4,6-trimethylphenyl)-6-benzothiazolecarboxamide

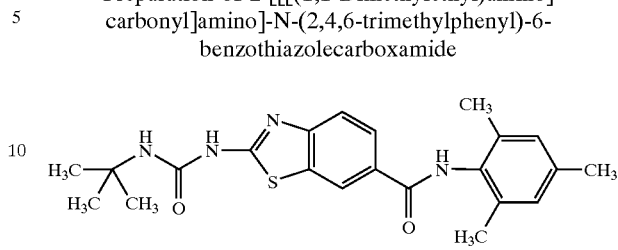

A. 2-[[[Phenoxy]carbonyl]amino]-N-(2,4,6-trimethylphenyl)-6-benzothiazolecarboxamide Phenyl chloroformate (470 mg, 3 mmol) was added dropwise to a stirred solution of the free base of 2 (311 mg, 1 mmol) in THF (20 ml) and saturated. aq. $KHCO_3$ solution (20 mL) at 0–5° C. The biphasic mixture was stirred for 3 h. The THF layer was separated and the aqueous layer was extracted with dichloromethane (30 mL, 2×). The organic extracts were combined, dried ($MgSO_4$), filtered and concentrated. The crude residue was diluted with EtOAc (25 mL) and the solid was filtered, washed with EtOAc (8 mL, 4×), and dried in vacuo to obtain the title compound of this step as a white solid (269 mg, 62%).

B. 2-[[[(1,1-Dimethylethyl)amino]carbonyl]amino]-N-(2,4,6-trimethylphenyl)-6-benzothiazolecarboxamide tert-Butyl amine (73 mg, 1 mmol) was added to a stirred solution of 7A (22 mg, 0.05 mmol) in THF (5 mL). The solution was stirred at RT for 16 h, diluted with dichloromethane (30 mL) and washed with 2 N aq. HCl solution (10 mL, 2×) and 0.5 N aq. NaOH solution (10 mL, 2×). The dichloromethane extract was dried ($MgSO_4$), filtered and concentrated to obtain the title compound of this Example (17 mg, 80%) as a white solid.

MS=411.1 ($M^+$+H).

EXAMPLE 8

Preparation of 2-[[[Bis(1-methylethyl)amino]carbonyl]amino]-N-(2,4,6-trimethylphenyl)-6-benzothiazolecarboxamide

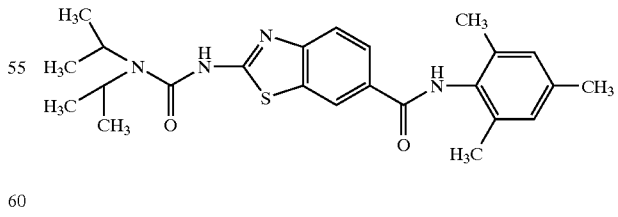

Analogous to the preparation of 7B except using diisopropyl amine to give the title compound 8 as an off-white solid (78.5%).

MS=439.2 ($M^+$+H).

EXAMPLE 9

Preparation of [6-Bromo-4-[[(2,4,6-Trimethylphenyl)amino]carbonyl]-2-benzothiazolyl] carbamic acid, 1,1-dimethylethyl ester

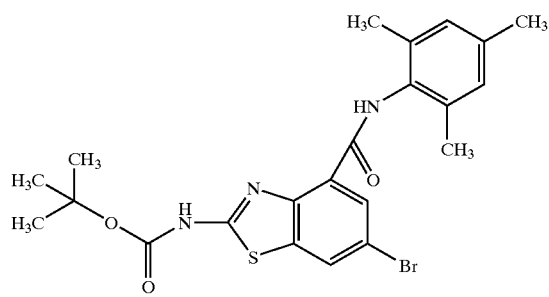

Analogous to the preparation of 1 except using methyl-2-amino-6-bromo-benzothiazole-4-carboxylate (U.S. Pat. No. 5,496,816) in place of 1A to give the title compound 9 as a white solid.

MS=491.8 (M$^+$+H).

EXAMPLE 10

Preparation of [4-[[(2,4,6-Trimethylphenyl)amino] carbonyl]-2-benzothiazolyl]carbamic acid, 1,1-dimethylethyl ester

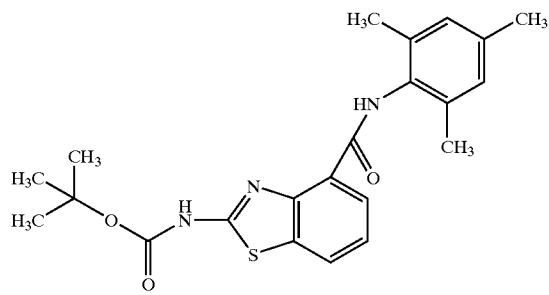

Palladium hydroxide (40 mg) was added to a stirred suspension of 9 (50 mg, 0.1 mmol) in absolute ethanol (60 mL). The reaction flask was equipped with a hydrogen filled balloon via a three way stopcock. Air inside the flask was evacuated under reduced pressure and then filled with hydrogen from the balloon. This operation was repeated (3x). Hydrogenolysis was continued overnight. The reaction mixture was filtered through a pad of anhydrous MgSO$_4$. Residual solid was washed with ethanol (10 mL, 3x). The filtrate was concentrated and the crude residue was chromatographed on a silica gel column. Elution with 5% EtOAc in hexanes, followed by 10% and 20% EtOAc in hexanes afforded the title compound 10 (37 mg, 88%) as a white solid.

MS=412.1 (M$^+$+H).

EXAMPLE 11

Preparation of [6-Bromo-7-[[(2,4,6-Trimethylphenyl)amino]carbonyl]-2-benzothiazolyl] carbamic acid, 1,1-dimethylethyl ester

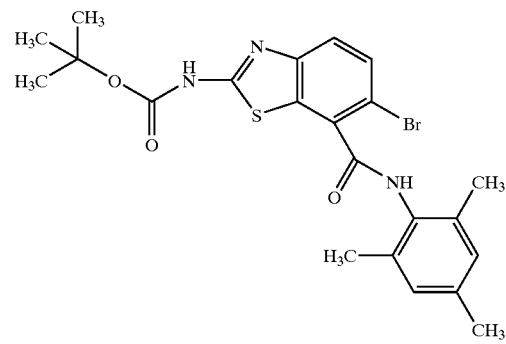

A. Methyl-3-amino-6-bromo-benzoate

Tin (II) chloride dihydrate (22.56 g, 100 mmol) was added to a stirred solution of methyl-2-bromo-5-nitrobenzoate (9 g, 34.61 mmol) in methanol (250 mL) and conc. HCl (25 mL). The solution was stirred at RT for 8 h and then treated with satd. aq. KHCO$_3$ solution (600 mL). Additional solid KHCO$_3$ (50 g) was added. The mixture was extracted with EtOAc (200 mL, 5x). The EtOAc extracts were combined, dried (MgSO$_4$), filtered and concentrated. The residue was diluted with EtOAc (250 mL) and washed with brine (50 mL, 2x), dried (MgSO$_4$), filtered and concentrated to obtain the title compound of this step (7.45 g, 94%) as a brown oil.

B. Methyl-2-amino-6-bromo-benzothiazole-7-carboxylate (11Ba) and Methyl-2-amino-6-bromo-benzothiazole-5-carboxylate (11Bb)

Analogous to the preparation of 1A except using 9A in place of ethyl-4-aminobenzoate as the starting aniline. Trituration of the crude residue with EtOAc afforded pure 11Ba (43%). The filtrate was concentrated and the residue was chromatographed on a silica gel column. Elution with 10% EtOAc in hexanes, followed by 20%, 30%, and 50% EtOAc in hexanes gave a 1:1 mixture of 11Ba and 11Bb (13%) as a yellow solid.

C. [6-Bromo-7-[[(2,4,6-Trimethylphenyl)amino]carbonyl]-2-benzothiazolyl]carbamic acid, 1,1-dimethylethyl ester Analogous to the preparation of 1D except using 11Ba in place of 1A afforded the title compound as a white solid.

MS=491.9 (M$^+$+H).

EXAMPLE 12

Preparation of [7-[[(2,4,6-Trimethylphenyl)amino] carbonyl]-2-benzothiazolyl]carbamic acid, 1,1-dimethylethyl ester

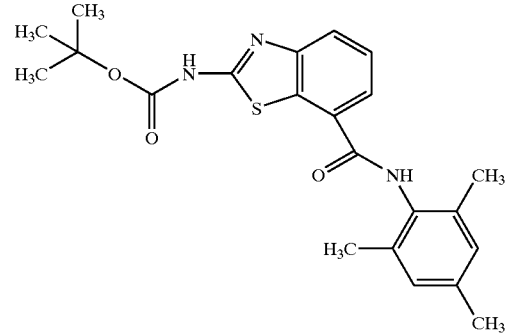

Analogous to the preparation of 10 except using 11C in place of 9 gave the title compound 12 (89%) as a white solid.

MS=412.1 (M$^+$+H).

EXAMPLE 13

Preparation of [6-Bromo-5-[[(2,4,6-Trimethylphenyl)amino]carbonyl]-2-benzothiazolyl]carbamic acid, 1,1-dimethylethyl ester

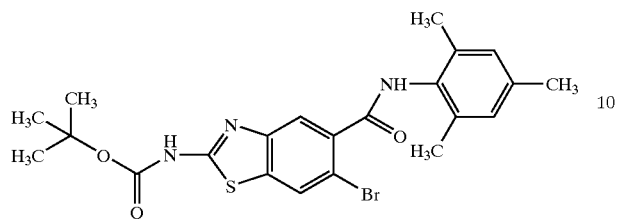

Analogous to the preparation of 1D except using a 1:1 mixture of 11Ba and 11Bb as the starting benzothiazole in place of 1A. The crude product obtained after work up was diluted with EtOAc and let stand at RT for 2 h. The precipitated solid was filtered, washed with EtOAc, and dried in vacuo to obtain the title compound 13 as a white solid.

MS=492.0 ($M^+ + H$).

EXAMPLE 14

Preparation of [5-[[(2,4,6-Trimethylphenyl)amino]carbonyl]-2-benzothiazolyl]carbamic acid, 1,1-dimethylethyl ester

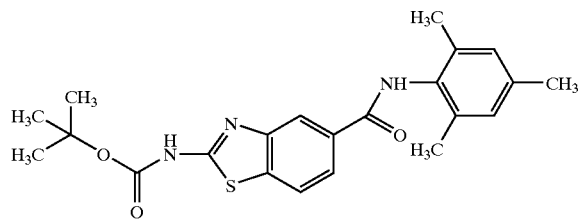

Analogous to the preparation of 10 except using 13 in place of 9 gave the title compound 14 (63%) as a white solid.

MS=412.1 ($M^+ + H$).

EXAMPLE 15

Preparation of 2-[[[Phenylamino]carbonyl]amino]-N-(2,4,6-trimethylphenyl)-6-benzothiazolecarboxamide

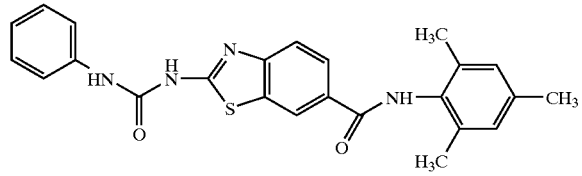

A solution of the free base of 2 (100 mg, 0.32 mmol), phenyl isocyanate (119 mg, 1 mmol) and 4-diethylaminopyridine (10 mg) in THF (2 mL) and pyridine (2 mL) was stirred at RT overnight. The mixture was diluted with dichloromethane (30 mL) and washed with 2 N aq. HCl solution (20 mL, 2×). The dichloromethane extract was diluted with methanol (10 mL), dried ($MgSO_4$), filtered and concentrated. The crude residue was diluted with EtOAc (25 mL) and the solid was filtered, and washed with EtOAc (5 mL, 3×). The white solid was suspended in dichloromethane (30 mL) and methanol (2 mL) and stirred for 20 min and filtered. Residual solid was washed with dichloromethane (5 mL, 3×), and dried in vacuo to obtain the title compound 15 (88 mg, 64%).

MS=431.1 ($M^+ + H$).

EXAMPLE 16

Preparation of 2-[[[(Phenylmethyl)amino]carbonyl]amino]-N-(2,4,6-trimethylphenyl)-6-benzothiazolecarboxamide

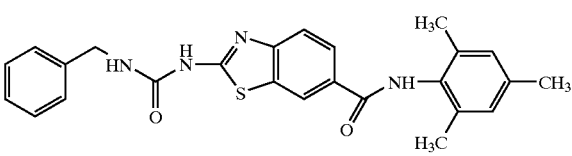

Analogous to the preparation of 15 except using benzyl isocyanate gave the title compound 16 as a white solid.

MS=445 ($M^+ + H$).

EXAMPLE 17

Preparation of 2-[[[Ethylamino]carbonyl]amino]-N-(2,4,6-trimethylphenyl)-6-benzothiazolecarboxamide

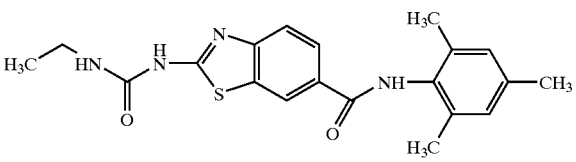

Analogous to the preparation of 15 except using ethyl isocyanate gave the title compound 17 as a white solid.

MS=383 ($M^+ + H$).

EXAMPLE 18

Preparation of 2-[[(Butylamino)carbonyl]amino]-N-2,4,6-trimethylphenyl)-6-benzothiazolecarboxamide

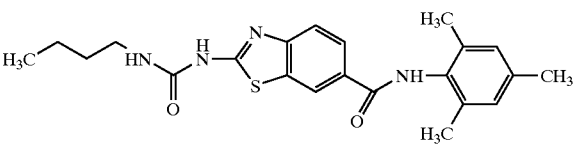

Analogous to the preparation of 15 except using n-butyl isocyanate gave the title compound 18 as a white solid.

MS=411 ($M^+ + H$).

EXAMPLES 19 TO 58

General Procedure

Compounds 19 to 58 were prepared following the procedure described below.

The appropriate amine (0.08 mmol) was added to a solution of 7A (20 mg, 0.054 mmol) in THF (3 mL). The solution was stirred at RT for 18 to 40 h. The reaction mixture was diluted with dichloromethane (5 mL) and washed with 1 N aq. HCl solution (1.5 mL, 2×), and 1 N aq. NaOH solution (1.5 mL, 2×). The organic extract was dried (MgSO$_4$), filtered and concentrated in vacuo to obtain the compounds of these Examples, identified in Table 1 below.

In Table 1, "HPLC Ret Time" was the HPLC retention time obtained under the following conditions: YMC S5 ODS 4.6×50 mm Ballastic Column, 4 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 4 mL/min, λ=220 nM for compounds 19 to 56. For compounds 57 to 58, HPLC conditions were: Zorbax SB-C18 4.5 mm×7.5 cm short column, 8 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 2.5 ml/min, λ=217 nM.

TABLE 1

| Ex. No. | Compound Structure | Compound Name | HPLC Ret Time (min) |
|---|---|---|---|
| 19 | 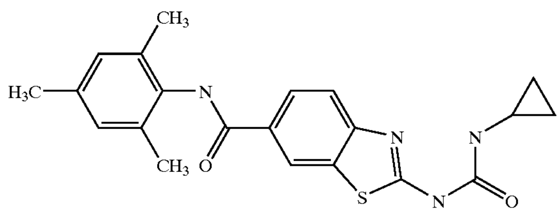 | 2-[[(Cyclopropylamino)-carbonyl]amino]-N-(2,4,6-trimethylphenyl)-6-benzothiazolecarboxamide | 3.88 |
| 20 | 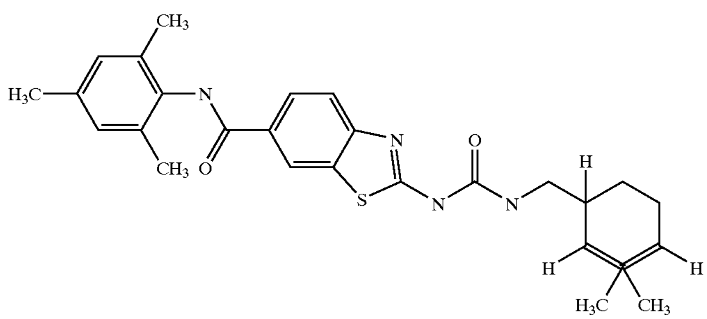 | (R)-2-[[[[(3,3-Dimethylcyclohexyl)methyl]amino]-carbonyl]amino]-N-(2,4,6-trimethylphenyl)-6-benzotiazolecarboxamide | 4.81 |
| 21 | 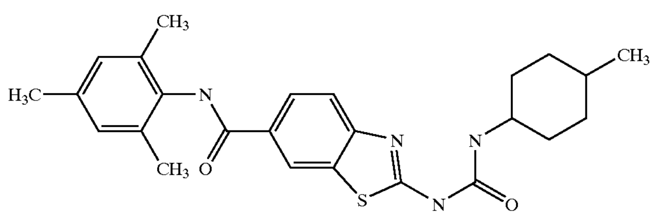 | 2-[[[(4-Methylcyclohexyl)-amino]carbonyl]amino]-N-(2,4,6-trimethylphenyl)-6-benzothiazolecarboxamide | 4.52 |
| 22 | 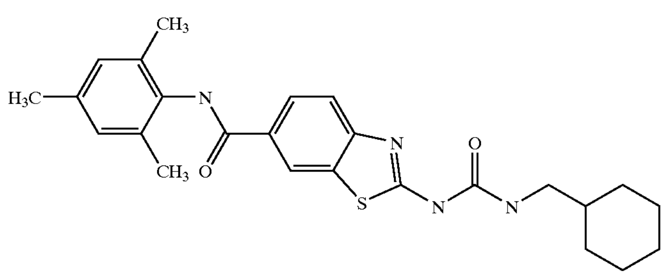 | 2-[[[(Cyclohexylmethyl)-amino]carbonyl]amino]-N-(2,4,6-trimethylphenyl)-6-benzothiazolecarboxamide | 4.53 |
| 23 | 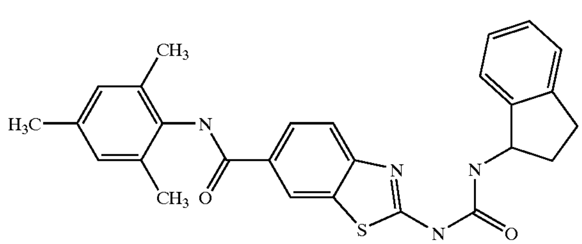 | 2-[[[(2,3-Dihydro-1H-inden-1-yl)amino]carbonyl]-amino]-N-(2,4,6-trimethylphenyl)-6-benzothiazolecarboxamide | 4.40 |

TABLE 1-continued

| Ex. No. | Compound Structure | Compound Name | HPLC Ret Time (min) |
|---|---|---|---|
| 24 | 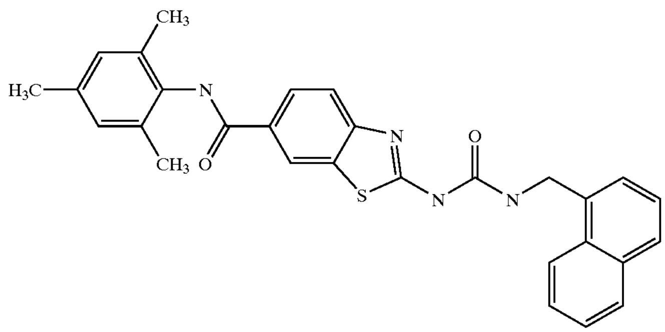 | 2-[[[(1-Naphthalenyl-methyl)amino]carbonyl]-amino]-N-(2,4,6-trimethyl-phenyl)-6-benzothiazole-carboxamide | 4.53 |
| 25 | 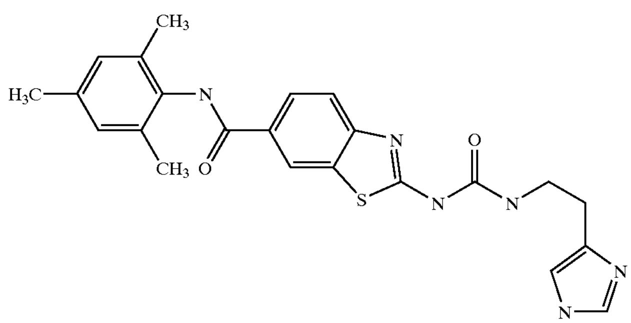 | 2-[[[[2-(1H-Imidazol-4-yl)-ethyl]amino]carbonyl]-amino]-N-(2,4,6-trimethyl-phenyl)-6-benzothiazole-carboxamide | 3.19 |
| 26 | 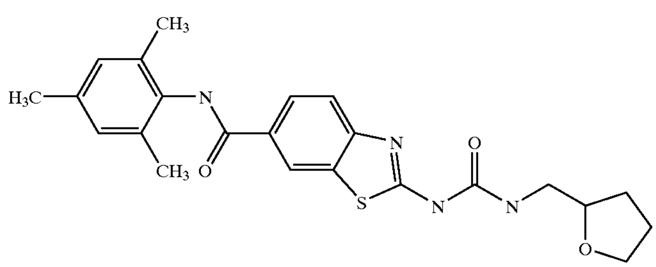 | 2-[[[[(Tetrahydro-2-furanyl)-methyl]amino]carbonyl]-amino]-N-(2,4,6-trimethyl-phenyl)-6-benzothiazole-carboxamide | 4.14 |
| 27 | 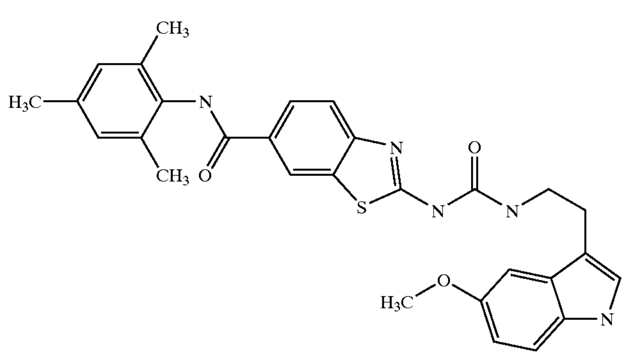 | 2-[[[[2-(5-Methoxy-1H-indol-3-yl)ethyl]amino]-carbonyl]amino]-N-(2,4,6-trimethylphenyl)-6-benzo-thiazolecarboxamide | 4.19 |

TABLE 1-continued

| Ex. No. | Compound Structure | Compound Name | HPLC Ret Time (min) |
|---|---|---|---|
| 28 | 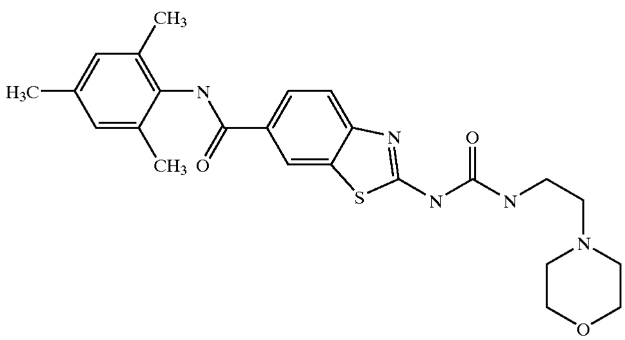 | 2-[[[[2-(4-Morpholinyl)-ethyl]amino]carbonyl]-amino]-N-(2,4,6-trimethyl-phenyl)-6-benzo-thiazolecarboxamide | 3.08 |
| 29 | 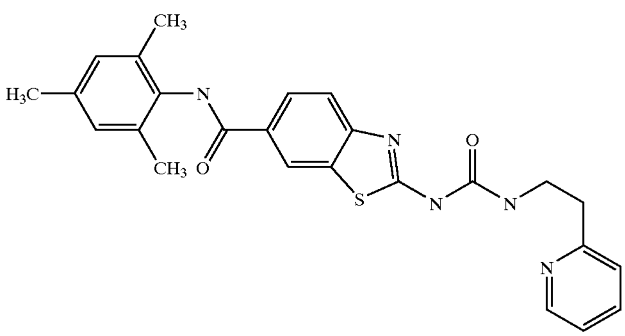 | 2-[[[[2-(2-Pyridinyl)ethyl]-amino]carbonyl]amino]-N-(2,4,6-trimethylphenyl)-6-benzothiazolecarboxamide | 3.17 |
| 30 | 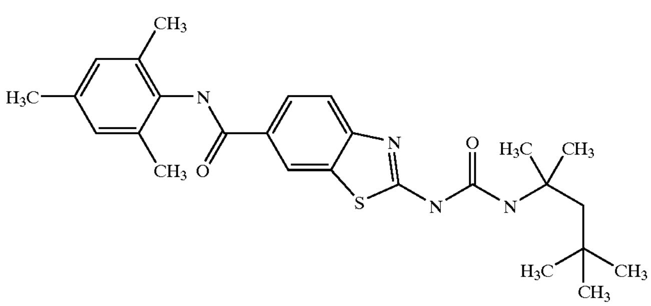 | 2-[[[(1,1,3,3-Tetramethyl-butyl)amino]carbonyl]-amino]-N-(2,4,6-trimethyl-phenyl)-6-benzothiazole-carboxamide | 4.64 |
| 31 | 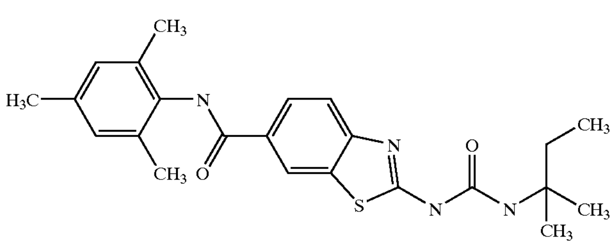 | 2-[[[(1,1-Dimethylpropyl)-amino]carbonyl]amino]-N-(2,4,6-trimethylphenyl)-6-benzothiazolecarboxamide | 4.32 |
| 32 | 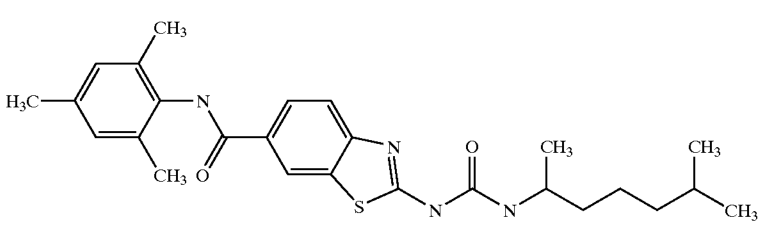 | 2-[[[(1,5-Dimethylhexyl)-amino]carbonyl]amino]-N-(2,4,6-trimethylphenyl)-6-benzothiazolecarboxamide | 4.74 |

TABLE 1-continued

| Ex. No. | Compound Structure | Compound Name | HPLC Ret Time (min) |
|---|---|---|---|
| 33 | 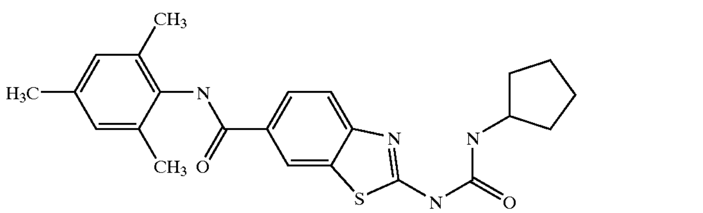 | 2-[[(Cyclopentylamino)-carbonyl]amino]-N-(2,4,6-trimethylphenyl)-6-benzothiazolecarboxamide | 4.28 |
| 34 | 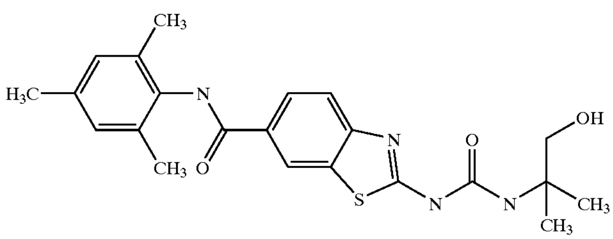 | 2-[[[(1,1-Dimethyl-2-hydroxyethyl)amino]-carbonyl]amino]-N-(2,4,6-trimethylphenyl)-6-benzothiazolecarboxamide | 3.90 |
| 35 | 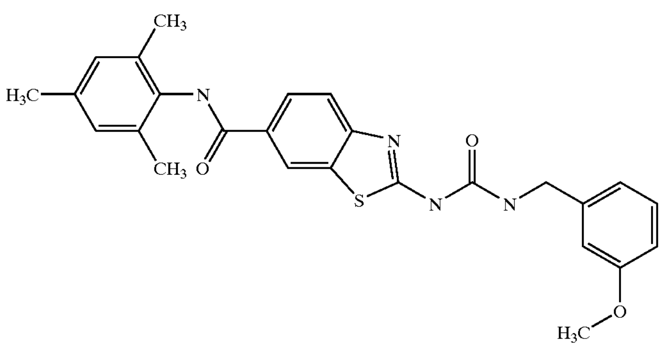 | 2-[[[[(3-Methoxyphenyl)-methyl]amino]carbonyl]-amino]-N-(2,4,6-trimethylphenyl)-6-benzothiazole-carboxamide | 4.19 |
| 36 | 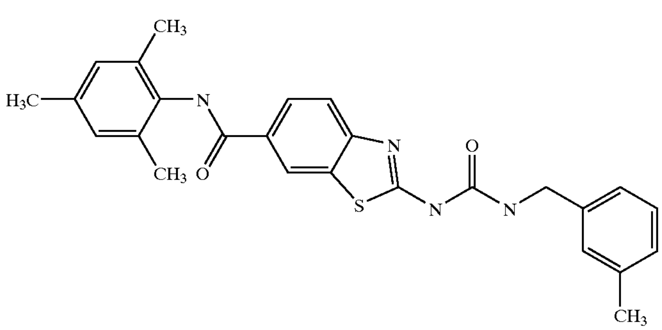 | 2-[[[[(3-Methylphenyl)-methyl]amino]carbonyl]-amino]-N-(2,4,6-trimethylphenyl)-6-benzothiazole-carboxamide | 4.34 |
| 37 | 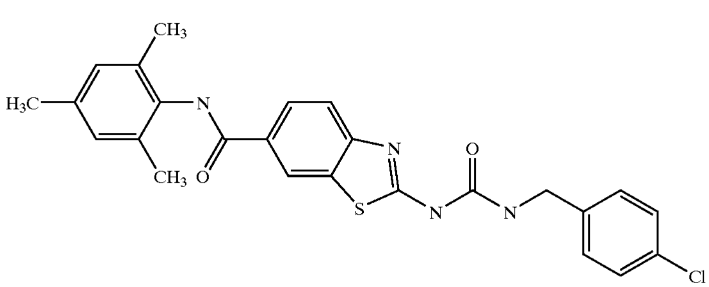 | 2-[[[[(4-Chlorophenyl)-methyl]amino]carbonyl]-amino]-N-(2,4,6-trimethylphenyl)-6-benzothiazole-carboxamide | 4.37 |

TABLE 1-continued

| Ex. No. | Compound Structure | Compound Name | HPLC Ret Time (min) |
|---|---|---|---|
| 38 | 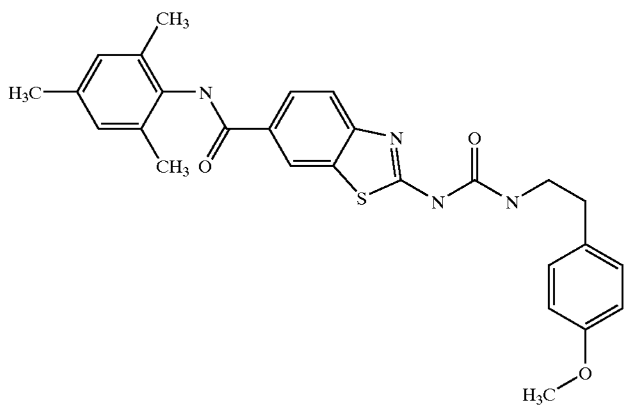 | 2-[[[[2-(4-Methoxyphenyl)-ethyl]amino]carbonyl]-amino]-N-(2,4,6-trimethyl-phenyl)-6-benzothiazole-carboxamide | 4.30 |
| 39 | 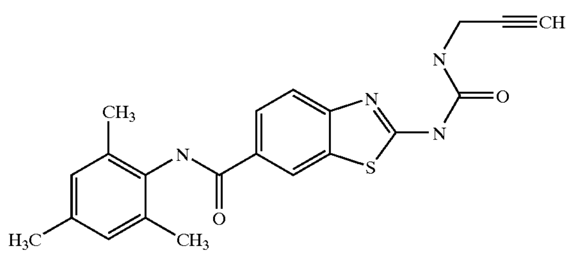 | 2-[[(2-Propynylamino)-carbonyl]amino]-N-(2,4,6-trimethylphenyl)-6-benzo-thiazolecarboxamide | 4.66 |
| 40 | 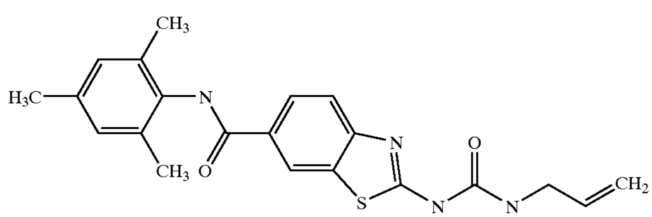 | 2-[[(2-Propenylamino)-carbonyl]amino]-N-(2,4,6-trimethylphenyl)-6-benzo-thiazolecarboxamide | 3.94 |
| 41 | 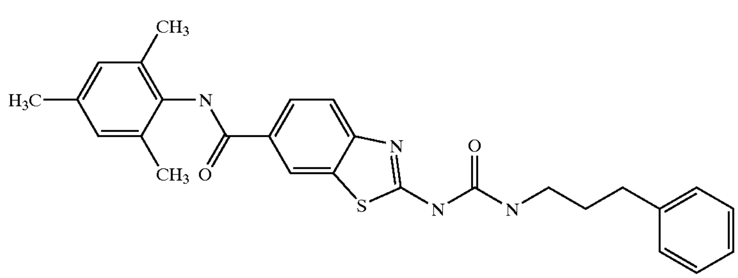 | 2-[[[(3-Phenylpropyl)-amino]carbonyl]amino]-N-(2,4,6-trimethylphenyl)-6-benzothiazolecarboxamide | 4.45 |
| 42 | 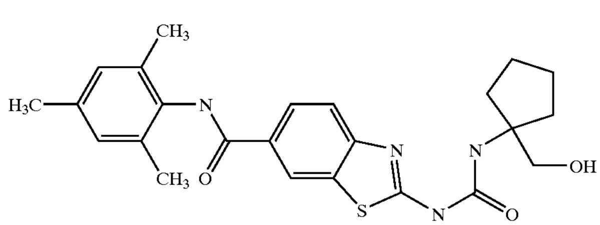 | 2-[[[[1-(Hydroxymethyl)-cyclopentyl]amino]-carbonyl]amino]-N-(2,4,6-trimethylphenyl)-6-benzo-thiazolecarboxamide | 4.07 |

TABLE 1-continued

| Ex. No. | Compound Structure | Compound Name | HPLC Ret Time (min) |
|---|---|---|---|
| 43 | 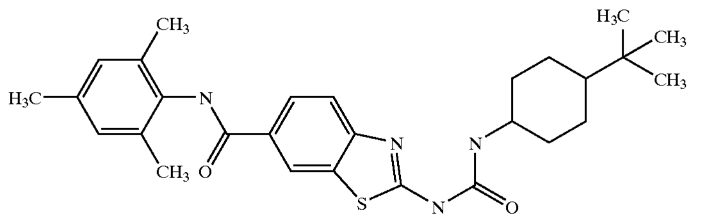 | 2-[[[[4-(Dimethylethyl)-cyclohexyl]amino]-carbonyl]amino]-N-(2,4,6-trimethylphenyl)-6-benzothiazolecarboxamide | 4.87 |
| 44 | 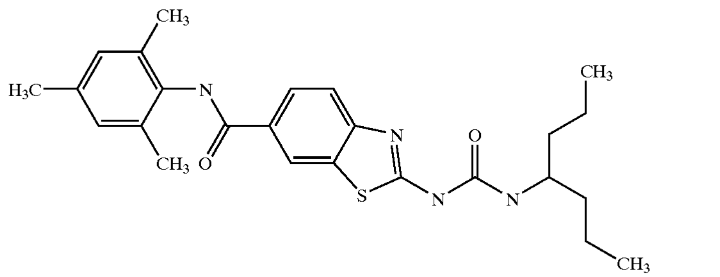 | 2-[[[(1-Propylbutyl)-amino]carbonyl]amino]-N-(2,4,6-trimethylphenyl)-6-benzothiazolecarboxamide | 4.54 |
| 45 | 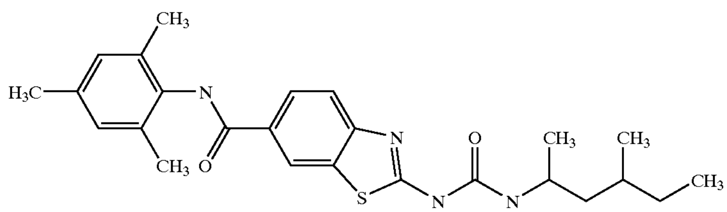 | 2-[[[(1,3-Dimethylpentyl)-amino]carbonyl]amino]-N-(2,4,6-trimethylphenyl)-6-benzothiazolecarboxamide | 4.57 |
| 46 | 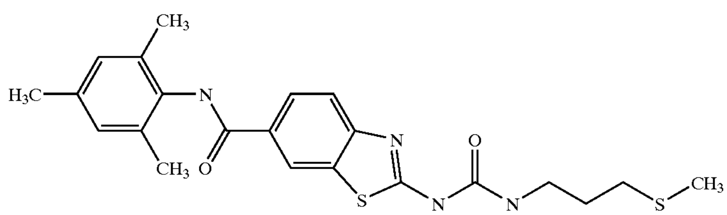 | 2-[[[[3-(Methylthio)propyl]-amino]carbonyl]amino]-N-(2,4,6-trimethylphenyl)-6-benzothiazolecarboxamide | 4.08 |
| 47 | 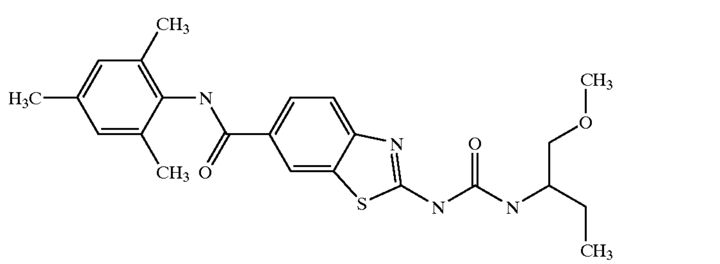 | 2-[[[[1-(Methoxymethyl)-propyl]amino]carbonyl]-amino]-N-(2,4,6-trimethyl-phenyl)-6-benzothiazole-carboxamide | 4.05 |
| 48 | 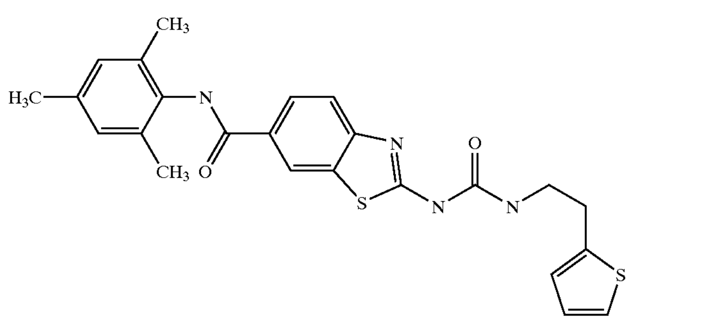 | 2-[[[[2-(2-Thienyl)ethyl]-amino]carbonyl]amino]-N-(2,4,6-trimethylphenyl)-6-benzothiazolecarboxamide | 4.24 |

TABLE 1-continued

| Ex. No. | Compound Structure | Compound Name | HPLC Ret Time (min) |
|---|---|---|---|
| 49 | 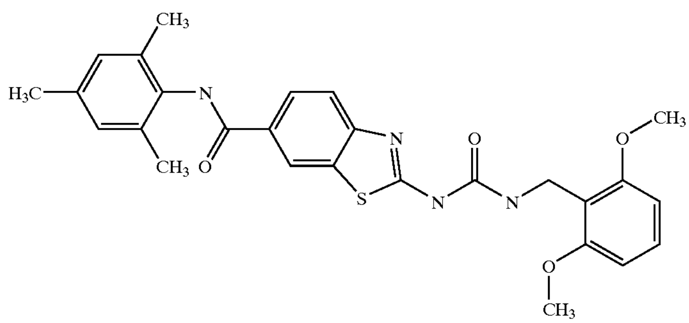 | 2-[[[[(2,6-Dimethoxy-phenyl)methyl]amino]-carbonyl]amino]-N-(2,4,6-trimethylphenyl)-6-benzothiazolecarboxamide | 4.31 |
| 50 | Chiral | (R)-2-[[[[1-(Hydroxy-methyl)-2-phenylethyl]-amino]carbonyl]amino]-N-(2,4,6-trimethylphenyl)-6-benzothiazolecarboxamide | 4.13 |
| 51 | Chiral | (R)-2-[[[(1-Phenylethyl)-amino]carbonyl]amino]-N-(2,4,6-trimethylphenyl)-6-benzothiazolecarboxamide | 4.28 |
| 52 | 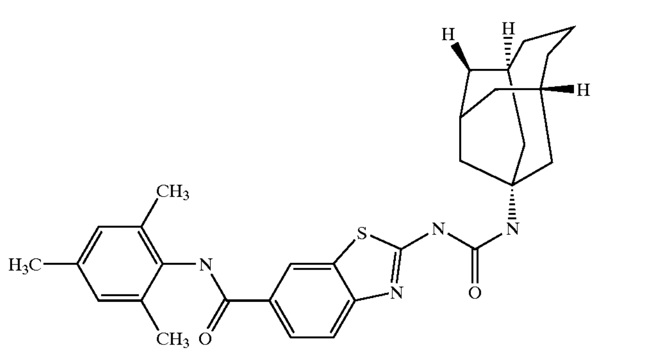 | 2-[[(1-Adamantylamino)-carbonyl]amino]-N-(2,4,6-trimethylphenyl)-6-benzothiazolecarboxamide | 4.74 |

TABLE 1-continued

| Ex. No. | Compound Structure | Compound Name | HPLC Ret Time (min) |
|---|---|---|---|
| 53 | 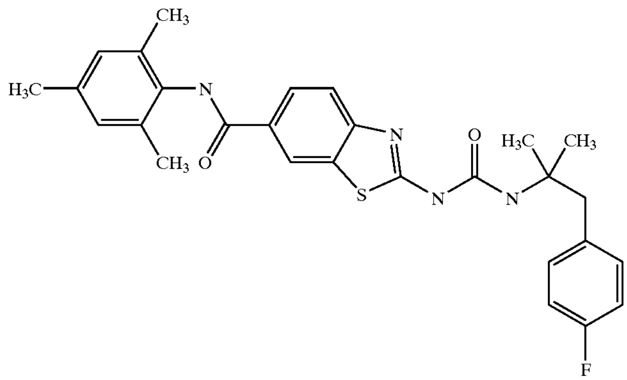 | 2-[[[[2-(4-Fluorophenyl)-1,1-dimethylethyl]amino]-carbonyl]amino]-N-(2,4,6-trimethylphenyl)-6-benzothiazolecarboxamide | 4.54 |
| 54 | 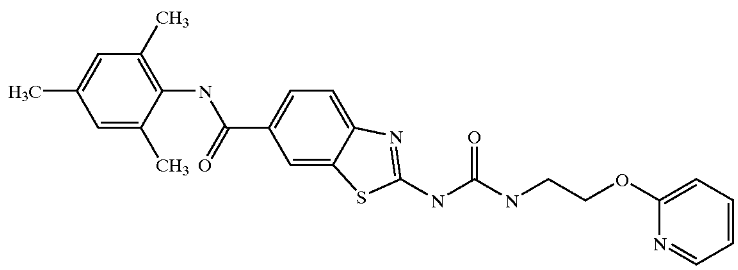 | 2-[[[[2-(2-Pyridinyloxy)-ethyl]amino]carbonyl]-amino]-N-(2,4,6-trimethyl-phenyl)-6-benzothiazole-carboxamide | 3.97 |
| 55 | 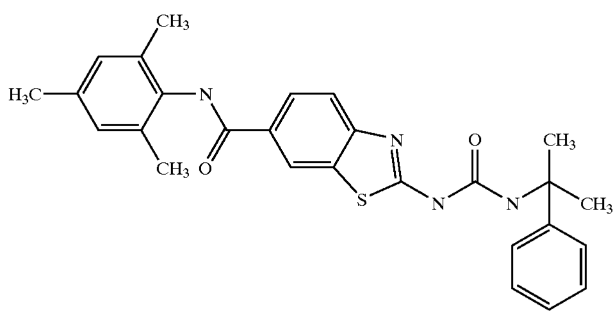 | 2-[[[(1-Methyl-1-phenyl-ethyl)amino]carbonyl]-amino]-N-(2,4,6-trimethyl-phenyl)-6-benzothiazole-carboxamide | 4.36 |
| 56 | Chiral | (R)-2-[[[[1-(4-Methyl-phenyl)ethyl]amino]-carbonyl]amino]-N-(2,4,6-trimethylphenyl)-6-benzothiazole-carboxamide | 4.44 |
| 57 | 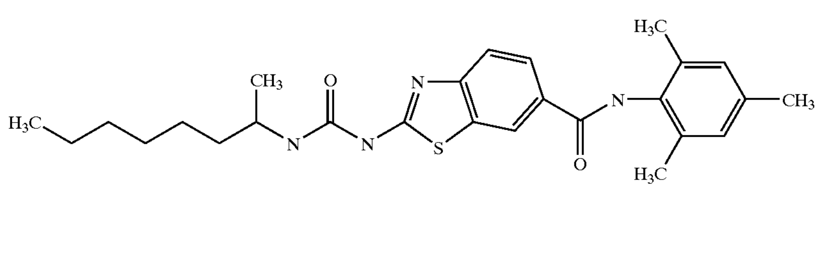 | 2-[[[(1-Methylheptyl)-amino]carbonyl]amino]-N-(2,4,6-trimethylphenyl)-6-benzothiazolecarboxamide | 9.75 |

TABLE 1-continued

| Ex. No. | Compound Structure | Compound Name | HPLC Ret Time (min) |
|---|---|---|---|
| 58 | 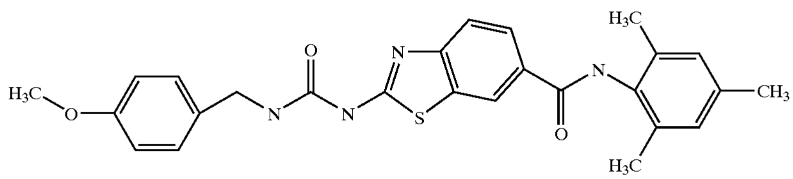 | 2-[[[[(4-Methoxyphenyl)-methyl]amino]carbonyl]-amino]-N-(2,4,6-trimethyl-phenyl)-6-benzothiazole-carboxamide | 8.38 |

EXAMPLES 59 TO 95

General Procedure

Compounds 59 to 95 were prepared following the procedure described below.

The appropriate arylamine (0.08 mmol) was added to a solution of 7A (20 mg, 0.054 mmol) in THF (3 mL). The solution was heated to 45° C. for 24 to 72 h. The reaction mixture was diluted with dichloromethane (5 mL) and washed with 1 N aq. HCl solution (3 mL, 2×), and 1 N aq. NaOH solution (3 mL, 2×). The organic extract was dried (MgSO$_4$), filtered and concentrated in vacuo to obtain in crude form the compounds of these Examples, which were purified by HPLC (automated preparative HPLC under the following conditions: YMC ODS A 20×100 mm column, 10 minute gradient starting from 30% solvent B (90% MeOH, 10% H$_2$O, 0.1% TFA) and 70% solvent A (10% MeOH, 90% H$_2$O, 0.1% TFA) to 100% solvent B, flow rate 20 mL/min, λ=220 nm), and are identified in Table 2 below.

In Table 2, "HPLC Ret Time" was the HPLC retention time obtained under the following conditions: YMC S5 ODS 4.6×50 mm Ballastic Column, 4 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 4 mL/min, λ=220 nM.

TABLE 2

| Ex. No. | Compound Structure | Compound Name | HPLC Ret Time (min) |
|---|---|---|---|
| 59 | 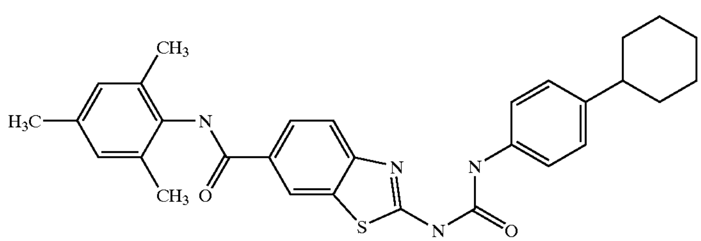 | 2-[[[(4-Cyclohexylphenyl)amino]-carbonyl]amino]-N-(2,4,6-trimethyl-phenyl)-6-benzothiazolecarboxamide | 4.99 |
| 60 | 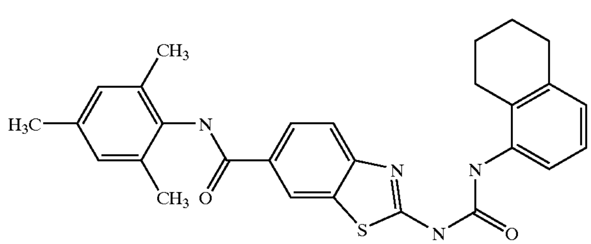 | 2-[[[(5,6,7,8-Tetrahydro-1-naphthalenyl)amino]carbonyl]amino]-N-(2,4,6-trimethylphenyl)-6-benzo-thiazolecarboxamide | 4.64 |
| 61 | 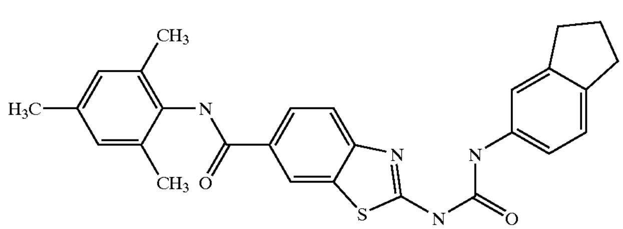 | 2-[[[(2,3-Dihydro-1H-inden-5-yl)amino]-carbonyl]amino]-N-(2,4,6-trimethyl-phenyl)-6-benzothiazolecarboxamide | 3.94 |

TABLE 2-continued

| Ex. No. | Compound Name | HPLC Ret Time (min) |
|---|---|---|
| 62 | 2-[[[(1,3-Benzodioxol-5-ylamino)-carbonyl]amino]-N-(2,4,6-trimethyl-phenyl)-6-benzothiazolecarboxamide | 4.20 |
| 63 | 2-[[[(2-Pyridinylamino)carbonyl]amino]-N-(2,4,6-trimethylphenyl)-6-benzo-thiazolecarboxamide | 3.95 |
| 64 | 2-[[[[(3-Methyl-2-pyridinyl)amino]-carbonyl]amino]-N-(2,4,6-trimethyl-phenyl)-6-benzothiazolecarboxamide | 3.75 |
| 65 | 2-[[[[(4-Methyl-2-pyridinyl)amino]-carbonyl]amino]-N-(2,4,6-trimethyl-phenyl)-6-benzothiazolecarboxamide | 3.89 |
| 66 | 2-[[[[(2-Chloro-5-methylphenyl)amino]-carbonyl]amino]-N-(2,4,6-trimethyl-phenyl)-6-benzothiazolecarboxamide | 4.62 |
| 67 | 2-[[[[(2,6-Dichlorophenyl)amino]-carbonyl]amino]-N-(2,4,6-trimethyl-phenyl)-6-benzothiazolecarboxamide | 5.03 |

TABLE 2-continued

| Ex. No. | Compound Structure | Compound Name | HPLC Ret Time (min) |
|---|---|---|---|
| 68 | 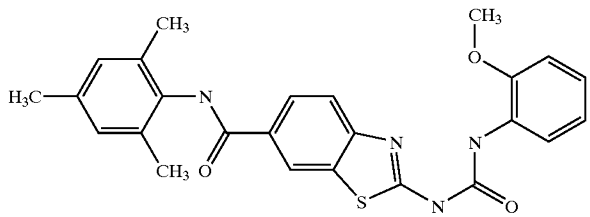 | 2-[[[(2-Methoxyphenyl)amino]-carbonyl]amino]-N-(2,4,6-trimethylphenyl)-6-benzothiazolecarboxamide | 4.37 |
| 69 | 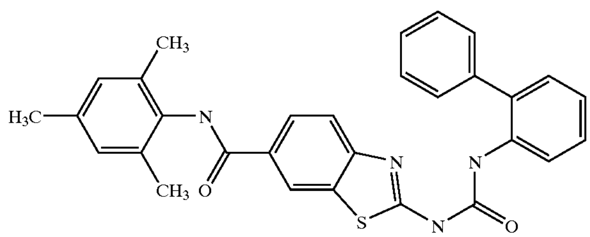 | 2-[[([1,1'-Biphenyl]-2-ylamino)-carbonyl]amino]-N-(2,4,6-trimethylphenyl)-6-benzothiazolecarboxamide | 4.57 |
| 70 | 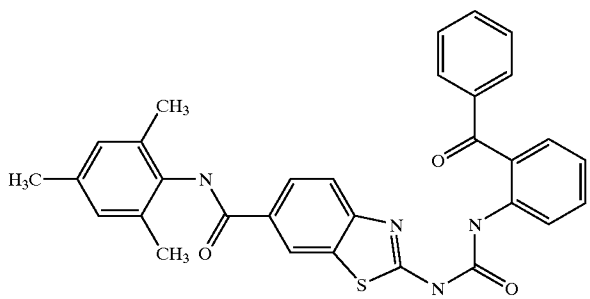 | 2-[[[(2-Benzoylphenyl)amino]-carbonyl]amino]-N-(2,4,6-trimethylphenyl)-6-benzothiazolecarboxamide | 3.53 |
| 71 | 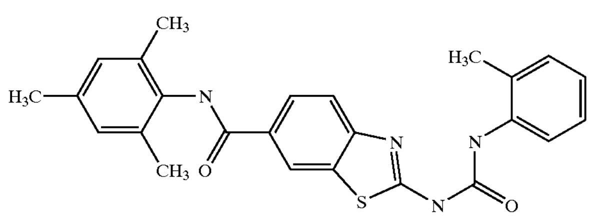 | 2-[[[(2-Methylphenyl)amino]-carbonyl]-amino]-N-(2,4,6-trimethylphenyl)-6-benzothiazolecarboxamide | 4.30 |
| 72 | 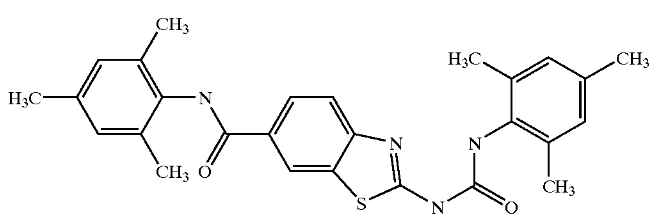 | N-(2,4,6-Trimethylphenyl)-2-[[[(2,4,6-trimethylphenyl)amino]carbonyl]-amino]-6-benzothiazolecarboxamide | 4.35 |
| 73 | 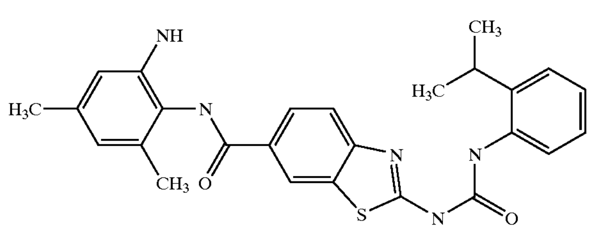 | 2-[[[[2-Methyl-6-(1-methylethyl)phenyl]-amino]carbonyl]amino]-N-(2,4,6-trimethylphenyl)-6-benzothiazole-carboxamide | 4.42 |

TABLE 2-continued

| Ex. No. | Compound Structure | Compound Name | HPLC Ret Time (min) |
|---|---|---|---|
| 74 | 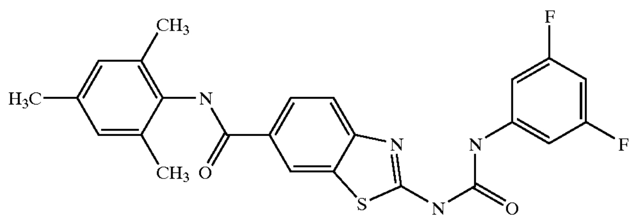 | 2-[[[(3,5-Difluorophenyl)amino]-carbonyl]amino]-N-(2,4,6-trimethyl-phenyl)-6-benzothiazolecarboxamide | 4.23 |
| 75 | 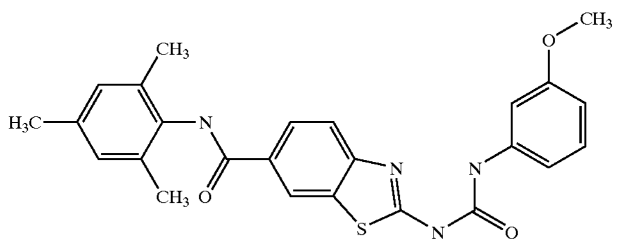 | 2-[[[(3-Methoxyphenyl)amino]carbonyl]-amino]-N-(2,4,6-trimethylphenyl)-6-benzothiazolecarboxamide | 4.25 |
| 76 | 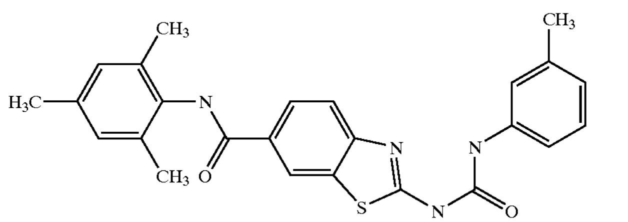 | 2-[[[(3-Methylphenyl)amino]carbonyl]-amino]-N-(2,4,6-trimethylphenyl)-6-benzothiazolecarboxamide | 4.38 |
| 77 | 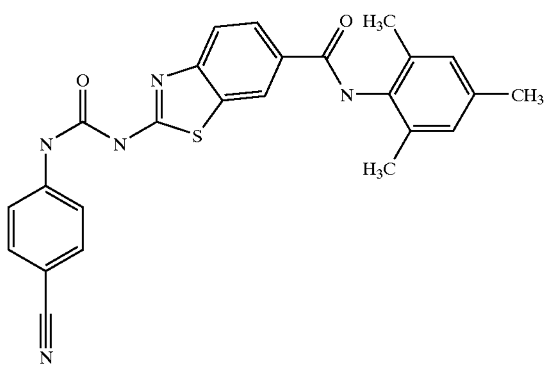 | 2-[[[(4-Cyanophenyl)amino]carbonyl]-amino]-N-(2,4,6-trimethylphenyl)-6-benzothiazolecarboxamide | 4.10 |
| 78 | 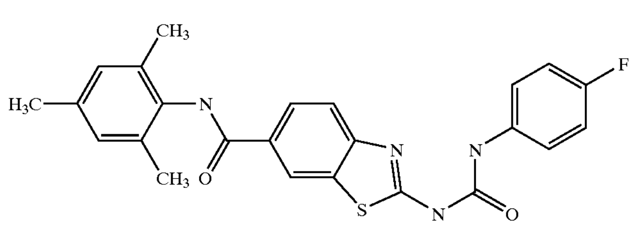 | 2-[[[(4-Fluorophenyl)amino]carbonyl]-amino]-N-(2,4,6-trimethylphenyl)-6-benzothiazolecarboxamide | 4.27 |
| 79 | 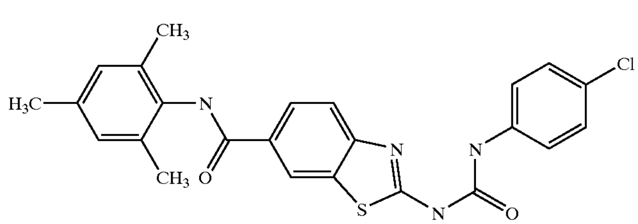 | 2-[[[(4-Chlorophenyl)amino]carbonyl]-amino]-N-(2,4,6-trimethylphenyl)-6-benzothiazolecarboxamide | 4.47 |

TABLE 2-continued

| Ex. No. | Compound Structure | Compound Name | HPLC Ret Time (min) |
|---|---|---|---|
| 80 | 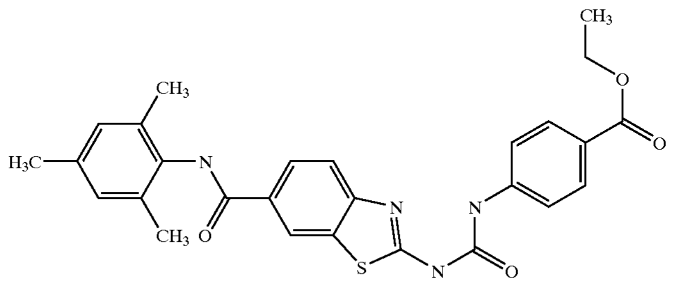 | 4-[[[[6-[[(2,4,6-Trimethylphenyl)amino]-carbonyl]-2-benzothiazolyl]amino]-carbonyl]amino]benzoic acid, ethyl ester | 4.50 |
| 81 | 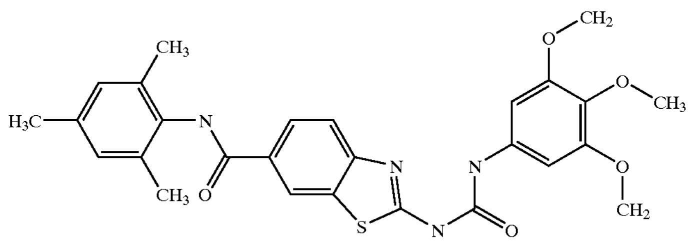 | 2-[[[(3,4,5-Trimethoxyphenyl)amino]-carbonyl]amino]-N-(2,4,6-trimethyl-phenyl)-6-benzothiazolecarboxamide | 4.16 |
| 82 | 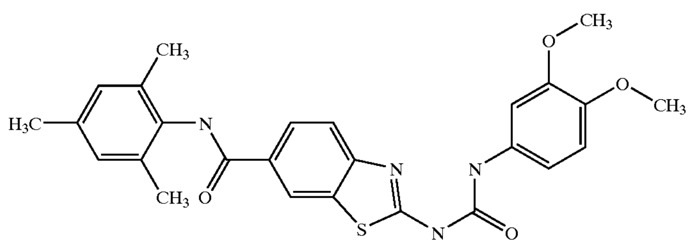 | 2-[[[(3,4-Dimethoxyphenyl)amino]-carbonyl]amino]-N-(2,4,6-trimethyl-phenyl)-6-benzothiazolecarboxamide | 4.10 |
| 83 | 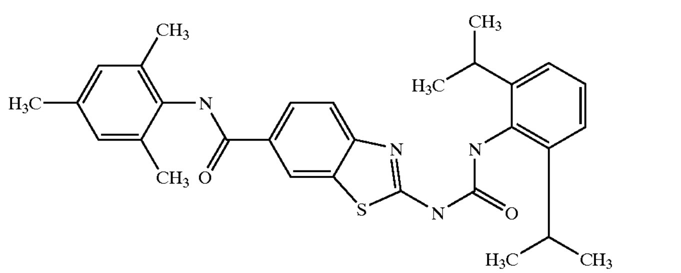 | 2-[[[[2,5-Bis(1-Methylethyl)phenyl]-amino]carbonyl]amino]-N-(2,4,6-trimethylphenyl)-6-benzothiazole-carboxamide | 5.03 |
| 84 | 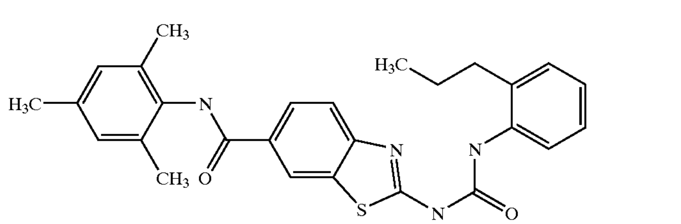 | 2-[[[(2-Propylphenyl)amino]carbonyl]-amino]-N-(2,4,6-trimethylphenyl)-6-benzothiazolecarboxamide | 4.52 |
| 85 | 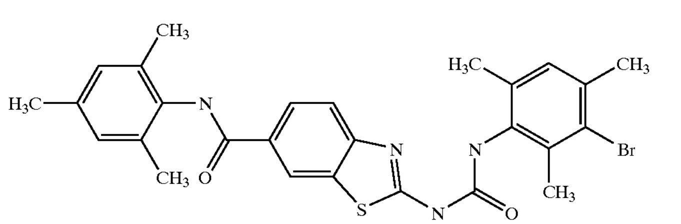 | 2-[[[(3-Bromo-2,4,6-trimethylphenyl)-amino]carbonyl]amino]-N-(2,4,6-trimethylphenyl)-6-benzothiazole-carboxamide | 4.59 |

TABLE 2-continued

| Ex. No. | Compound Structure | Compound Name | HPLC Ret Time (min) |
|---|---|---|---|
| 86 | 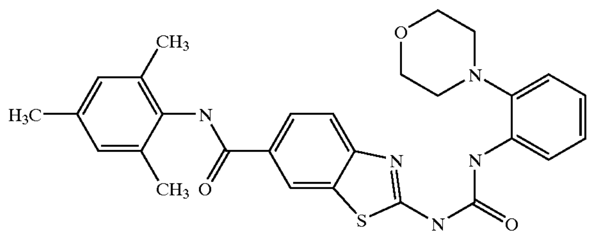 | 2-[[[[2-(4-Morpholinyl)phenyl]amino]-carbonyl]amino]-N-(2,4,6-trimethyl-phenyl)-6-benzothiazolecarboxamide | 4.70 |
| 87 | 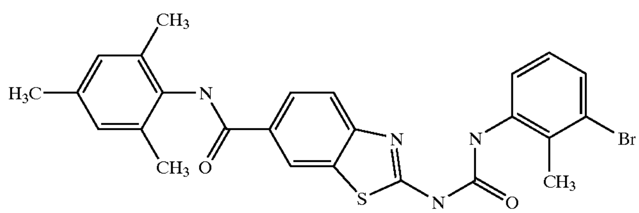 | 2-[[[(3-Bromo-2-methylphenyl)amino]-carbonyl]amino]-N-(2,4,6-trimethyl-phenyl)-6-benzothiazolecarboxamide | 4.59 |
| 88 | 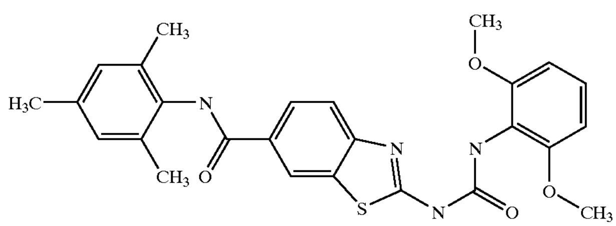 | 2-[[[(2,6-Dimethoxyphenyl)amino]-carbonyl]amino]-N-(2,4,6-trimethyl-phenyl)-6-benzothiazolecarboxamide | 3.91 |
| 89 | 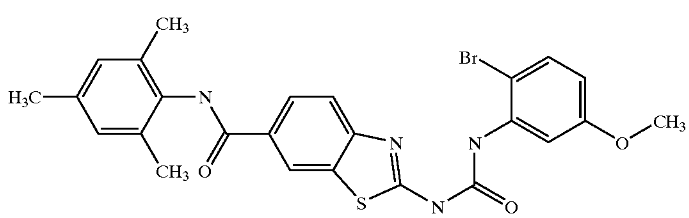 | 2-[[[(2-Bromo-5-methoxyphenyl)amino]-carbonyl]amino]-N-(2,4,6-trimethyl-phenyl)-6-benzothiazolecarboxamide | 4.61 |
| 90 | 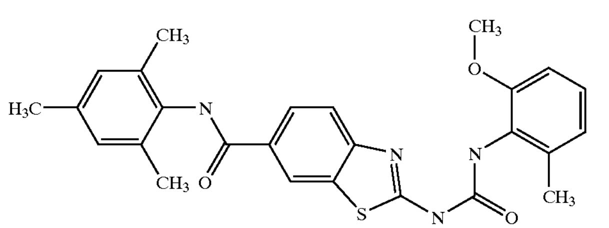 | 2-[[[(2-Methoxy-6-methylphenyl)-amino]carbonyl]amino]-N-(2,4,6-trimethylphenyl)-6-benzothiazole-carboxamide | 4.10 |
| 91 | 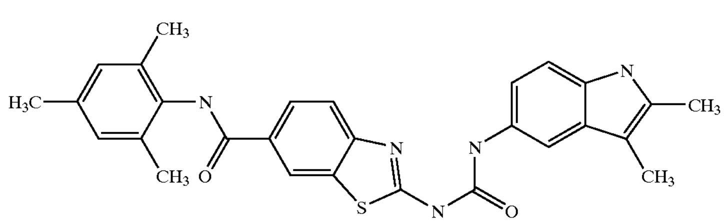 | 2-[[[(2,3-Dimethyl-1H-indol-5-yl)-amino]carbonyl]amino]-N-(2,4,6-trimethylphenyl)-6-benzothiazole-carboxamide | 4.28 |

TABLE 2-continued

| Ex. No. | Compound Structure | Compound Name | HPLC Ret Time (min) |
|---|---|---|---|
| 92 | 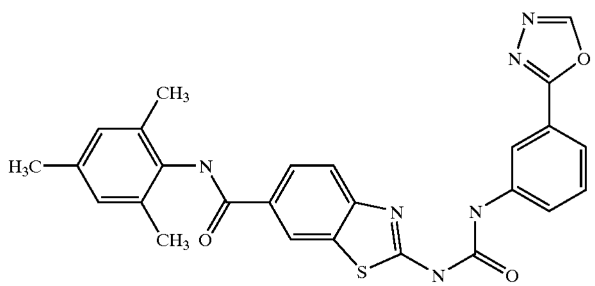 | 2-[[[[3-(1,3,4-Oxadiazol-2-yl)phenyl]-amino]carbonyl]amino]-N-(2,4,6-trimethylphenyl)-6-benzothiazole-carboxamide | 3.76 |
| 93 | 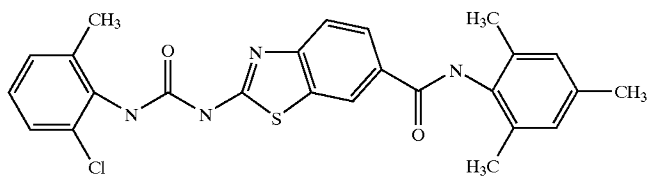 | 2-[[[(2-Chloro-6-methylphenyl)amino]-carbonyl]amino]-N-(2,4,6-trimethyl-phenyl)-6-benzothiazolecarboxamide | 4.08 |
| 94 | 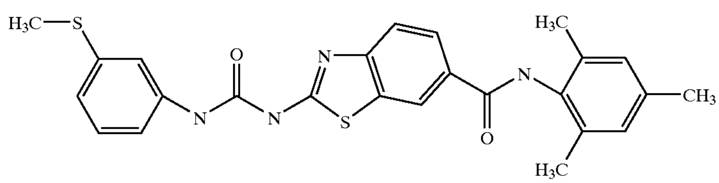 | 2-[[[[3-(Methylthio)phenyl]amino]-carbonyl]amino]-N-(2,4,6-trimethyl-phenyl)-6-benzothiazolecarboxamide | 4.48 |
| 95 | 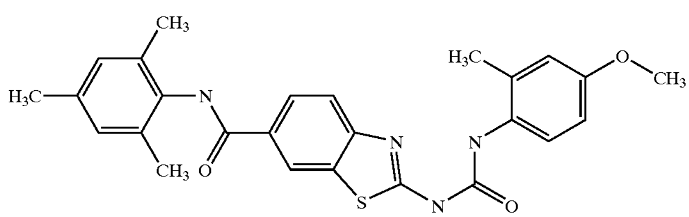 | 2-[[[(4-Methoxy-2-methylphenyl)-amino]carbonyl]amino]-N-(2,4,6-trimethylphenyl)-6-benzothiazole-carboxamide | 4.59 |

EXAMPLES 96 TO 140

General Procedure

Compounds 96 to 140 were prepared following the procedure described below.

Diisopropylethyl amine (50 μl, 0.288 mmol) was added to a mixture of the free base of 2 (30 mg, 0.096 mmol), the appropriate carboxylic acid (0.115 mmol), 1-hydroxy-7-azabenzotriazole (17 mg, 0.125 mmol), and ethyl-3-(3-dimethylamino)-propyl carbodiimide hydrochloride (24 mg, 0.125 mmol) in THF (1 mL). The mixture was heated at 45° C. for 18–72 h. The reaction mixture was diluted with dichloromethane (5 mL) and washed with 1 N aq. HCl solution (2×), and 1 N aq. NaOH solution (2×). The organic extract was dried (MgSO$_4$), filtered and concentrated in vacuo. The crude products were purified either by trituration with dichloromethane-ether or by automatic preparative HPLC (conditions: YMC ODS A 20×100 mm column, 10 minute gradient starting from 30% solvent B (90% MeOH, 10% H$_2$O, 0.1% TFA) and 70% solvent A (10% MeOH, 90% H$_2$O, 0.1% TFA) to 100% solvent B, flow rate 20 mL/min, λ=220 nm) to obtain the compounds of these Examples which are identified in Table 3 below.

In Table 3, "HPLC Ret Time" was the HPLC retention time obtained under the following conditions: YMC S5 ODS 4.6×50 mm Ballastic Column, 4 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 4 mL/min, λ=220 nM for compounds 99 to 140. For compound 98 the HPLC conditions were: Zorbax SB-C18 4.5 mm×7.5 cm short column, 8 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 2.5 mL/min, λ=217 nM. For compound 96 the HPLC conditions were: YMC S5 ODS 4.6×50 mm Ballastic Column, 4 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 3 mL/min, λ=220 nM. For compound 97 the HPLC conditions were: YMC S5 ODS 4.6×50 mm Ballastic Column, 8 min gradient starting from 100% solvent A (10% MeOH, 90% 140, 0.2% H$_3$PO$_4$) to 100% solvent B (90% MeOH, 10% H$_2$O, 0.2% H$_3$PO$_4$), flow rate 3 mL/min, λ=220 nM.

TABLE 3

| Ex. No. | Compound Structure | Compound Name | HPLC Ret Time (min) |
|---|---|---|---|
| 96 | 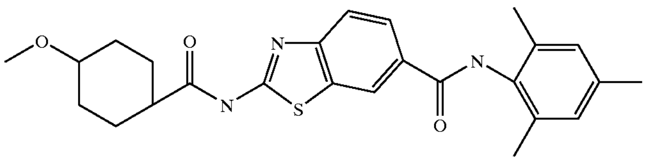 | 2-[[(4-Methoxycyclohexyl)carbonyl]amino]-N-(2,4,6-trimethylphenyl)-6-benzothiazolecarboxamide | 4.73 |
| 97 | 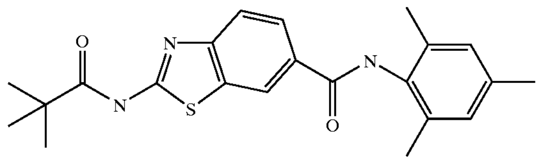 | 2-[(2,2-Dimethyl-1-oxopropyl)amino]-N-(2,4,6-trimethylphenyl)-6-benzothiazolecarboxamide | 8.62 |
| 98 | 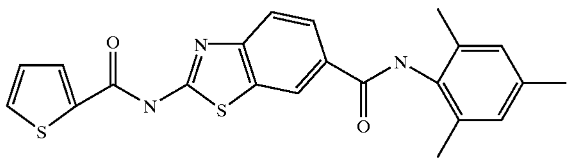 | 2-[(2-Thienylacetyl)amino]-N-(2,4,6-trimethylphenyl)-6-benzothiazolecarboxamide | 8.58 |
| 99 | 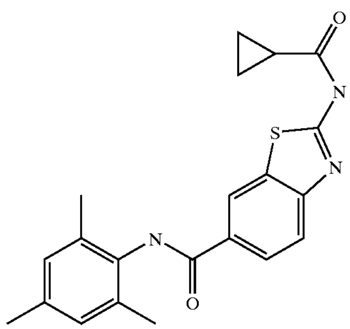 | 2-[(Cyclopropylcarbonyl)amino]-N-(2,4,6-trimethylphenyl)-6-benzothiazolecarboxamide | 3.93 |
| 100 | 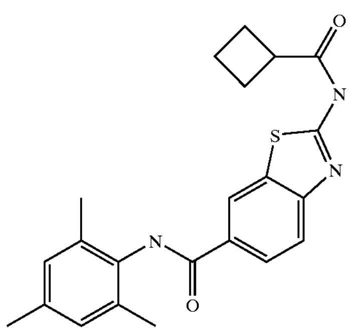 | 2-[(Cyclobutylcarbonyl)amino]-N-(2,4,6-trimethylphenyl)-6-benzothiazolecarboxamide | 4.00 |
| 101 | 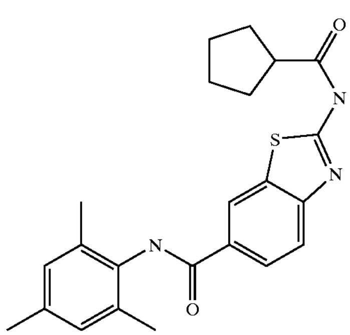 | 2-[(Cyclopentylcarbonyl)amino]-N-(2,4,6-trimethylphenyl)-6-benzothiazolecarboxamide | 3.97 |

TABLE 3-continued

| Ex. No. | Compound Structure | Compound Name | HPLC Ret Time (min) |
|---|---|---|---|
| 102 | 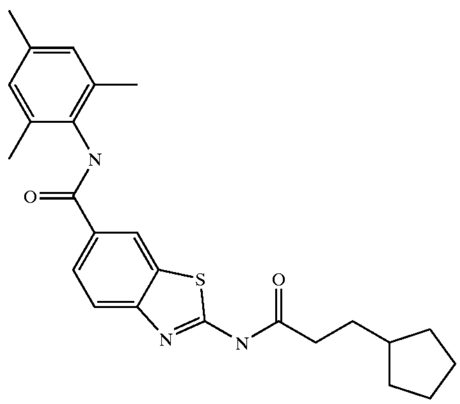 | 2-[(3-Cyclopentyl-1-oxopropyl)amino]-N-(2,4,6-trimethylphenyl)-6-benzothiazolecarboxamide | 4.52 |
| 103 | 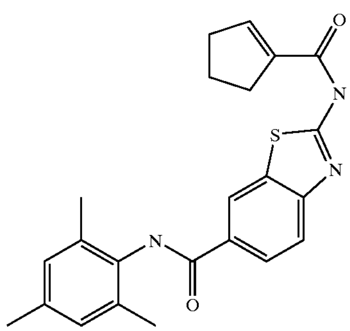 | 2-[(1-Cyclopenten-1-ylcarbonyl)amino]-N-(2,4,6-trimethylphenyl)-6-benzothiazolecarboxamide | 4.27 |
| 104 | 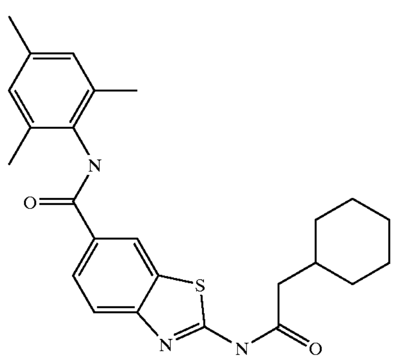 | 2-[(Cyclohexylacetyl)amino]-N-(2,4,6-trimethylphenyl)-6-benzothiazolecarboxamide | 4.51 |
| 105 | 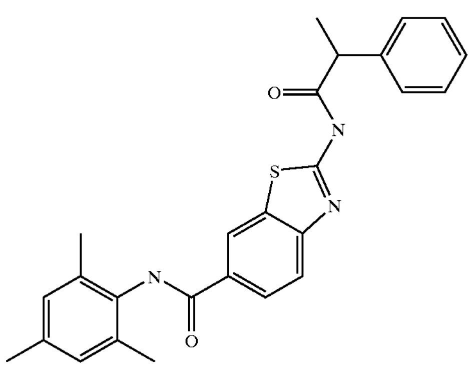 | 2-[(1-Oxo-2-phenylpropyl)amino]-N-(2,4,6-trimethylphenyl)-6-benzothiazolecarboxamide | 4.20 |

TABLE 3-continued
| Ex. No. | Compound Structure | Compound Name | HPLC Ret Time (min) |
|---|---|---|---|
| 106 | 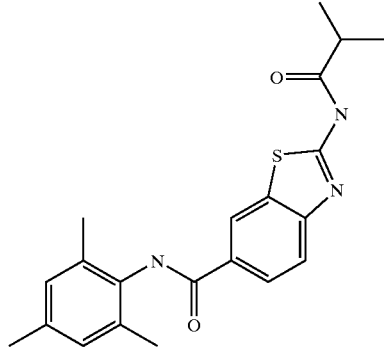 | 2-[(2-Methyl-1-oxopropyl)amino]-N-(2,4,6-trimethylphenyl)-6-benzothiazolecarboxamide | 3.89 |
| 107 | 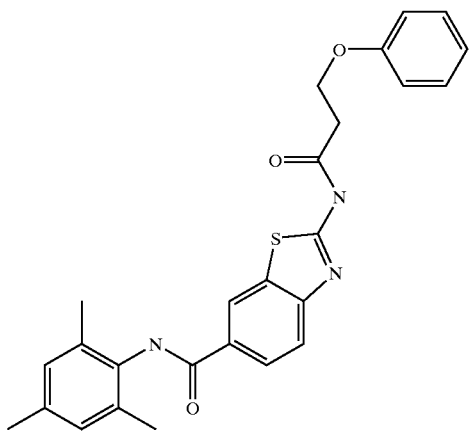 | 2-[(1-Oxo-3-phenoxypropyl)amino]-N-(2,4,6-trimethylphenyl)-6-benzothiazolecarboxamide | 4.34 |
| 108 | 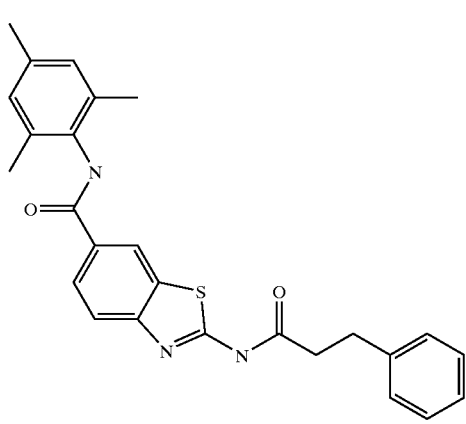 | 2-[(1-Oxo-3-phenylpropyl)amino]-N-(2,4,6-trimethylphenyl)-6-benzothiazolecarboxamide | 4.22 |

TABLE 3-continued

| Ex. No. | Compound Structure | Compound Name | HPLC Ret Time (min) |
|---|---|---|---|
| 109 | 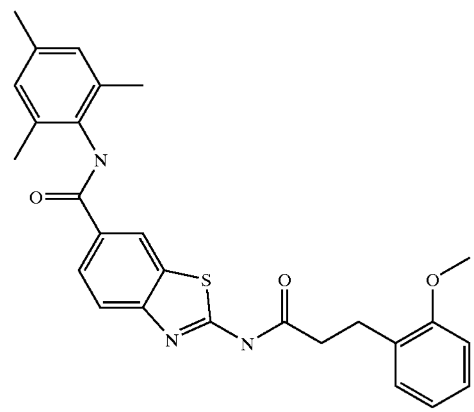 | 2-[[3-(2-Methoxyphenyl)-1-oxopropyl]amino]-N-(2,4,6-trimethylphenyl)-6-benzothiazolecarboxamide | 4.25 |
| 110 | 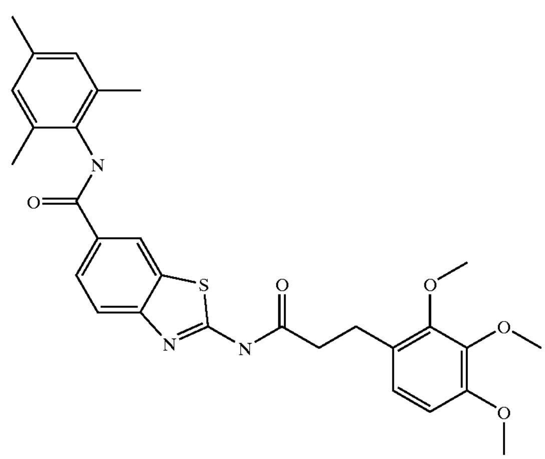 | 2-[[3-(2,3,4-Trimethoxyphenyl)-1-oxopropyl]amino]-N-(2,4,6-trimethylphenyl)-6-benzothiazolecarboxamide | 4.15 |
| 111 | 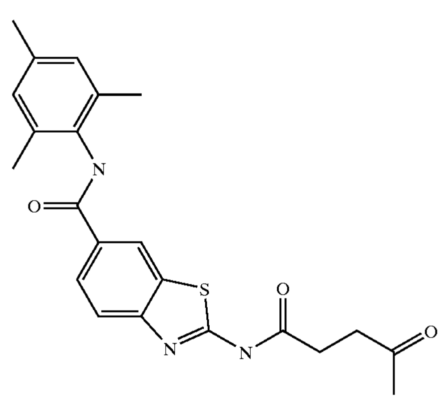 | 2-[(1,4-Dioxopentyl)amino]-N-(2,4,6-trimethylphenyl)-6-benzothiazolecarboxamide | 3.98 |

TABLE 3-continued

| Ex. No. | Compound Structure | Compound Name | HPLC Ret Time (min) |
|---|---|---|---|
| 112 | 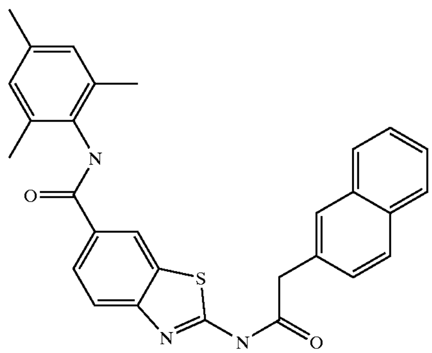 | 2-[(2-Naphthalenylacetyl)amino]-N-(2,4,6-trimethylphenyl)-6-benzothiazolecarboxamide | 4.42 |
| 113 | 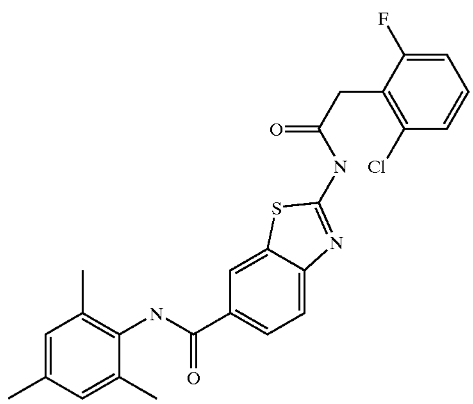 | 2-[[(2-Chloro-6-fluorophenyl)acetyl]amino]-N-(2,4,6-trimethylphenyl)-6-benzothiazolecarboxamide | 4.21 |
| 114 | 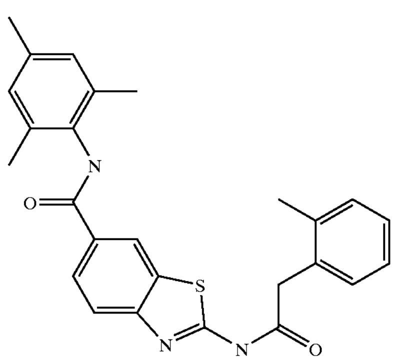 | 2-[[(2-Methylphenyl)acetyl]amino]-N-(2,4,6-trimethylphenyl)-6-benzothiazolecarboxamide | 4.31 |
| 115 | 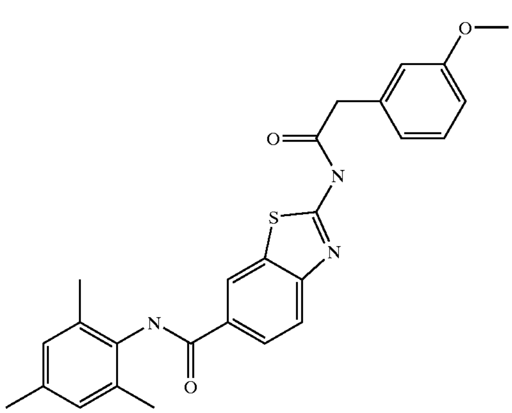 | 2-[[(3-Methoxyphenyl)acetyl]amino]-N-(2,4,6-trimethylphenyl)-6-benzothiazolecarboxamide | 4.07 |

TABLE 3-continued

| Ex. No. | Compound Structure | Compound Name | HPLC Ret Time (min) |
|---|---|---|---|
| 116 | 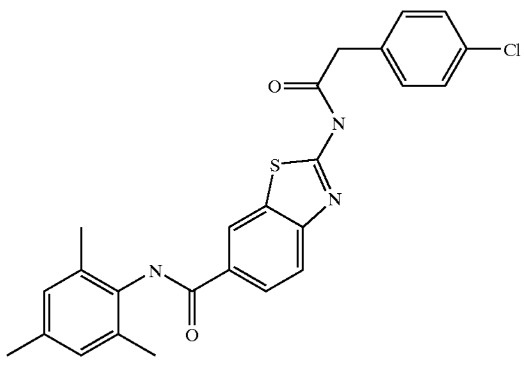 | 2-[[(4-Chlorophenyl)acetyl]amino]-N-(2,4,6-trimethylphenyl)-6-benzothiazolecarboxamide | 4.30 |
| 117 | 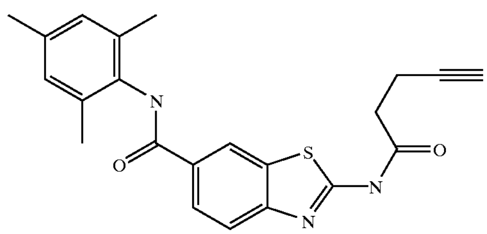 | 2-[(1-Oxo-4-pentynyl)amino]-N-(2,4,6-trimethylphenyl)-6-benzothiazolecarboxamide | 3.76 |
| 118 | 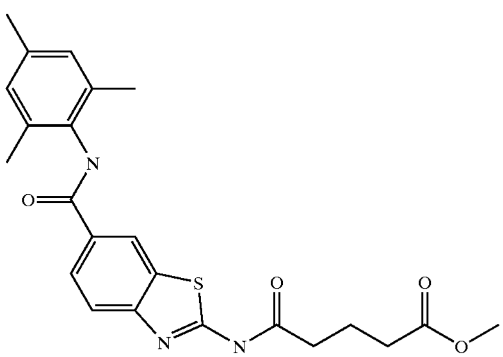 | 5-Oxo-5-[[6-[[(2,4,6-trimethylphenyl)amino]carbonyl]-2-benzothiazolyl]amino]pentanoic acid, methyl ester | 3.96 |
| 119 | 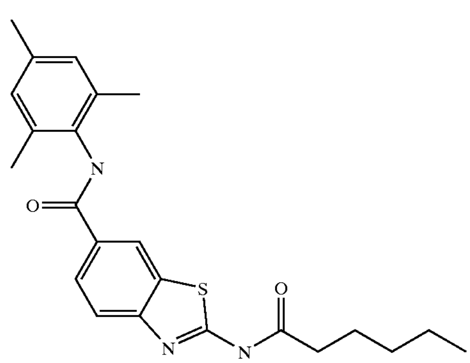 | 2-[(1-Oxohexyl)amino]-N-(2,4,6-trimethylphenyl)-6-benzothiazolecarboxamide | 4.36 |

TABLE 3-continued

| Ex. No. | Compound Structure | Compound Name | HPLC Ret Time (min) |
|---|---|---|---|
| 120 | 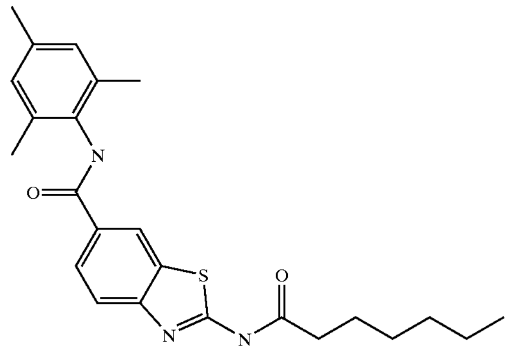 | 2-[(1-Oxoheptyl)amino]-N-(2,4,6-trimethylphenyl)-6-benzothiazolecarboxamide | 4.49 |
| 121 | 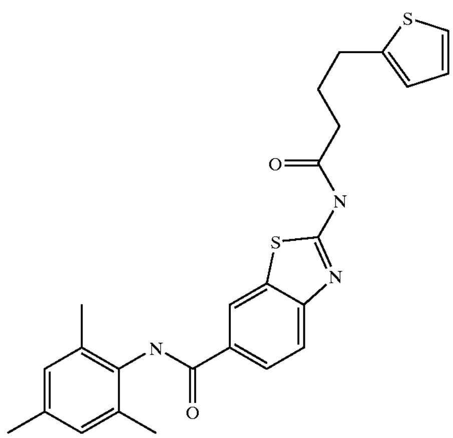 | 2-[[1-Oxo-4-(2-thienyl)butyl]amino]-N-(2,4,6-trimethylphenyl)-6-benzothiazolecarboxamide | 4.42 |
| 122 | 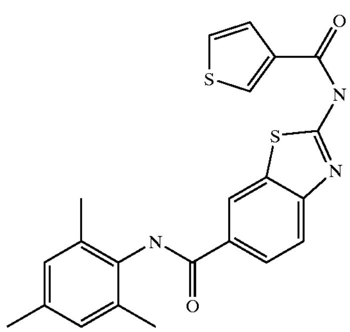 | 2-[(3-Thienylcarbonyl)amino]-N-(2,4,6-trimethylphenyl)-6-benzothiazolecarboxamide | 4.06 |
| 123 | 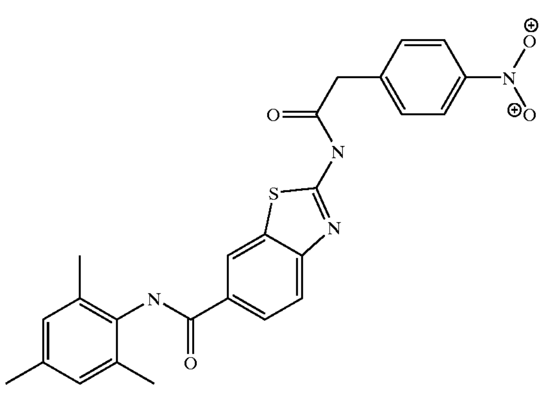 | 2-[[(4-Nitrophenyl)acetyl]amino]-N-(2,4,6-trimethylphenyl-6-benzothiazolecarboxamide | 4.17 |

TABLE 3-continued

| Ex. No. | Compound Structure | Compound Name | HPLC Ret Time (min) |
|---|---|---|---|
| 124 | 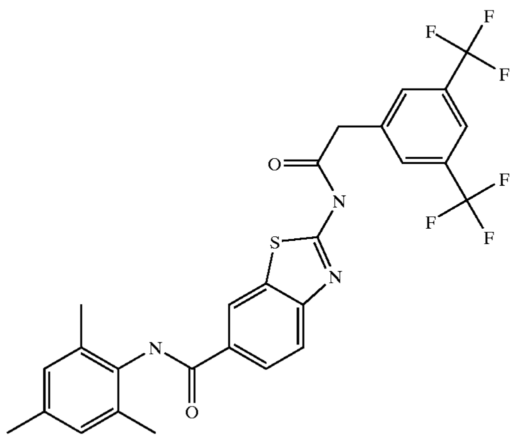 | 2-[[3,5-Bis(trifluoromethyl)phenyl]acetyl]amino]-N-(2,4,6-trimethylphenyl)-6-benzothiazolecarboxamide | 4.65 |
| 125 | 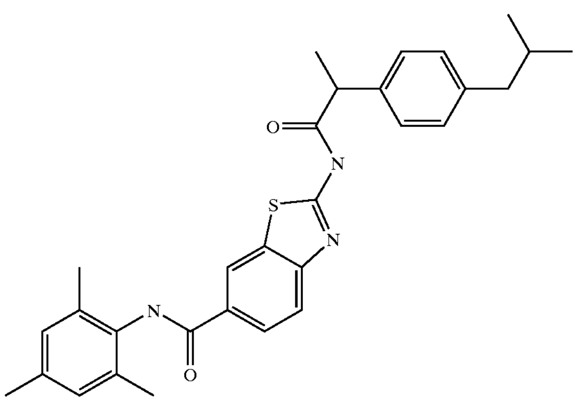 | 2-[[2-[4-(2-Methypropyl)phenyl]-1-oxopropyl]amino]-N-(2,4,6-trimethylphenyl)-6-benzothiazolecarboxamide | 4.80 |
| 126 | 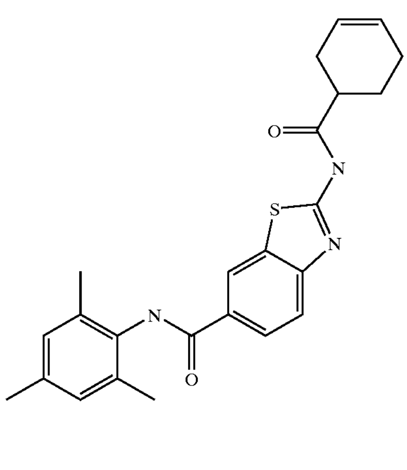 | 2-[[(3-Cyclohexen-1-yl)carbonyl]amino]-N-(2,4,6-trimethylphenyl)-6-benzothiazolecarboxamide | 4.20 |

TABLE 3-continued

| Ex. No. | Compound Structure | Compound Name | HPLC Ret Time (min) |
| --- | --- | --- | --- |
| 127 | 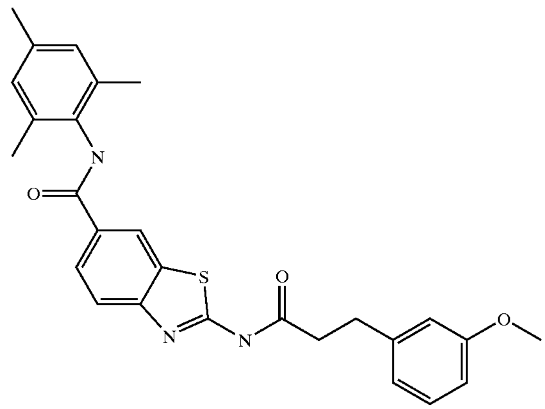 | 2-[[3-(3-Methoxyphenyl)-1-oxopropyl]amino]-N-(2,4,6-trimethylphenyl)-6-benzothiazolecarboxamide | 4.22 |
| 128 | 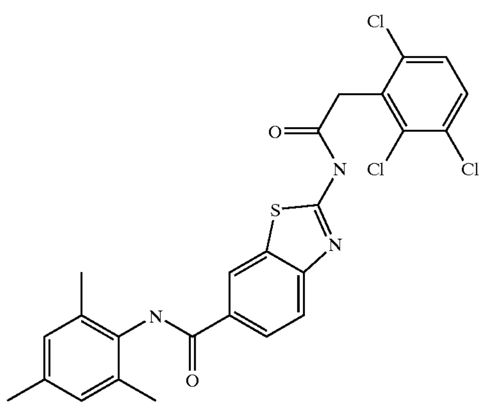 | 2-[[(2,3,6-Trichlorophenyl)acetyl]amino]-N-(2,4,6-trimethylphenyl)-6-benzothiazolecarboxamide | 4.50 |
| 129 | 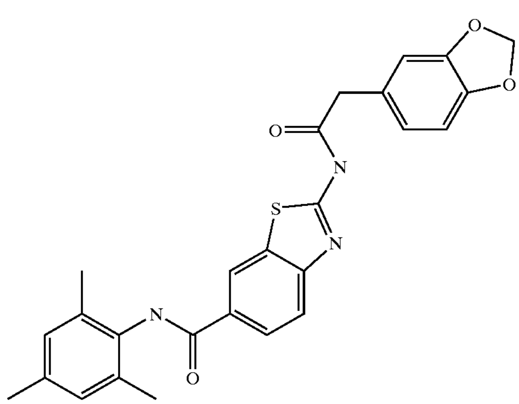 | 2-[[(1,3-Benzodioxol-5-yl)acetyl]amino]-N-(2,4,6-trimethylphenyl)-6-benzothiazolecarboxamide | 4.04 |

TABLE 3-continued

| Ex. No. | Compound Structure | Compound Name | HPLC Ret Time (min) |
|---|---|---|---|
| 130 | 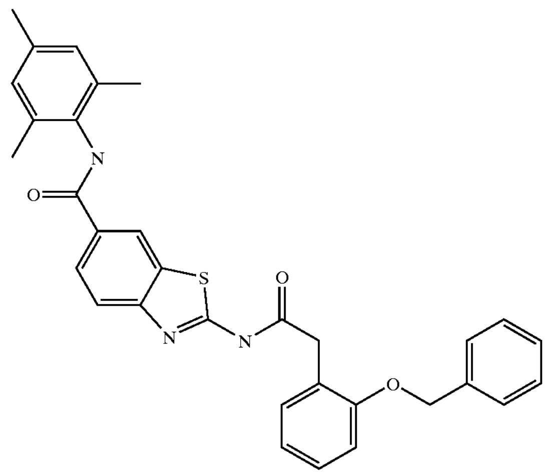 | 2-[[[2-(Phenylmethoxy)phenyl]acetyl]amino]-N-(2,4,6-trimethylphenyl)-6-benzothiazolecarboxamide | 4.35 |
| 131 | 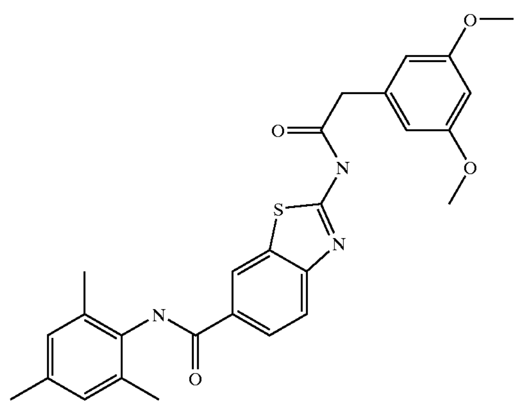 | 2-[[(3,5-Dimethoxyphenyl)acetyl]amino]-N-(2,4,6-trimethylphenyl)-6-benzothiazolecarboxamide | 4.09 |
| 132 | 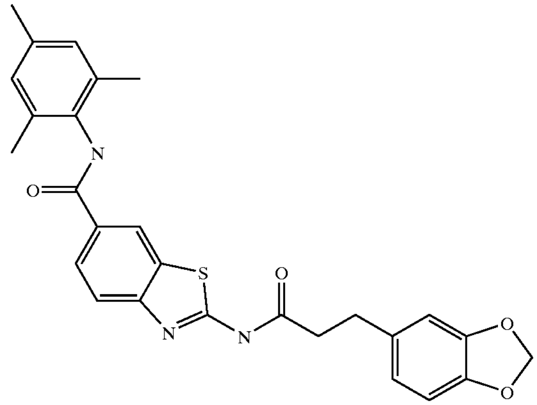 | 2-[[3-(1,3-Benzodioxol-5-yl)-1-oxopropyl]amino]-N-(2,4,6-trimethylphenyl)-6-benzothiazolecarboxamide | 4.18 |

TABLE 3-continued

| Ex. No. | Compound Structure | Compound Name | HPLC Ret Time (min) |
|---|---|---|---|
| 133 | 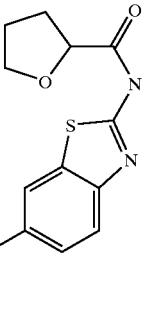 | 2-[[(Tetrahydro-2-furanyl)carbonyl]amino]-N-(2,4,6-trimethylphenyl)-6-benzothiazolecarboxamide | 3.93 |
| 134 | 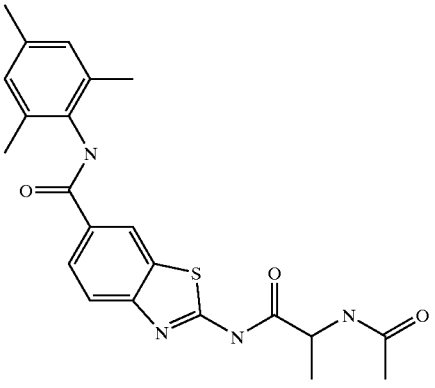 | 2-[[2-(Acetylamino)-1-oxopropyl]amino]-N-(2,4,6-trimethylphenyl)-6-benzothiazolecarboxamide | 3.63 |
| 135 | 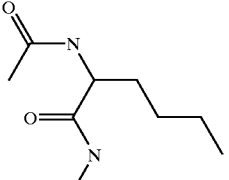 | 2-[[2-(Acetylamino)-1-oxohexyl]amino]-N-(2,4,6-trimethylphenyl)-6-benzothiazolecarboxamide | 3.97 |
| 136 | 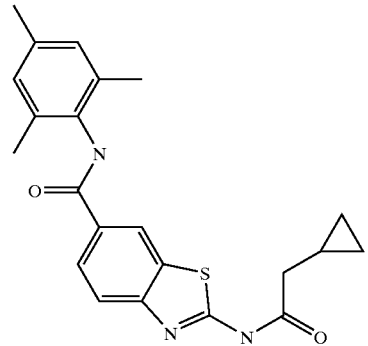 | 2-[(Cyclopropylacetyl)amino]-N-(2,4,6-trimethylphenyl)-6-benzothiazolecarboxamide | 3.92 |

TABLE 3-continued

| Ex. No. | Compound Structure | Compound Name | HPLC Ret Time (min) |
|---|---|---|---|
| 137 | 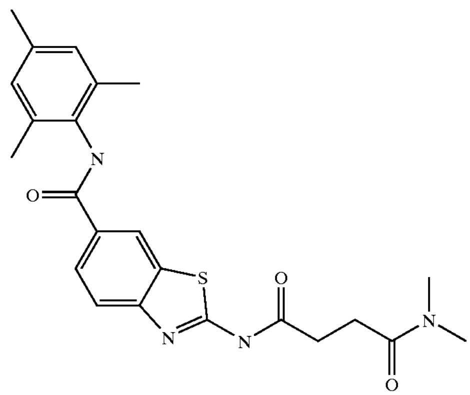 | N,N-Dimethyl-N'-[6-[[(2,4,6-trimethylphenyl)amino]carbonyl]-2-benzothiazolyl]butanediamide | 3.66 |
| 138 | 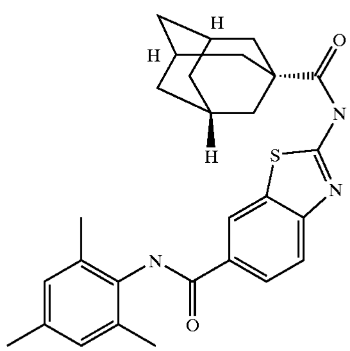 | 2-[(1-Adamantylcarbonyl)amino]-N-(2,4,6-trimethylphenyl)-6-benzothiazolecarboxamide | 4.59 |
| 139 | 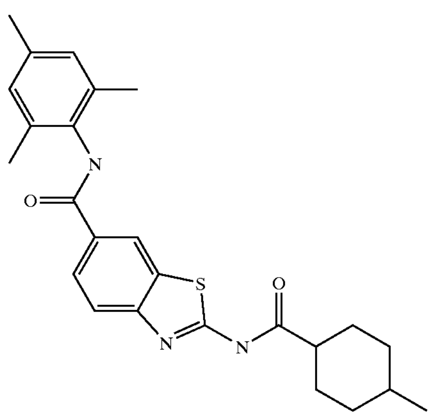 | 2-[[(4-Methylcyclohexyl)carbonyl]amino]-N-(2,4,6-trimethylphenyl)-6-benzothiazolecarboxamide | 4.42 |
| 140 | 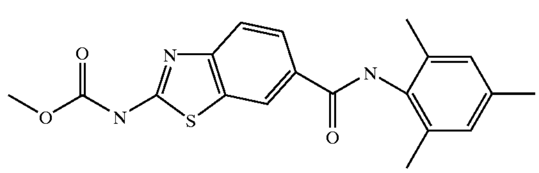 | 2-[(3-Methoxy-1-oxopropyl)amino]-N-(2,4,6-trimethylphenyl)-6-benzothiazolecarboxamide | 3.34 |

EXAMPLES 141 TO 163

General Procedure

Compounds 141 to 163 were prepared following the procedure described below.

A. 2-tert-Butoxycarbonyloxyamino-benzothiazole-6-carboxylic acid chloride

A 2 M solution of oxalyl chloride in dichloromethane (6.8 mL, 13.59 mmol) was added to a suspension of 1C (2 g, 6.79 mmol) in dichloromethane (25 mL) at 0° C. Dimethylformamide (3 drops) was added. The ice bath was removed and the suspension was stirred at RT for 3 h and then heated to 32° C. for an additional 3 h. The mixture was diluted with ether (25 mL) and the solid was collected by filtration. The solid was washed with ether several times, and dried in vacuo to obtain the title compound of this step (1.75 g, 82%). An additional crop of the title acid chloride was obtained by the trituration of the filtrate after concentration, with ether (250 mg, 12%).

B. Compounds 141 to 163

Diisopropylethyl amine (23 μL, 0.288 mmol) was added to a mixture of 2-tert-butoxycarbonyloxyamino-benzothiazole-6-carboxylic acid chloride (34.41 mg, 0.11 mmol), and the appropriate aniline (0.12 mmol) in THF (1 mL). The mixture was stirred at RT for 22 h. The reaction mixture was diluted with dichloromethane (4 mL) and washed with 2 N aq. HCl solution (2×), dried (Na$_2$SO$_4$), filtered and concentrated in vacuo. The crude products were purified either by trituration with dichloromethane-ether (1:1) and/or by silica gel chromatography (eluting solvent: 2–5% MeOH in dichloromethane), and the compounds obtained in these Examples are identified in Table 4 below.

In Table 4, "HPLC Ret Time" was the HPLC retention time obtained under the following conditions: YMC S5 ODS 4.6×50 mm Ballastic Column, 4 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 4 ml/min, λ=220 nM.

TABLE 4

| Ex. No. | Compound Structure | Compound Name | HPLC Ret Time (min) |
|---|---|---|---|
| 141 | 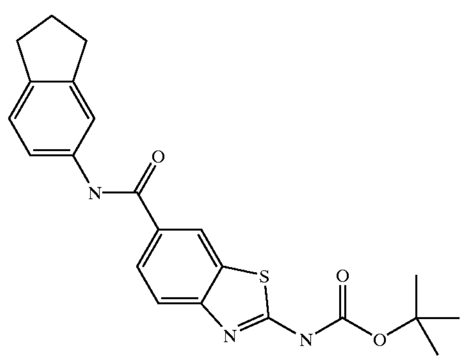 | [6-[[(2,3-Dihydro-1H-inden-5-yl)amino]carbonyl]-2-benzothiazolyl]carbamic acid, 1,1-dimethylethyl ester | 4.44 |
| 142 | 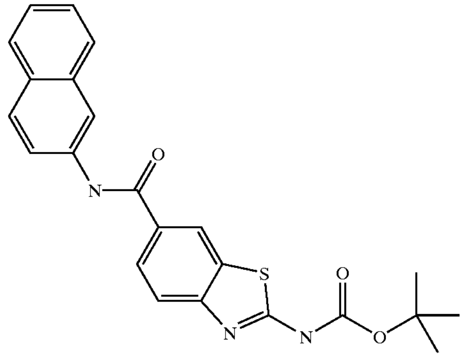 | [6-[(2-Naphthylenylamino)carbonyl]-2-benzothiazolyl]carbamic acid, 1,1-dimethylethyl ester | 4.46 |

TABLE 4-continued

| Ex. No. | Compound Structure | Compound Name | HPLC Ret Time (min) |
|---|---|---|---|
| 143 | 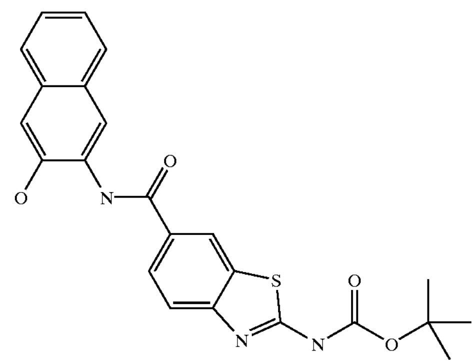 | [6-[[(3-Hydroxy-2-naphthalenyl)amino]carbonyl]-2-benzothiazolyl]carbamic acid, 1,1-dimethylethyl ester | 4.46 |
| 144 | 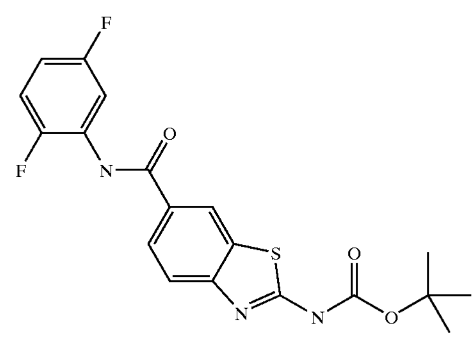 | [6-[[(2-Fluoro-5-methylphenyl)amino]carbonyl]-2-benzothiazolyl]carbamic acid, 1,1-dimethylethyl ester | 4.21 |
| 145 | 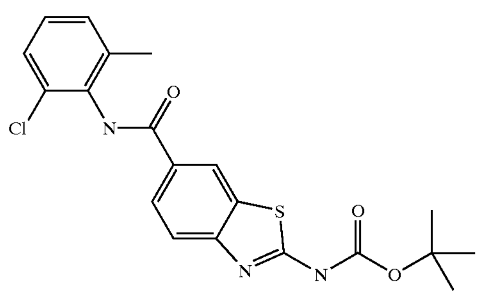 | [6-[[(2-Chloro-6-methylphenyl)amino]carbonyl]-2-benzothiazolyl]carbamic acid, 1,1-dimethylethyl ester | 4.05 |
| 146 | 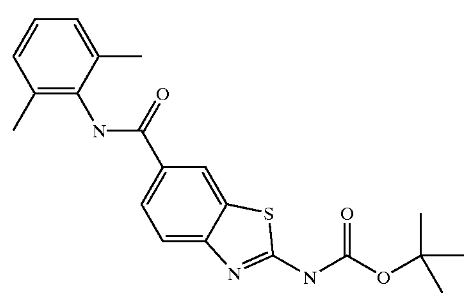 | [6-[[(2,6-Dimethylphenyl)amino]carbonyl]-2-benzothiazolyl]carbamic acid, 1,1-dimethylethyl ester | 4.07 |

TABLE 4-continued

| Ex. No. | Compound Structure | Compound Name | HPLC Ret Time (min) |
|---|---|---|---|
| 147 | 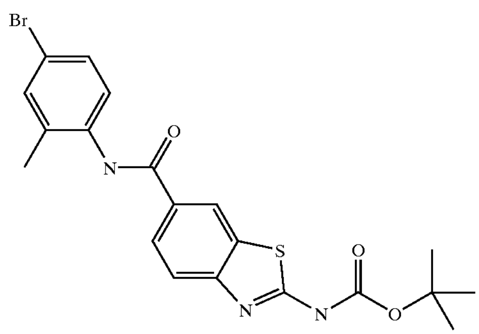 | [6-[[(4-Bromo-2-methylphenyl)amino]carbonyl]-2-benzothiazolyl]carbamic acid, 1,1-dimethylethyl ester | 4.34 |
| 148 | 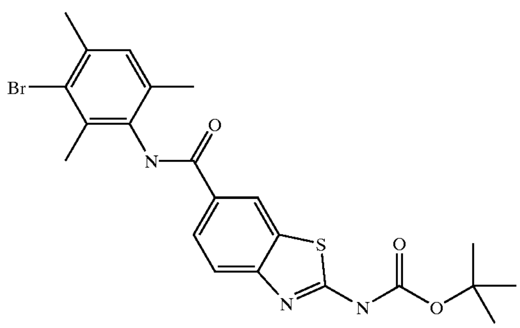 | [6-[[(3-Bromo-2,4,6-trimethylphenyl)amino]carbonyl]-2-benzothiazolyl]carbamic acid, 1,1-dimethylethyl ester | 4.45 |
| 149 | 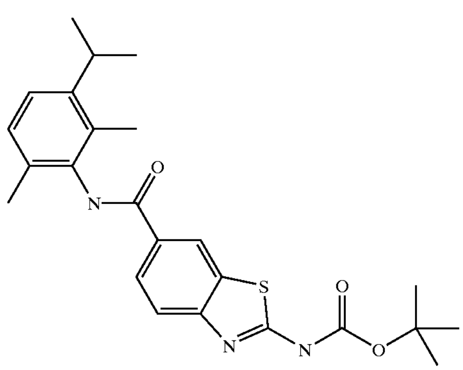 | [6-[[[2,6-Dimethyl-3-(1-methylethyl)phenyl]amino]carbonyl]-2-benzothiazolyl]carbamic acid, 1,1-dimethylethyl ester | 4.44 |
| 150 | 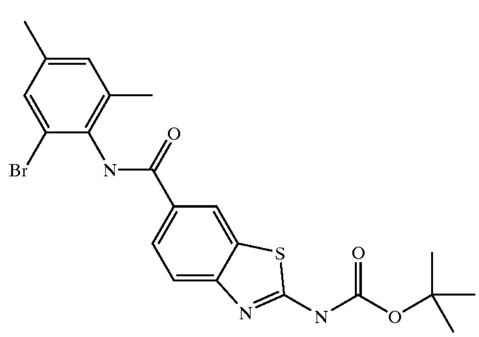 | [6-[[(2-Bromo-4,6-dimethylphenyl)amino]carbonyl]-2-benzothiazolyl]carbamic acid, 1,1-dimethylethyl ester | 4.22 |

TABLE 4-continued

| Ex. No. | Compound Structure | Compound Name | HPLC Ret Time (min) |
|---|---|---|---|
| 151 | 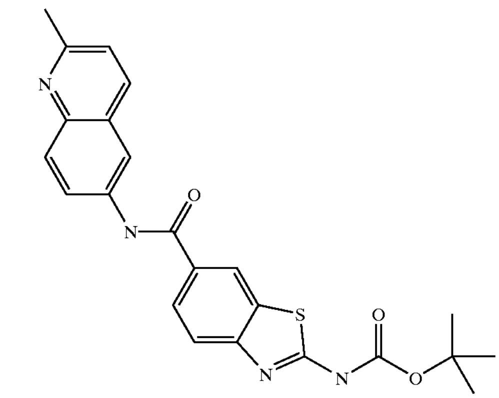 | [6-[[(2-Methyl-6-quinolinyl)amino]carbonyl]-2-benzothiazolyl]carbamic acid, 1,1-dimethylethyl ester | 3.41 |
| 152 | 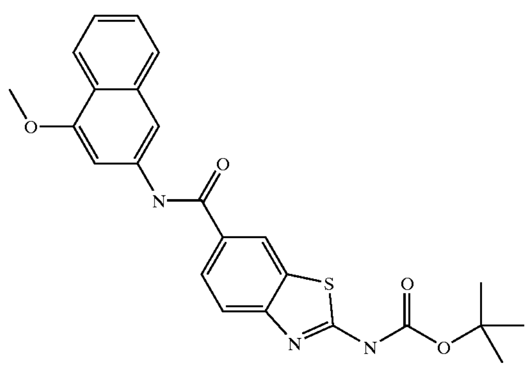 | [6-[[(4-Methoxy-2-naphthalenyl)amino]carbonyl]-2-benzothiazolyl]carbamic acid, 1,1-dimethylethyl ester | 4.58 |
| 153 | 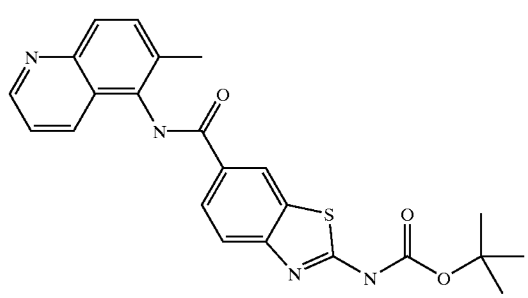 | [6-[[(6-Methyl-5-quinolinyl)amino]carbonyl]-2-benzothiazolyl]carbamic acid, 1,1-dimethylethyl ester | 3.26 |
| 154 | 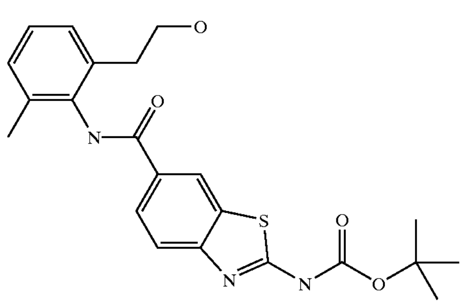 | [6-[[[2-(2-Hydroxyethyl)-6-methylphenyl]amino]carbonyl]-2-benzothiazolyl]carbamic acid, 1,1-dimethylethyl ester | 3.85 |

TABLE 4-continued

| Ex. No. | Compound Structure | Compound Name | HPLC Ret Time (min) |
|---|---|---|---|
| 155 | 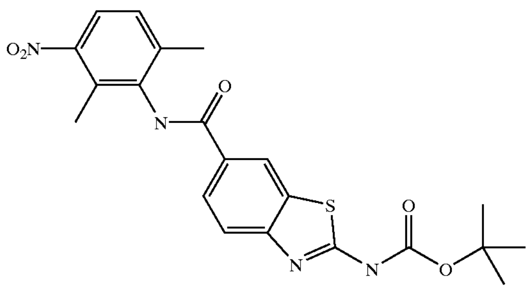 | [6-[[(2,6-Dimethyl-3-nitrophenyl)amino]carbonyl]-2-benzothiazolyl]carbamic acid, 1,1-dimethylethyl ester | 4.03 |
| 156 | 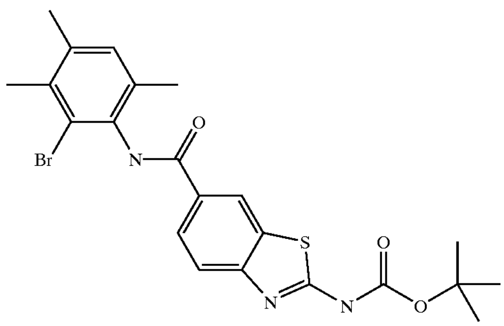 | [6-[[(2-Bromo-3,4,6-trimethylphenyl)amino]carbonyl]-2-benzothiazolyl]carbamic acid, 1,1-dimethylethyl ester | 4.32 |
| 157 | 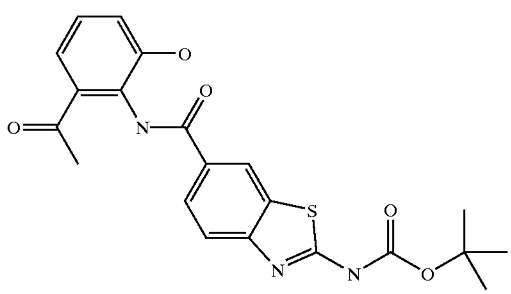 | [6-[[(2-Acetyl-6-hydroxyphenyl)amino]carbonyl]-2-benzothiazolyl]carbamic acid, 1,1-dimethylethyl ester | 4.26 |
| 158 | 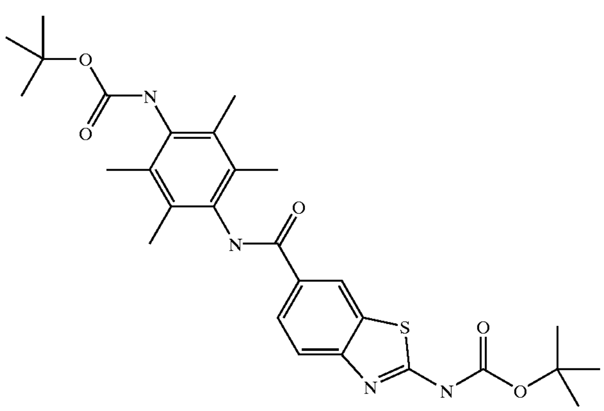 | [6-[[[4-[[(1,1-Dimethylethoxy)carbonyl]amino]-2,3,5,6-tetramethylphenyl]amino]carbonyl]-2-benzothiazolyl]carbamic acid, 1,1-dimethylethyl ester | 4.31 |
| 159 | 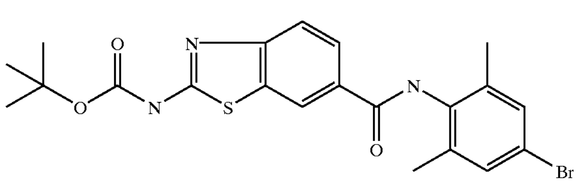 | [6-[[(4-Bromo-2,6-dimethylphenyl)amino]carbonyl]-2-benzothiazolyl]carbamic acid, 1,1-dimethylethyl ester | 5.13 |

TABLE 4-continued

| Ex. No. | Compound Structure | Compound Name | HPLC Ret Time (min) |
|---|---|---|---|
| 160 | 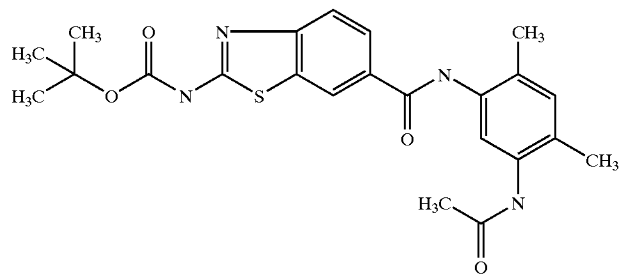 | [6-[[[3-Acetylamino]-4,6-dimethylphenyl]amino]carbonyl]-2-benzothiazolyl]carbamic acid, 1,1-dimethylethyl ester | 4.27 |
| 161 | 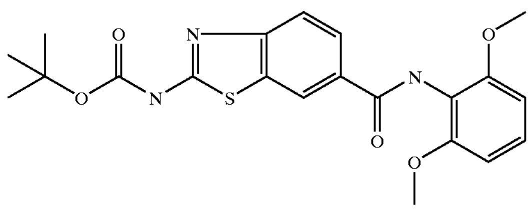 | [6-[[2,6-Dimethoxyphenyl)amino]carbonyl]-2-benzothiazolyl]carbamic acid, 1,1-dimethylethyl ester | 3.73 |
| 162 | 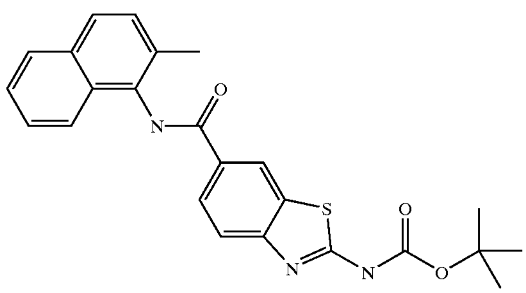 | [6-[[(2-Methyl-1-naphthalenyl)amino]carbonyl]-2-benzothiazolyl]carbamic acid, 1,1-dimethylethyl ester | 4.18 |
| 163 | 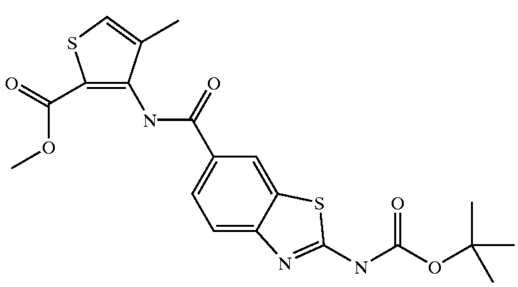 | 3-[[[2-[[(1,1-Dimethylethoxy)carbonyl]amino]-6-benzothiazolyl]carbonyl]amino]-4-methyl-2-thiophenecarboxylic acid, methyl ester | 4.09 |

EXAMPLE 164

Preparation of [6-[[(2,4,6-Trimethylphenyl)amino]carbonyl]-2-benzothiazolyl]carbamic acid, methyl ester

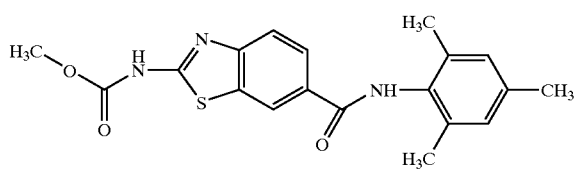

Methyl chloroformate (250 μL) was added dropwise to a stirred solution of the free base of 2 (62 mg, 0.2 mmol) in THF (10 mL) and 10% aq. $KHCO_3$ solution (15 mL) at 0 to 5° C. The biphasic mixture was stirred for 2 h, and then diluted with dichloromethane (25 mL) and water (20 mL). The organic extracts were dried ($MgSO_4$), filtered and concentrated. The crude residue was chromatographed on a silica gel column and eluted with 30% EtOAc in hexanes, followed by 50% and 70% EtOAc in hexanes, and 10% MeOH in dichloromethane to obtain the title compound (42 mg, 57%) as a white solid.

MS=370 ($M^+$+H).

EXAMPLE 165

Preparation of 2-[[(Acetylamino)acetyl]amino]-N-(2,4,6-trimethylphenyl)-6-benzothiazolecarboxamide

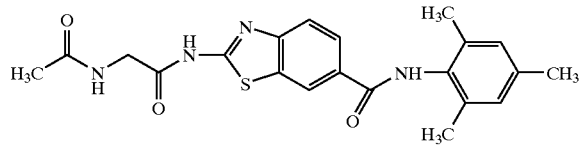

Diisopropylethyl amine (400 μL, 2.3 mmol) was added to a mixture of the free base of 2 (50 mg, 0.16 mmol), N-acetylglycine (42 mg, 0.36 mmol), 1-hydroxy-7-azabenzotriazole (49 mg, 0.36 mmol), and ethyl-3-(3-dimethylamino)-propyl carbodiimide hydrochloride (72 mg, 0.36 mmol) in THF (6 mL). The mixture was heated to 50° C. overnight, cooled to RT, diluted with dichloromethane (60 mL) and washed with 2 N aq. HCl solution (20 mL), and satd. NaHCO$_3$ solution (15 mL, 2×). The dichloromethane extract was dried (MgSO$_4$), filtered and concentrated. The residue was diluted with dichloromethane-methanol (20 mL, 4:1) and EtOAc (5 mL) was added. The precipitated solid was filtered, washed with EtOAc (5 mL, 3×), and dried in vacuo to obtain the title compound of this Example (15 mg, 22.8%).

MS=411.1 (M$^+$+H).

EXAMPLE 166

Preparation of N-(2-Chloro-6-methylphenyl)-2-[[[(1,1-dimethylethyl)amino]carbonyl]amino]-6-benzothiazolecarboxamide

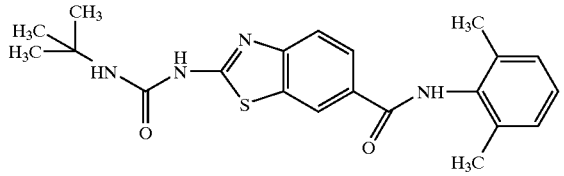

A. Ethyl-2-[[(phenoxylcarbonyl]amino]-benzothiazole-6-carboxylate

Phenyl chloroformate (14.25 mL, 113.6 mmol) was added dropwise to a stirred solution of 1A (8.6 g, 37.86 mmol) in THF (300 mL) and satd. aq. KHCO$_3$ solution (300 mL) at 0 to 5° C. The biphasic mixture was stirred for 3.5 h. The THF layer was separated and the aq. layer was extracted with dichloromethane (150 mL, 2×). A yellow solid which precipitated during the work up was collected by filtration, washed with dichloromethane, water and ether. Organic extracts were combined, dried (Na$_2$SO$_4$), filtered and concentrated to obtain a yellow solid. The crude solids were combined, diluted with ether (100 mL), filtered, and dried in vacuo to obtain the title compound of this step as a yellow solid (11.24 g, 85%).

B. Ethyl-2-[[[(1,1-Dimethylethyl)amino]carbonyl]amino]-benzothiazole-6-carboxylate tert-Butyl amine (6.66 mL, 63.4 mmol) was added to a stirred suspension of 166A (11.23 g, 32.33 mmol) in TBF (163 mL). The suspension was stirred at RT for 16 h, and the yellow solid was filtered, washed with THF, 2 N aq. HCl solution, 0.1 N aq. NaOH solution, water and ether. The filtrate was diluted with dichloromethane and washed with 2 N aq. HCl solution (2×) and 0.1 N aq. NaOH solution (2×) and brine. The dichloromethane extract was dried (Na$_2$SO$_4$), filtered and concentrated to obtain a yellow solid. Solids were combined, suspended in ether, filtered, washed several times with ether and dried in vacuo to obtain the title compound of this step (10.41 g, 100%).

C. 2-[[[(1,1-Dimethylethyl)amino]carbonyl]amino]-benzothiazole-6-carboxlic acid

An aq. 2 N potassium hydroxide solution (405 mL) was added to a suspension of 166B (10.41 g, 32.4 mmol) in THF (90 mL) and ethanol (135 mL). The mixture was heated to 60° C., cooled to 0° C. and concentrated. The residue was cooled to 0° C. and acidified to pH 1.0 with conc. HCl solution. The precipitated solid was filtered, washed with water and ether. The solid was suspended in toluene (2×) and concentrated under reduced pressure. This operation was repeated with ether (2×). The solid was collected and dried in vacuo over phosphorus pentoxide to obtain the title acid of this step (10 g, 100% yield).

D. 2-[[[(1,1-Dimethylethyl)amino]carbonyl]amino]-benzothiazole-6-carboxylic acid-7-aza-benzotriazole ester ("HOAT ester")

Diisopropylethyl amine (958 μL, 6.84 mmol) was added to a solution of 166C (500 mg, 1.71 mmol), and HATU (778 mg, 2.05 mmol) in dimethylformamide (10 mL). The solution was stirred at RT overnight, diluted with dichloromethane and washed with 1 N aq. HCl solution and water. The dichloromethane extract was separated, dried (MgSO$_4$) and concentrated. The crude solid was triturated with methanol (2×) to obtain the title compound of this step (380 mg, 54.3%). A second crop of the title compound (152 mg, 21.7%) was obtained after trituration of the residual filtrate.

E. N-(2-Chloro-6-methylphenyl)-2-[[[(1,1-dimethylethyl)amino]carbonyl]amino]-6-benzothiazolecarboxamide A 1 M solution of sodium bis-trimethylsilyl amide (366 μL, 0.37 mmol) was added to a stirred solution of 2-chloro-6-methylaniline (33.1 μL, 0.268 mmol) in THF (2 mL). The mixture was stirred at RT for 10 min, and 166D (100 mg, 0.244 mmol) was added. Dimethylformamide (2 mL) was added to dissolve the precipitate obtained during the reaction. The mixture was stirred at RT overnight, diluted with dichloromethane and washed with 1 N aq. HCl solution (30 mL, 3×), 5% aq. KHCO$_3$ solution (20 mL, 2×). The organic extract was dried (MgSO$_4$), filtered and concentrated. The crude residue was purified by automated preparative HPLC (conditions: YMC ODS A 20×100 mm column, 10 minute gradient starting from 30% solvent B (90% MeOH, 10% H$_2$O, 0.1% TFA) and 70% solvent A (10% MeOH, 90% H$_2$O, 0.1% TFA) to 100% solvent B, flow rate 20 mL/min, λ=220 nm) to obtain the title compound of this Example (19.5 mg, 19%).

MS=417 (M$^+$+H).

Alternative Method

A(Alt). [6-[[(2-Chloro-6-methylphenyl)amino]carbonyl]-2-benzothiazolyl]carbamic acid, 1,1-dimethylethyl ester Diisopropylethyl amine (1.67 mL, 6.02 mmol) was added to a stirred suspension of 141A [2-tert-butoxycarbonyloxy-amino-benzothiazole-6-carboxylic acid chloride] (1.88 g, 6.02 mmol), 2-chloro-6-methylaniline (960 μL, 7.83 mmol) in THF (40 mL). The mixture was stirred at RT overnight and then diluted with dichloromethane (100 mL). The reaction mixture was washed with 1 N aq. HCl solution (2×), 1 N aq. NaOH solution, and brine. The organic layer was dried (Na$_2$SO$_4$), filtered, and concentrated. The residue was diluted with EtOAc (10 ml), stirred for 20 min, and diethyl ether (5 mL) was added. After 5 min, the solid was filtered, and dried in vacuo to obtain the title compound of this step (940 mg, 37%).

B(Alt). 2-Amino-N-(2-chloro-6-methylphenyl)-6-benzothiazolecarboxamide

A solution of 166A(Alt) (940 mg, 2.25 mmol) in trifluoroacetic acid (5 mL) and dichloromethane (2 mL) was stirred at RT overnight. The mixture was concentrated, diluted in dichloromethane (100 mL), and washed with satd. sodium bicarbonate solution (2×), water and brine. The dichloromethane extract was dried (Na$_2$SO$_4$), filtered, and concentrated in vacuo to obtain the title compound of this step (750 mg, 98%).

C(Alt). [6-[[(2-Chloro-6-methylphenyl)amino]carbonyl]-2-benzothiazolyl]carbamic acid phenyl ester Analogous to the preparation of Example 7A except using 166B(Alt) in place of the free base of 2 gave the title compound of this step (92%) after trituration with diethyl ether/EtOAc (1:1).

D(Alt). N-(2-Chloro-6-methylphenyl)-2-[[[(1,1-dimethylethyl)amino]carbonyl]amino]-6-benzothiazolecarboxamide A solution of 166C(Alt) (680 mg, 1.57 mmol) and tert-butyl amine (196 μL, 1.87 mmol) in THF (50 mL) was stirred for 7 h. The mixture was diluted with dichloromethane (200 mL) and washed with 1 N aq. HCl solution (50 mL), 1 N aq. NaOH solution (50 mL, 2×). The organic extract was dried (Na$_2$SO$_4$), filtered, and concentrated. The residue was triturated with diethyl ether to obtain the title compound of this Example (488 mg, 75%).

EXAMPLE 167

Preparation of N-(2,6-Dichlorophenyl)-2-[[[(1,1-dimethylethyl)amino]carbonyl]amino]-6-benzothiazolecarboxamide

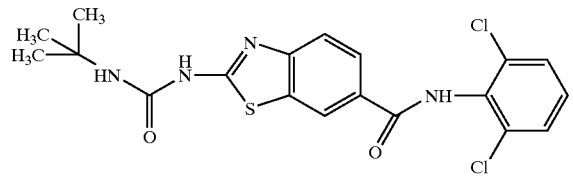

Analogous to the preparation of compound 166E except using 2,6-dichloroaniline gave the title compound (17%) after purification by automated preparative HPLC (conditions: YMC ODS A 20×100 mm column, 10 minute gradient starting from 30% solvent B (90% MeOH, 10% H$_2$O, 0.1% TFA) and 70% solvent A (10% MeOH, 90% H$_2$O, 0.1% TFA) to 100% solvent B, flow rate 20 mL/min, λ=220 nm).
MS=438 (M$^+$+H).

EXAMPLE 168

Preparation of N-(4-Bromo-2,6-dimethylphenyl)-2-[[[(1,1-dimethylethyl)amino]carbonyl]amino]-6-benzothiazolecarboxamide

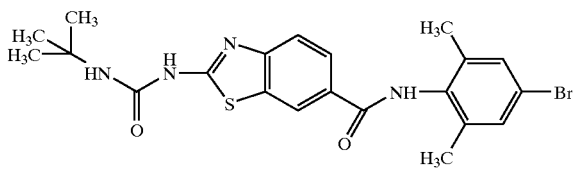

Analogous to the preparation of compound 166E except using 4-bromo-2,6-dimethylaniline gave the title compound (19%) after purification by automated preparative HPLC (conditions: same as in Example 167).
MS=477 (M$^+$+H).

EXAMPLE 169

Preparation of N-(4-Carbomethoxy-2,6-Dimethylphenyl)-2-[[[1,1-dimethylethoxy]carbonyl]amino]-6-benzothiazolecarboxamide

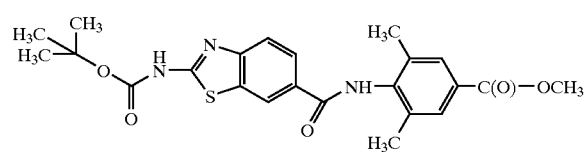

Analogous to the preparation of the compounds of Table 4 using 4-carbomethoxy-2,6-diethylaniline gave the title compound of this Example (53%).
MS=428.1 (M$^+$+H).

EXAMPLE 170

Preparation of N-(4-Hydroxymethyl-2,6-Dimethylphenyl)-2-[[[1,1-dimethylethoxy]carbonyl]amino]-6-benzothiazolecarboxamide

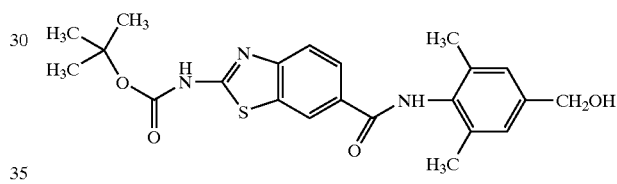

Analogous to the preparation of compounds 141 to 163 except using 4-hydroxymethyl-2,6-dimethylaniline gave the title compound of this Example (71%).
MS=456.1 (M$^+$+H).

EXAMPLE 171

Preparation of [4-Methyl-6-[[(2,4,6-trimethylphenyl)amino]carbonyl]-2-benzothiazolyl]carbamic acid, 1,1-dimethylethyl ester

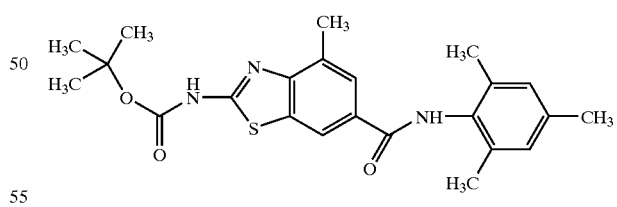

A. Methyl-2-amino-4-methyl-benzothiazole-6-carboxylate
Analogous to the preparation of compound 1A except using methyl-4-amino-3-methylbenzoate gave the title compound of this step.

B. Methyl-2,2-bis-tert-butoxycarbonyloxyamino-4-methyl-benzothiazole-6-carboxylate A suspension of 171A (1.16 g, 5.2 mmol, 85% pure), di-t-butylcarbonate (2.37 g, 10.87 mmol) and 4-dimethylaminopyridine (93 mg, 0.76 mmol) in THF (80 mL) was heated to 60° C. for 3.5 h. The mixture was cooled, washed with 1 N aq. HCl solution (50 mL, 2×), and water.

The organic extract was dried (MgSO₄), filtered and concentrated to obtain the title compound of this step (693 mg, 31.5%).

C. 2-tert-Butoxycarbonyloxyamino-4-methyl-benzothiazole-6-carboxylic acid

Analogous to the preparation of 1C except using 171B gave the title compound (95%) of this step as a white solid.

D. [4-Methyl-6-[[(2,4,6-trimethylphenyl)amino]carbonyl]-2-benzothiazolyl]carbamic acid, 1,1-dimethylethyl ester Diisopropylethyl amine (65 μL, 0.51 mmol) was added to a stirred solution of 171C (50 mg, 0.17 mmol), 2,4,6-trimethylaniline (28.4 μL, 0.203 mmol) and benzotriazolo-1-yloxytris(dimethylamino)phosphonium hexafluorophosphate (Castro's reagent, 89.6 mg, 0.203 mmol) in dimethylformamide (2 mL). The solution was stirred at RT for 40 h and then diluted with dichloromethane (50 mL). The mixture was washed with 1 N aq. HCl solution (25 mL, 2×) and water, dried (MgSO₄), filtered and concentrated. The crude residue was triturated with a mixture of ether and EtOAc. Solid was collected and dried in vacuo to obtain the title compound of this Example (43 mg, 62%).

MS=426 (M⁺+H).

EXAMPLE 172

Preparation of 2-Amino-4-methyl-N-(2,4,6-trimethylphenyl)-6-benzothiazolecarboxamide, trifluoroacetate (1:1)

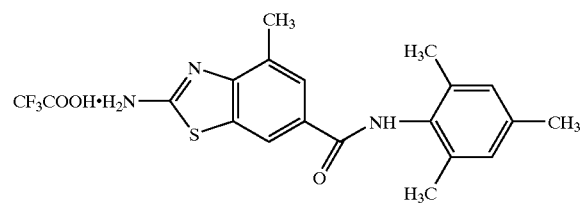

Analogous to the preparation of compound 2 except using 171D afforded the title compound of this Example (74%).

MS=326(M⁺+H).

EXAMPLE 173

Preparation of 4-Methoxy-[6-[[(2,4,6-trimethylphenyl)amino]carbonyl]-2-benzothiazolyl] carbamic acid, 1,1-dimethylethyl ester

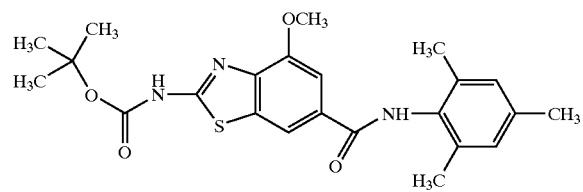

Analogous to the preparation of 171D except using methyl-4-amino-3-methoxybenzoate gave the title compound of this Example.

MS=442 (M⁺+H).

EXAMPLE 174

Preparation of 2-Amino-4-methoxy-N-(2,4,6-trimethylphenyl)-6-benzothiazolecarboxamide, trifluoroacetate (1:1)

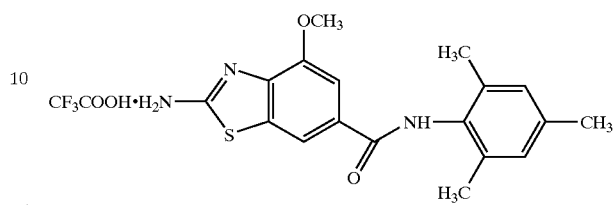

Analogous to the preparation of 2 except using 173 afforded the title compound (82%) as a white solid.

MS=342 (M⁺+H).

EXAMPLE 175

Preparation of 2-[[(Methylamino)carbonyl]amino]-N-(2,4,6-trimethylphenyl)-6-benzothiazolecarboxamide

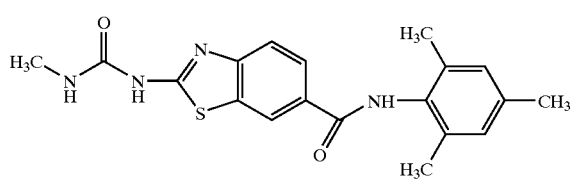

Analogous to the preparation of 15 except using methyl isocyanate gave the title compound (71%) as a white solid.

MS=369 (M⁺+H).

EXAMPLE 176

Preparation of 2-[[[Methylamino]carbonyl]amino]-4-methoxy-N-(2,4,6-trimethylphenyl)-6-benzothiazolecarboxamide

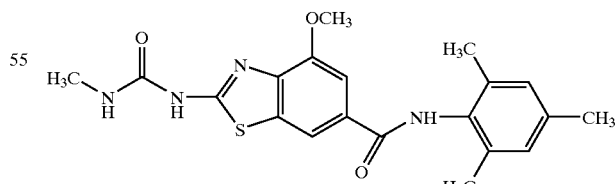

Analogous to the preparation of 175 except using 174 gave the title compound (39%) as a white solid.

MS 399 (M⁺+H).

EXAMPLE 177

Preparation of 5-Methoxy-[6-[[(2,4,6-trimethylphenyl)amino]carbonyl]-2-benzothiazolyl]carbamic acid, 1,1-dimethylethyl ester

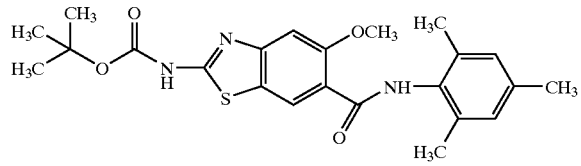

Analogous to the preparation of 171D except using methyl-4-amino-2-methoxybenzoate gave the title compound of this Example.

MS=442 (M$^+$+H).

EXAMPLE 178

Preparation of 2-Amino-N-(4-N,N-dimethylamino-2,3,5,6-tetramethylphenyl)-6-benzothiazolecarboxamide, trifluoroacetate (1:1)

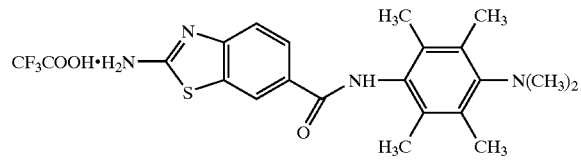

Analogous to the preparation of the compounds of Table 4 using using N$_1$,N$_1$,2,3,5,6-hexamethyl-1,4-phenylenediaminedihydrochloride gave the title compound of this Example after purification by automated preparative HPLC (conditions: same as in Example 167).

MS=369.2 (M$^+$+H).

EXAMPLES 179 and 180

Preparation of 5-Chloro-[6-[[(2,4,6-trimethylphenyl)amino]carbonyl]-2-benzothiazolyl]carbamic acid, 1,1-dimethylethyl ester (179)

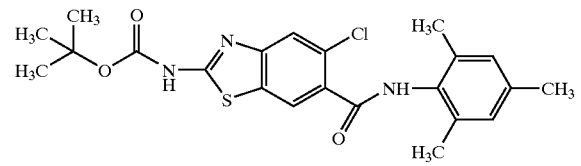

and

7-Chloro-[6-[[(2,4,6-trimethylphenyl)amino]carbonyl]-2-benzothiazolyl]carbamic acid, 1,1-diethylethyl ester (180)

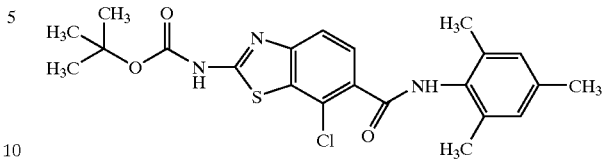

A. Methyl-2-amino-5-chloro-benzothiazole-6-carboxylate (179A) and Methyl-2-amino-7-chloro-benzothiazole-6-carboxylate (180A Analogous to the preparation of compound 1A except using ethyl-2-amino-4-chlorobenzoate gave a mixture of the title compounds 179A and 180A in 2:1 ratio (71%).

B. Methyl-2-tert-butoxycarbonyloxyamino-5-chloro-benzothiazole-6-carboxylate (179B) and Methyl-2-tert-butoxycarbonyloxyamino-7-chloro-benzothiazole-6-carboxylate (180B)

Analogous to the preparation of compound 1B except using a mixture of compounds 179A and 180A gave a mixture of the title compounds 179B and 180B (2:1) as a yellow solid (63%).

C. 2-tert-Butoxycarbonyloxyamino-5-chloro-benzothiazole-6-carboxylic acid (179C) and 2-tert-Butoxycarbonyloxyamino-7-chloro-benzothiazole-6-carboxylic acid (180C)

A solution of a mixture of compounds 179B and 180B (3.75 g, 10.9 mmol) in ethanol (50 mL) and 2 N aq. sodium hydroxide solution (27.5 mL, 55 mmol) was stirred at RT for 18 h. Most of the ethanol was removed in vacuo and the residue was cooled to 0° C. and acidified with satd. aq. potassium hydrogen sulfate to pH 1–2. The precipitate was filtered, washed with water and dried in vacuo to obtain a mixture of the title acids 179C and 180C (4.3 g, 100%, 2:1 ratio) as a yellow solid.

D. 5-Chloro-[6-[[(2,4,6-trimethylphenyl)amino]carbonyl]-2-benzothiazolyl]carbamic acid, 1,1-dimethylethyl ester (179D) and 7-Chloro-[6-[[(2,4,6-trimethylphenyl)amino]carbonyl]-2-benzothiazolyl]carbamic acid, 1,1-dimethylethyl ester (180D)

Diisopropylethyl amine (400 µL, 2.2 mmol) was added to a stirred suspension of compounds 179C and 180C (328 mg, 1 mmol), 2,4,6-trimethylaniline (170 µL, 1.1 mmol) and benzotriazolo-1-yloxytris(dimethylamino)phosphonium hexafluorophosphate (Castro's reagent, 485 mg, 1.1 mmol) in dichloromethane (5 mL). The solution was stirred at RT for 18 h, filtered and dried to obtain a mixture of intermediate benzotriazolo-esters (400 mg) which was dissolved in dimethylformamide (5 mL) and 2,4,6-trimethylaniline (560 µL, 4 mmol) was added. The solution was heated to 50° C. for 72 h, cooled and diluted with EtOAc (100 mL) and water (100 mL). The EtOAc layer was separated, washed with 1 N aq. HCl solution (100 mL, 3x), brine (50 mL), dried (MgSO$_4$), filtered and concentrated. The orange-yellow solid was dissolved in dimethylsulfoxide (1 mL) and diluted with methanol (5 mL), followed by water (5 mL). The solution was let stand at RT for several hours. The precipitated solid was filtered, washed with water (20 mL), dried and then recrystallized from DMSO—MeOH—H$_2$O mixture to obtain the pure title compound 179D (45 mg, 10%).

MS=447 (M$^+$+H).

A second crop of solid was obtained from the mother liquor which was collected by filtration and dried in vacuo to obtain the title compound 180D (44 mg, 10%).

MS=447 (M$^+$+H).

EXAMPLE 181

Preparation of 2-Amino-5-hydroxy-N-[2,4,6-trimethylphenyl]-6-benzothiazolecarboxamide

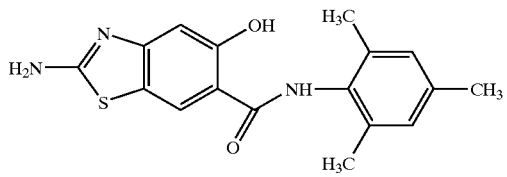

Boron tribromide (300 µL, 3 mmol) was added to a solution of 177 (441 mg, 1 mmol) in dichloromethane (7 mL) at −78° C. The solution was stirred at −78° C. for 1 h and at RT for 1 h, diluted with satd. aq. NaHCO$_3$ solution and concentrated in vacuo. The residue was diluted with water and filtered. The white solid was washed thoroughly with water, ether and dried in vacuo to obtain the title compound of this Example (260 mg, 80%).

MS=328 (M$^+$+H).

EXAMPLE 182

Preparation of 5-tert-Butoxycarbonyloxy-[6-[[(2,4,6-trimethylphenyl)amino]carbonyl]-2-benzothiazolyl]carbamic acid, 1,1-dimethylethyl ester

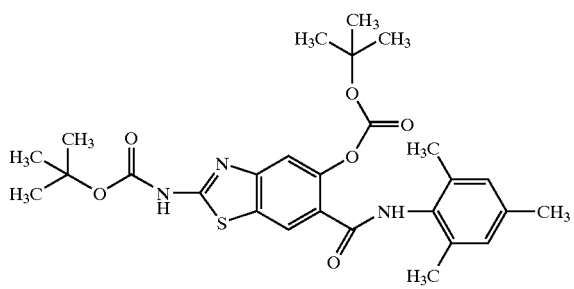

Analogous to the preparation of 1B except using 181 afforded the title compound 182 (25%) after purification by silica gel chromatography and elution with a gradient of dichloromethane to 5% MeOH in dichloromethane in 1% increment with MeOH.

MS=428 (M$^+$+H).

EXAMPLE 183

Preparation of 2-[[[(1,1-Dimethylethyl)amino]carbonyl]amino]-N-(2,6-dimethylphenyl)-6-benzothiazolecarboxamide

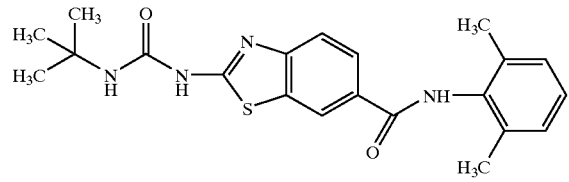

Analogous to the preparation of 166E except using 2,6-dimethylaniline gave the title compound (19%) after purification by automated preparative HPLC (conditions: same as in Example 167).

MS=397 (M$^+$+H).

Alternative Method

A(Alt). [6-[[(2,6-Dimethylphenyl)amino]carbonyl]-2-benzothiazolyl]carbamic acid, 1,1-dimethylethyl ester Diisopropylethyl amine (1.17 mL, 6.42 mmol) was added to a stirred suspension of 141A [2-tert-butoxycarbonyloxyamino-benzothiazole-6-carboxylic acid chloride] (1 g, 3.21 mmol), 2,6-dimethylaniline (473 µL, 3.84 mmol) in THF (25 mL). The mixture was stirred at RT overnight and then diluted with dichloromethane (70 mL). The reaction mixture was washed with 1 N aq. HCl solution (30 mL, 2×), water and brine. The organic layer was dried (Na$_2$SO$_4$), filtered, and concentrated. The residue was triturated with diethyl ether/EtOAc (1:1), filtered, and dried in vacuo to obtain the title compound of this step (475 mg, 37%).

B(Alt). 2-Amino-N-(2,6-dimethylphenyl)-6-benzothiazolecarboxamide

A solution of 183A(Alt) (1 g, 2.5 mmol) in trifluoroacetic acid (6 mL) and dichloromethane (5 mL) was stirred at RT for 2.5 h. The mixture was concentrated, dissolved in dichloromethane and washed with satd. sodium bicarbonate solution (25 mL, 2×), water and brine. The dichloromethane extract was dried (Na$_2$SO$_4$), filtered, and concentrated. The residue was triturated with ether to obtain the title compound of this step (570 mg, 76%).

C(Alt). [6-[[(2,6-Dimethylphenyl)amino]carbonyl]-2-benzothiazolyl]carbamic acid, phenyl ester Analogous to the preparation of Example 7A except using 183B(Alt) in place of the free base of 2 gave the title compound of this step (98%) after trituration with diethyl ether/EtOAc (10:1).

D(Alt). 2-[[[(1,1-Dimethylethyl)amino]carbonyl]amino]-N-(2,6-dimethylphenyl)-6-benzothiazolecarboxamide A solution of 183C(Alt) (46 mg, 0.11 mmol) and tert-butyl amine (14 µL, 0.13 mmol) in THF (4 mL) was stirred at RT overnight. The mixture was diluted with dichloromethane (50 mL) and washed with 1 N aq. HCl solution (30 mL), 1 N aq. NaOH solution (25 mL, 2×), water. The organic extract was dried (NaSO$_4$), filtered, and concentrated. The residue was triturated with diethyl ether to obtain the title compound of this Example (23 mg, 66%).

EXAMPLES 184 TO 204

General Procedure

Compounds 184 to 204 were prepared following the procedure described below.

The appropriate amine (0.086 mmol) was added to a solution of 183C(Alt) (30 mg, 0.072 mmol) in THF (3 mL). In the case of aliphatic amines, the solution was stirred at RT for 48–72 h. For anilines, the solution was heated to 60° C. for 72 h. The reaction mixture was diluted with dichloromethane (5 mL) and washed with 1 N aq. HCl solution (2×), 1 N aq. NaOH solution (2×). The organic extract was dried (Na$_2$SO$_4$), filtered and concentrated in vacuo to obtain the title compounds of these Examples. Some of the title compounds required purification achieved by automated preparative HPLC under the following conditions: YMC ODS 20×100 mm Column, 10 min gradient starting from 70% solvent A (10% MeOH, 90% H$_2$O, 0.2% H$_3$PO$_4$) and 30% solvent B to 100% solvent B (90% MeOH, 10% H$_2$O, 0.2% H$_3$PO$_4$), flow rate 20 mL/min, λ=220 nM. "HPLC Ret Time" is the HPLC retention time under the following conditions: YMC SS ODS 4.6×50 mm Ballastic Column, 4 min gradient starting from 100% solvent A (10% MeOH, 90% H$_2$O, 0.2% H$_3$PO$_4$) to 100% solvent B (90% MeOH, 10% H$_2$O, 0.2% H$_3$PO$_4$), flow rate 4 mL/min, λ=220 nM.

| Ex. No. | Compound Structure | Compound Name | HPLC Ret Time (min) |
|---|---|---|---|
| 184 | 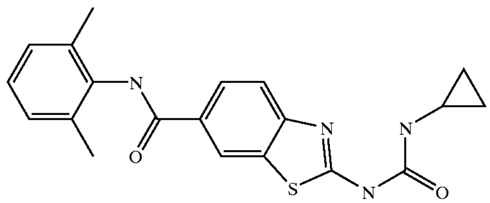 | 2-[[[(Cyclopropylamino)carbonyl]amino]-N-(2,6-dimethylphenyl)-6-benzothiazolecarboxamide | 3.62 |
| 185 | 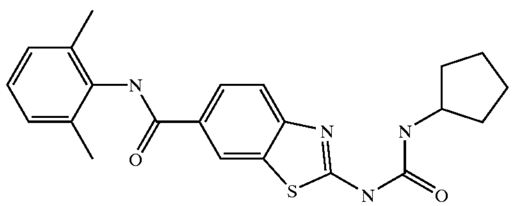 | 2-[[[(Cyclopentylamino)carbonyl]amino]-N-(2,6-dimethylphenyl)-6-benzothiazolecarboxamide | 4.04 |
| 186 | 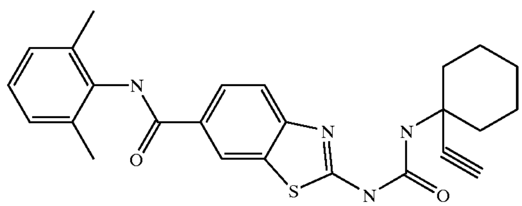 | 2-[[[[1-(ethynyl)cyclohexyl]amino]carbonyl]amino]-N-(2,6-dimethylphenyl)-6-benzothiazolecarboxamide | 4.13 |
| 187 | 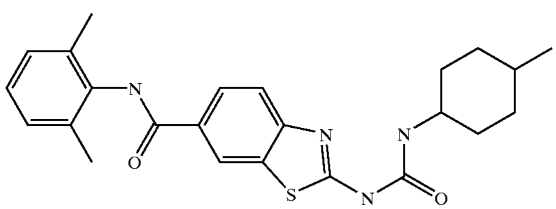 | 2-[[[(4-Methyl-cyclohexyl)amino]carbonyl]amino]-N-(2,6-dimethylphenyl)-6-benzothiazolecarboxamide | 4.39 |
| 188 | 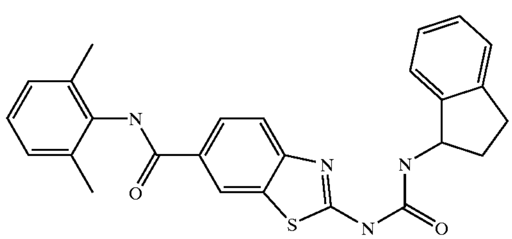 | 2-[[[(2,3-Dihydro-1H-inden-1-yl)amino]carbonyl]amino]-N-(2,6-dimethylphenyl)-6-benzothiazolecarboxamide | 4.25 |
| 189 | 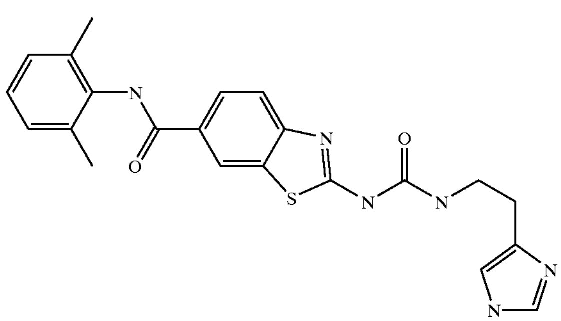 | 2-[[[[2-(1H-Imidazol-4-yl)ethyl]amino]carbonyl]amino]-N-(2,6-dimethylphenyl)-6-benzothiazolecarboxamide | 2.84 |

-continued

| Ex. No. | Compound Structure | Compound Name | HPLC Ret Time (min) |
|---|---|---|---|
| 190 | 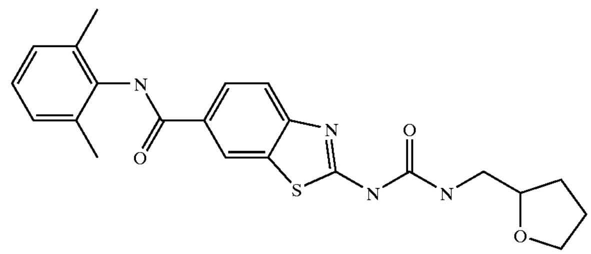 | 2-[[[[(Tetrahydro-2-furanyl)methyl]amino]carbonyl]amino]-N-(2,6-dimethylphenyl)-6-benzothiazolecarboxamide | 3.68 |
| 191 | 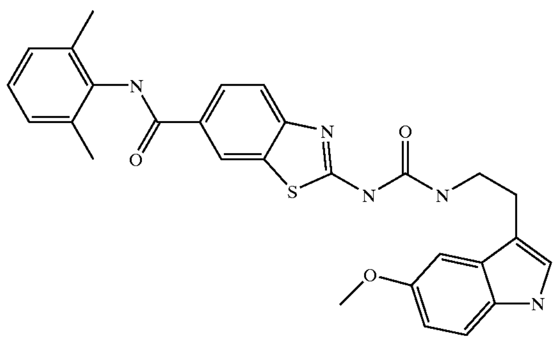 | 2-[[[[2-(5-Methoxy-1H-indol-3-yl)ethyl]amino]carbonyl]amino]-N-(2,6-dimethylphenyl)-6-benzothiazolecarboxamide | 3.99 |
| 192 | 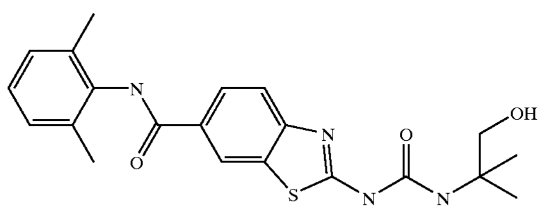 | 2-[[[(1,1-Dimethyl-2-hydroxyethyl)amino]carbonyl]amino]-N-(2,6-dimethylphenyl)-6-benzothiazolecarboxamide | 4.07 |
| 193 | 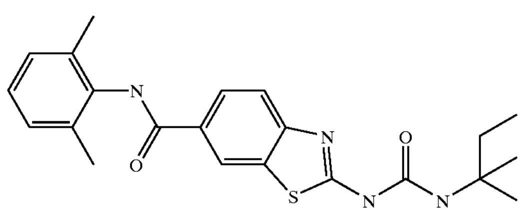 | 2-[[[(1,1-Dimethylpropyl)amino]carbonyl]amino]-N-(2,6-dimethylphenyl)-6-benzothiazolecarboxamide | 4.14 |
| 194 | 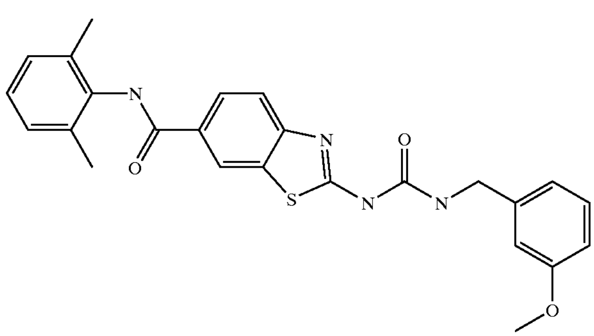 | 2-[[[[(3-Methoxyphenyl)methyl]amino]carbonyl]amino]-N-(2,6-dimethylphenyl)-6-benzothiazolecarboxamide | 4.02 |

-continued

| Ex. No. | Compound Structure | Compound Name | HPLC Ret Time (min) |
|---|---|---|---|
| 195 | 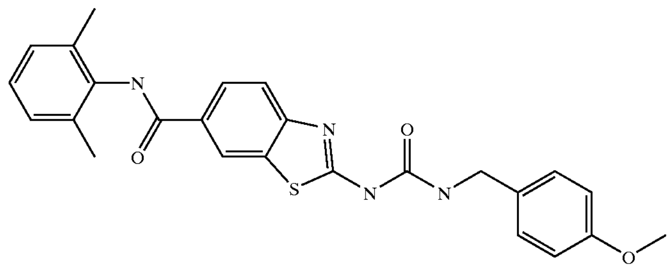 | 2-[[[[(4-Methoxyphenyl)methyl]amino]carbonyl]amino]-N-(2,6-dimethylphenyl)-6-benzothiazolecarboxamide | 4.00 |
| 196 | 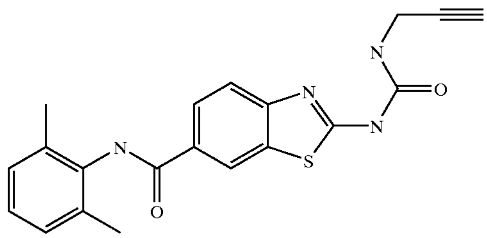 | 2-[[(2-Propynylamino)carbonyl]amino]-N-(2,6-dimethylphenyl)-6-benzothiazolecarboxamide | 4.06 |
| 197 | 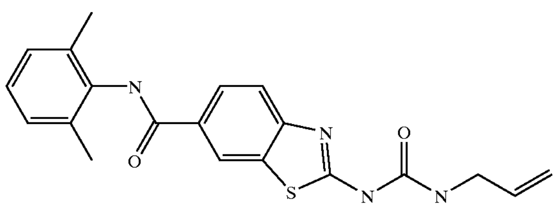 | 2-[[(2-Propenylamino)carbonyl]amino]-N-(2,6-dimethylphenyl)-6-benzothiazolecarboxamide | 3.69 |
| 198 | 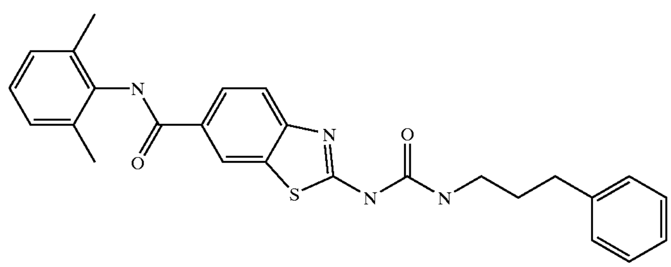 | 2-[[[(3-Phenylpropyl)amino]carbonyl]amino]-N-(2,6-dimethylphenyl)-6-benzothiazolecarboxamide | 4.29 |
| 199 | 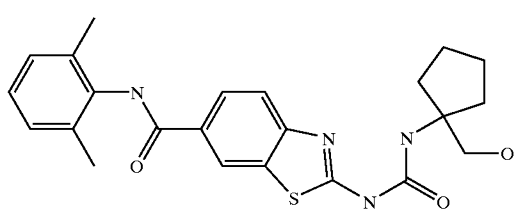 | 2-[[[[1-(Hydroxymethyl)cyclopentyl]amino]carbonyl]amino]-N-(2,6-dimethylphenyl)-6-benzothiazolecarboxamide | 3.90 |
| 200 | 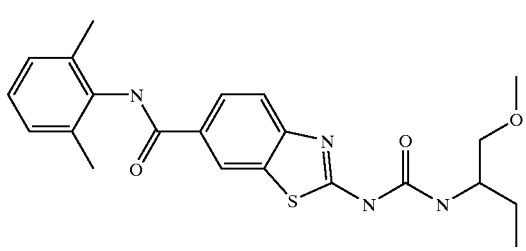 | 2-[[[[1-(Methoxymethyl)propyl]amino]carbonyl]amino]-N-(2,6-dimethylphenyl)-6-benzothiazolecarboxamide | 3.86 |

-continued

| Ex. No. | Compound Structure | Compound Name | HPLC Ret Time (min) |
|---|---|---|---|
| 201 | 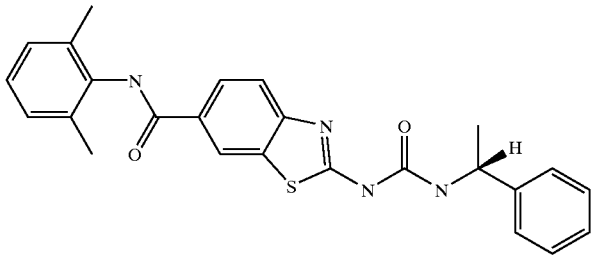 | (R)-2-[[[(1-Phenylethyl)amino]carbonyl]amino]-N-(2,6-dimethylphenyl)-6-benzothiazolecarboxamide | 4.12 |
| 202 | 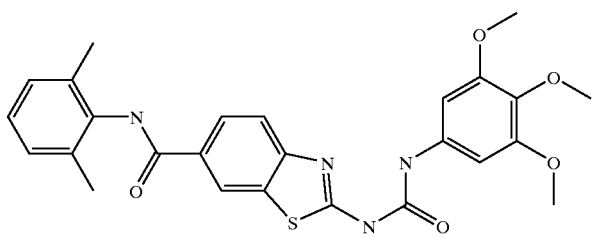 | 2-[[[(3,4,5-Trimethoxyphenyl)amino]carbonyl]amino]-N-(2,6-dimethylphenyl)-6-benzothiazolecarboxamide | 4.15 |
| 203 | 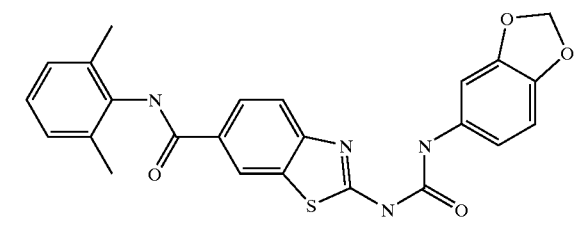 | 2-[[(1,3-Benzodioxol-5-ylamino)carbonyl]amino]-N-(2,6-dimethylphenyl)-6-benzothiazolecarboxamide | 4.02 |
| 204 | 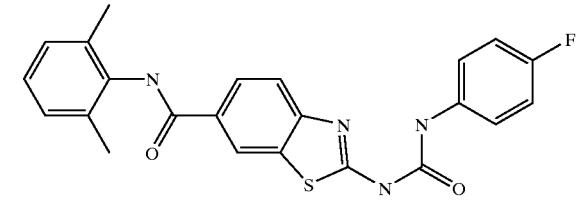 | 2-[[[(4-Fluorophenyl)amino]carbonyl]amino]-N-(2,6-dimethylphenyl)-6-benzothiazolecarboxamide | 4.05 |

EXAMPLES 205 TO 226

General Procedure

Compounds 205 to 226 were prepared following the procedure described below.

The appropriate amine (0.086 mmol) was added to a solution of 166C(Alt) (30 mg, 0.072 mmol) in THF (3 mL). In case of the aliphatic amines, the solution was stirred at RT for 48–72 h. For anilines, the solution was heated to 60° C. for 72 h. The reaction mixture was diluted with dichloromethane (5 mL) and washed with 1 N aq. HCl solution (2×), 1 N aq. NaOH solution (2×). The organic extract was dried ($Na_2SO_4$), filtered and concentrated in vacuo to obtain the title compounds of these Examples. Some of the title compounds required purification achieved by automated preparative HPLC under the following conditions: YMC ODS 20×100 mm Column, 10 min gradient starting from 70% solvent A (10% MeOH, 90% $H_2O$, 0.2% $H_3PO_4$) and 30% solvent B to 100% solvent B (90% MeOH, 10% $H_2O$, 0.2% $H_3PO_4$), flow rate 20 mL/min, λ=220 nM. "HPLC Ret Time" is the HPLC retention time under the following conditions: YMC S5 ODS 4.6×50 mm Ballastic Column, 4 min gradient starting from 100% solvent A (10% MeOH, 90% $H_2O$, 0.2% $H_3PO_4$) to 100% solvent B (90% MeOH, 10% $H_2O$, 0.2% $H_3PO_4$), flow rate 4 mL/min, λ=220 nM.

| Ex. No. | Compound Structure | Compound Name | HPLC Ret Time (min) |
|---|---|---|---|
| 205 | 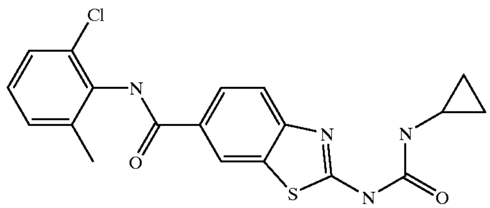 | 2-[[[(Cyclopropylamino)carbonyl]amino]-N-(2-chloro-6-methylphenyl)-6-benzothiazolecarboxamide | 4.15 |
| 206 | 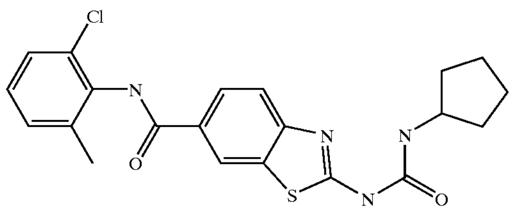 | 2-[[[(Cyclopentylamino)carbonyl]amino]-N-(2-chloro-6-methylphenyl)-6-benzothiazolecarboxamide | 4.08 |
| 207 | 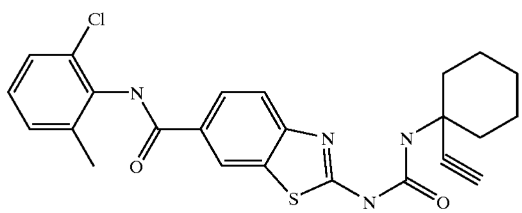 | 2-[[[[1-(ethynyl)cyclohexyl]amino]carbonyl]amino]-N-(2-chloro-6-methylphenyl)-6-benzothiazolecarboxamide | 4.17 |
| 208 | 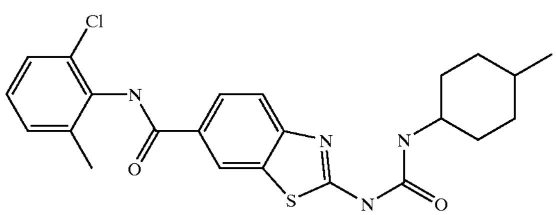 | 2-[[[[(4-Methyl-cyclohexyl)amino]carbonyl]amino]-N-(2-chloro-6-methylphenyl)-6-benzothiazolecarboxamide | 4.37 |
| 209 | 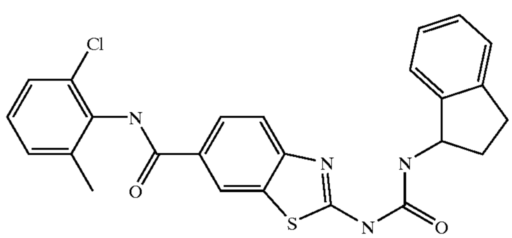 | 2-[[[(2,3-Dihydro-1H-inden-1-yl)amino]carbonyl]amino]-N-(2-chloro-6-methylphenyl)-6-benzothiazolecarboxamide | 4.23 |
| 210 | 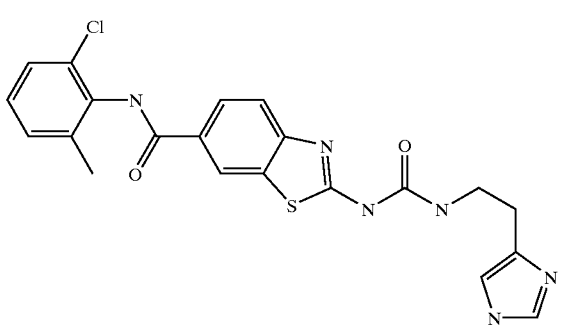 | 2-[[[[2-(1H-Imidazol-4-yl)ethyl]amino]carbonyl]amino]-N-(2-chloro-6-methylphenyl)-6-benzothiazolecarboxamide | 2.87 |

| Ex. No. | Compound Structure | Compound Name | HPLC Ret Time (min) |
|---|---|---|---|
| 211 | 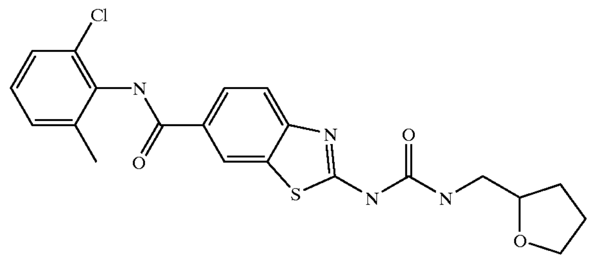 | 2-[[[[(Tetrahydro-2-furanyl)methyl]amino]carbonyl]amino]-N-(2-chloro-6-methylphenyl)-6-benzothiazolecarboxamide | 4.00 |
| 212 | 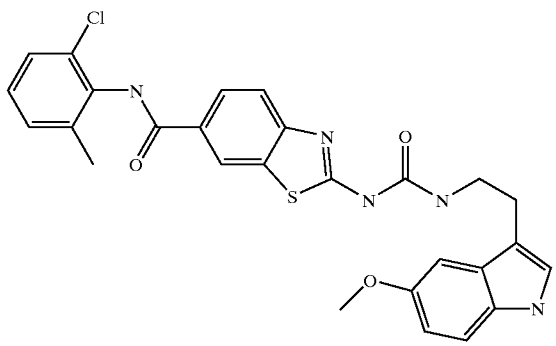 | 2-[[[[2-(5-Methoxy-1H-indol-3-yl)ethyl]amino]carbonyl]amino]-N-(2-chloro-6-methylphenyl)-6-benzothiazolecarboxamide | 3.97 |
| 213 | 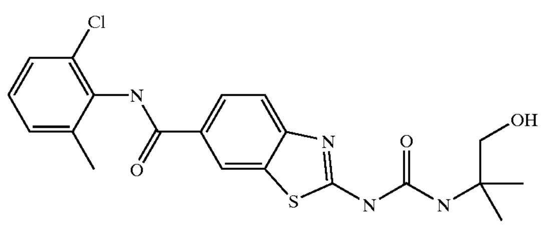 | 2-[[[(1,1-Dimethyl-2-hydroxyethyl)amino]carbonyl]amino]-N-(2-chloro-6-methylphenyl)-6-benzothiazolecarboxamide | 4.29 |
| 214 | 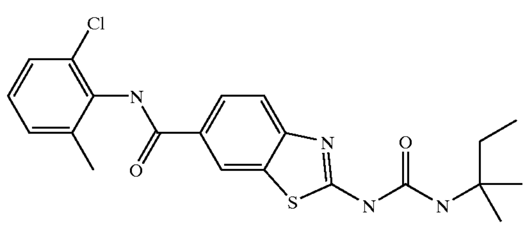 | 2-[[[(1,1-Dimethyl-propyl)amino]carbonyl]amino]-N-(2-chloro-6-methylphenyl)-6-benzothiazolecarboxamide | 4.12 |
| 215 | 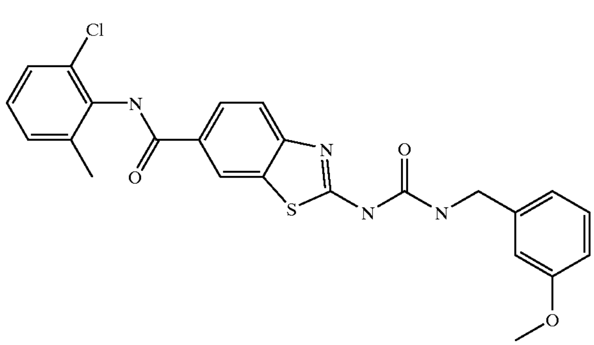 | 2-[[[[(3-Methoxyphenyl)methyl]amino]carbonyl]amino]-N-(2-chloro-6-methylphenyl)-6-benzothiazolecarboxamide | 4.01 |

-continued

| Ex. No. | Compound Structure | Compound Name | HPLC Ret Time (min) |
|---|---|---|---|
| 216 | 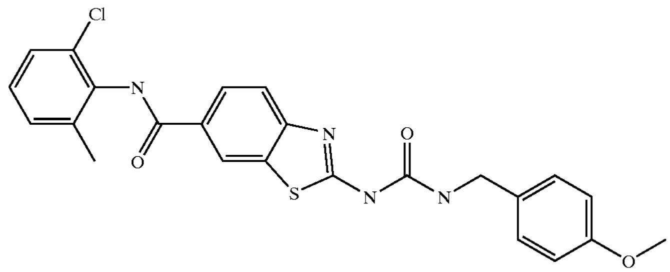 | 2-[[[[(4-Methoxyphenyl)methyl]amino]carbonyl]amino]-N-(2-chloro-6-methylphenyl)-6-benzothiazolecarboxamide | 3.98 |
| 217 | 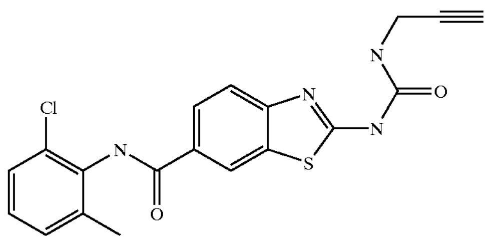 | 2-[[(2-Propynylamino)carbonyl]amino]-N-(2-chloro-6-methylphenyl)-6-benzothiazolecarboxamide | 4.37 |
| 218 | 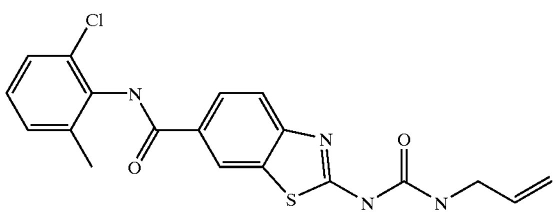 | 2-[[(2-Propenylamino)carbonyl]amino]-N-(2-chloro-6-methylphenyl)-6-benzothiazolecarboxamide | 3.67 |
| 219 | 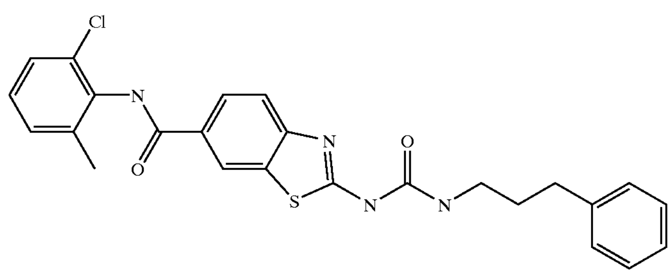 | 2-[[[(3-Phenylpropyl)amino]carbonyl]amino]-N-(2-chloro-6-methylphenyl)-6-benzothiazolecarboxamide | 4.27 |
| 220 | 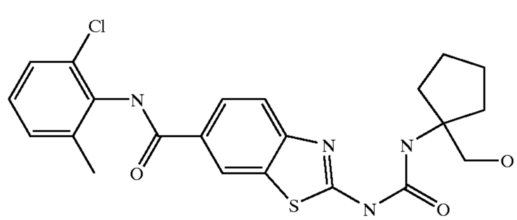 | 2-[[[[1-(Hydroxymethyl)cyclopentyl]amino]carbonyl]amino]-N-(2-chloro-6-methylphenyl)-6-benzothiazolecarboxamide | 4.28 |
| 221 | 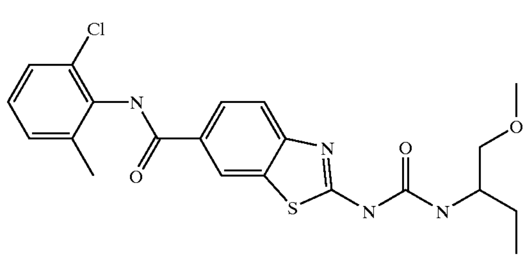 | 2-[[[[1-(Methoxymethyl)propyl]amino]carbonyl]amino]-N-(2-chloro-6-methylphenyl)-6-benzothiazolecarboxamide | 3.84 |

-continued

| Ex. No. | Compound Structure | Compound Name | HPLC Ret Time (min) |
|---|---|---|---|
| 222 | 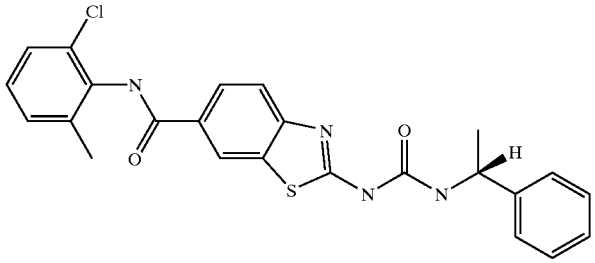 | (R)-2-[[[(1-Phenylethyl)amino]carbonyl]amino]-N-(2-chloro-6-methylphenyl)-6-benzothiazolecarboxamide | 4.10 |
| 223 | 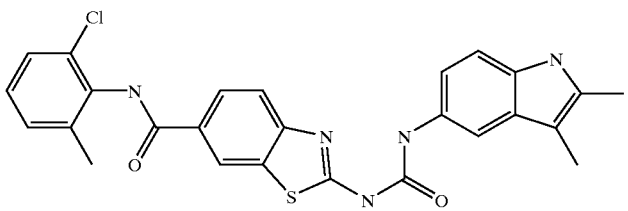 | 2-[[[(2,3-Dimethyl-1H-indol-5-yl)amino]carbonyl]amino]-N-(2-chloro-6-methylphenyl)-6-benzothiazolecarboxamide | 4.32 |
| 224 | 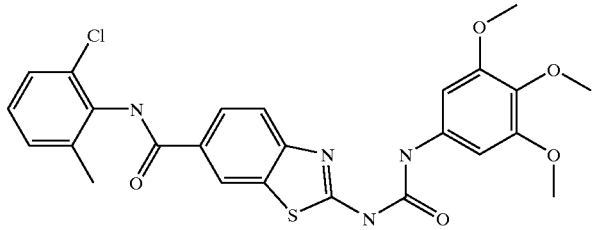 | 2-[[[(3,4,5-Trimethoxyphenyl)amino]carbonyl]amino]-N-(2-chloro-6-methylphenyl)-6-benzothiazolecarboxamide | 4.03 |
| 225 | 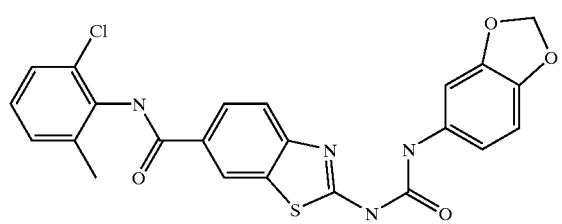 | 2-[[[(1,3-Benzodioxol-5-ylamino)carbonyl]amino]-N-(2-chloro-6-methylphenyl)-6-benzothiazolecarboxamide | 4.01 |
| 226 | 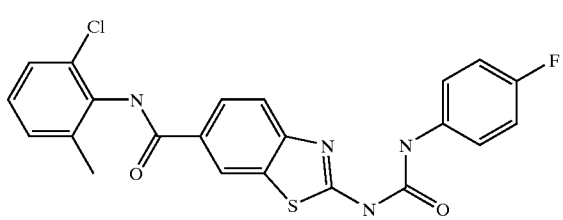 | 2-[[[(4-Fluorophenyl)amino]carbonyl]amino]-N-(2-chloro-6-methylphenyl)-6-benzothiazolecarboxamide | 4.37 |

EXAMPLE 227

Preparation of 2-[[[[(1-methoxycarbonyl)cyclopropyl]amino]carbonyl]amino-N-(2,4,6-trimethylphenyl)-6-benzothiazolecarboxamide

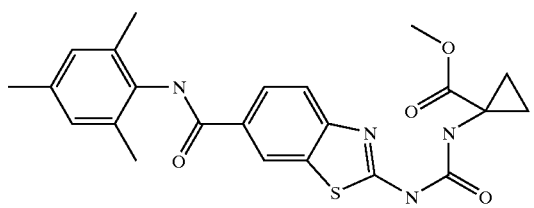

Analogous to the preparation of the compounds of Table 1 using 1-methoxycarbonyl-cyclopropyl amine gave the title compound of this Example (6%) after purification by preparative HPLC under the following conditions: YMC ODS 20×100 mm Column, 10 min gradient starting from 70% solvent A (10% MeOH, 90% $H_2O$, 0.2% $H_3PO_4$) and 30% solvent B to 100% solvent B (90% MeOH, 10% $H_2O$, 0.2% $H_3PO_4$), flow rate 20 mL/min, λ=220 nM. MS: 453 $(M+H)^+$.

EXAMPLE 228

Preparation of [6-[[[(2,6-Dimethyl-4-phenyl)phenyl]amino]carbonyl]-2-benzothiazolyl]carbamic acid, 1,1-dimethylethyl ester

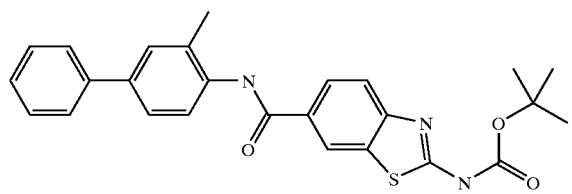

Analogous to the preparation of the compounds of Table 4 using 2,6-dimethyl-4-phenyl aniline gave the title compound of this Example (45%) after purification by silica gel chromatography and elution with 1–5% methanol in chloroform. MS: 474.1 $(M+H)^+$.

EXAMPLE 229

Preparation of [6-[[[(2,6-Dimethyl-4-(2-N,N-dimethylethoxy)phenyl]amino]carbonyl]-2-benzothiazolyl]carbamic acid, 1,1-dimethylethyl ester

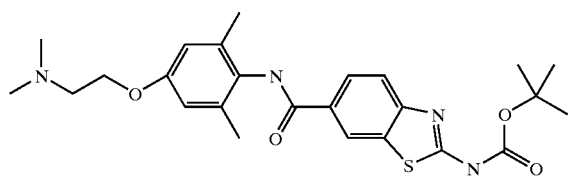

Analogous to the preparation of the compounds of Table 4 using 2,6-dimethyl-4-(2-N,N-dimethylethoxy) aniline gave the title compound of this Example (45%) after purification by silica gel chromatography and elution with 2–5% methanol in chloroform and 95:4:1 chloroform:methanol:triethyl amine. MS: 485.1 $(M+H)^+$.

EXAMPLE 230

Preparation of [6-[[[(2-Dimethyl-4-(2-morpholinoethoxy)phenyl]amino]carbonyl]-2-benzothiazolyl]carbamic acid, 1,1-dimethylethyl ester

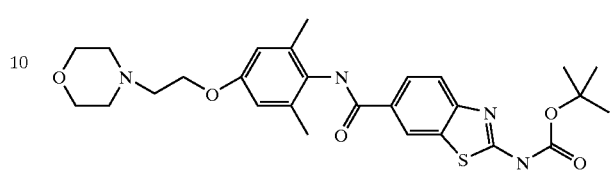

Analogous to the preparation of the compounds of Table 4 using 2,6-dimethyl-4-(2-morpholinoethoxy) aniline gave the title compound of this Example (18%) after purification by silica gel chromatography and elution with 95:4:1 chloroform:methanol:triethyl amine. MS: 527.7 $(M+H)^+$.

EXAMPLE 231

Preparation of 2-[(Cyclopropylcarbonyl)amino]-N-(2-chloro-6-methylphenyl)-6-benzothiazolecarboxamide

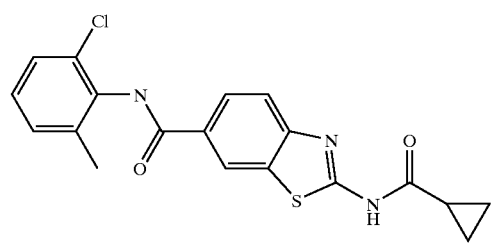

Analogous to the preparation of 99 in Table 3 except using 166B(Alt) afforded the title compound of this Example. MS: 386 $(M+H)^+$.

EXAMPLE 232

Preparation of 2-[(2-Methyl-cyclopropylcarbonyl)amino]-N-(2-chloro-6-methylphenyl)-6-benzothiazolecarboxamide

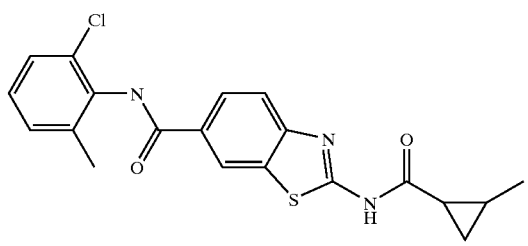

Analogous to the preparation of 231 except using 2-methyl-cyclopropane carboxylic acid afforded the title compound of this Example. MS: 400 $(M+H)^+$.

EXAMPLE 233

Preparation of 2-[(2,2-Dichloro-1-methyl-cyclopropylcarbonyl)amino]-N-(2-chloro-6-methylphenyl)-6-benzothiazolecarboxamide

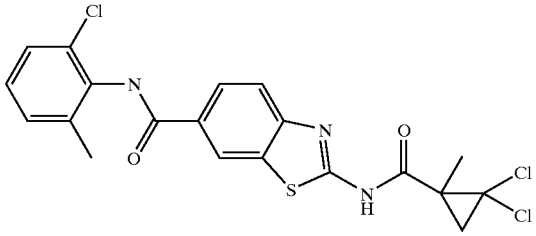

Analogous to the preparation of 231 except using 2,2-dichloro-1-methylcyclopropane carboxylic acid afforded the title compound of this Example. MS: 469 (M+H)$^+$.

EXAMPLE 234

Preparation of 2-[(1-Hydroxy-cyclopropylcarbonyl)amino]-N-(2-chloro-6-methylphenyl)-6-benzothiazolecarboxamide

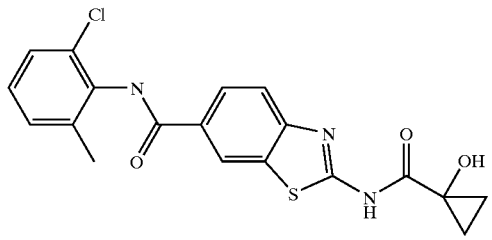

Analogous to the preparation of 231 except using 1-hydroxy-cyclopropane carboxylic acid afforded the title compound of this Example. MS: 402 (M+H)$^+$.

EXAMPLES 235 TO 282 & 467 TO 478

General Procedure

Compounds 235 to 282 and 467 to 478 were prepared following the procedure described below. Diisopropylethyl amine (50 μL, 0.288 mmol) was added to a mixture of compound 166B(Alt) (30 mg, 0.096 mmol), carboxylic acid (0.115 mmol), 1-hydroxy-7-azabenzotriazole (17 mg, 0.125 mmol), and ethyl-3-(3-dimethylamino)-propyl carbodiimide hydrochloride (24 mg, 0.125 mmol) in THF (1 mL). The mixture was heated at 45° C. for 18–72 h. The reaction mixture was diluted with dichloromethane (5 mL) and washed with 1 N aq. HCl solution (2×), 1 N aq. NaOH solution (2×). The organic extract was dried (MgSO4), filtered and concentrated in speedvac. The crude products were purified either by trituration with dichloromethane-ether or by automated preparative HPLC under the following conditions: YMC ODS 20×100 mm Column, 10 min gradient starting from 70% solvent A (10% MeOH, 90% H2O, 0.2% H3PO4) and 30% solvent B to 100% solvent B (90% MeOH, 10% H2O, 0.2% H3PO4), flow rate 20 mL/min, λ=220 nM.

"HPLC Ret Time" is the HPLC retention time under the following conditions: YMC S5 ODS 4.6×50 mm Ballastic Column, 4 min gradient starting from 100% solvent A (10% MeOH, 90% H2O, 0.2% H3PO4) to 100% solvent B (90% MeOH, 10% H2O, 0.2% H3PO4) with 2 min hold, flow rate 4 mL/min, λ=220 nM for compounds 235–271, and and compounds 467–478, and Phenomenex-Prime S5, 4.6×50 mm Column, 2 min gradient starting from 100% solvent A (10% MeOH, 90% H2O, 0.2% H3PO4) to 100% solvent B (90% MeOH, 10% H2O, 0.2% H3PO4) with 1 min hold, flow rate 5 mL/min, λ=220 nM for compounds 272–282.

| EX. NO. | Compound Structure | Compound Name | HPLC Ret Time (min) |
|---|---|---|---|
| 235 | 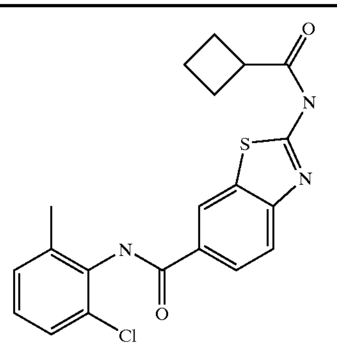 | N-(2-Chloro-6-methylphenyl)-2-[(cyclobutylcarbonyl)amino]-6-benzothiazolecarboxamide | 3.84 |

-continued

| EX. NO. | Compound Structure | Compound Name | HPLC Ret Time (min) |
|---|---|---|---|
| 236 | 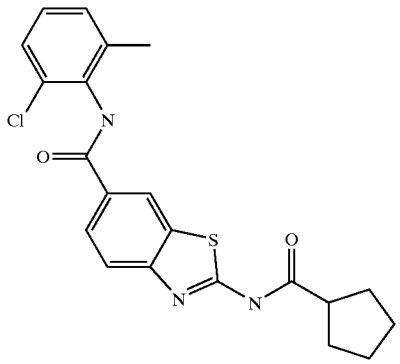 | N-(2-Chloro-6-methylphenyl)-2-[(cyclopentylcarbonyl)amino]-6-benzothiazolecarboxamide | 4.00 |
| 237 | 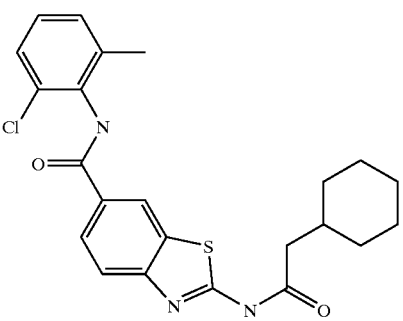 | N-(2-Chloro-6-methylphenyl)-2-[(cyclohexylacetyl)amino]-6-benzothiazolecarboxamide | 4.32 |
| 238 | 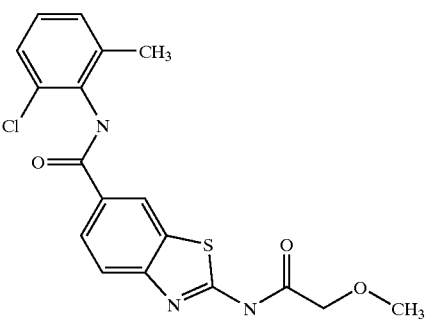 | N-(2-Chloro-6-methylphenyl)-2-[(methoxyacetyl)amino]-6-benzothiazolecarboxamide | 3.39 |
| 239 | 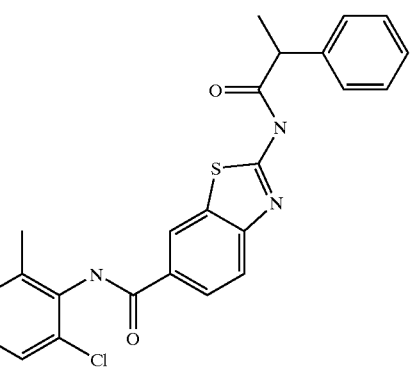 | N-(2-Chloro-6-methylphenyl)-2-[(1-oxo-2-phenylpropyl)amino]-6-benzothiazolecarboxamide | 4.1 |

-continued

| EX. NO. | Compound Structure | Compound Name | HPLC Ret Time (min) |
|---|---|---|---|
| 240 | 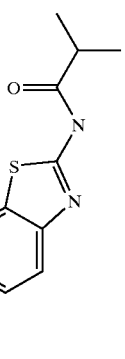 | N-(2-Chloro-6-methylphenyl)-2-[(1-oxo-2-methylpropyl)amino]-6-benzothiazolecarboxamide | 4.06 |
| 241 | 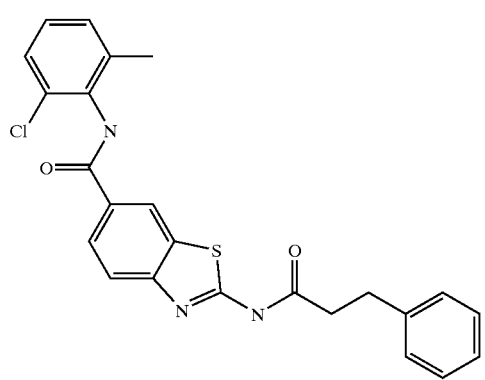 | N-(2-Chloro-6-methylphenyl)-2-[(1-oxo-3-phenylpropyl)amino]-6-benzothiazolecarboxamide | 4.11 |
| 242 | 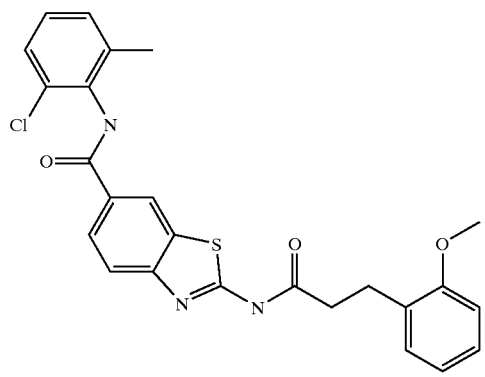 | N-(2-Chloro-6-methylphenyl-2-[[3-(2-methoxyphenyl)-1-oxopropyl]amino]-6-benzothiazolecarboxamide | 4.16 |
| 243 | 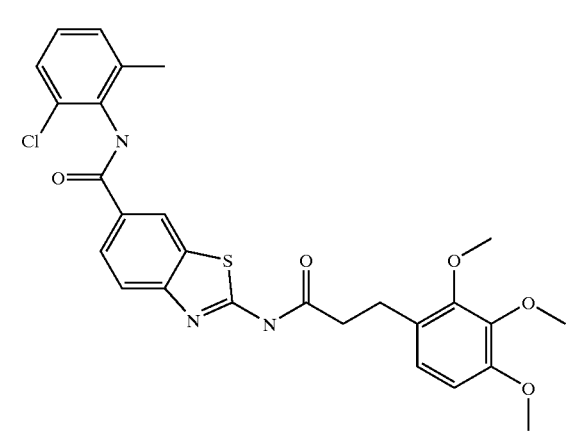 | N-(2-Chloro-6-methylphenyl)-2-[[1-oxo-3-(2,3,4-trimethoxyphenyl)propyl]amino]-6-benzothiazolecarboxamide | 4.03 |

| EX. NO. | Compound Structure | Compound Name | HPLC Ret Time (min) |
|---|---|---|---|
| 244 | 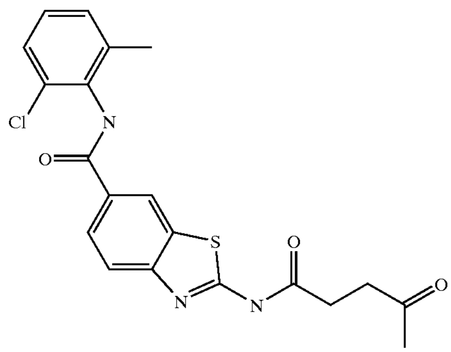 | N-(2-Chloro-6-methylphenyl)-2-[(1,4-dioxopentyl)amino]-6-benzothiazolecarboxamide | 3.37 |
| 245 | 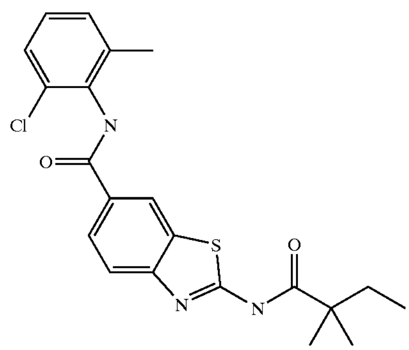 | N-(2-Chloro-6-methylphenyl)-2-[(2,2-dimethyl-1-oxobutyl)amino]-6-benzothiazolecarboxamide | 4.04 |
| 246 | 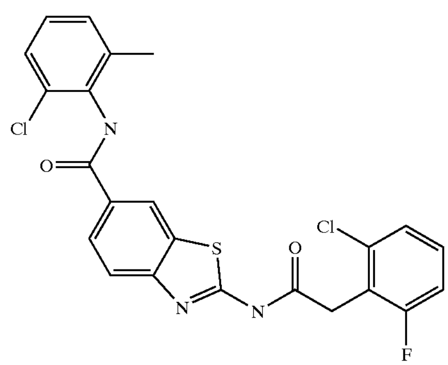 | 2-[[(2-Chloro-6-fluorophenyl)acetyl]amino]-N-(2-chloro-6-methylphenyl)-6-benzothiazolecarboxamide | 4.05 |
| 247 | 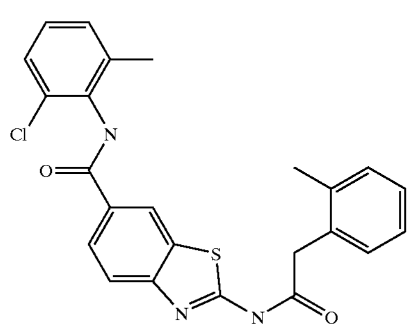 | N-(2-Chloro-6-methylphenyl)-2-[[(2-methylphenyl)acetyl]amino]-6-benzothiazolecarboxamide | 4.06 |

| EX. NO. | Compound Structure | Compound Name | HPLC Ret Time (min) |
|---|---|---|---|
| 248 | 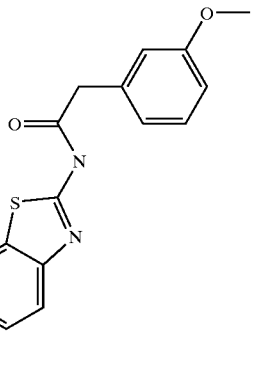 | N-(2-Chloro-6-methylphenyl)-2-[[(3-methoxyphenyl)acetyl]amino]-6-benzothiazolecarboxamide | 3.94 |
| 249 | 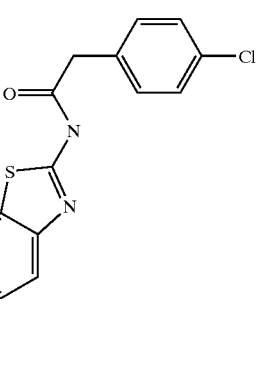 | N-(2-Chloro-6-methylphenyl)-2-[[(4-chlorophenyl)acetyl]amino]-6-benzothiazolecarboxamide | 4.19 |
| 250 | 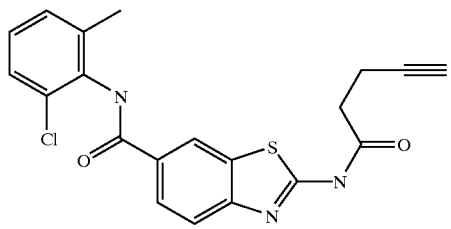 | N-(2-Chloro-6-methylphenyl)-2-[(1-oxo-4-pentynyl)amino]-6-benzothiazolecarboxamide | 3.58 |
| 251 | 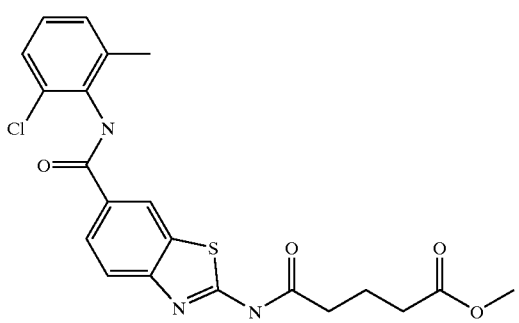 | 5-[[6-[[(2-Chloro-6-methylphenyl)amino]carbonyl]-2-benzothiazolyl]amino]-5-oxopentanoic acid methyl ester | 3.63 |

-continued

| EX. NO. | Compound Structure | Compound Name | HPLC Ret Time (min) |
|---|---|---|---|
| 252 | 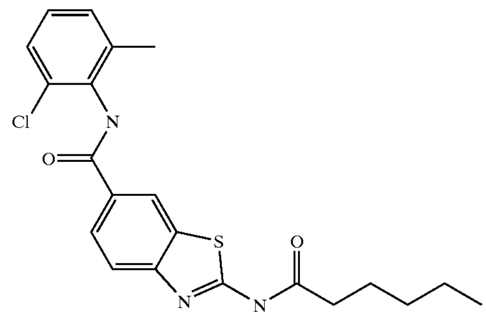 | N-(2-Chloro-6-methylphenyl)-2-[(1-oxohexyl)amino]-6-benzothiazolecarboxamide | 4.17 |
| 253 | 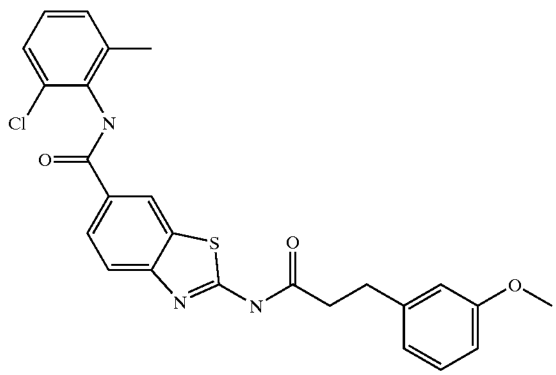 | N-(2-Chloro-6-methylphenyl)-2-[[3-(3-methoxyphenyl)-1-oxopropyl]amino]-6-benzothiazolecarboxamide | 4.1 |
| 254 | 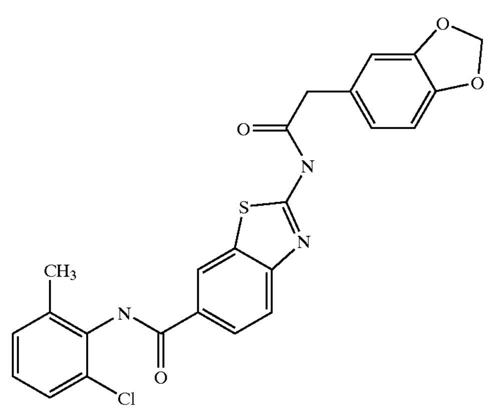 | 2-[[(1,3-Benzodioxol-5-yl)acetyl]amino]-N-(2-chloro-6-methylphenyl)-6-benzothiazolecarboxamide | 3.89 |
| 255 | 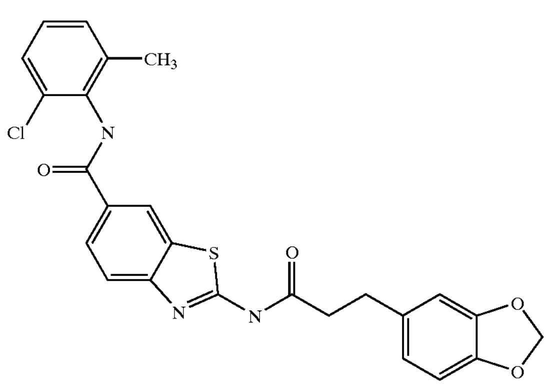 | 2-[[3-(1,3-Benzodioxol-5-yl)-1-oxopropyl]amino]-N-(2-chloro-6-methylphenyl)-6-benzothiazolecarboxamide | 4.08 |

| EX. NO. | Compound Structure | Compound Name | HPLC Ret Time (min) |
|---|---|---|---|
| 256 | 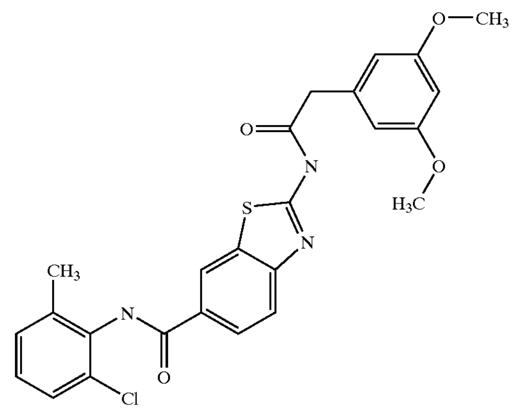 | N-(2-Chloro-6-methylphenyl)-2-[[(3,5-dimethoxyphenyl)acetyl]amino]-6-benzothiazolecarboxamide | 3.95 |
| 257 | 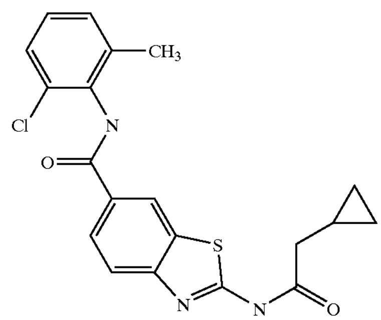 | N-(2-Chloro-6-methylphenyl)-2-[(cyclopropylacetyl)amino]-6-benzothiazolecarboxamide | 3.76 |
| 258 | 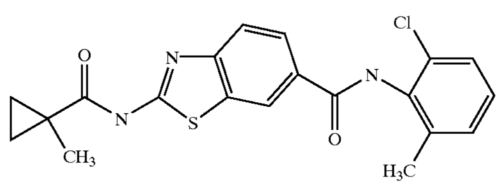 | N-(2-Chloro-6-methylphenyl)-2-[[(1-methylcyclopropyl)carbonyl]amino]-6-benzothiazolecarboxamide | 3.82 |
| 259 | 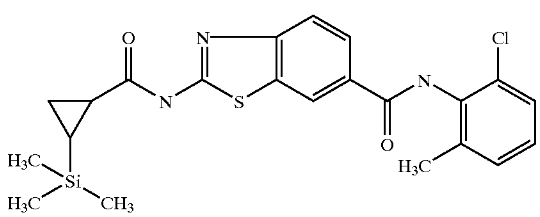 | N-(2-Chloro-6-methylphenyl)-2-[[[2-(trimethylsilyl)cyclopropyl]carbonyl]amino]-6-benzothiazolecarboxamide | 4.55 |
| 260 | 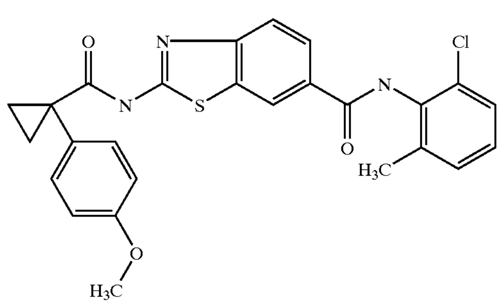 | N-(2-Chloro-6-methylphenyl)-2-[[[1-(4-methoxyphenyl)cyclopropyl]carbonyl]amino]-6-benzothiazolecarboxamide | 4.41 |

-continued

| EX. NO. | Compound Structure | Compound Name | HPLC Ret Time (min) |
|---|---|---|---|
| 261 | 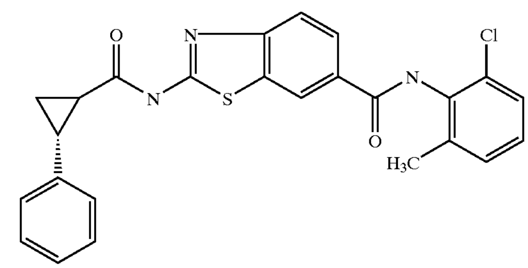 | trans-N-(2-Chloro-6-methylphenyl)-2-[[(2-phenylcyclopropyl)carbonyl]amino]-6-benzothiazolecarboxamide | 4.37 |
| 262 | 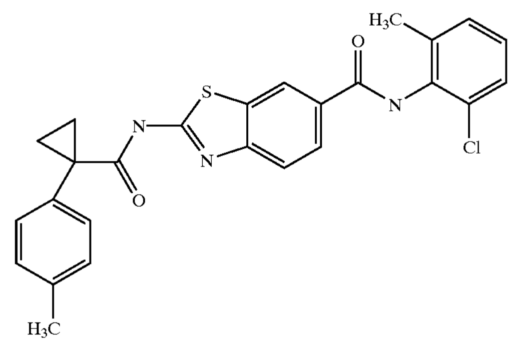 | N-(2-Chloro-6-methylphenyl)-2-[[[1-(4-methylphenyl)cyclopropyl]carbonyl]amino]-6-benzothiazolecarboxamide | 4.51 |
| 263 | 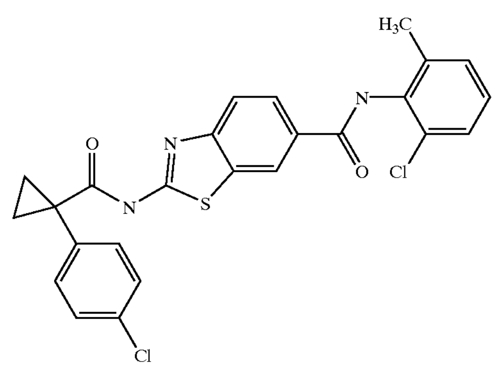 | N-(2-Chloro-6-methylphenyl)-2-[[[1-(4-chlorophenyl)cyclopropyl]carbonyl]amino]-6-benzothiazolecarboxamide | 4.49 |
| 264 | 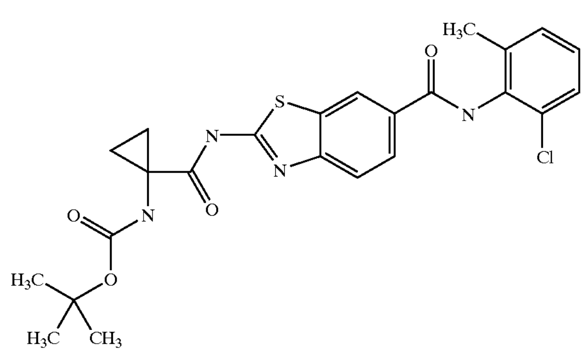 | [1-[[[6-[[(2-Chloro-6-methylphenyl)amino]carbonyl]-2-benzothiazolyl]amino]carbonyl]cyclopropyl]carbamic acid 1,1-dimethylethyl ester | 3.96 |

| EX. NO. | Compound Structure | Compound Name | HPLC Ret Time (min) |
|---|---|---|---|
| 265 | Chiral | (1S-trans)-N-(2-Chloro-6-methylphenyl)-2-[[[2,2-diethyl-3-(2-methyl-1-propenyl)cyclopropyl]carbonyl]amino]-6-benzothiazolecarboxamide | 4.52 |
| 266 | Chiral | (1S-cis)-N-(2-Chloro-6-methylphenyl)-2-[[[2,2-dimethyl-3-(2-methyl-1-propenyl)cyclopropyl]carbonyl]amino]-6-benzothiazolecarboxamide | 4.48 |
| 267 | 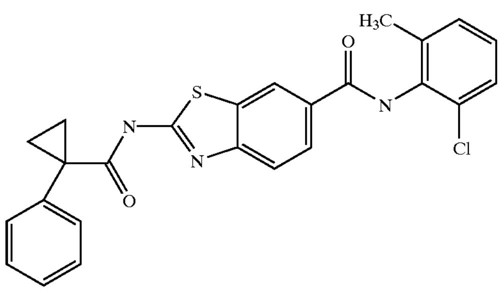 | N-(2-Chloro-6-methylphenyl)-2-[[(1-phenylcyclopropyl)carbonyl]amino]-6-benzothiazolecarboxamide | 4.30 |
| 268 | 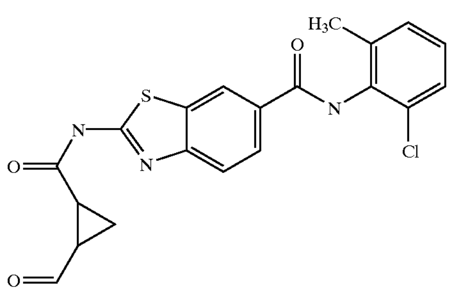 | N-(2-Chloro-6-methylphenyl)-2-[[(2-formylcyclopropyl)carbonyl]amino]-6-benzothiazolecarboxamide | 4.28 |
| 269 | 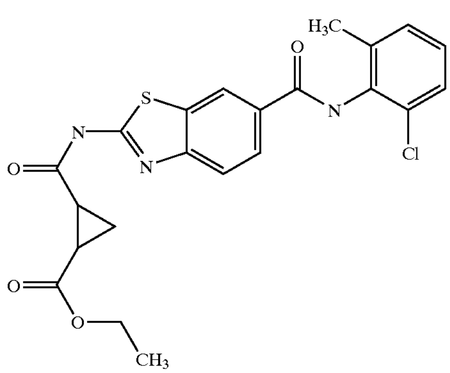 | 2-[[[6-[[(2-Chloro-6-methylphenyl)amino]carbonyl]-2-benzothiazolyl]amino]carbonyl]cyclopropanecarboxylic acid ethyl ester | 4.04 |

-continued

| EX. NO. | Compound Structure | Compound Name | HPLC Ret Time (min) |
|---|---|---|---|
| 270 | 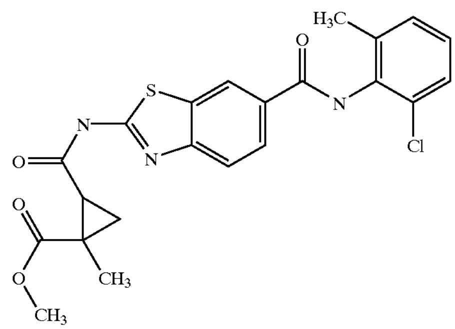 | 2-[[[6-[[(2-Chloro-6-methylphenyl)amino]carbonyl]-2-benzothiazolyl]amino]carbonyl]-1-methylcyclopropanecarboxylic acid methyl ester | 3.95 3.98 |
| 271 | 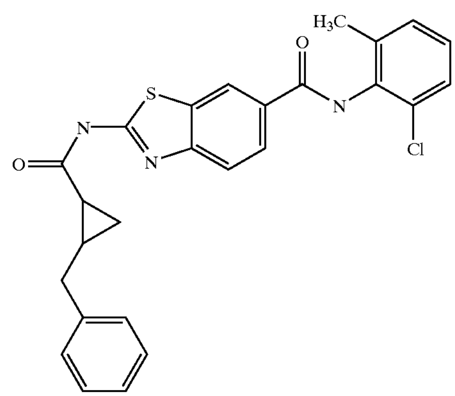 | N-(2-Chloro-6-methylphenyl)-2-[[[2-(phenylmethyl)cyclopropyl]carbonyl]amino]-6-benzothiazolecarboxamide | 4.36 |
| 272 | 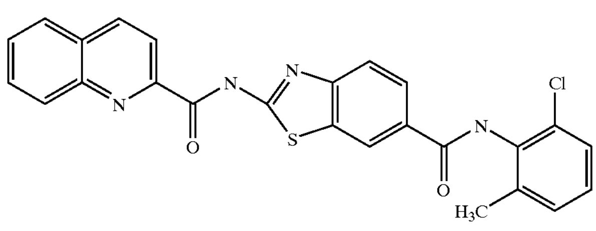 | N-[6-[[(2-Chloro-6-methylphenyl)amino]carbonyl]-2-benzothiazolyl]-2-quinolinecarboxamide | 2.39 |
| 273 | 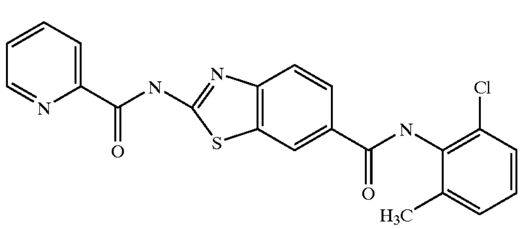 | N-(2-Chloro-6-methylphenyl)-2-[(2-pyridinylcarbonyl)amino]-6-benzothiazolecarboxamide | 2.14 |

-continued

| EX. NO. | Compound Structure | Compound Name | HPLC Ret Time (min) |
|---|---|---|---|
| 274 | 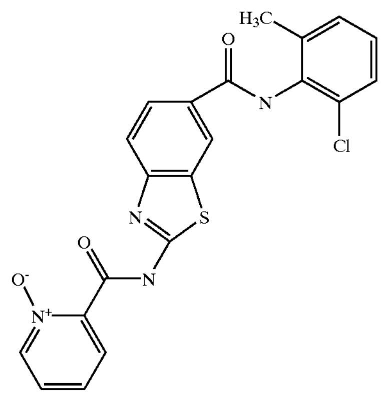 | N-(2-Chloro-6-methylphenyl)-2-[(2-pyridinylcarbonyl)amino]-6-benzothiazolecarboxamide, 1-oxide | 2.02 |
| 275 | 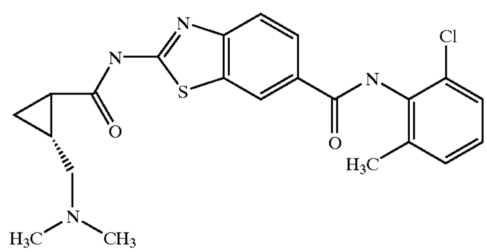 | trans-N-(2-Chloro-6-methylphenyl)-2-[[[2-[(dimethylamino)methyl]cyclopropyl]carbonyl]amino]-6-benzothiazolecarboxamide | 1.66 |
| 276 | 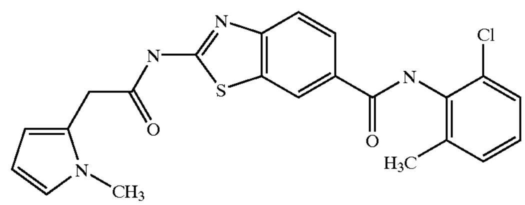 | N-(2-Chloro-6-methylphenyl)-2-[[(1-methyl-1H-pyrrol-2-yl)acetyl]amino]-6-benzothiazolecarboxamide | 2.07 |
| 277 | 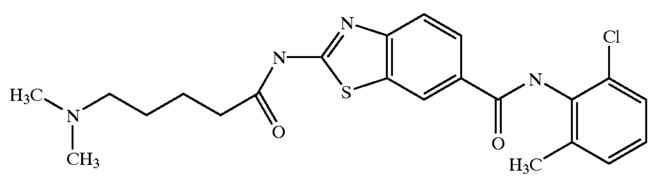 | N-(2-Chloro-6-methylphenyl)-2-[[5-(dimethylamino)-1-oxopentyl]amino]-6-benzothiazolecarboxamide | 1.65 |
| 278 | 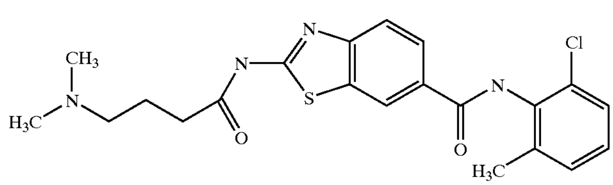 | N-(2-Chloro-6-methylphenyl)-2-[[4-(dimethylamino)-1-oxobutyl]amino]-6-benzothiazolecarboxamide | 1.58 |
| 279 | 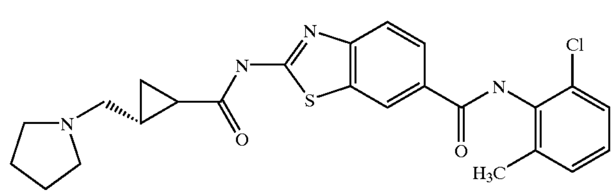 | trans-N-(2-Chloro-6-methylphenyl)-2-[[[2-(1-pyrrolidinylmethyl)cyclopropyl]carbonyl]amino]-6-benzothiazolecarboxamide | 1.67 |

| EX. NO. | Compound Structure | Compound Name | HPLC Ret Time (min) |
|---|---|---|---|
| 280 | 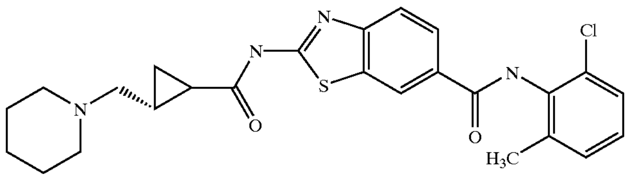 | trans-N-(2-Chloro-6-methylphenyl)-2-[[[2-(1-piperidinylmethyl)cyclopropyl]carbonyl]amino]-6-benzothiazolecarboxamide | 1.70 |
| 281 | 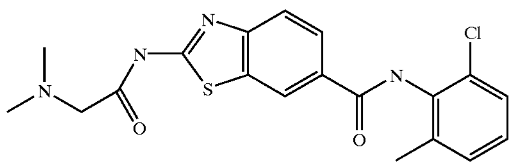 | N-(2-Chloro-6-methylphenyl)-2-[[[(dimethylamino)acetyl]amino]-6-benzothiazolecarboxamide | 1.49 |
| 282 | 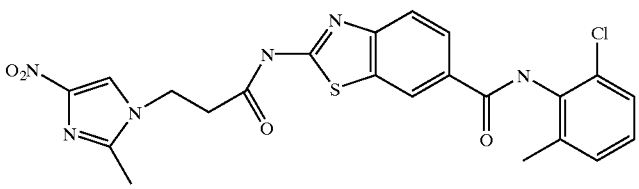 | N-(2-Chloro-6-methylphenyl)-2-[[3-(2-methyl-4-nitro-1H-imidazol-1-yl)-1-oxopropyl]amino]-6-benzothiazolecarboxamide | 1.91 |
| 467 | 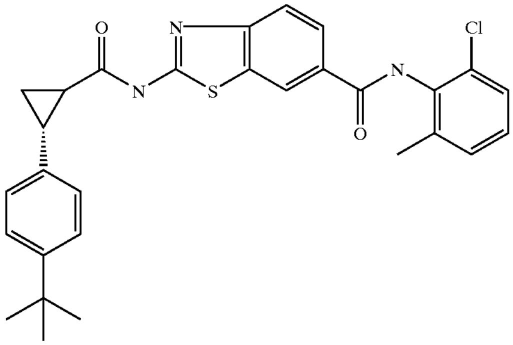 | trans-N-(2-Chloro-6-methylphenyl)-2-[[[2-[4-(1,1-dimethylethyl)phenyl]cyclopropyl]carbonyl]amino]-6-benzothiazolecarboxamide | 4.87 |
| 468 | 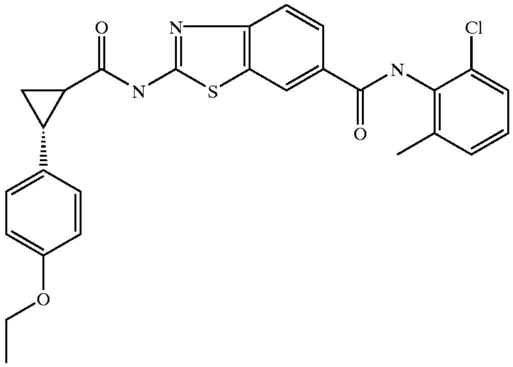 | trans-N-(2-Chloro-6-methylphenyl)-2-[[[2-(4-ethoxyphenyl)cyclopropyl]carbonyl]amino]-6-benzothiazolecarboxamide | 4.51 |

-continued

| EX. NO. | Compound Structure | Compound Name | HPLC Ret Time (min) |
|---|---|---|---|
| 469 | 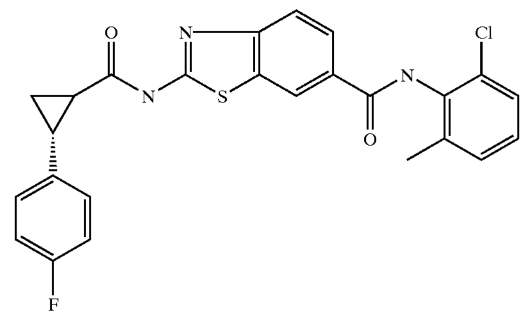 | trans-N-(2-Chloro-6-methylphenyl)-2-[[[2-(4-fluorophenyl)cyclopropyl]carbonyl]amino]-6-benzothiazolecarboxamide | 4.39 |
| 470 | 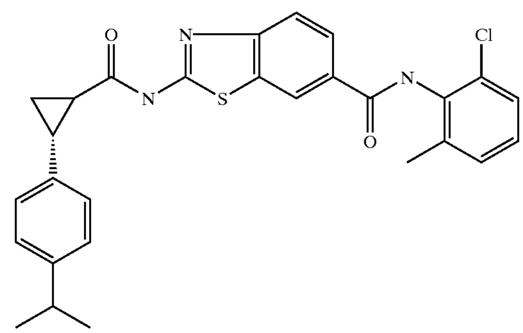 | trans-N-(2-Chloro-6-methylphenyl)-2-[[[2-[4-(1-methylethyl)phenyl]cyclopropyl]carbonyl]amino]-6-benzothiazolecarboxamide | 4.77 |
| 471 | 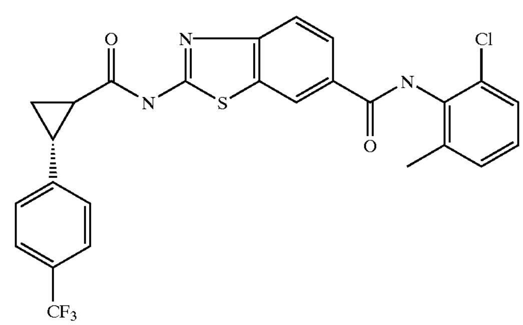 | trans-N-2-Chloro-6-methylphenyl)-2-[[[2-[4-(trifluoromethyl)phenyl]cyclopropyl]carbonyl]amino]-6-benzothiazolecarboxamide | 4.57 |
| 472 | 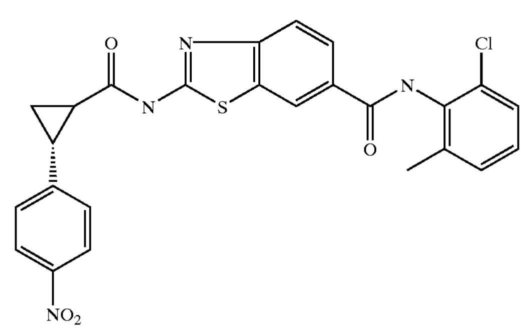 | trans-N-(2-Chloro-6-methylphenyl)-2-[[[2-(2-nitrophenyl)cyclopropyl]carbonyl]amino]-6-benzothiazolecarboxamide | 4.36 |

| EX. NO. | Compound Name | HPLC Ret Time (min) |
|---|---|---|
| 473 | trans-N-(2-Chloro-6-methylphenyl)-2-[[[2-(4-cyanophenyl)cyclopropyl]carbonyl]amino]-6-benzothiazolecarboxamide | 4.20 |
| 474 | trans-2-[[[(2-[1,1'-Biphenyl]-4-ylcyclopropyl)carbonyl]amino]-N-(2-chloro-6-methylphenyl)-6-benzothiazolecarboxamide | 4.80 |
| 475 | trans-2-[[[2-(1,3-Benzodioxol-4-yl)cyclopropyl]carbonyl]amino]-N-(2-chloro-6-methylphenyl)-6-benzothiazolecarboxamide | 4.37 |
| 476 | trans-N-(2-Chloro-6-methylphenyl)-2-[[[2-(3-chlorophenyl)cyclopropyl]carbonyl]amino]-6-benzothiazolecarboxamide | 4.59 |
| 477 | trans-N-(2-Chloro-6-methylphenyl)-2-[[[2-(3-cyanophenyl)cyclopropyl]carbonyl]amino]-6-benzothiazolecarboxamide | 4.21 |

| EX. NO. | Compound Structure | Compound Name | HPLC Ret Time (min) |
|---|---|---|---|
| 478 | 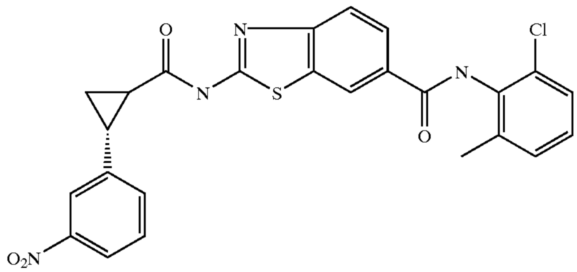 | trans-N-(2-Chloro-6-methylphenyl)-2-[[[2-(3-nitrophenyl)cyclopropyl]carbonyl]amino]-6-benzothiazolecarboxamide | 4.37 |

EXAMPLES 283 TO 322

General Procedure

Compounds 283 to 322 were prepared following the procedure described below. Diisopropylethyl amine (50 μL, 0.288 mmol) was added to a mixture of compound 183B (Alt) (30 mg, 0.096 mmol), carboxylic acid (0.115 mmol), 1-hydroxy-7-azabenzotriazole (17 mg, 0.125 mmol), and ethyl-3-(3-dimethylamino)-propyl carbodiimide hydrochloride (24 mg, 0.125 mmol) in TBF (1 mL). The mixture was heated at 45° C. for 18–72 h. The reaction mixture was diluted with dichloromethane (5 mL) and washed with 1 N aq. HCl solution (2×), 1 N aq. NaOH solution (2×). The organic extract was dried (MgSO4), filtered and concentrated in speedvac. The crude products were purified either by trituration with dichloromethane-ether or by automated preparative HPLC under the following conditions: YMC ODS 20×100 mm Column, 10 min gradient starting from 70% solvent A (10% MeOH, 90% H2O, 0.2% H3PO4) and 30% solvent B to 100% solvent B (90% MeOH, 10% H2O, 0.2% H3PO4), flow rate 20 mL/min, λ=220 nM.

"HPLC Ret Time" is the HPLC retention time under the following conditions: YMC S5 ODS 4.6×50 mm Ballastic Column, 4 min gradient starting from 100% solvent A (10% MeOH, 90% H2O, 0.2% H3PO4) to 100% solvent B (90% MeOH, 10% H2O, 0.2% H3PO4) with 2 min hold, flow rate 4 mL/min, λ=220 nM.

| EX. NO. | Compound Structure | Compound Name | HPLC Ret Time (min) |
|---|---|---|---|
| 283 | 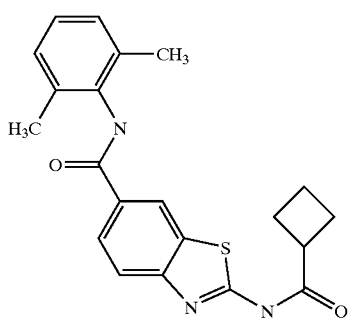 | 2-[(Cyclobutylcarbonyl)amino]-N-(2,6-dimethylphenyl)-6-benzothiazolecarboxamide | 3.86 |
| 284 | 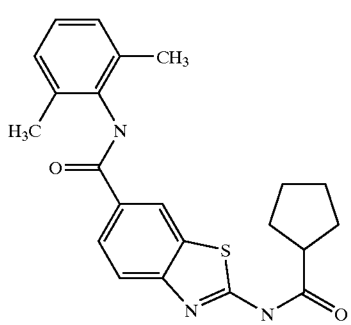 | 2-[(Cyclopentylcarbonyl)amino]-N-(2,6-dimethylphenyl)-6-benzothiazolecarboxamide | 4.01 |

-continued

| EX. NO. | Compound Structure | Compound Name | HPLC Ret Time (min) |
|---|---|---|---|
| 285 | 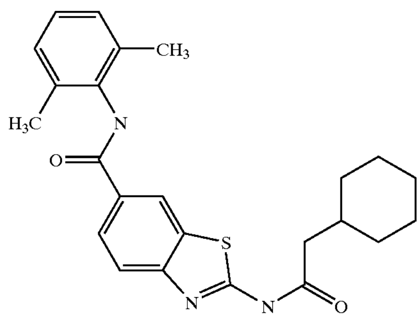 | 2-[(Cyclohexylacetyl)amino]-N-(2,6-dimethylphenyl)-6-benzothiazolecarboxamide | 4.45 |
| 286 | 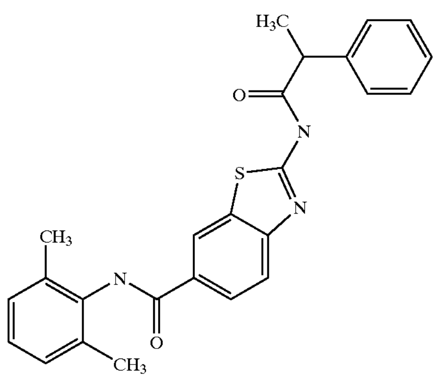 | N-(2,6-Dimethylphenyl)-2-[(1-oxo-2-phenylpropyl)amino]-6-benzothiazolecarboxamide | 4.1 |
| 287 | 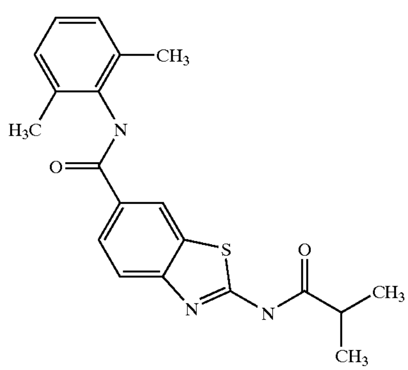 | N-(2,6-Dimethylphenyl)-2-[(2-methyl-1-oxopropyl)amino]-6-benzothiazolecarboxamide | 3.73 |
| 288 | 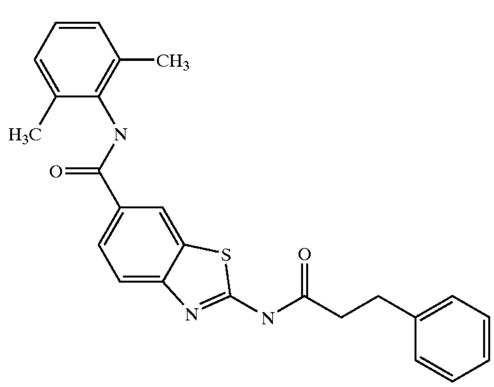 | N-(2,6-Dimethylphenyl)-2-[(1-oxo-3-phenylpropyl)amino]-6-benzothiazolecarboxamide | 4.11 |

-continued

| EX. NO. | Compound Structure | Compound Name | HPLC Ret Time (min) |
|---|---|---|---|
| 289 | 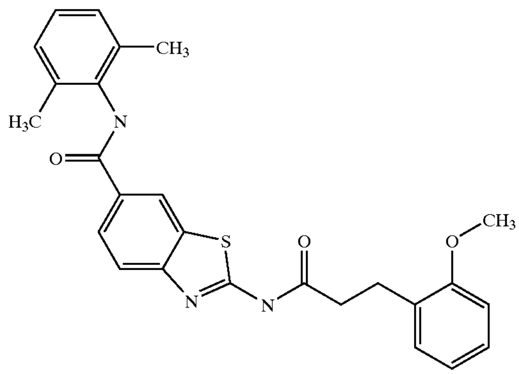 | N-(2,6-Dimethylphenyl)-2-[[3-(2-methoxyphenyl)-1-oxopropyl]amino]-6-benzothiazolecarboxamide | 4.15 |
| 290 | 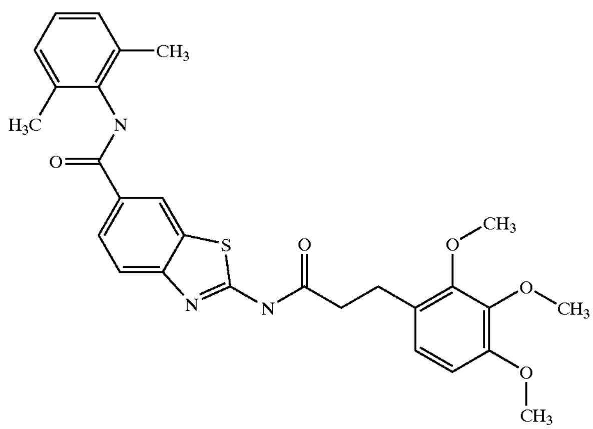 | N-(2,6-Dimethylphenyl)-2-[[3-(2,3,4-trimethoxyphenyl)-1-oxopropyl]amino]-6-benzothiazolecarboxamide | 4.00 |
| 291 | 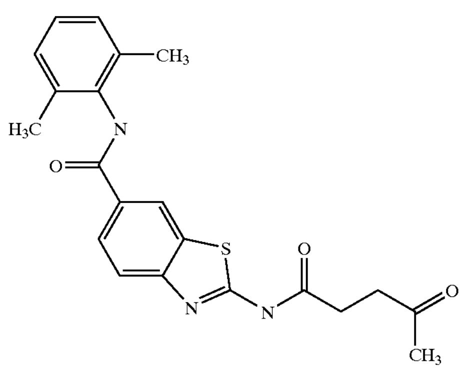 | N-(2,6-Dimethylphenyl)-2-[(1,4-dioxopentyl)amino]-6-benzothiazolecarboxamide | 3.37 |
| 292 | 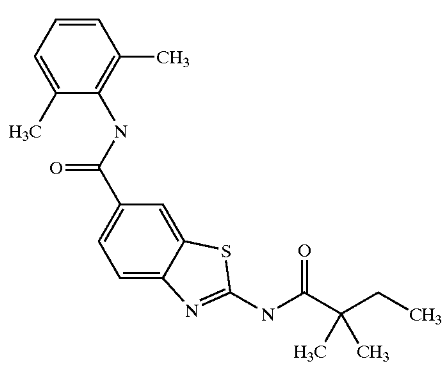 | 2-[(2,2-Dimethyl-1-oxobutyl)amino]-N-(2,6-dimethylphenyl)-6-benzothiazolecarboxamide | 4.05 |

-continued

| EX. NO. | Compound Structure | Compound Name | HPLC Ret Time (min) |
|---|---|---|---|
| 293 | 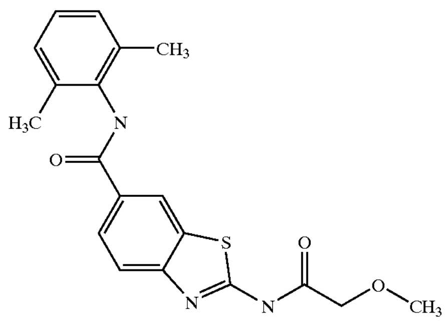 | N-(2,6-Dimethylphenyl)-2-[(methoxyacetyl)-amino]-6-benzothiazolecarboxamide | 3.39 |
| 294 | 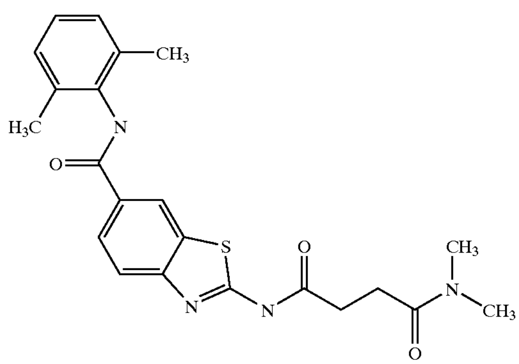 | N,N-Dimethyl-N'-[6-[[(2,6-dimethylphenyl)-amino]carbonyl]-2-benzothiazolyl]butanediamide | 3.34 |
| 295 | 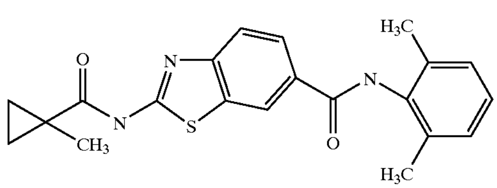 | N-(2,6-Dimethylphenyl)-2-[[(1-methylcyclopropyl)carbonyl]amino]-6-benzothiazole-carboxamide | 3.83 |
| 296 | 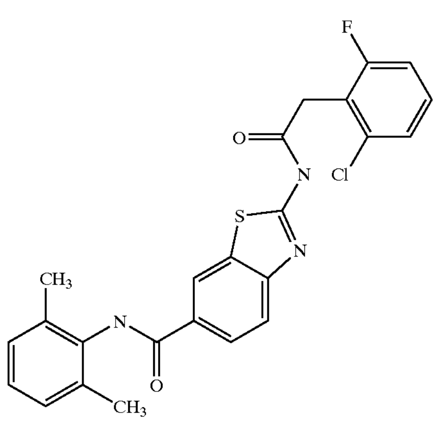 | 2-[[(2-Chloro-6-fluorophenyl)acetyl]amino]-N-(2,6-dimethylphenyl)-6-benzothiazole-carboxamide | 4.03 |

-continued

| EX. NO. | Compound Structure | Compound Name | HPLC Ret Time (min) |
|---|---|---|---|
| 297 | 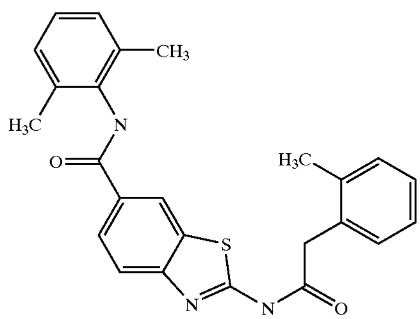 | N-(2,6-Dimethylphenyl)-2-[[(2-methylphenyl)-acetyl]amino]-6-benzothiazolecarboxamide | 4.07 |
| 298 | 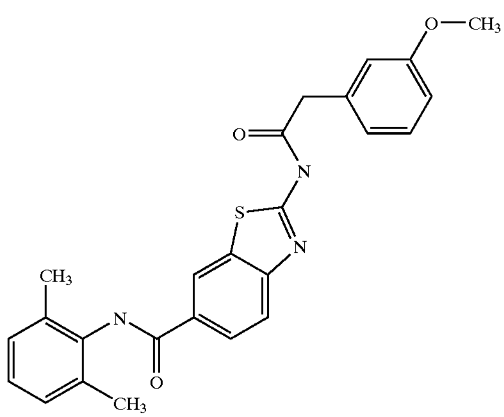 | N-(2,6-Dimethylphenyl)-2-[[(3-methoxyphenyl)-acetyl]amino]-6-benzothiazolecarboxamide | 3.94 |
| 299 | 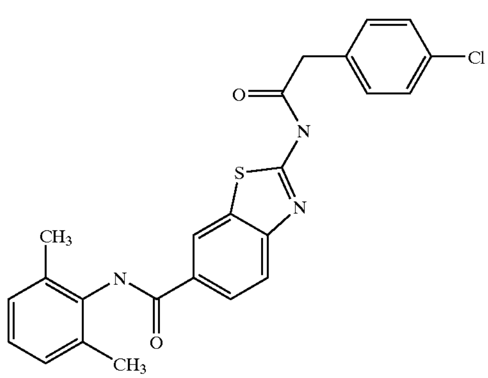 | 2-[[(4-Chlorophenyl)acetyl]amino]-N-(2,6-dimethylphenyl)-6-benzothiazolecarboxamide | 4.19 |
| 300 | 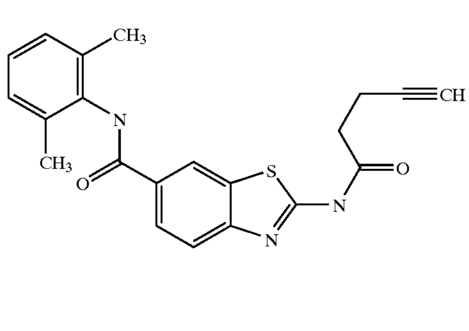 | N-(2,6-Dimethylphenyl)-2-[(1-oxo-4-pentynyl)-amino]-6-benzothiazolecarboxamide | 3.58 |

-continued

| EX. NO. | Compound Structure | Compound Name | HPLC Ret Time (min) |
|---|---|---|---|
| 301 | 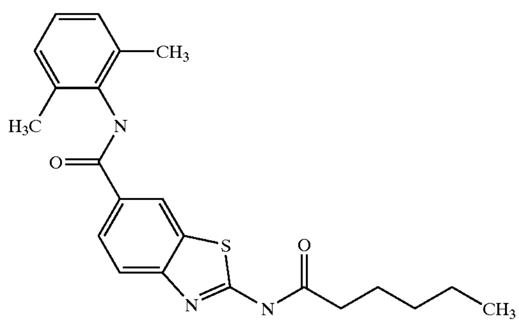 | N-(2,6-Dimethylphenyl)-2-[[(1-oxohexyl)amino]-6-benzothiazolecarboxamide | 4.18 |
| 302 | 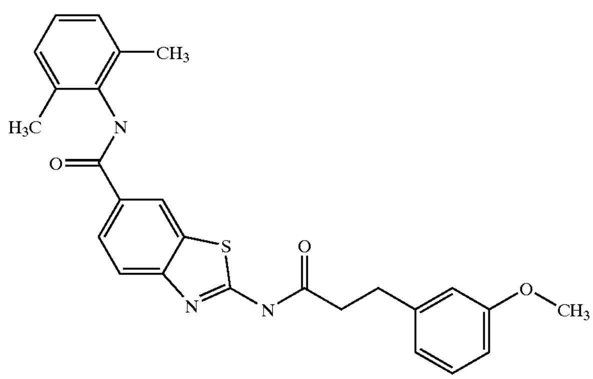 | N-(2,6-Dimethylphenyl)-2-[[3-(3-methoxy-phenyl)-1-oxopropyl]amino]-6-benzothiazole-carboxamide | 4.11 |
| 303 | 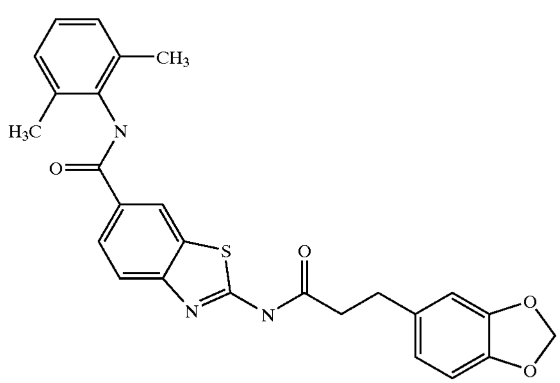 | 2-[[3-(1,3-Benzodioxol-5-yl)-1-oxopropyl]-amino]-N-(2,6-dimethylphenyl)-6-benzothiazole-carboxamide | 4.09 |
| 304 | 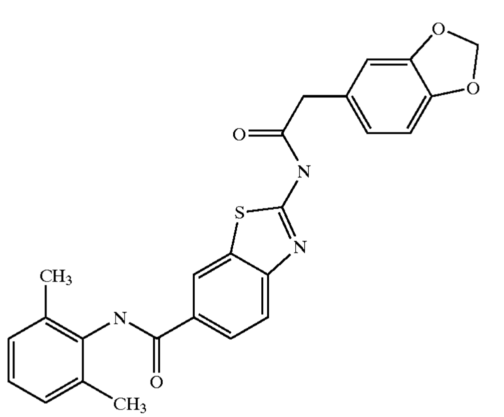 | 2-[[(1,3-Benzodioxol-5-yl)acetyl]amino]-N-(2,6-dimethylphenyl)-6-benzothiazolecarboxamide | 3.91 |

-continued

| EX. NO. | Compound Structure | Compound Name | HPLC Ret Time (min) |
|---|---|---|---|
| 305 | 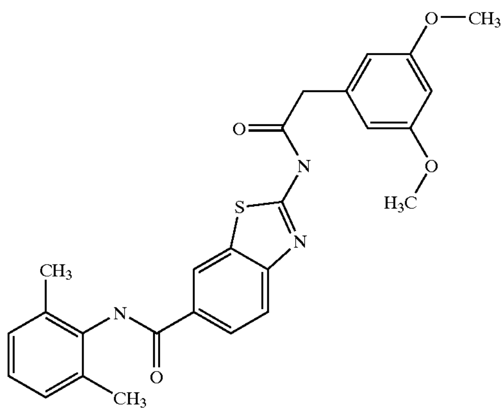 | 2-[[(3,5-Dimethoxyphenyl)acetyl]amino]-N-(2,6-dimethylphenyl)-6-benzothiazolecarboxamide | 3.97 |
| 306 | 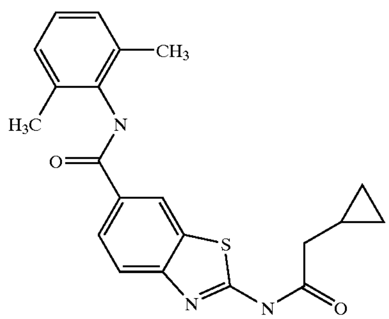 | 2-[(Cyclopropylacetyl)amino]-N-(2,6-dimethylphenyl)-6-benzothiazolecarboxamide | 3.79 |
| 307 | 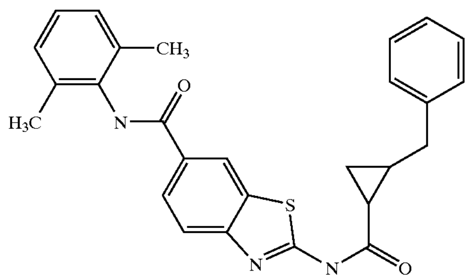 | N-(2,6-Dimethylphenyl)-2-[[[2-(phenylmethyl)-cyclopropyl]carbonyl]amino]-6-benzothiazole-carboxamide | 4.48 |
| 308 | 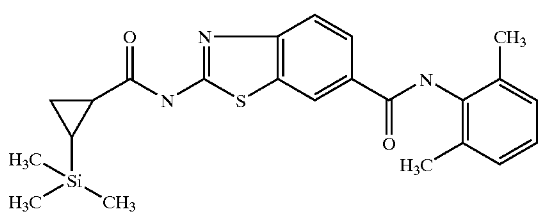 | N-(2,6-Dimethylphenyl)-2-[[[2-(trimethylsilyl)-cyclopropyl]carbonyl]amino]-6-benzothiazole-carboxamide | 4.58 |
| 309 | 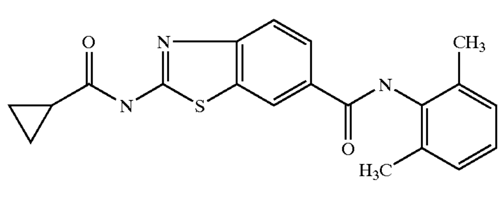 | 2-[(Cyclopropylcarbonyl)amino]-N-(2,6-dimethylphenyl)-6-benzothiazolecarboxamide | 3.82 |

-continued

| EX. NO. | Compound Structure | Compound Name | HPLC Ret Time (min) |
|---|---|---|---|
| 310 | 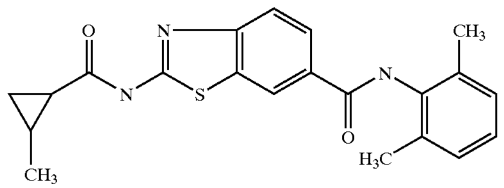 | N-(2,6)-Dimethylphenyl)-2-[[(2-methylcyclo-propyl)carbonyl]amino]-6-benzothiazole-carboxamide | 4.02 |
| 311 | 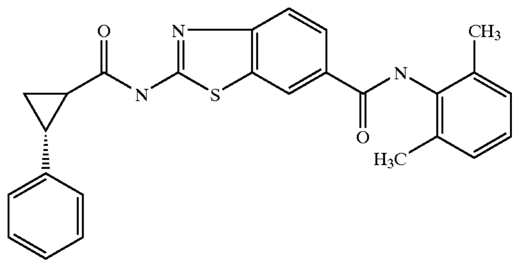 | trans-N-(2,6-Dimethylphenyl)-2-[[(2-phenyl-cyclopropyl)caronyl]amino]-6-benzothiazole-carboxamide | 4.38 |
| 312 | 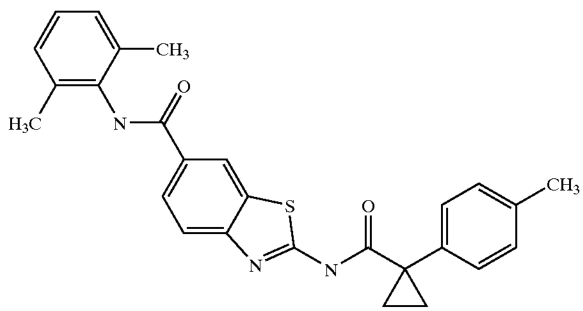 | N-(2,6-Dimethylphenyl)-2-[[[1-(4-methylphenyl)-cyclopropyl]carbonyl]amino]-6-benzothiazole-carboxamide | 4.50 |
| 313 | 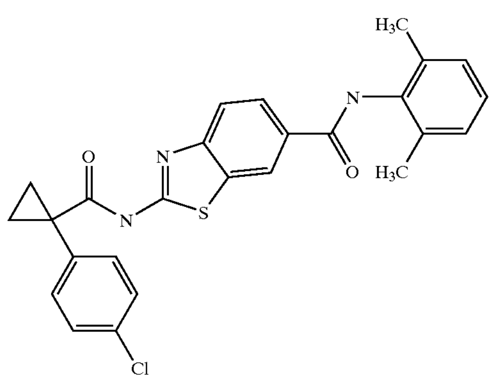 | 2-[[[1-(4-Chlorophenyl)cyclopropyl]carbonyl]-amino]-N-(2,6-dimethylphenyl)-6-benzothiazole-carboxamide | 4.47 |
| 314 | 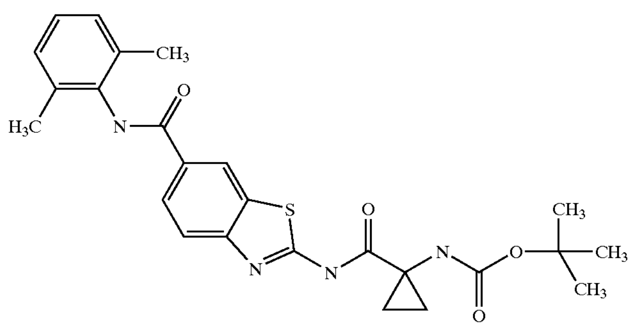 | [1-[[[6-[[(2,6-Dimethylphenyl)amino]carbonyl]-2-benzothiazolyl]amino]carbonyl]cyclopropyl]-carbamic acid 1,1-dimethylethyl ester | 3.97 |

-continued

| EX. NO. | Compound Structure | Compound Name | HPLC Ret Time (min) |
|---|---|---|---|
| 315 | Chiral | (1S-cis)-2-[[[2,2-Dimethyl-3-(2-methyl-1-propenyl)cyclopropyl]carbonyl]amino]-N-(2,6-dimethylphenyl)-6-benzothiazolecarboxamide | 4.50 |
| 316 | 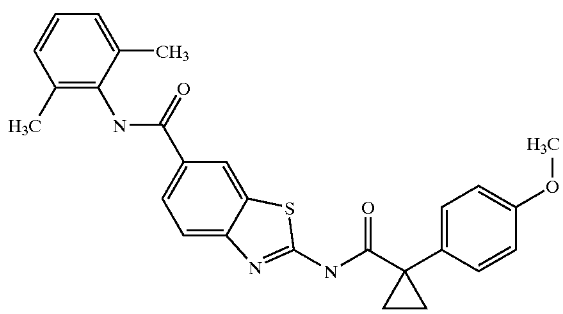 | N-(2,6-Dimethylphenyl)-2-[[[1-(4-methoxyphenyl)cyclopropyl]carbonyl]amino]-6-benzothiazolecarboxamide | 4.36 |
| 317 | 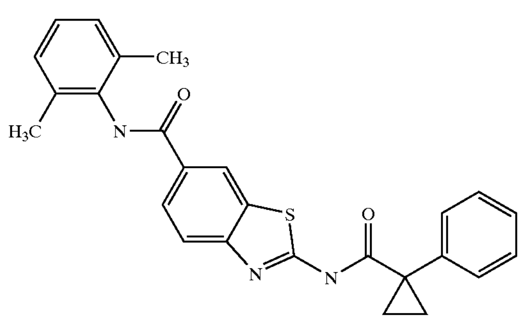 | N-(2,6-Dimethylphenyl)-2-[[(1-phenylcyclopropyl)carbonyl]amino]-6-benzothiazole-carboxamide | 4.32 |
| 318 | 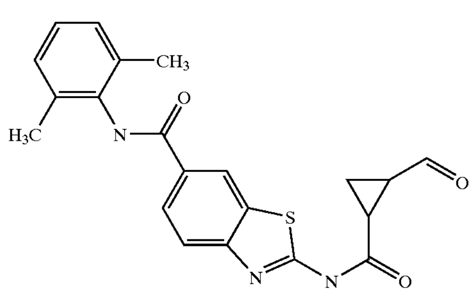 | N-(2,6-Dimethylphenyl)-2-[[(2-formylcyclopropyl)carbonyl]amino]-6-benzothiazole-carboxamide | 4.29 |

-continued

| EX. NO. | Compound Structure | Compound Name | HPLC Ret Time (min) |
|---|---|---|---|
| 319 | 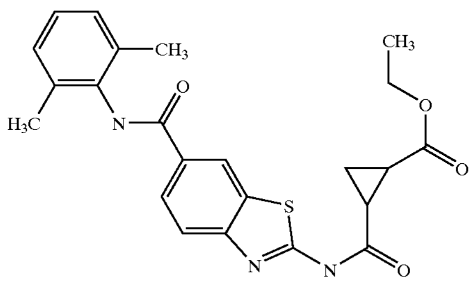 | 2-[[[6-[[(2,6-Dimethylphenyl)amino]carbonyl]-2-benzothiazolyl]amino]carbonyl]cyclopropane-carboxylic acid ethyl ester | 4.03 |
| 320 | 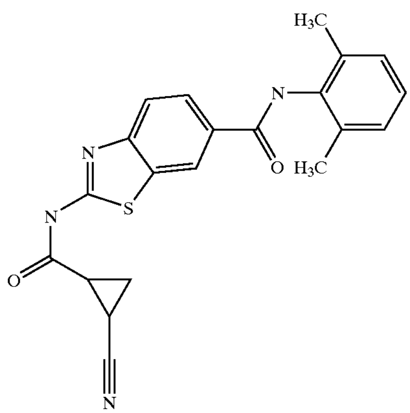 | 2-[[(2-Cyanocyclopropyl)carbonyl]amino]-N-(2,6-dimethylphenyl)-6-benzothiazole-carboxamide | 2.5 |
| 321 | 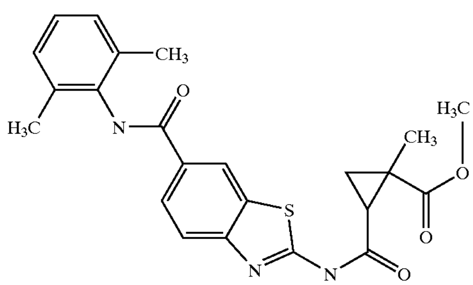 | 2-[[[6-[[(2,6-Dimethylphenyl)amino]carbonyl]-2-benzothiazolyl]amino]carbonyl]-1-methylcyclo-propanecarboxylic acid methyl ester | 3.97  4.00 |
| 322 | Chiral | (1S-trans)-2-[[[2,2-Dimethyl-3-(2-methyl-1-propenyl)cyclopropyl]carbonyl]amino]-N-(2,6-dimethylphenyl)-6-benzothiazolecarboxamide | 4.53 |

EXAMPLE 323 TO 337

General Procedure

Compounds 323 to 337 were prepared following the procedure described below. Diisopropylethyl amine (50 μL, 0.288 mmol) was added to a mixture of the free base of compound 2 (30 mg, 0.096 mmol), carboxylic acid (0.115 mmol), 1-hydroxy-7-azabenzotriazole (17 mg, 0.125 mmol), and ethyl-3-(3-dimethylamino)-propyl carbodiimide hydrochloride (24 mg, 0.125 mmol) in THF (1 mL). The mixture was heated at 45° C. for 18–72 h. The reaction mixture was diluted with dichloromethane (5 mL) and washed with 1 N aq. HCl solution (2×), 1 N aq. NaOH solution (2×). The organic extract was dried (MgSO₄), filtered and concentrated in speedvac. The crude products were purified either by trituration with dichloromethane-ether or by automated preparative HPLC under the following conditions: YMC ODS 20×100 mm Column, 10 min gradient starting from 70% solvent A (10% MeOH, 90% H2O, 0.2% H3PO4) and 30% solvent B to 100% solvent B (90% MeOH, 10% H2O, 0.2% H3PO4), flow rate 20 mL/min, λ=220 nM.

"HPLC Ret Time" is the HPLC retention time under the following conditions: For compounds 327–334 the conditions are YMC S5 ODS 4.6×50 mm Ballastic Column, 4 min gradient starting from 100% solvent A (10% MeOH, 90% H2O, 0.2% H3PO4) to 100% solvent B (90% MeOH, 10% H2O, 0.2% H3PO4) with 2 min hold, flow rate 4 mL/min, λ=220 nM; for compounds 323–326 and 335–337 the conditions are YMC S5 ODS 4.6×50 mm Ballastic Column, 4 min gradient starting from 100% solvent A (10% MeOH, 90% H2O, 0.1% TFA) to 100% solvent B (90% MeOH, 10% H2O, 0.1% H3PO4) with 2 min hold, flow rate 4 mL/min, λ=220 nM.

| EX. NO. | Compound Structure | Compound Name | HPLC Ret Time (min) |
|---|---|---|---|
| 323 | 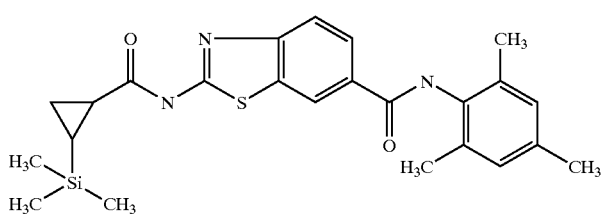 | N-(2,4,6-Trimethylphenyl)-2-[[[2-(trimethyl-silyl)cyclopropyl]carbonyl]amino]-6-benzo-thiazolecarboxamide | 4.70 |
| 324 | 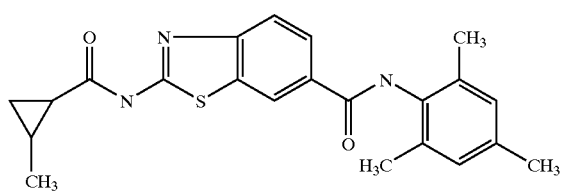 | 2-[[(2-Methylcyclopropyl)carbonyl]amino]-N-(2,4,6-trimethylphenyl)-6-benzothiazole-carboxamide | 4.18 |
| 325 | 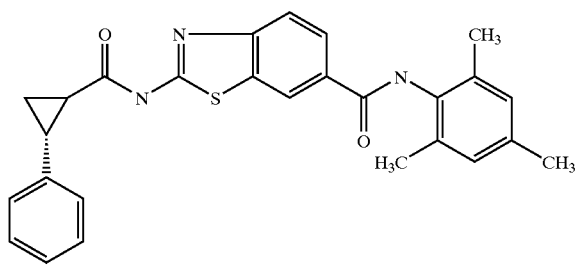 | trans-2-[[(2-Phenylcyclopropyl)carbonyl]amino]-N-(2,4,6-trimethylphenyl)-6-benzothiazole-carboxamide | 4.54 |
| 326 | 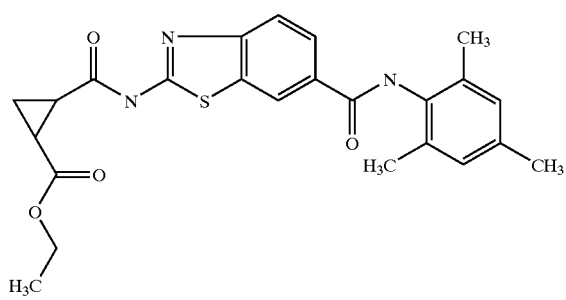 | 2-[[[6-[[(2,4,6-Trimethylphenyl)amino]carbonyl-2-benzothiazolyl]amino]carbonyl]cyclopropane-carboxylic acid ethyl ester | 4.32 |

-continued

| EX. NO. | Compound Structure | Compound Name | HPLC Ret Time (min) |
|---|---|---|---|
| 327 | 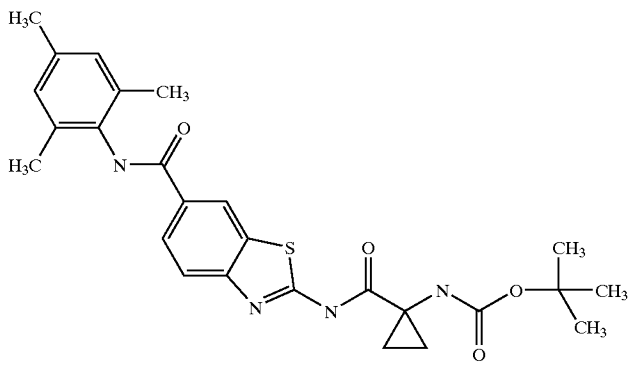 | [1-[[[6-[[(2,4,6-Trimethylphenyl)amino]-carbonyl]-2-benzothiazolyl]amino]carbonyl]-cyclopropyl]carbamic acid 1,1-dimethylethyl ester | 4.15 |
| 328 | Chiral | (1S-trans)-2-[[[2,2-Dimethyl-3-(2-methyl-1-propenyl)cyclopropyl]carbonyl]amino]-N-(2,4,6-trimethylphenyl)-6-benzothiazolecarboxamide | 4.65 |
| 329 | Chiral | (1S-cis)-2-[[[2,2-Dimethyl-3-(2-methyl-1-propenyl)cyclopropyl]carbonyl]amino]-N-(2,4,6-trimethylphenyl)-6-benzothiazolecarboxamide | 4.63 |

-continued

| EX. NO. | Compound Structure | Compound Name | HPLC Ret Time (min) |
|---|---|---|---|
| 330 | 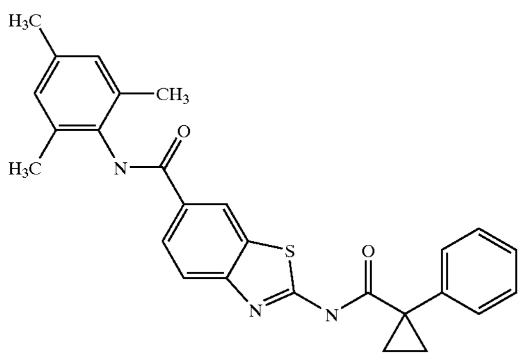 | 2-[[(1-Phenylcyclopropyl)carbonyl]amino]-N-(2,4,6-trimethylphenyl)-6-benzothiazole-carboxamide | 4.45 |
| 331 | 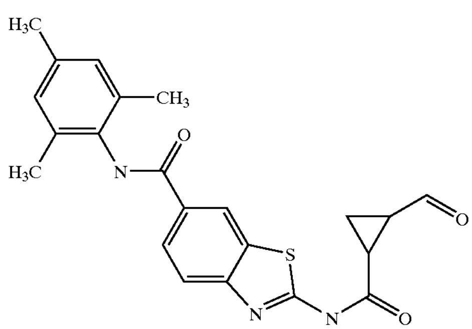 | 2-[[(2-Formylcyclopropyl)carbonyl]amino]-N-(2,4,6-trimethylphenyl)-6-benzothiazole-carboxamide | 4.43 |
| 332 | 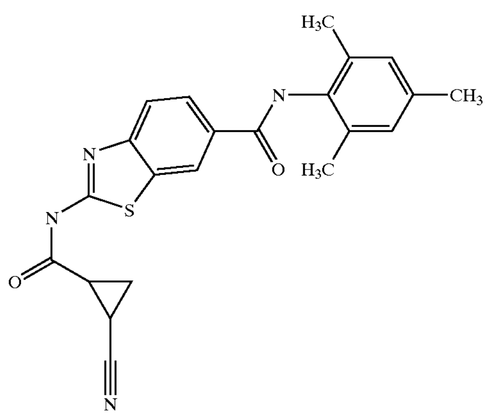 | 2-[[(2-Cyanocyclopropyl)carbonyl]amino]-N-(2,4,6-triethylphenyl)-6-benzothiazole-carboxamide | 4.42 |
| 333 | 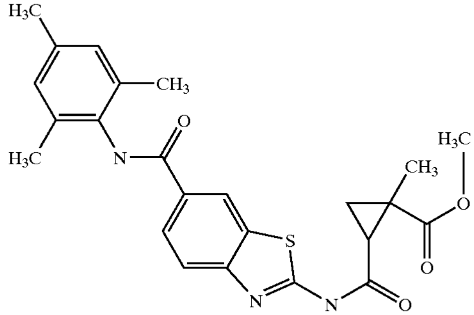 | 2-[[[6-[[(2,4,6-Trimethylphenyl)amino]carbonyl]-2-benzothiazolyl]amino]carbonyl]-1-methylcyclopropanecarboxylic acid methyl ester | 4.14 |

-continued

| EX. NO. | Compound Structure | Compound Name | HPLC Ret Time (min) |
|---|---|---|---|
| 334 | 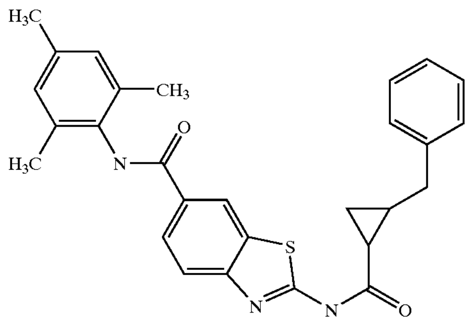 | 2-[[[2-(Phenylmethyl)cyclopropyl]carbonyl]-amino]-N-(2,4,6-trimethylphenyl)-6-benzothiazole-carboxamide | 4.48 |
| 335 | 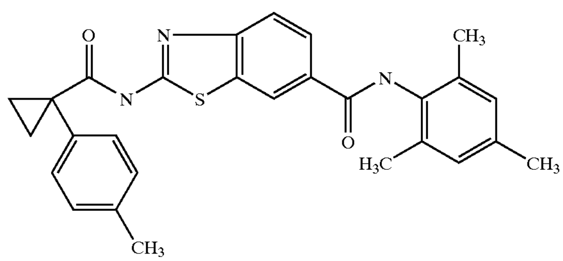 | 2-[[[1-(4-Methylphenyl)cyclopropyl]carbonyl]-amino]-N-(2,4,6-triethylphenyl)-6-benzothiazole-carboxamide | 4.73 |
| 336 | 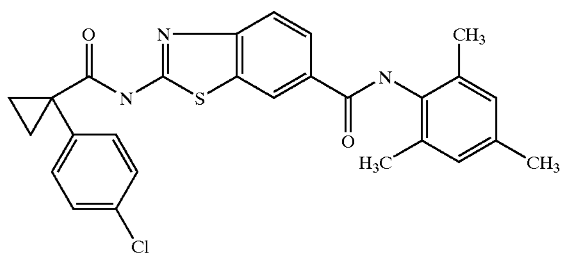 | 2-[[[1-(4-Chlorophenyl)cyclopropyl]carbonyl]-amino]-N-(2,4,6-trimethylphenyl)-6-benzothiazole-carboxamide | 4.68 |
| 337 | 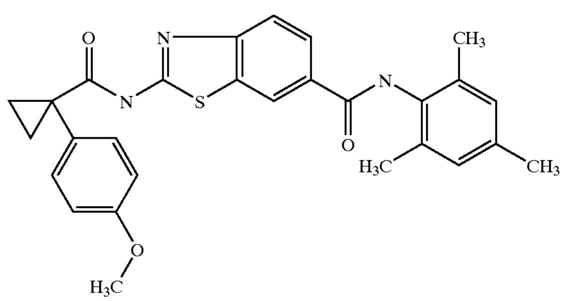 | 2-[[[1-(4-Methoxyphenyl)cyclopropyl]carbonyl]-amino]-N-(2,4,6-trimethylphenyl)-6-benzothiazole-carboxamide | 4.59 |

EXAMPLE 338 TO 466

General Procedure

Compounds 338 to 466 were prepared following the procedure described below. Appropriate amine (0.086 mmol) was added to a solution of 166A (30 mg, 0.072 mmol) in THF (3 mL). The solution was stirred at 57° C. for 48–72 h. The reaction mixture was diluted with dichloromethane (5 mL) and washed with 1 N aq. HCl solution (2×), 1 N aq. NaOH solution (2×). The organic extract was dried (Na$_2$SO$_4$), filtered and concentrated in vacuo to obtain the titled compounds. Some of the analogs required purification by automated preparative HPLC under the following conditions: YMC ODS 20×100 mm Column, 10 min gradient starting from 70% solvent A (10% MeOH, 90%o H2O, 0.2% H3PO4) and 30% solvent B to 100% solvent B (90% MeOH, 10% H2O, 0.2% H3PO4), flow rate 20 mL/min, λ=220 nM.

"HPLC Ret Time" is the HPLC retention time under the following conditions: Phenomenex-Prime S5 C18 4.6×30 mm, 2 min gradient starting from 100% solvent A (10% MeOH, 90% H2O, 0.2% H3PO4) to 100% solvent B (90% MeOH, 10% H2O, 0.2% H3PO4) with 1 min hold, flow rate 5 mL/min, λ=220 nM for compounds 387–388; 3905; 422; 426–428; 431–466; Phenomenex-LUNA S5 C18 4.6×30 mm, 2 min gradient starting from 100% solvent A (10% MeOH, 90% H2O, 0.1% TFA ) to 100% solvent B (90% MeOH, 10% H2O, 0.1% TFA) with 1 min hold, flow rate 5 mL/min, λ=220 nM for compounds 338–340; 344–345;

347–386; 389; 406–421; 423–425; 429–430; and YMC S5 ODS 4.6×50 mm Ballastic Column, 4 min gradient starting from 100% solvent A (10% MeOH, 90% H2O, 0.2% H3PO4) to 100% solvent B (90% MeOH, 10% H2O, 0.2% H3PO4) with 2 min hold, flow rate 4 mL/min, λ=220 nM for compounds 341–343; and 346.

| EX. NO. | Compound Structure | Compound Name | HPLC Ret Time (min) |
|---|---|---|---|
| 338 | 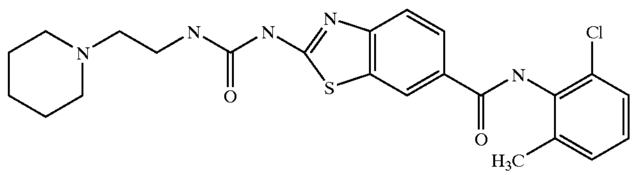 | N-(2-Chloro-6-methylphenyl-2-[[[[2-(1-piperidinyl)ethyl]amino]carbonyl]amino]-6-benzothiazole-carboxamide | 1.76 |
| 339 | 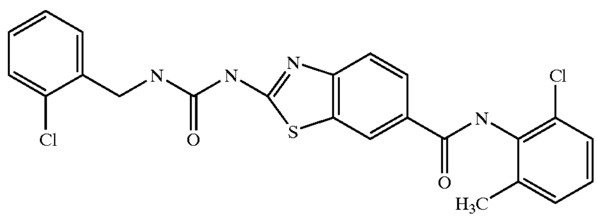 | N-(2-Chloro-6-methylphenyl)-2-[[[[(2-chlorophenyl)methyl]amino]carbonyl]amino]-6-benzothiazole-carboxamide | 2.55 |
| 340 | 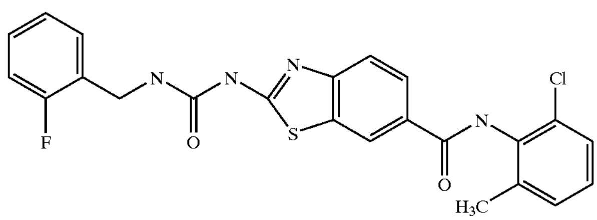 | N-(2-Chloro-6-methylphenyl)-2-[[[[(2-fluorophenyl)methyl]amino]carbonyl]amino]-6-benzothiazole-carboxamide | 2.23 |
| 341 | 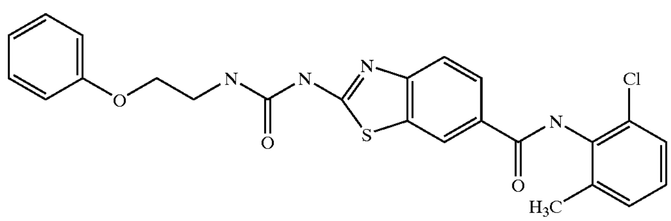 | N-(2-Chloro-6-methylphenyl)-2-[[[(2-phenoxyethyl)amino]carbonyl]amino]-6-benzothiazole-carboxamide | 4.16 |
| 342 | 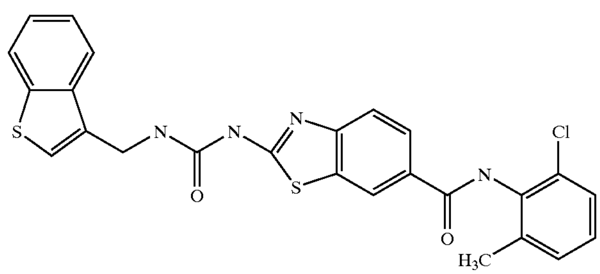 | 2-[[[(Benzo[b]thiophen-3-ylmethyl)amino]carbonyl]amino]-N-(2-chloro-6-methylphenyl)-6-benzothiazolecarboxamide | 4.31 |
| 343 | 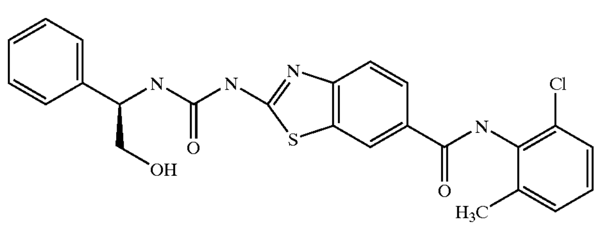 | (R)-N-(2-Chloro-6-methylphenyl)-2-[[[(2-hydroxy-1-phenylethyl)amino]carbonyl]amino]-6-benzothiazolecarboxamide | 3.82 |

Chiral

-continued

| EX. NO. | Compound Structure | Compound Name | HPLC Ret Time (min) |
|---|---|---|---|
| 344 | 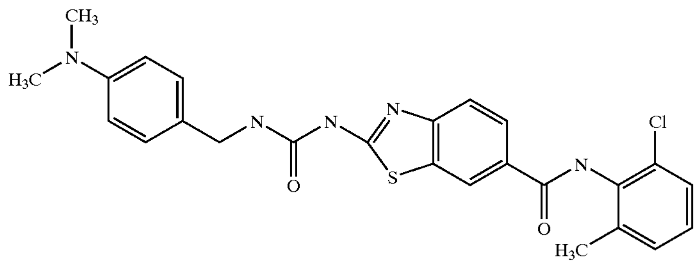 | N-(2-Chloro-6-methylphenyl)-2-[[[[4-(dimethylamino)phenyl]methyl]amino]carbonyl]amino]-6-benzothiazolecarboxamide | 1.81 |
| 345 | Chiral | (S)-N-(2-Chloro-6-methylphenyl)-2-[[[(2-hydroxy-1-phenylethyl)amino]carbonyl]amino]-6-benzothiazolecarboxamide | 2.13 |
| 346 | 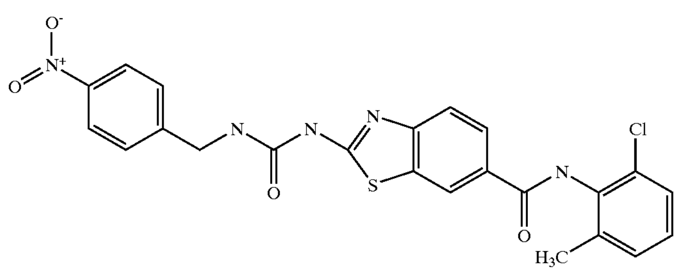 | N-(2-Chloro-6-methylphenyl)-2-[[[[(4-nitrophenyl)methyl]amino]carbonyl]amino]-6-benzothiazolecarboxamide | 3.96 |
| 347 | 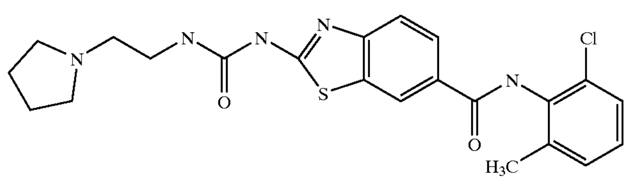 | N-(2-Chloro-6-methylphenyl)-2-[[[[2-(1-pyrrolidinyl)ethyl]amino]carbonyl]amino]-6-benzothiazolecarboxamide | 1.73 |
| 348 | 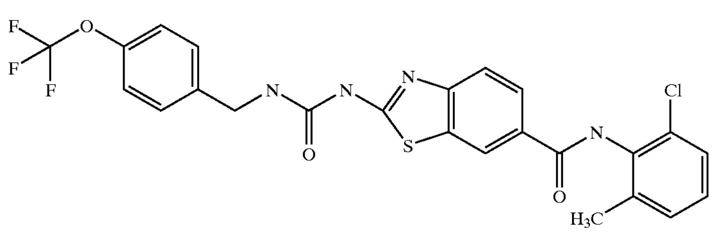 | N-(2-Chloro-6-methylphenyl)-2-[[[[[4-(trifluoromethoxy)phenyl]methyl]amino]carbonyl]amino]-6-benzothiazolecarboxamide | 2.38 |
| 349 | 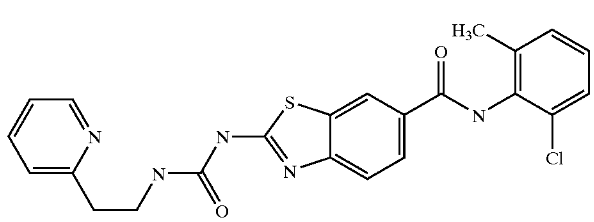 | N-(2-Chloro-6-methylphenyl)-2-[[[[2-(2-pyridinyl)ethyl]amino]carbonyl]amino]-6-benzothiazolecarboxamide | 1.61 |

-continued

| EX. NO. | Compound Structure | Compound Name | HPLC Ret Time (min) |
|---|---|---|---|
| 350 | 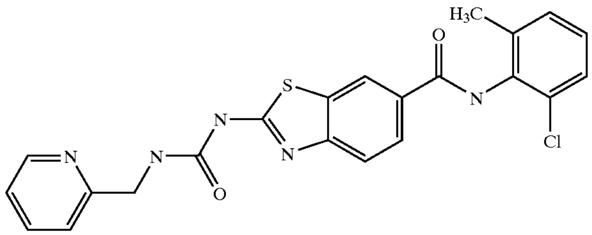 | N-(2-Chloro-6-methylphenyl)-2-[[[(2-pyridinylmethyl)amino]carbonyl]amino]-6-benzothiazolecarboxamide | 1.62 |
| 351 | 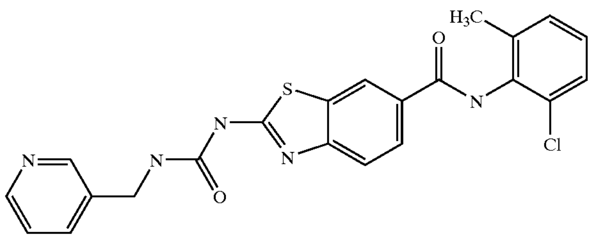 | N-(2-Chloro-6-methylphenyl)-2-[[[(3-pyridinylmethyl)amino]carbonyl]amino]-6-benzothiazolecarboxamide | 1.59 |
| 352 | 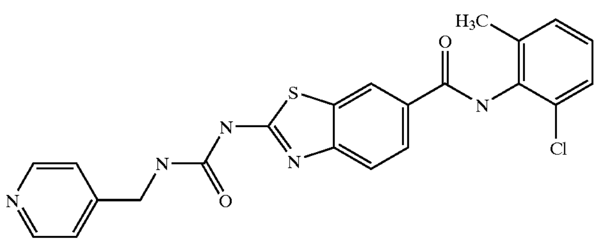 | N-(2-Chloro-6-methylphenyl)-2-[[[(4-pyridinylmethyl)amino]carbonyl]amino]-6-benzothiazolecarboxamide | 1.58 |
| 353 | 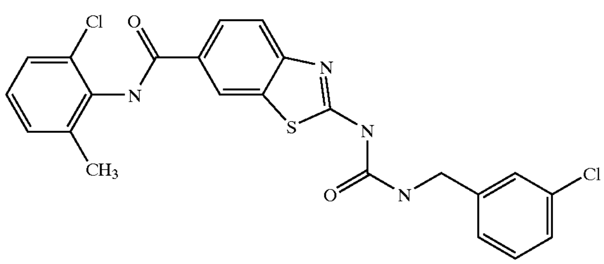 | N-(2-Chloro-6-methylphenyl)-2-[[[[(3-chlorophenyl)methyl]amino]carbonyl]amino]-6-benzothiazolecarboxamide | 2.27 |
| 354 | 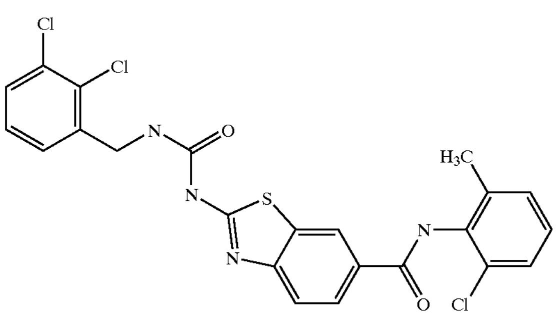 | N-(2-Chloro-6-methylphenyl)-2-[[[[(2,3-dichlorophenyl)methyl]amino]carbonyl]amino]-6-benzothiazolecarboxamide | 2.35 |
| 355 | 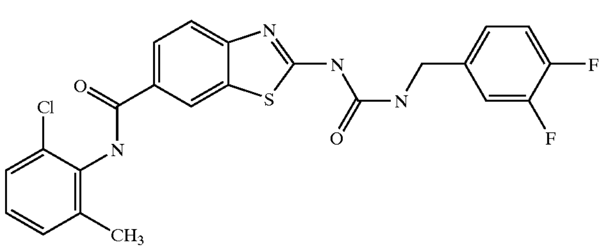 | N-(2-Chloro-6-methylphenyl)-2-[[[[(3,4-difluorophenyl)methyl]amino]carbonyl]amino]-6-benzothiazolecarboxamide | 2.22 |

-continued

| EX. NO. | Compound Structure | Compound Name | HPLC Ret Time (min) |
|---|---|---|---|
| 356 | 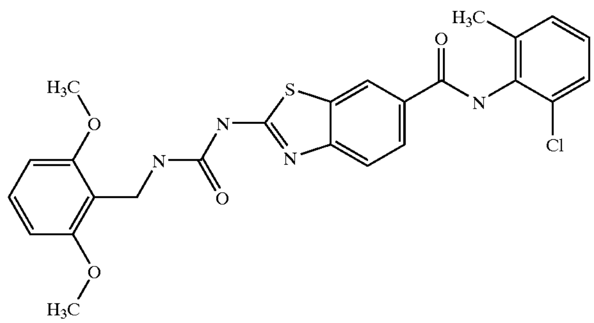 | N-(2-Chloro-6-methylphenyl)-2-[[[[(2,6-dimethoxyphenyl)methyl]amino]carbonyl]amino]-6-benzothiazolecarboxamide | 2.24 |
| 357 | 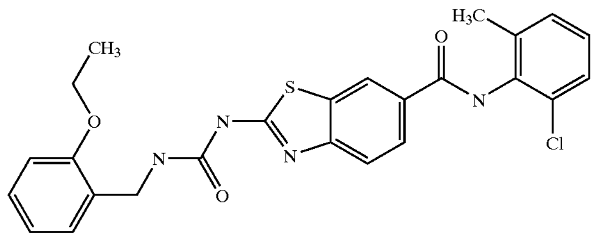 | N-(2-Chloro-6-methylphenyl)-2-[[[[(2-ethoxyphenyl)methyl]amino]carbonyl]amino]-6-benzothiazolecarboxamide | 2.29 |
| 358 | 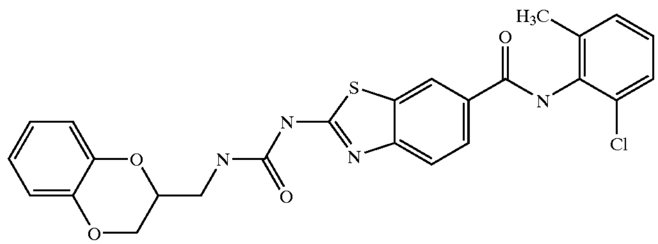 | N-(2-Chloro-6-methylphenyl)-2-[[[[(2,3-dihydro-1,4-benzodioxin-2-yl)methyl]amino]carbonyl]amino]-6-benzothiazole-carboxamide | 2.25 |
| 359 | 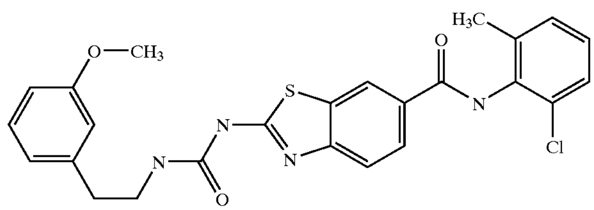 | N-(2-Chloro-6-methylphenyl)-2-[[[[2-(3-methoxyphenyl)ethyl]amino]carbonyl]amino]-6-benzothiazolecarboxamide | 2.23 |
| 360 | 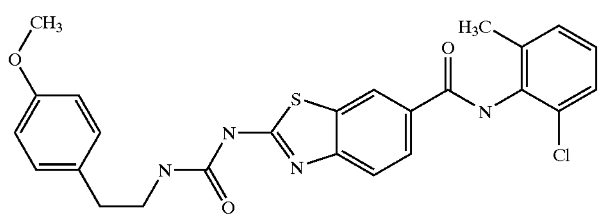 | N-(2-Chloro-6-methylphenyl)-2-[[[[2-(4-methoxyphenyl)ethyl]amino]carbonyl]amino]-6-benzothiazolecarboxamide | 2.22 |
| 361 | 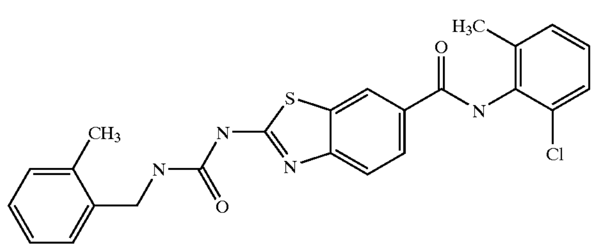 | N-(2-Chloro-6-methylphenyl)-2-[[[[(2-methylphenyl)methyl]amino]carbonyl]amino]-6-benzothiazolecarboxamide | 2.24 |

| EX. NO. | Compound Structure | Compound Name | HPLC Ret Time (min) |
|---|---|---|---|
| 362 | 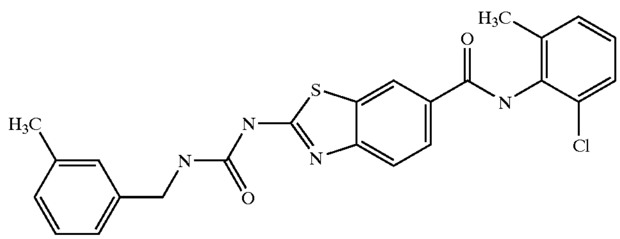 | N-(2-Chloro-6-methylphenyl)-2-[[[[(3-methylphenyl)methyl]amino]carbonyl]amino]-6-benzothiazolecarboxamide | 2.25 |
| 363 | 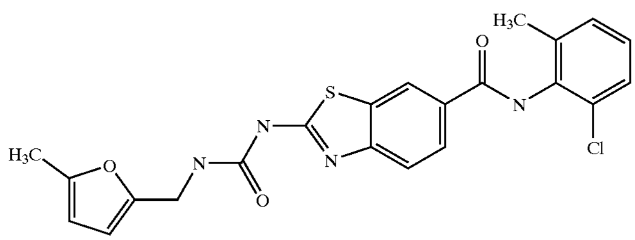 | N-(2-Chloro-6-methylphenyl)-2-[[[[(5-methyl-2-furanyl)methyl]amino]carbonyl]amino]-6-benzothiazolecarboxamide | 2.14 |
| 364 | Chiral | (S)-N-(2-Chloro-6-methylphenyl)-2-[[[[1-(hydroxymethyl)-2-phenylethyl]amino]carbonyl]amino]-6-benzothiazolecarboxamide | 2.13 |
| 365 | 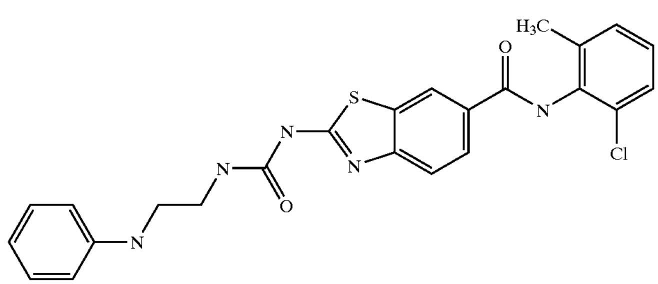 | N-(2-Chloro-6-methylphenyl)-2-[[[[2-(phenylamino)ethyl]amino]carbonyl]amino]-6-benzothiazolecarboxamide | 1.96 |
| 366 | 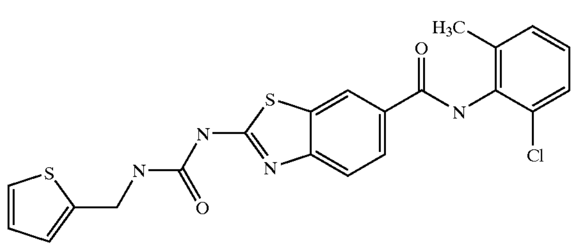 | N-(2-Chloro-6-methylphenyl)-2-[[[(2-thienylmethyl)amino]carbonyl]amino]-6-benzothiazolecarboxamide | 2.11 |

-continued

| EX. NO. | Compound Structure | Compound Name | HPLC Ret Time (min) |
|---|---|---|---|
| 367 | 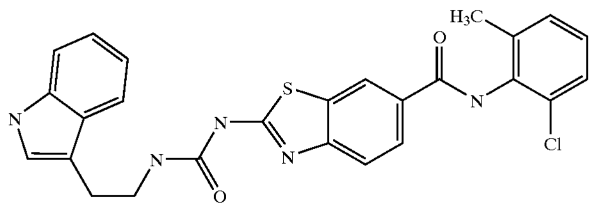 | N-(2-Chloro-6-methylphenyl)-2-[[[[2-(1H-indol-3-yl)ethyl]amino]carbonyl]amino]-6-benzothiazolecarboxamide | 2.19 |
| 368 | 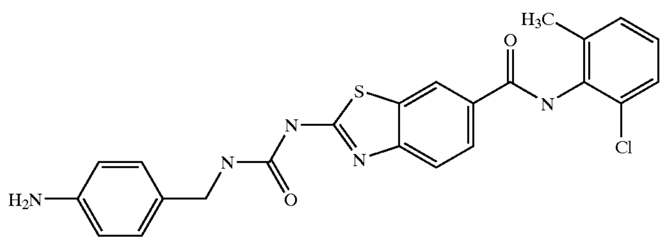 | 2-[[[[(4-Aminophenyl)methyl]amino]carbonyl]amino]-N-(2-chloro-6-methylphenyl)-6-benzothiazolecarboxamide | 1.69 |
| 369 | 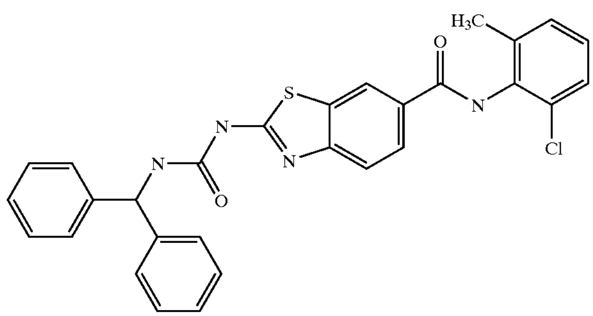 | N-(2-Chloro-6-methylphenyl)-2-[[[(diphenylmethyl)amino]carbonyl]amino]-6-benzothiazolecarboxamide | 2.34 |
| 370 | Chiral | (1R-exo)-2-[[(Bicyclo[2.2.1]heptan-2-ylamino)carbonyl]amino]-N-(2-chloro-6-methylphenyl)-6-benzothiazolecarboxamide | 2.29 |
| 371 | 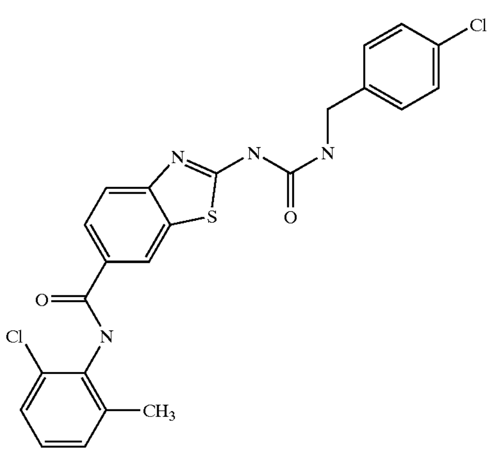 | N-(2-Chloro-6-methylphenyl)-2-[[[[(4-chlorophenyl)methyl]amino]carbonyl]amino]-6-benzothiazolecarboxamide | 2.26 |

-continued

| EX. NO. | Compound Structure | Compound Name | HPLC Ret Time (min) |
|---|---|---|---|
| 372 | 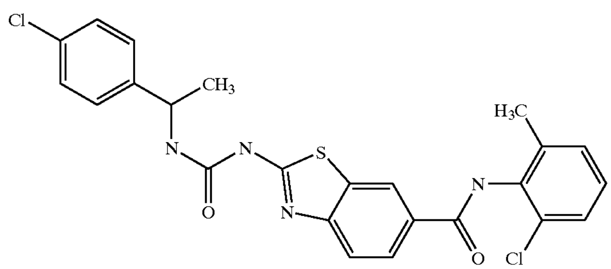 | N-(2-Chloro-6-methylphenyl)-2-[[[[1-(4-chlorophenyl)ethyl]amino]carbonyl]amino]-6-benzothiazole-carboxamide | 2.31 |
| 373 | Chiral | (R)-N-(2-Chloro-6-methylphenyl)-2-[[[[1-(4-methylphenyl)ethyl]amino]carbonyl]amino]-6-benzothiazolecarboxamide | 2.30 |
| 374 | Chiral | (S)-N-(2-Chloro-6-methylphenyl)-2-[[[[1-(4-methylphenyl)ethyl]amino]carbonyl]amino]-6-benzothiazolecarboxamide | 2.30 |
| 375 | 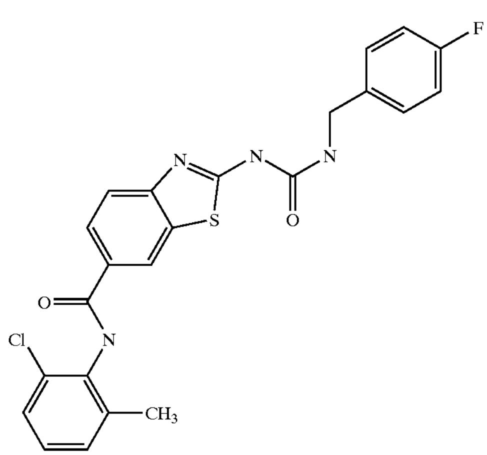 | N-(2-Chloro-6-methylphenyl)-2-[[[[(4-fluorophenyl)methyl]amino]carbonyl]amino]-6-benzothiazolecarboxamide | 2.17 |

-continued

| EX. NO. | Compound Structure | Compound Name | HPLC Ret Time (min) |
|---|---|---|---|
| 376 | 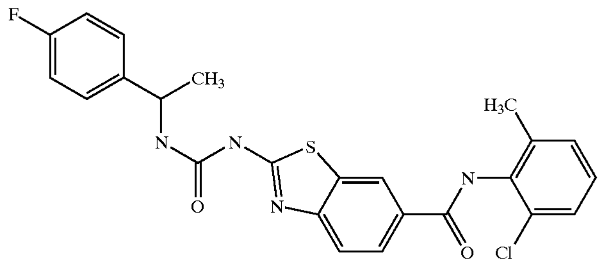 | N-(2-Chloro-6-methylphenyl)-2-[[[[1-(4-fluorophenyl)ethyl]amino]carbonyl]amino]-6-benzothiazolecarboxamide | 2.22 |
| 377 | 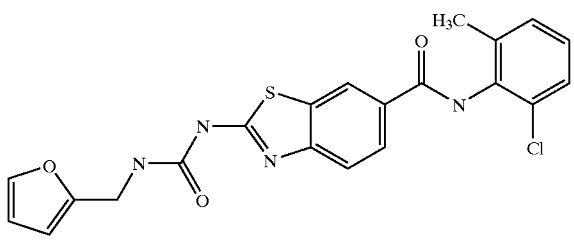 | N-(2-Chloro-6-methylphenyl)-2-[[[(2-furanylmethyl)amino]carbonyl]amino]-6-benzothiazolecarboxamide | 2.05 |
| 378 | 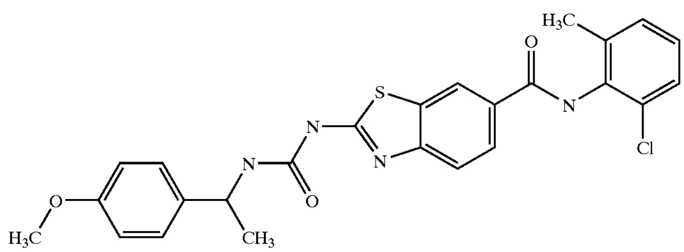 | N-(2-Chloro-6-methylphenyl)-2-[[[[1-(4-methoxyphenyl)ethyl]amino]carbonyl]amino]-6-benzothiazolecarboxamide | 2.20 |
| 379 | Chiral | (S)-N-(2-Chloro-6-methylphenyl)-2-[[[(1-phenylethyl)amino]carbonyl]amino]-6-benzothiazole-carboxamide | 2.20 |
| 380 | 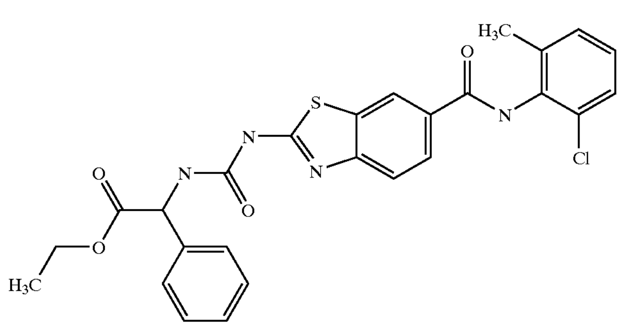 | α-[[[[6-[[(2-Chloro-6-methylphenyl)amino]carbonyl]-2-benzothiazolyl]amino]carbonyl]amino]benzeneacetic acid ethyl ester | 2.22 |

-continued

| EX. NO. | Compound Name | HPLC Ret Time (min) |
|---|---|---|
| 381 | N-(2-Chloro-6-methylphenyl)-2-[[[[2-(4-methylphenyl)-1-phenylethyl]amino]carbonyl]amino]-6-benzothiazolecarboxamide | 2.44 |
| 382 | (R)-N-(2-Chloro-6-methylphenyl)-2-[[[(1-phenylpropyl)amino]carbonyl]amino]-6-benzothiazole-carboxamide | 2.27 |
| 383 | N-(2-Chloro-6-methylphenyl)-2-[[[[(4-methylphenyl)methyl]amino]carbonyl]amino]-6-benzothiazolecarboxamide | 2.30 |
| 384 | (R)-N-(2-Chloro-6-methylphenyl)-2-[[[[1-(4-nitrophenyl)ethyl]amino]carbonyl]amino]-6-benzothiazolecarboxamide | 2.26 |
| 385 | N-(2-Chloro-6-methylphenyl)-2-[[[[(4-chlorophenyl)phenylmethyl]amino]carbonyl]amino]-6-benzothiazolecarboxamide | 2.49 |

-continued

| EX. NO. | Compound Structure | Compound Name | HPLC Ret Time (min) |
|---|---|---|---|
| 386 | 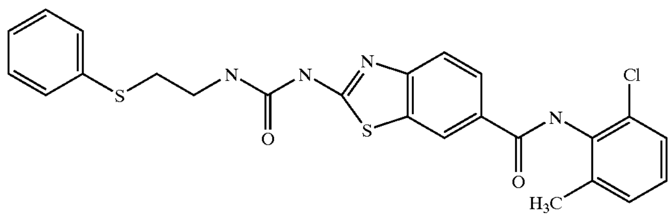 | N-(2-Chloro-6-methylphenyl)-2-[[[[2-(phenylthio)ethyl]amino]carbonyl]amino]-6-benzothiazolecarboxamide | 2.33 |
| 387 | 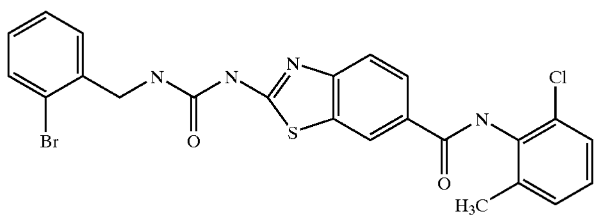 | 2-[[[[(2-Bromophenyl)methyl]amino]carbonyl]amino]-N-(2-chloro-6-methylphenyl)-6-benzothiazolecarboxamide | 2.26 |
| 388 | 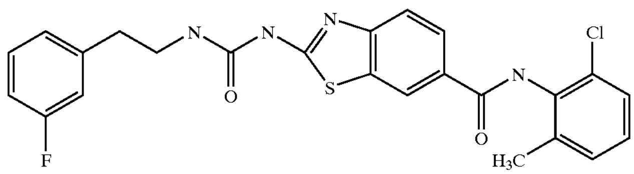 | N-(2-Chloro-6-methylphenyl)-2-[[[[2-(3-fluorophenyl)ethyl]amino]carbonyl]amino]-6-benzothiazolecarboxamide | 2.23 |
| 389 | 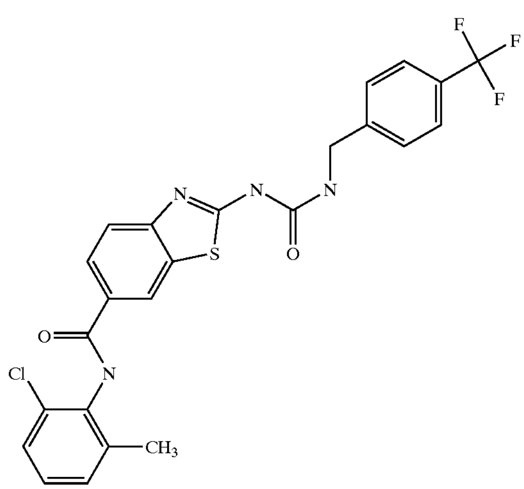 | N-(2-Chloro-6-methylphenyl)-2-[[[[[4-(trifluoromethyl)phenyl]methyl]amino]carbonyl]amino]-6-benzothiazolecarboxamide | 2.28 |
| 390 | 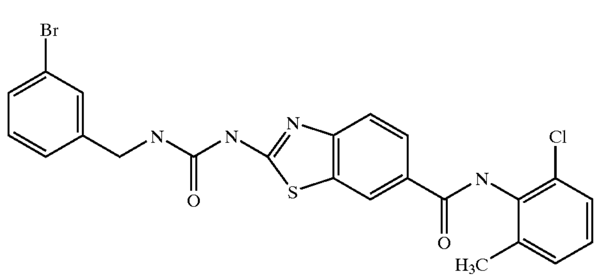 | 2-[[[[(3-Bromophenyl)methyl]amino]carbonyl]amino]-N-(2-chloro-6-methylphenyl)-6-benzothiazolecarboxamide | 2.28 |

-continued

| EX. NO. | Compound Structure | Compound Name | HPLC Ret Time (min) |
|---|---|---|---|
| 391 | 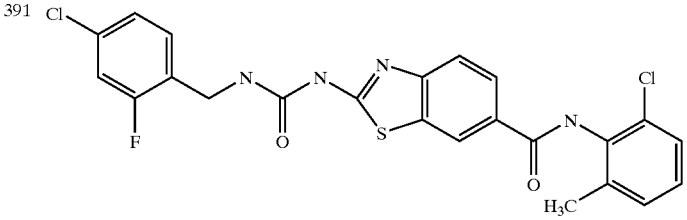 | 2-[[[[(4-Chloro-2-fluorophenyl) methyl]amino]carbonyl]amino]-N-(2-chloro-6-methylphenyl)-6-benzothiazolecarboxamide | 2.28 |
| 392 | 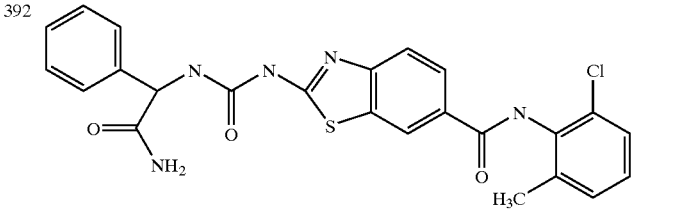 | 2-[[[(2-Amino-2-oxo-1-phenylethyl)amino]carbonyl] amino]-N-(2-chloro-6-methylphenyl)-6-benzothiazole-carboxamide | 2.36 |
| 393 | 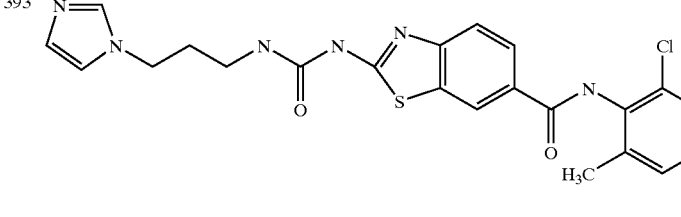 | N-(2-Chloro-6-methylphenyl)-2-[[[[3-(1H-imidazol-1-yl)propyl] amino]carbonyl]amino]-6-benzothiazolecarboxamide | 1.61 |
| 394 | 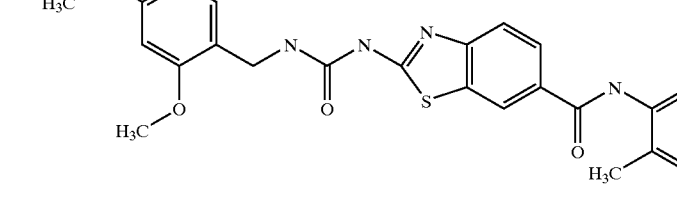 | N-(2-Chloro-6-methylphenyl)-2-[[[[(2,4-dimethoxyphenyl)methyl] amino]carbonyl]amino]-6-benzothiazolecarboxamide | 2.19 |
| 395 | 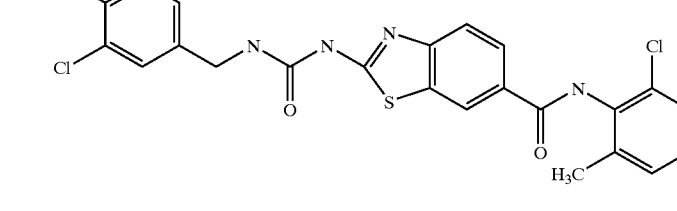 | N-(2-Chloro-6-methylphenyl)-2-[[[[(3-chloro-4-methylphenyl) methyl]amino]carbonyl]amino]-6-benzothiazolecarboxamide | 2.34 |
| 396 | 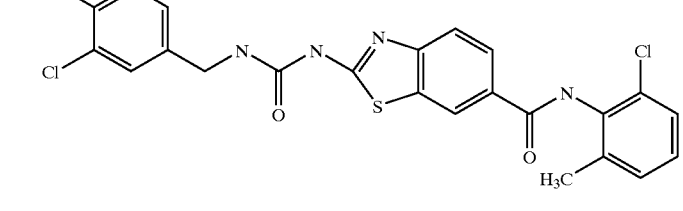 | 2-[[[[(3-Chloro-4-fluorophenyl) methyl]amino]carbonyl]amino]-N-(2-chloro-6-methylphenyl)-6-benzothiazolecarboxamide | 2.27 |

-continued

| EX. NO. | Compound Structure | Compound Name | HPLC Ret Time (min) |
|---|---|---|---|
| 397 | 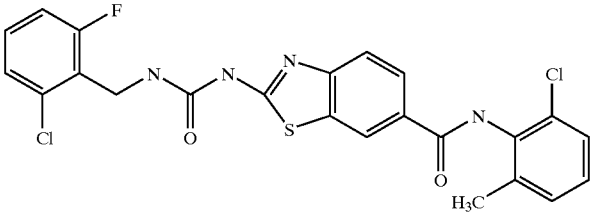 | 2-[[[[(2-Chloro-6-fluorophenyl)methyl]amino]carbonyl]amino]-N-(2-chloro-6-methylphenyl)-6-benzothiazolecarboxamide | 2.22 |
| 398 | 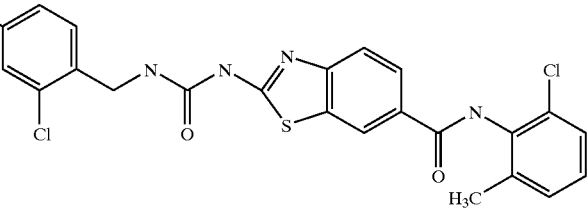 | 2-[[[[(2-Chloro-4-fluorophenyl)methyl]amino]carbonyl]amino]-N-(2-chloro-6-methylphenyl)-6-benzothiazolecarboxamide | 2.28 |
| 399 | 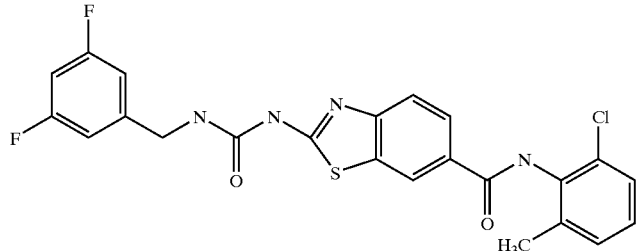 | N-(2-Chloro-6-methylphenyl)-2-[[[[(3,5-difluorophenyl)methyl]amino]carbonyl]amino]-6-benzothiazolecarboxamide | 2.20 |
| 400 | 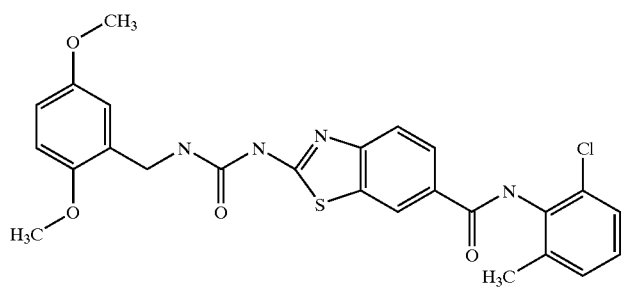 | N-(2-Chloro-6-methylphenyl)-2-[[[[(2,5-dimethoxyphenyl)methyl]amino]carbonyl]amino]-6-benzothiazolecarboxamide | 2.18 |
| 401 | 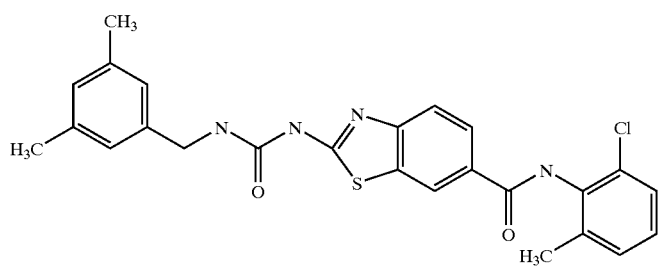 | N-(2-Chloro-6-methylphenyl)-2-[[[[(3,5-dimethylphenyl)methyl]amino]carbonyl]amino]-6-benzothiazolecarboxamide | 2.32 |
| 402 | 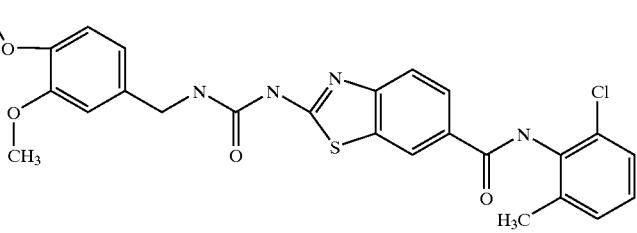 | N-(2-Chloro-6-methylphenyl)-2-[[[[(3,4-dimethoxyphenyl)methyl]amino]carbonyl]amino]-6-benzothiazolecarboxamide | 2.04 |

-continued

| EX. NO. | Compound Structure | Compound Name | HPLC Ret Time (min) |
|---|---|---|---|
| 403 | 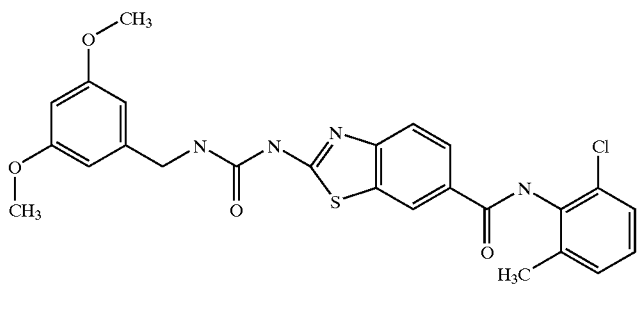 | N-(2-Chloro-6-methylphenyl)-2-[[[[(3,5-dimethoxyphenyl)methyl]amino]carbonyl]amino]-6-benzothiazolecarboxamide | 2.15 |
| 404 | 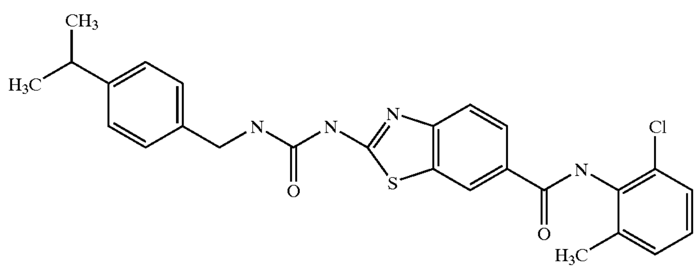 | N-(2-Chloro-6-methylphenyl)-2-[[[[4-(1-methylethyl)phenyl]methyl]amino]carbonyl]amino]-6-benzothiazolecarboxamide | 2.38 |
| 405 | 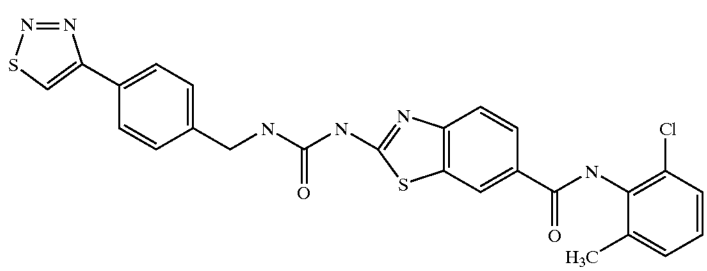 | N-(2-Chloro-6-methylphenyl)-2-[[[[4-(1,2,3-thiadiazol-4-yl)phenyl]methyl]amino]carbonyl]amino]-6-benzothiazolecarboxamide | 2.10 |
| 406 | 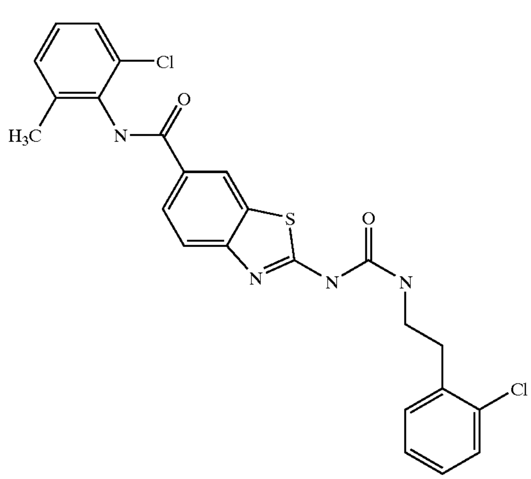 | N-(2-Chloro-6-methylphenyl)-2-[[[[2-(2-chlorophenyl)ethyl]amino]carbonyl]amino]-6-benzothiazolecarboxamide | 2.29 |

-continued

| EX. NO. | Compound Structure | Compound Name | HPLC Ret Time (min) |
|---|---|---|---|
| 407 | 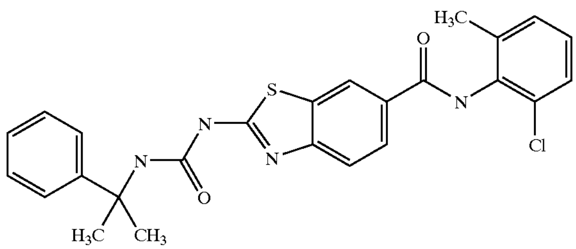 | N-(2-Chloro-6-methylphenyl)-2-[[[(1-methyl-1-phenylethyl)amino]carbonyl]amino]-6-benzothiazolecarboxamide | 2.24 |
| 408 | 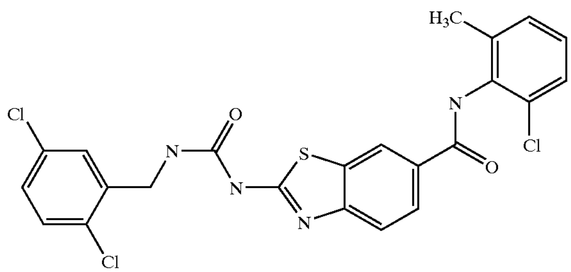 | N-(2-Chloro-6-methylphenyl)-2-[[[[(2,5-dichlorophenyl)methyl]amino]carbonyl]amino]-6-benzothiazolecarboxamide | 2.34 |
| 409 | 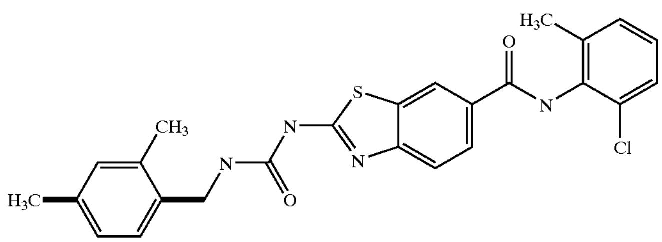 | N-(2-Chloro-6-methylphenyl)-2-[[[[(2,4-dimethylphenyl)methyl]amino]carbonyl]amino]-6-benzothiazolecarboxamide | 2.32 |
| 410 | 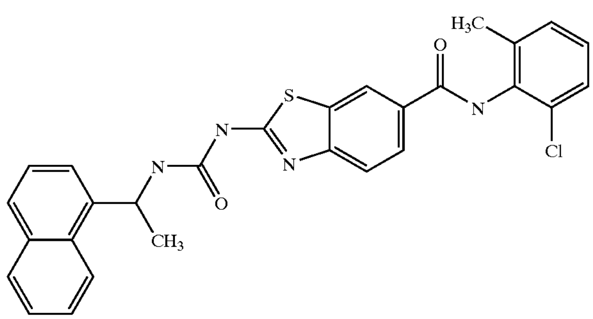 | N-(2-Chloro-6-methylphenyl)-2-[[[[1-(1-naphthalenyl)ethyl]amino]carbonyl]amino]-6-benzothiazolecarboxamide | 2.34 |
| 411 | 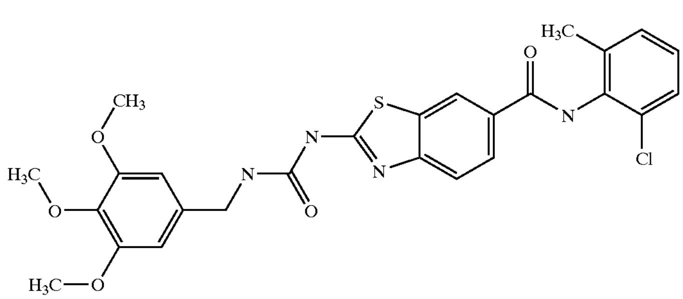 | N-(2-Chloro-6-methylphenyl)-2-[[[[(3,4,5-trimethoxyphenyl)methyl]amino]carbonyl]amino]-6-benzothiazolecarboxamide | 2.06 |

-continued

| EX. NO. | Compound Structure | Compound Name | HPLC Ret Time (min) |
|---|---|---|---|
| 412 | 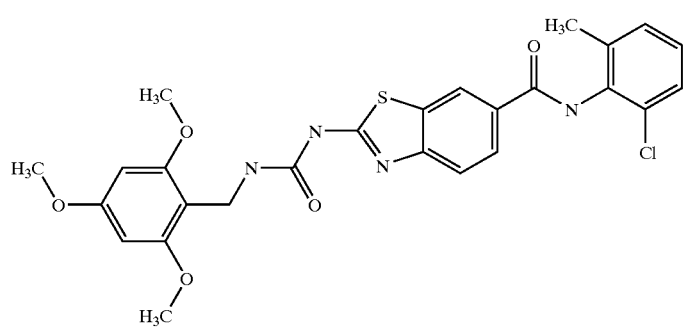 | N-(2-Chloro-6-methylphenyl)-2-[[[[(2,4,6-trimethoxyphenyl)methyl]amino]carbonyl]amino]-6-benzothiazolecarboxamide | 2.22 |
| 413 | 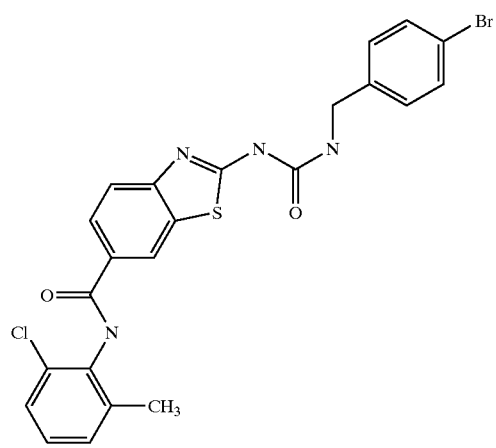 | 2-[[[[(4-Bromophenyl)methyl]amino]carbonyl]amino]-N-(2-chloro-6-methylphenyl)-6-benzothiazolecarboxamide | 2.29 |
| 414 | 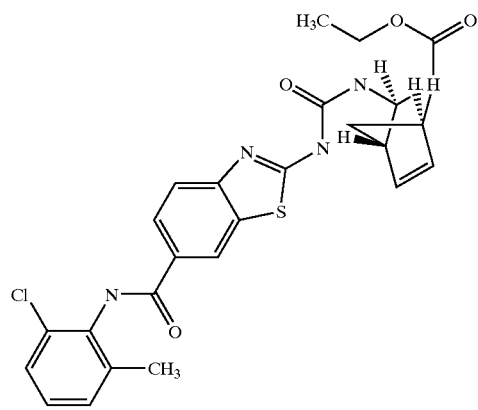 Chiral | [1R-(endo,endo)]-3-[[[[6-[[(2-Chloro-6-methylphenyl)amino]carbonyl]-2-benzothiazolyl]amino]carbonyl]amino]bicylo[2.2.1]hept-5-ene-2-carboxylic acid ethyl ester | 2.19 |

-continued

| EX. NO. | Compound Structure | Compound Name | HPLC Ret Time (min) |
|---|---|---|---|
| 415 | 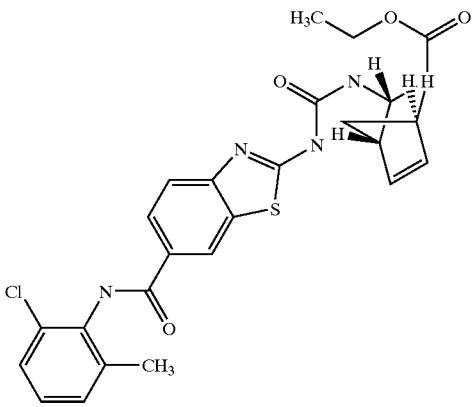<br>Chiral | [1S-(exo,exo)]-3-[[[[6-[[(2-Chloro-6-methylphenyl)amino]carbonyl]-2-benzothiazolyl]amino]carbonyl]amino]bicyclo[2.2.1]heptane-2-carboxylic acid ethyl ester | 2.25 |
| 416 | 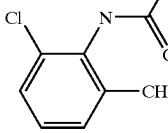<br>Chiral | [1R-(exo,exo)]-3-[[[[6-[[(2-Chloro-6-methylphenyl)amino]carbonyl]-2-benzothiazolyl]amino]carbonyl]amino]bicyclo[2.2.1]hept-5-ene-2-carboxylic acid ethyl ester | 2.22 |
| 417 | 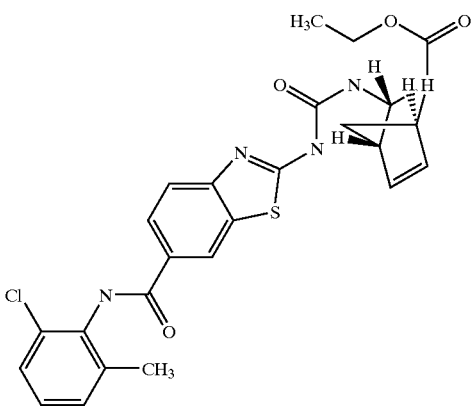<br>Chiral | [1R-(endo,endo)]-N-(2-Chloro-6-methylphenyl)-2-[[[[3-(hydroxymethyl)bicyclo[2.2.1]hept-5-en-2-yl]amino]carbonyl]amino]-6-benzothiazole-carboxamide | 2.07 |

| EX. NO. | Compound Structure | Compound Name | HPLC Ret Time (min) |
|---|---|---|---|
| 418 | 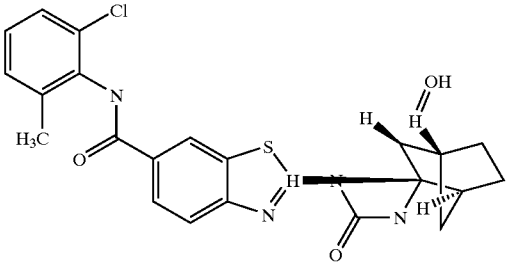 Chiral | [1S-(endo,endo)]-N-(2-Chloro-6-methylphenyl)-2-[[[[3-(hydroxymethyl)bicyclo[2.2.1]heptan-2-yl]amino]carbonyl]amino]-6-benzothiazolecarboxamide | 2.11 |
| 419 | 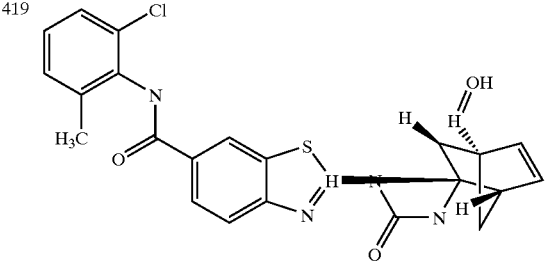 Chiral | [1R-(exo,exo)]-N-(2-Chloro-6-methylphenyl)-2-[[[[3-(hydroxymethyl)bicyclo[2.2.1]heptan-2-yl]amino]carbonyl]amino]-6-benzothiazolecarboxamide | 2.14 |
| 420 | 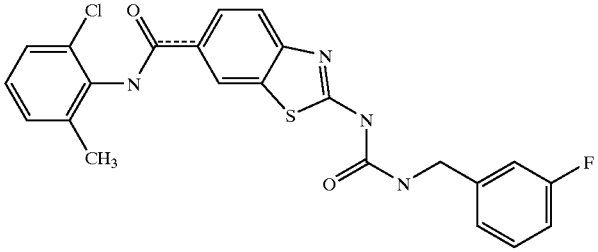 | N-(2-Chloro-6-methylphenyl)-2-[[[[(3-fluorophenyl)methyl]amino]carbonyl]amino]-6-benzothiazolecarboxamide | 2.17 |
| 421 | 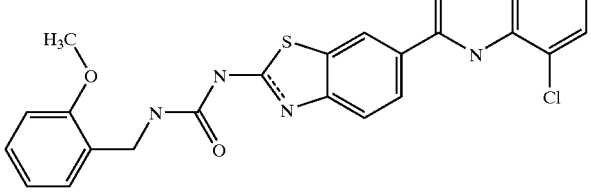 | N-(2-Chloro-6-methylphenyl)-2-[[[[(2-methoxyphenyl)methyl]amino]carbonyl]amino]-6-benzothiazolecarboxamide | 2.19 |
| 422 | 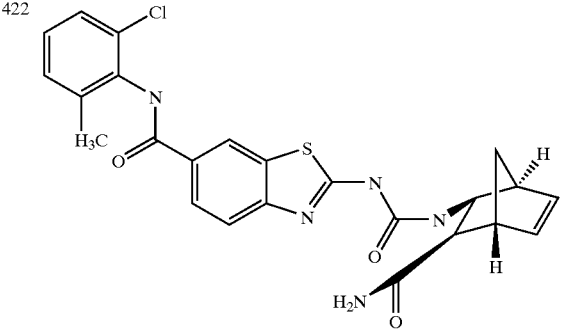 | (exo,exo)-2-[[[[3-(Aminocarbonyl)bicyclo[2.2.1]hept-5-en-2-yl]amino]carbonyl]amino]-N-(2-chloro-6-methylphenyl)-6-benzothiazolecarboxamide | 2.07 |

-continued

| EX. NO. | Compound Structure | Compound Name | HPLC Ret Time (min) |
|---|---|---|---|
| 423 | Chiral | (S)-N-(2-Chloro-6-methylphenyl)-2-[[[[1-(1-naphthalenyl)ethyl]amino]carbonyl]amino]-6-benzothiazolecarboxamide | 2.34 |
| 424 | 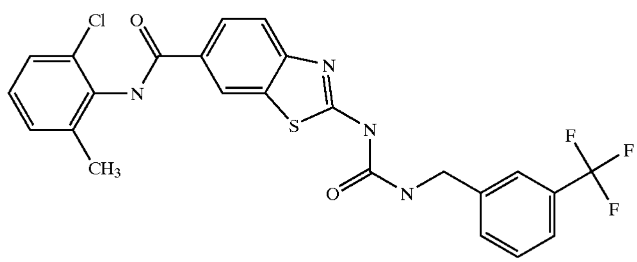 | N-(2-Chloro-6-methylphenyl)-2-[[[[[3-(trifluoromethyl)phenyl]methyl]amino]carbonyl]amino]-6-benzothiazolecarboxamide | 2.27 |
| 425 | 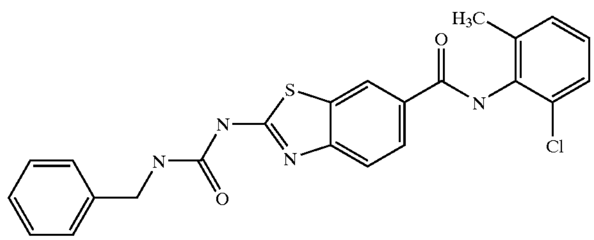 | N-(2-Chloro-6-methylphenyl)-2-[[[[(phenylmethyl)amino]carbonyl]amino]-6-benzothiazole-carboxamide | 2.15 |
| 426 | 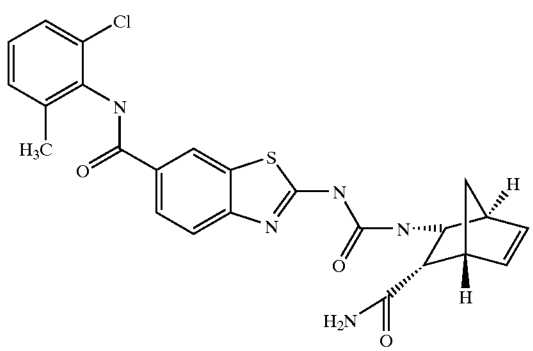 | (endo,endo)-2-[[[[3-(Aminocarbonyl)bicyclo[2.2.1]hept-5-en-2-yl]amino]carbonyl]amino]-N-(2-chloro-6-methylphenyl)-6-benzothiazole-carboxamide | 2.06 |
| 427 | 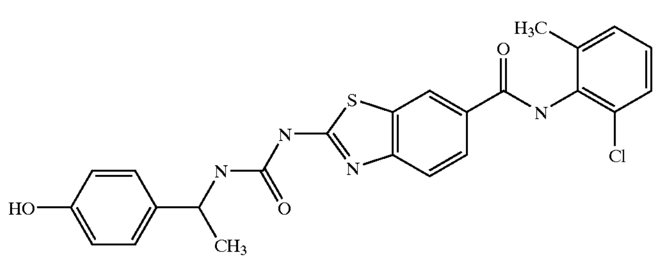 | N-(2-Chloro-6-methylphenyl)-2-[[[[1-(4-hydroxyphenyl)ethyl]amino]carbonyl]amino]-6-benzothiazolecarboxamide | 2.05 |

| EX. NO. | Compound Structure | Compound Name | HPLC Ret Time (min) |
|---|---|---|---|
| 428 | 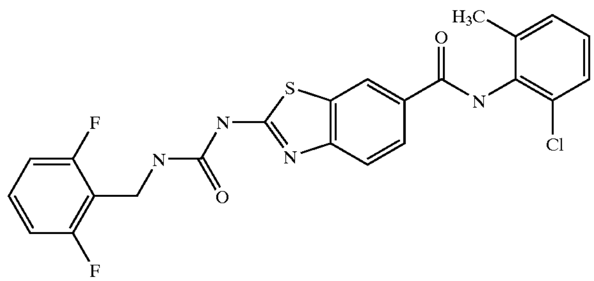 | N-(2-Chloro-6-methylphenyl)-2-[[[[(2,6-difluorophenyl)methyl]amino]carbonyl]amino]-6-benzothiazolecarboxamide | 2.22 |
| 429 | 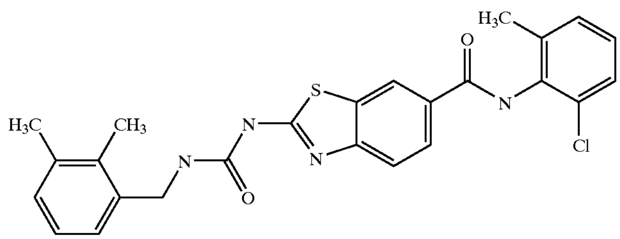 | N-(2-Chloro-6-methylphenyl)-2-[[[[(2,3-dimethylphenyl)methyl]amino]carbonyl]amino]-6-benzothiazolecarboxamide | 2.30 |
| 430 | Chiral | (R)-N-(2-Chloro-6-methylphenyl)-2-[[[[1-(1-naphthalenyl)ethyl]amino]carbonyl]amino]-6-benzothiazolecarboxamide | 2.34 |
| 431 | 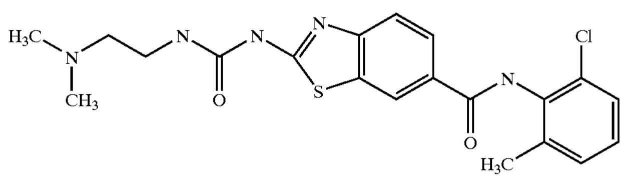 | N-(2-Chloro-6-methylphenyl-2-[[[[2-(dimethylamino)ethyl]amino]carbonyl]amino]-6-benzothiazolecarboxamide | 1.70 |
| 432 | 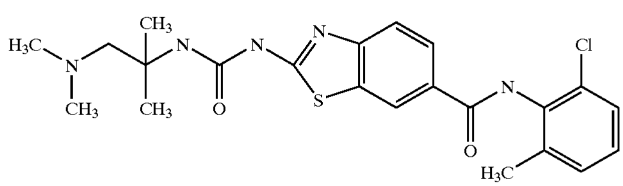 | N-(2-Chloro-6-methylphenyl)-2-[[[[1,1-dimethyl-2-(dimethylamino)ethyl]amino]carbonyl]amino]-6-benzothiazolecarboxamide | 1.71 |
| 433 | 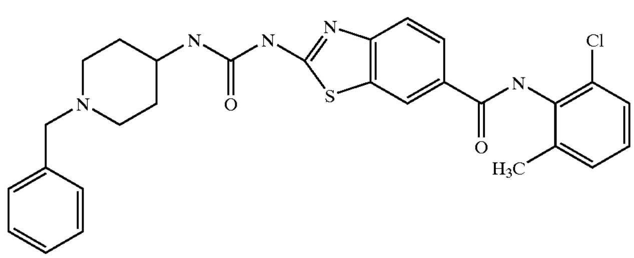 | N-(2-Chloro-6-methylphenyl)-2-[[[[1-(phenylmethyl)-4-piperidinyl]amino]carbonyl]amino]-6-benzothiazolecarboxamide | 1.62 |

-continued

| EX. NO. | Compound Structure | Compound Name | HPLC Ret Time (min) |
|---|---|---|---|
| 434 | 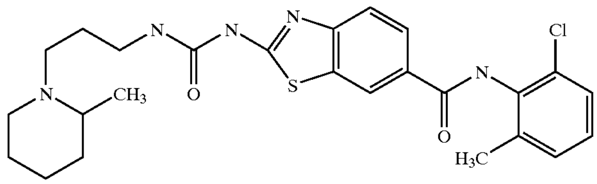 | N-(2-Chloro-6-methylphenyl-2-[[[[3-(2-methyl-1-piperidinyl)propyl]amino]carbonyl]amino]-6-benzothiazolecarboxamide | 1.70 |
| 435 | 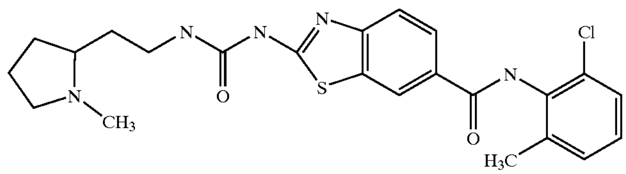 | N-(2-Chloro-6-methylphenyl)-2-[[[[2-(1-methyl-2-pyrrolidinyl)ethyl]amino]carbonyl]amino]-6-benzothiazolecarboxamide | 1.65 |
| 436 | 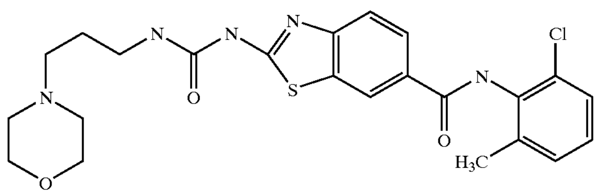 | N-(2-Chloro-6-methylphenyl)-2-[[[[3-(4-morpholinyl)propyl]amino]carbonyl]amino]-6-benzothiazolecarboxamide | 1.60 |
| 437 | 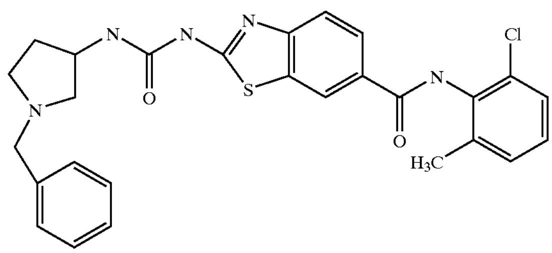 | N-(2-Chloro-6-methylphenyl)-2-[[[[1-(phenylmethyl)-3-pyrrolidinyl]amino]carbonyl]amino]-6-benzothiazolecarboxamide | 1.81 |
| 438 | 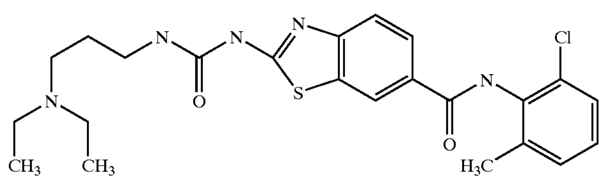 | N-(2-Chloro-6-methylphenyl)-2-[[[[3-(diethylamino)propyl]amino]carbonyl]amino]-6-benzothiazolecarboxamide | 1.65 |
| 439 | 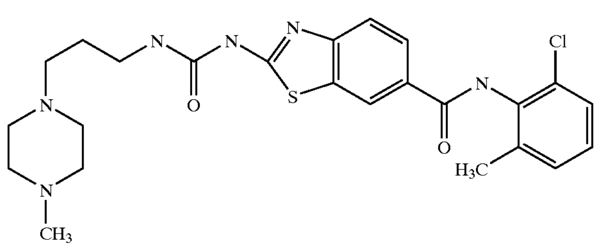 | N-(2-Chloro-6-methylphenyl)-2-[[[[3-(4-methyl-1-piperazinyl)propyl]amino]carbonyl]amino]-6-benzothiazolecarboxamide | 1.51 |
| 440 | 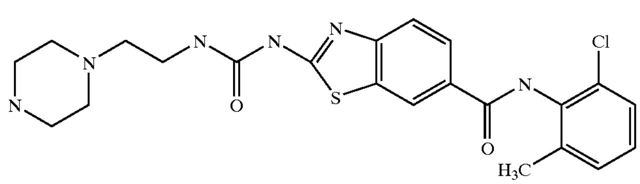 | N-(2-Chloro-6-methylphenyl)-2-[[[[2-(1-piperazinyl)ethyl]amino]carbonyl]amino]-6-benzothiazolecarboxamide | 1.46 |

-continued

| EX. NO. | Compound Structure | Compound Name | HPLC Ret Time (min) |
|---|---|---|---|
| 441 | 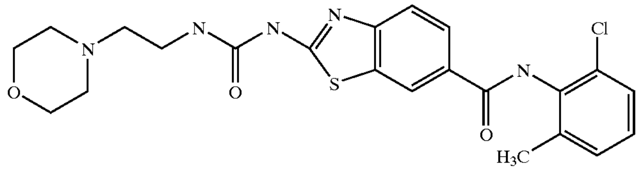 | N-(2-Chloro-6-methylphenyl)-2-[[[[2-(4-morpholinyl)ethyl]amino]carbonyl]amino]-6-benzothiazolecarboxamide | 1.58 |
| 442 | 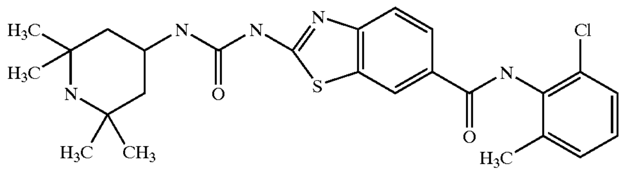 | N-(2-Chloro-6-methylphenyl)-2-[[[(2,2,6,6-tetramethyl-4-piperidinyl)amino]carbonyl]amino]-6-benzothiazolecarboxamide | 1.77 |
| 443 | Chiral | (R)-N-(2-Chloro-6-methylphenyl)-2-[[[[1-(phenylmethyl)-3-pyrrolidinyl]amino]carbonyl]amino]-6-benzothiazolecarboxamide | 1.80 |
| 444 | Chiral | (S)-N-(2-Chloro-6-methylphenyl)-2-[[[[1-(phenylmethyl)-3-pyrrolidinyl]amino]carbonyl]amino]-6-benzothiazolecarboxamide | 1.80 |
| 445 | 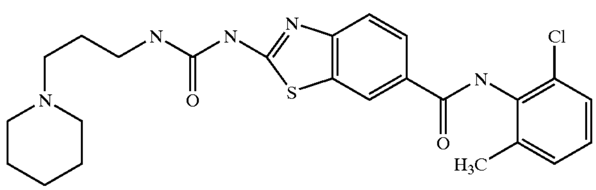 | N-(2-Chloro-6-methylphenyl)-2-[[[[3-(1-piperidinyl)propyl]amino]carbonyl]amino]-6-benzothiazolecarboxamide | 1.65 |
| 446 | 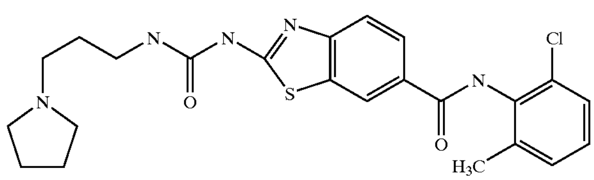 | N-(2-Chloro-6-methylphenyl)-2-[[[[3-(1-pyrrolidinyl)propyl]amino]carbonyl]amino]-6-benzothiazolecarboxamide | 1.62 |
| 447 | 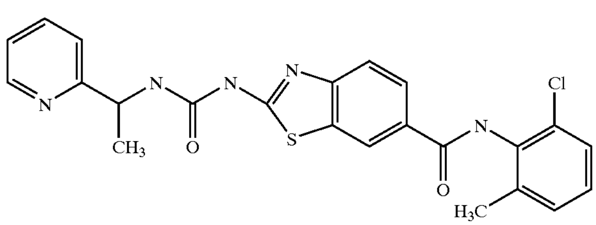 | N-(2-Chloro-6-methylphenyl)-2-[[[[1-(2-pyridinyl)ethyl]amino]carbonyl]amino]-6-benzothiazolecarboxamide | 1.70 |

-continued

| EX. NO. | Compound Structure | Compound Name | HPLC Ret Time (min) |
|---|---|---|---|
| 448 | 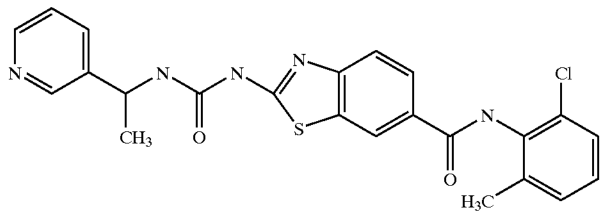 | N-(2-Chloro-6-methylphenyl)-2-[[[[1-(3-pyridinyl)ethyl]amino]carbonyl]amino]-6-benzothiazolecarboxamide | 1.65 |
| 449 | 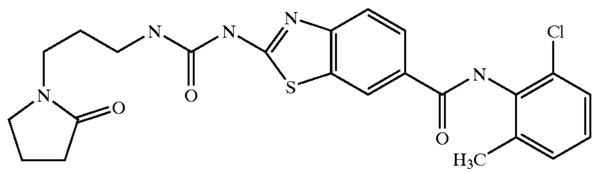 | N-(2-Chloro-6-methylphenyl)-2-[[[[3-(2-oxo-1-pyrrolidinyl)propyl]amino]carbonyl]amino]-6-benzothiazolecarboxamide | 1.91 |
| 450 | 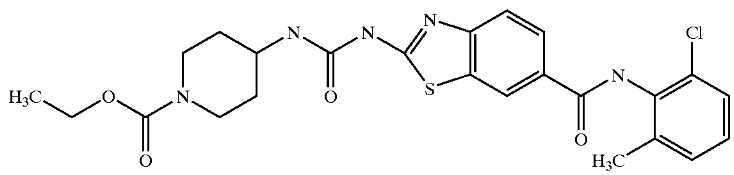 | 4-[[[[6-[[(2-Chloro-6-methylphenyl)amino]carbonyl]-2-benzothiazolyl]amino]carbonyl]amino]-1-piperidinecarboxylic acid ethyl ester | 2.12 |
| 451 | 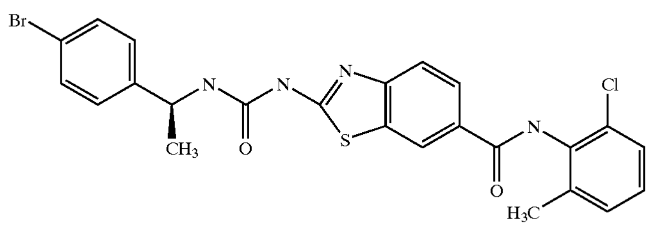 | (S)-2-[[[[1-(4-Bromophenyl)ethyl]amino]carbonyl]amino]-N-(2-chloro-6-methylphenyl)-6-benzothiazolecarboxamide | 2.34 |
| 452 | Chiral | (1S-cis)-2-[[[[2-(Aminocarbonyl)cyclohexyl]amino]carbonyl]amino]-N-(2-chloro-6-methylphenyl)-6-benzothiazole-carboxamide | 2.02 |
| 453 | 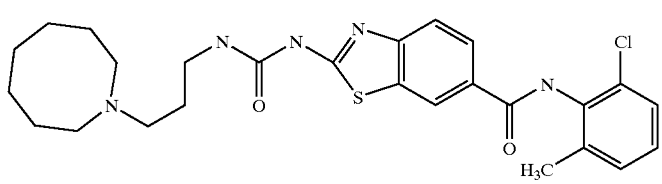 | 2-[[[[3-(1H-Azepin-1-yl)propyl]amino]carbonyl]amino]-N-(2-chloro-6-methylphenyl)-6-benzothiazolecarboxamide | 1.70 |
| 454 | 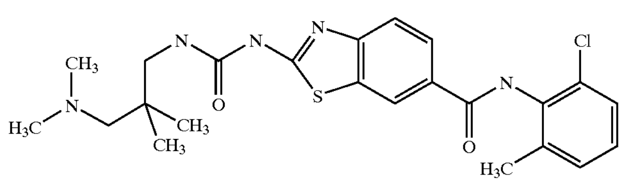 | N-(2-Chloro-6-methylphenyl)-2-[[[[2,2-dimethyl-3-(dimethylamino)propyl]amino]carbonyl]amino]-6-benzothiazolecarboxamide | 1.65 |

-continued

| EX. NO. | Compound Structure | Compound Name | HPLC Ret Time (min) |
|---|---|---|---|
| 455 | 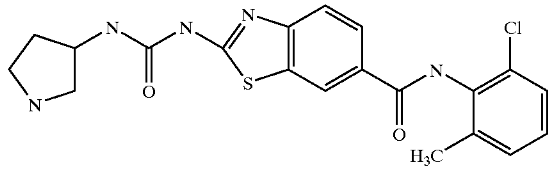 | N-(2-Chloro-6-methylphenyl)-2-[[(3-pyrrolidinylamino)carbonyl]amino]-6-benzothiazole-carboxamide | 1.54 |
| 456 | 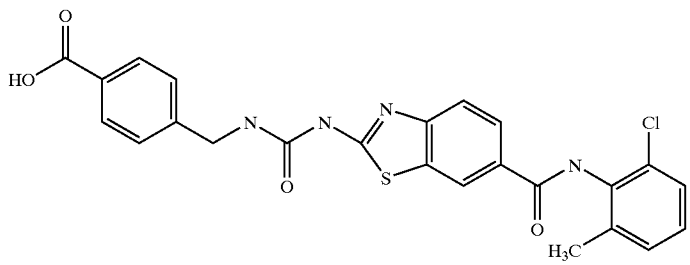 | 4-[[[[[6-[[(2-Chloro-6-methylphenyl)amino]carbonyl]-2-benzothiazolyl]amino]carbonyl]amino]methyl]benzoic acid | 2.02 |
| 457 | 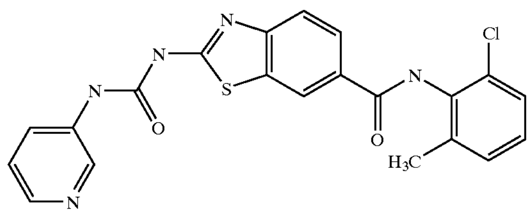 | N-(2-Chloro-6-methylphenyl)-2-[[(3-pyridinylamino)carbonyl]amino]-6-benzothiazole-carboxamide | 1.74 |
| 458 | 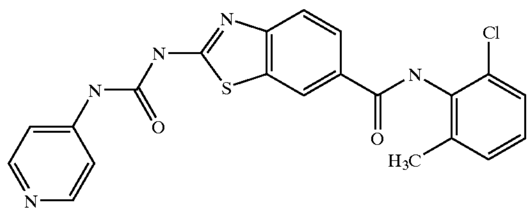 | N-(2-Chloro-6-methylphenyl)-2-[[(4-pyridinylamino)carbonyl]amino]-6-benzothiazole-carboxamide | 1.73 |
| 459 | 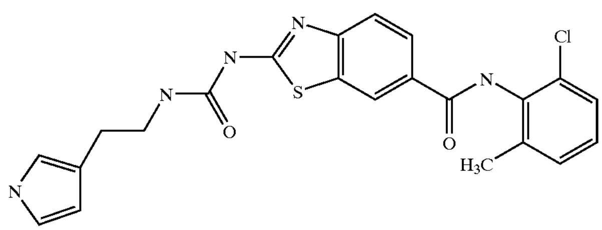 | N-(2-Chloro-6-methylphenyl-2-[[[[2-(1H-pyrrol-3-yl)ethyl]amino]carbonyl]amino]-6-benzothiazolecarboxamide | 1.75 |
| 460 | 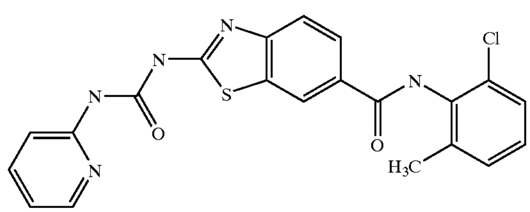 | N-2-Chloro-6-methylphenyl)-2-[[(2-pyridinylamino)carbonyl]amino]-6-benzothiazole-carboxamide | 2.06 |
| 461 | 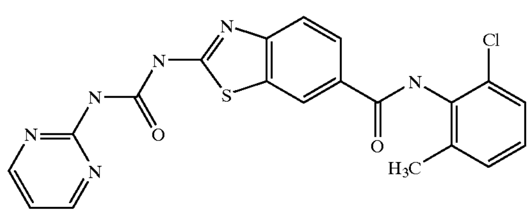 | N-(2-Chloro-6-methylphenyl)-2-[[(2-pyrimidinylamino)carbonyl]amino]-6-benzothiazole-carboxamide | 2.03 |

| EX. NO. | Compound Structure | Compound Name | HPLC Ret Time (min) |
|---|---|---|---|
| 462 | 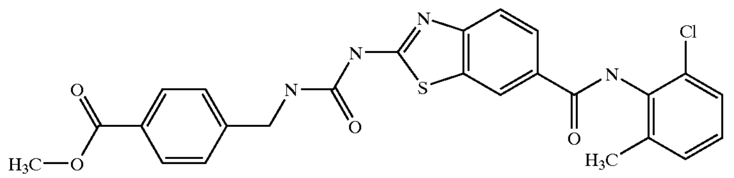 | 4-[[[[[6-[[(2-Chloro-6-methylphenyl)amino]carbonyl]-2-benzothiazolyl]amino]carbonyl]amino]methyl]benzoic acid methyl ester | 2.14 |
| 463 | 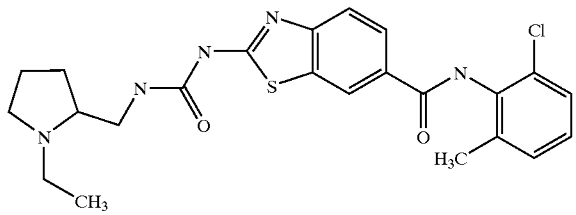 | N-(2-Chloro-6-methylphenyl)-2-[[[[(1-ethyl-2-pyrrolidinyl)methyl]amino]carbonyl]amino]-6-benzothiazolecarboxamide | 1.63 |
| 464 | 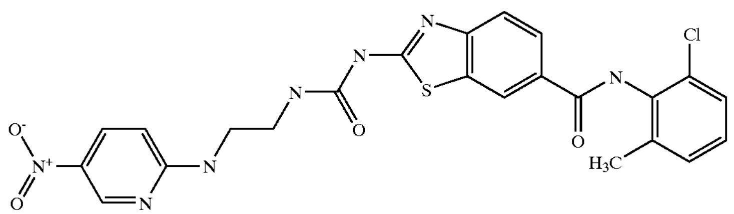 | N-(2-Chloro-6-methylphenyl)-2-[[[[2-[(5-nitro-2-pyridinyl)amino]ethyl]amino]carbonyl]amino]-6-benzothiazolecarboxamide | 2.07 |
| 465 | 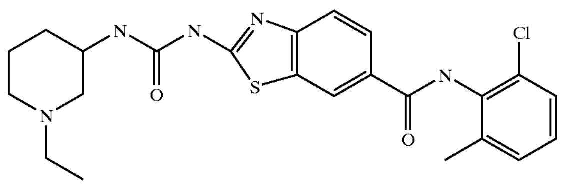 | N-(2-Chloro-6-methylphenyl)-2-[[[(1-ethyl-3-piperidinyl)amino]carbonyl]amino]-6-benzothiazolecarboxamide | 1.65 |
| 466 | 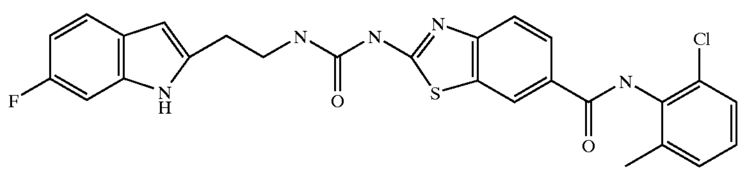 | N-(2-Chloro-6-methylphenyl)-2-[[[[2-(6-fluoro-1H-indol-2-yl)ethyl]amino]carbonyl]amino]-6-benzothiazolecarboxamide | 2.22 |

What is claimed is:

1. A compound or salt thereof selected from the group consisting of:

[6-[[(2,4,6-Trimethylphenyl)amino]carbonyl]-2-benzothiazolyl]carbamic acid, 1,1-dimethylethyl ester;

2-Amino-N-(2,4,6-trimethylphenyl)-6-benzothiazolecarboxamide, trifluoroacetate (1:1);

2-(Acetylamino)-N-(2,4,6-trimethylphenyl)-6-benzothiazolecarboxamide;

2-(Benzoylamino)-N-(2,4,6-trimethylphenyl)-6-benzothiazolecarboxamide;

2-[(1-Oxopropyl)amino]-N-(2,4,6-trimethylphenyl)-6-benzothiazolecarboxamide;

2-[(1-Oxobutyl)amino]-N-(2,4,6-trimethylphenyl)-6-benzothiazolecarboxamide;

2-[[[(1,1-Dimethylethyl)amino]carbonyl]amino]-N-(2,4,6-trimethylphenyl)-6-benzothiazolecarboxamide;

2-[[[Bis(1-methylethyl)amino]carbonyl]amino]-N-(2,4,6-trimethylphenyl)-6-benzothiazolecarboxamide;

[6-Bromo-4-[[(2,4,6-Trimethylphenyl)amino]carbonyl]-2-benzothiazolyl]carbamic acid, 1,1-dimethylethyl ester;

[4-[[(2,4,6-Trimethylphenyl)amino]carbonyl]-2-benzothiazolyl]carbamic acid, 1,1-dimethylethyl ester;

[6-Bromo-7-[[(2,4,6-Trimethylphenyl)amino]carbonyl]-2-benzothiazolyl]carbamic acid, 1,1-dimethylethyl ester;

[7-[[(2,4,6-Trimethylphenyl)amino]carbonyl]-2-benzothiazolyl]carbamic acid, 1,1-dimethylethyl ester;

[6-Bromo-5-[[(2,4,6-Trimethylphenyl)amino]carbonyl]-2-benzothiazolyl]carbamic acid, 1,1-dimethylethyl ester;

[5-[[(2,4,6-Trimethylphenyl)amino]carbonyl]-2-benzothiazolyl]carbamic acid, 1,1-dimethylethyl ester;

2-[[[Phenylamino]carbonyl]amino]-N-(2,4,6-trimethylphenyl)-6-benzothiazolecarboxamide;

2-[[[(Phenylmethyl)amino]carbonyl]amino]-N-(2,4,6-trimethylphenyl)-6-benzothiazolecarboxamide;

2-[[[Ethylamino]carbonyl]amino]-N-(2,4,6-trimethylphenyl)-6-benzothiazolecarboxamide;

2-[[(Butylamino)carbonyl]amino]-N-(2,4,6-trimethylphenyl)-6-benzothiazolecarboxamide;

2-[[(Cyclopropylamino)carbonyl]amino]-N-(2,4,6-trimethylphenyl)-6-benzothiazolecarboxamide;

(R)-2-[[[[(3,3-Dimethylcyclohexyl)methyl]amino]carbonyl]amino]-N-(2,4,6-trimethylphenyl)-6-benzothiazolecarboxamide;

2-[[[(4-Methylcyclohexyl)amino]carbonyl]amino]-N-(2,4,6-trimethylphenyl)-6-benzothiazolecarboxamide;

2-[[[(Cyclohexylmethyl)amino]carbonyl]amino]-N-(2,4,6-trimethylphenyl)-6-benzothiazolecarboxamide;

2-[[[(2,3-Dihydro-1H-inden-1-yl)amino]carbonyl]amino]-N-(2,4,6-trimethylphenyl)-6-benzothiazolecarboxamide;

2-[[[(1-Naphthalenylmethyl)amino]carbonyl]amino]-N-(2,4,6-trimethylphenyl)-6-benzothiazolecarboxamide;

2-[[[[2-(1H-Imidazol-4-yl)ethyl]amino]carbonyl]amino]-N-(2,4,6-trimethylphenyl)-6-benzothiazolecarboxamide;

2-[[[[(Tetrahydro-2-furanyl)methyl]amino]carbonyl]amino]-N-(2,4,6-trimethylphenyl)-6-benzothiazolecarboxamide;

2-[[[[2-(5-Methoxy-1H-indol-3-yl)ethyl]amino]carbonyl]amino]-N-(2,4,6-trimethylphenyl)-6-benzothiazolecarboxamide;

2-[[[[2-(4-Morpholinyl)ethyl]amino]carbonyl]amino]-N-(2,4,6-trimethylphenyl)-6-benzothiazolecarboxamide;

2-[[[[2-(2-Pyridinyl)ethyl]amino]carbonyl]amino]-N-(2,4,6-trimethylphenyl)-6-benzothiazolecarboxamide;

2-[[[(1,1,3,3-Tetramethylbutyl)amino]carbonyl]amino]-N-(2,4,6-trimethylphenyl)-6-benzothiazolecarboxamide;

2-[[[(1,1-Dimethyl-propyl)amino]carbonyl]amino]-N-(2,4,6-trimethylphenyl)-6-benzothiazolecarboxamide;

2-[[[(1,5-Dimethylhexyl)amino]carbonyl]amino]-N-(2,4,6-trimethylphenyl)-6-benzothiazolecarboxamide;

2-[[(Cyclopentylamino)carbonyl]amino]-N-(2,4,6-trimethylphenyl)-6-benzothiazolecarboxamide;

2-[[[(1,1-Dimethyl-2-hydroxyethyl)amino]carbonyl]amino]-N-(2,4,6-trimethylphenyl)-6-benzothiazolecarboxamide;

2-[[[[(3-Methoxyphenyl)methyl]amino]carbonyl]amino]-N-(2,4,6-trimethylphenyl)-6-benzothiazolecarboxamide;

2-[[[[(3-Methylphenyl)methyl]amino]carbonyl]amino]-N-(2,4,6-trimethylphenyl)-6-benzothiazolecarboxamide;

2-[[[[(4-Chlorophenyl)methyl]amino]carbonyl]amino]-N-(2,4,6-trimethylphenyl)-6-benzothiazolecarboxamide;

2-[[[[2-(4-Methoxyphenyl)ethyl]amino]carbonyl]amino]-N-(2,4,6-trimethylphenyl)-6-benzothiazolecarboxamide;

2-[[(2-Propynylamino)carbonyl]amino]-N-(2,4,6-trimethylphenyl)-6-benzothiazolecarboxamide;

2-[[(2-Propenylamino)carbonyl]amino]-N-(2,4,6-trimethylphenyl)-6-benzothiazolecarboxamide;

2-[[[(3-Phenylpropyl)amino]carbonyl]amino]-N-(2,4,6-trimethylphenyl)-6-benzothiazolecarboxamide;

2-[[[[1-(Hydroxymethyl)cyclopentyl]amino]carbonyl]amino]-N-(2,4,6-trimethylphenyl)-6-benzothiazolecarboxamide;

2-[[[[4-(1,1-Dimethylethyl)cyclohexyl]amino]carbonyl]amino]-N-(2,4,6-trimethylphenyl)-6-benzothiazolecarboxamide;

2-[[[(1-Propylbutyl)amino]carbonyl]amino]-N-(2,4,6-trimethylphenyl)-6-benzothiazolecarboxamide;

2-[[[(1,3-Dimethylpentyl)amino]carbonyl]amino]-N-(2,4,6-trimethylphenyl)-6-benzothiazolecarboxamide;

2-[[[[3-(Methylthio)propyl]amino]carbonyl]amino]-N-(2,4,6-trimethylphenyl)-6-benzothiazolecarboxamide;

2-[[[[1-(Methoxymethyl)propyl]amino]carbonyl]amino]-N-(2,4,6-trimethylphenyl)-6-benzothiazolecarboxamide;

2-[[[[2-(2-Thienyl)ethyl]amino]carbonyl]amino]-N-(2,4,6-trimethylphenyl)-6-benzothiazolecarboxamide;

2-[[[[(2,6-Dimethoxyphenyl)methyl]amino]carbonyl]amino]-N-(2,4,6-trimethylphenyl)-6-benzothiazolecarboxamide;

(R)-2-[[[[1-(Hydroxymethyl)-2-phenylethyl]amino]carbonyl]amino]-N-(2,4,6-trimethylphenyl)-6-benzothiazolecarboxamide;

(R)-2-[[[(1-Phenylethyl)amino]carbonyl]amino]-N-(2,4,6-trimethylphenyl)-6-benzothiazolecarboxamide;

2-[[(1-Adamantylamino)carbonyl]amino]-N-(2,4,6-trimethylphenyl)-6-benzothiazolecarboxamide;

2-[[[[2-(4-Fluorophenyl)-1,1-dimethylethyl]amino]carbonyl]amino]-N-(2,4,6-trimethylphenyl)-6-benzothiazolecarboxamide;

2-[[[[2-(2-Pyridinyloxy)ethyl]amino]carbonyl]amino]-N-(2,4,6-trimethylphenyl)-6-benzothiazolecarboxamide;

2-[[[(1-Methyl-1-phenylethyl)amino]carbonyl]amino]-N-(2,4,6-trimethylphenyl)-6-benzothiazolecarboxamide;

(R)-2-[[[[1-(4-Methylphenyl)ethyl]amino]carbonyl]amino]-N-(2,4,6-trimethylphenyl)-6-benzothiazolecarboxamide;

2-[[[(1-Methylheptyl)amino]carbonyl]amino]-N-(2,4,6-trimethylphenyl)-6-benzothiazolecarboxamide;

2-[[[[(4-Methoxyphenyl)methyl]amino]carbonyl]amino]-N-(2,4,6-trimethylphenyl)-6-benzothiazolecarboxamide;

2-[[[(4-Cyclohexylphenyl)amino]carbonyl]amino]-N-(2,4,6-trimethylphenyl)-6-benzothiazolecarboxamide;

2-[[[(5,6,7,8-Tetrahydro-1-naphthalenyl)amino]carbonyl]amino]-N-(2,4,6-trimethylphenyl)-6-benzothiazolecarboxamide;

2-[[[(2,3-Dihydro-1H-inden-5-yl)amino]carbonyl]amino]-N-(2,4,6-trimethylphenyl)-6-benzothiazolecarboxamide;

2-[[(1,3-Benzodioxol-5-ylamino)carbonyl]amino]-N-(2,4,6-trimethylphenyl)-6-benzothiazolecarboxamide;

2-[[(2-Pyridinylamino)carbonyl]amino]-N-(2,4,6-trimethylphenyl)-6-benzothiazolecarboxamide;

2-[[[(3-Methyl-2-pyridinyl)amino]carbonyl]amino]-N-(2,4,6-trimethylphenyl)-6-benzothiazolecarboxamide;

2-[[[(4-Methyl-2-pyridinyl)amino]carbonyl]amino]-N-(2,4,6-trimethylphenyl)-6-benzothiazolecarboxamide;

2-[[[(2-Chloro-5-methylphenyl)amino]carbonyl]amino]-N-(2,4,6-trimethylphenyl)-6-benzothiazolecarboxamide;

2-[[[(2,6-Dichlorophenyl)amino]carbonyl]amino]-N-(2,4,6-trimethylphenyl)-6-benzothiazolecarboxamide;

2-[[[(2-Methoxyphenyl)amino]carbonyl]amino]-N-(2,4,6-trimethylphenyl)-6-benzothiazolecarboxamide;

2-[[([1,1'-Biphenyl]-2-ylamino)carbonyl]amino]-N-(2,4,6-trimethylphenyl)-6-benzothiazolecarboxamide;
2-[[[(2-Benzoylphenyl)amino]carbonyl]amino]-N-(2,4,6-trimethylphenyl)-6-benzothiazolecarboxamide;
2-[[[(2-Methylphenyl)amino]carbonyl]amino]-N-(2,4,6-trimethylphenyl)-6-benzothiazolecarboxamide;
N-(2,4,6-Trimethylphenyl)-2-[[[(2,4,6-trimethylphenyl)amino]carbonyl]amino]-6-benzothiazolecarboxamide;
2-[[[[2-Methyl-6-(1-methylethyl)phenyl]amino]carbonyl]amino]-N-(2,4,6-trimethylphenyl)-6-benzothiazolecarboxamide;
2-[[[(3,5-Difluorophenyl)amino]carbonyl]amino]-N-(2,4,6-trimethylphenyl)-6-benzothiazolecarboxamide;
2-[[[(3-Methoxyphenyl)amino]carbonyl]amino]-N-(2,4,6-trimethylphenyl)-6-benzothiazolecarboxamide;
2-[[[(3-Methylphenyl)amino]carbonyl]amino]-N-(2,4,6-trimethylphenyl)-6-benzothiazolecarboxamide;
2-[[[(4-Cyanophenyl)amino]carbonyl]amino]-N-(2,4,6-trimethylphenyl)-6-benzothiazolecarboxamide;
2-[[[(4-Fluorophenyl)amino]carbonyl]amino]-N-(2,4,6-trimethylphenyl)-6-benzothiazolecarboxamide;
2-[[[(4-Chlorophenyl)amino]carbonyl]amino]-N-(2,4,6-trimethylphenyl)-6-benzothiazolecarboxamide;
4-[[[[6-[[(2,4,6-Trimethylphenyl)amino]carbonyl]-2-benzothiazolyl]amino]carbonyl]amino]benzoic acid, ethyl ester;
2-[[[(3,4,5-Trimethoxyphenyl)amino]carbonyl]amino]-N-(2,4,6-trimethylphenyl)-6-benzothiazolecarboxamide;
2-[[[(3,4-Dimethoxyphenyl)amino]carbonyl]amino]-N-(2,4,6-trimethylphenyl)-6-benzothiazolecarboxamide;
2-[[[[2,6-Bis(1-Methylethyl)phenyl]amino]carbonyl]amino]-N-(2,4,6-trimethylphenyl)-6-benzothiazolecarboxamide;
2-[[[(2-Propylphenyl)amino]carbonyl]amino]-N-(2,4,6-trimethylphenyl)-6-benzothiazolecarboxamide;
2-[[[(3-Bromo-2,4,6-trimethylphenyl)amino]carbonyl]amino]-N-(2,4,6-trimethylphenyl)-6-benzothiazolecarboxamide;
2-[[[[2-(4-Morpholinyl)phenyl]amino]carbonyl]amino]-N-(2,4,6-trimethylphenyl)-6-benzothiazolecarboxamide;
2-[[[(3-Bromo-2-methylphenyl)amino]carbonyl]amino]-N-(2,4,6-trimethylphenyl)-6-benzothiazolecarboxamide;
2-[[[(2,6-Dimethoxyphenyl)amino]carbonyl]amino]-N-(2,4,6-trimethylphenyl)-6-benzothiazolecarboxamide;
2-[[[(2-Bromo-5-methoxyphenyl)amino]carbonyl]amino]-N-(2,4,6-trimethylphenyl)-6-benzothiazolecarboxamide;
2-[[[(2-Methoxy-6-methylphenyl)amino]carbonyl]amino]-N-(2,4,6-trimethylphenyl)-6-benzothiazolecarboxamide;
2-[[[(2,3-Dimethyl-1H-indol-5-yl)amino]carbonyl]amino]-N-(2,4,6-trimethylphenyl)-6-benzothiazolecarboxamide;
2-[[[[3-(1,3,4-Oxadiazol-2-yl)phenyl]amino]carbonyl]amino]-N-(2,4,6-trimethylphenyl)-6-benzothiazolecarboxamide;
2-[[[(2-Chloro-6-methylphenyl)amino]carbonyl]amino]-N-(2,4,6-trimethylphenyl)-6-benzothiazolecarboxamide;
2-[[[[3-(Methylthio)phenyl]amino]carbonyl]amino]-N-(2,4,6-trimethylphenyl)-6-benzothiazolecarboxamide;
2-[[[(4-Methoxy-2-methylphenyl)amino]carbonyl]amino]-N-(2,4,6-trimethylphenyl)-6-benzothiazolecarboxamide;
2-[[[(4-Methoxycyclohexyl)carbonyl]amino]-N-(2,4,6-trimethylphenyl)-6-benzothiazolecarboxamide;
2-[(2,2-Dimethyl-1-oxopropyl)amino]-N-(2,4,6-trimethylphenyl)-6-benzothiazolecarboxamide;
2-[(2-Thienylacetyl)amino]-N-(2,4,6-trimethylphenyl)-6-benzothiazolecarboxamide;
2-[(Cyclopropylcarbonyl)amino]-N-(2,4,6-trimethylphenyl)-6-benzothiazolecarboxamide;
2-[(Cyclobutylcarbonyl)amino]-N-(2,4,6-trimethylphenyl)-6-benzothiazolecarboxamide;
2-[(Cyclopentylcarbonyl)amino]-N-(2,4,6-trimethylphenyl)-6-benzothiazolecarboxamide;
2-[(3-Cyclopentyl-1-oxopropyl)amino]-N-(2,4,6-trimethylphenyl)-6-benzothiazolecarboxamide;
2-[(1-Cyclopenten-1-ylcarbonyl)amino]-N-(2,4,6-trimethylphenyl)-6-benzothiazolecarboxamide;
2-[(Cyclohexylacetyl)amino]-N-(2,4,6-trimethylphenyl)-6-benzothiazolecarboxamide;
2-[(1-Oxo-2-phenylpropyl)amino]-N-(2,4,6-trimethylphenyl)-6-benzothiazolecarboxamide;
2-[(2-Methyl-1-oxopropyl)amino]-N-(2,4,6-trimethylphenyl)-6-benzothiazolecarboxamide;
2-[(1-Oxo-3-phenoxypropyl)amino]-N-(2,4,6-trimethylphenyl)-6-benzothiazolecarboxamide;
2-[(1-Oxo-3-phenylpropyl)amino]-N-(2,4,6-trimethylphenyl)-6-benzothiazolecarboxamide;
2-[[3-(2-Methoxyphenyl)-1-oxopropyl]amino]-N-(2,4,6-trimethylphenyl)-6-benzothiazolecarboxamide;
2-[[3-(2,3,4-Trimethoxyphenyl)-1-oxopropyl]amino]-N-(2,4,6-trimethylphenyl)-6-benzothiazolecarboxamide;
2-[(1,4-Dioxopentyl)amino]-N-(2,4,6-trimethylphenyl)-6-benzothiazolecarboxamide;
2-[(2-Naphthalenylacetyl)amino]-N-(2,4,6-trimethylphenyl)-6-benzothiazolecarboxamide;
2-[[(2-Chloro-6-fluorophenyl)acetyl]amino]-N-(2,4,6-trimethylphenyl)-6-benzothiazolecarboxamide;
2-[[(2-Methylphenyl)acetyl]amino]-N-(2,4,6-trimethylphenyl)-6-benzothiazolecarboxamide;
2-[[(3-Methoxyphenyl)acetyl]amino]-N-(2,4,6-trimethylphenyl)-6-benzothiazolecarboxamide;
2-[[(4-Chlorophenyl)acetyl]amino]-N-(2,4,6-trimethylphenyl)-6-benzothiazolecarboxamide;
2-[(1-Oxo-4-pentynyl)amino]-N-(2,4,6-trimethylphenyl)-6-benzothiazolecarboxamide;
5-Oxo-5-[[6-[[(2,4,6-trimethylphenyl)amino]carbonyl]-2-benzothiazolyl]amino]pentanoic acid, methyl ester;
2-[(1-Oxohexyl)amino]-N-(2,4,6-trimethylphenyl)-6-benzothiazolecarboxamide;
2-[(1-Oxoheptyl)amino]-N-(2,4,6-trimethylphenyl)-6-benzothiazolecarboxamide 2-[[1-Oxo-4-(2-thienyl)butyl]amino]-N-(2,4,6-trimethylphenyl)-6-benzothiazolecarboxamide;
2-[(3-Thienylcarbonyl)amino]-N-(2,4,6-trimethylphenyl)-6-benzothiazolecarboxamide;
2-[[(4-Nitrophenyl)acetyl]amino]-N-(2,4,6-trimethylphenyl)-6-benzothiazolecarboxamide;
2-[[3,5-Bis(trifluoromethyl)phenyl]acetyl]amino)-N-(2,4,6-trimethylphenyl)-6-benzothiazolecarboxamide;
2-[[2-[4-(2-Methypropyl)phenyl]-1-oxopropyl]amino]-N-(2,4,6-trimethylphenyl)-6-benzothiazolecarboxamide;

2-[[(3-Cyclohexen-1-yl)carbonyl]amino]-N-(2,4,6-trimethylphenyl)-6-benzothiazolecarboxamide;

2-[[3-(3-Methoxyphenyl)-1-oxopropyl]amino]-N-(2,4,6-trimethylphenyl)-6-benzothiazolecarboxamide;

2-[[(2,3,6-Trichlorophenyl)acetyl]amino]-N-(2,4,6-trimethylphenyl)-6-benzothiazolecarboxamide;

2-[[(1,3-Benzodioxol-5-yl)acetyl]amino]-N-(2,4,6-trimethylphenyl)-6-benzothiazolecarboxamide;

2-[[[2-(Phenylmethoxy)phenyl]acetyl]amino]-N-(2,4,6-trimethylphenyl)-6-benzothiazolecarboxamide;

2-[[(3,5-Dimethoxyphenyl)acetyl]amino]-N-(2,4,6-trimethylphenyl)-6-benzothiazolecarboxamide;

2-[[3-(1,3-Benzodioxol-5-yl)-1-oxopropyl]amino]-N-(2,4,6-trimethylphenyl)-6-benzothiazolecarboxamide;

2-[[(Tetrahydro-2-furanyl)carbonyl]amino]-N-(2,4,6-trimethylphenyl)-6-benzothiazolecarboxamide;

2-[[2-(Acetylamino)-1-oxopropyl]amino]-N-(2,4,6-trimethylphenyl)-6-benzothiazolecarboxamide;

2-[[2-(Acetylamino)-1-oxohexyl]amino]-N-(2,4,6-trimethylphenyl)-6-benzothiazolecarboxamide;

2-[(Cyclopropylacetyl)amino]-N-(2,4,6-trimethylphenyl)-6-benzothiazolecarboxamide;

N,N-Dimethyl-N'-[6-[[(2,4,6-trimethylphenyl)amino]carbonyl]-2-benzothiazolyl]butanediamide;

2-[(1-Adamantylcarbonyl)amino]-N-(2,4,6-trimethylphenyl)-6-benzothiazolecarboxamide;

2-[[(4-Methylcyclohexyl)carbonyl]amino]-N-(2,4,6-trimethylphenyl)-6-benzothiazolecarboxamide;

2-[(3-Methoxy-1-oxopropyl)amino]-N-(2,4,6-trimethylphenyl)-6-benzothiazolecarboxamide;

[6-[[(2,3-Dihydro-1H-inden-5-yl)amino]carbonyl]-2-benzothiazolyl]carbamic acid, 1,1-dimethylethyl ester;

[6-[(2-Naphthylenylamino)carbonyl]-2-benzothiazolyl]carbamic acid, 1,1-dimethylethyl ester;

[6-[[(3-Hydroxy-2-naphthalenyl)amino]carbonyl]-2-benzothiazolyl]carbamic acid, 1,1-dimethylethyl ester;

[6-[[(2-Fluoro-5-methylphenyl)amino]carbonyl]-2-benzothiazolyl]carbamic acid, 1,1-dimethylethyl ester;

[6-[[(2-Chloro-6-methylphenyl)amino]carbonyl]-2-benzothiazolyl]carbamic acid, 1,1-dimethylethyl ester;

[6-[[(2,6-Dimethylphenyl)amino]carbonyl]-2-benzothiazolyl]carbamic acid, 1,1-dimethylethyl ester;

[6-[[(4-Bromo-2-methylphenyl)amino]carbonyl]-2-benzothiazolyl]carbamic acid, 1,1-dimethylethyl ester;

[6-[[(3-Bromo-2,4,6-trimethylphenyl)amino]carbonyl]-2-benzothiazolyl]carbamic acid, 1,1-dimethylethyl ester;

[6-[[[2,6-Dimethyl-3-(1-methylethyl)phenyl]amino]carbonyl]-2-benzothiazolyl]carbamic acid, 1,1-dimethylethyl ester;

[6-[[(2-Bromo-4,6-dimethylphenyl)amino]carbonyl]-2-benzothiazolyl]carbamic acid, 1,1-dimethylethyl ester;

[6-[[(2-Methyl-6-quinolinyl)amino]carbonyl]-2-benzothiazolyl]carbamic acid, 1,1-dimethylethyl ester;

[6-[[(4-Methoxy-2-naphthalenyl)amino]carbonyl]-2-benzothiazolyl]carbamic acid, 1,1-dimethylethyl ester;

[6-[[(6-Methyl-5-quinolinyl)amino]carbonyl]-2-benzothiazolyl]carbamic acid, 1,1-dimethylethyl ester;

[6-[[[2-(2-Hydroxyethyl)-6-methylphenyl]amino]carbonyl]-2-benzothiazolyl]carbamic acid, 1,1-dimethylethyl ester;

[6-[[(2,6-Dimethyl-3-nitrophenyl)amino]carbonyl]-2-benzothiazolyl]carbamic acid, 1,1-dimethylethyl ester;

[6-[[(2-Bromo-3,4,6-trimethylphenyl)amino]carbonyl]-2-benzothiazolyl]carbamic acid, 1,1-dimethylethyl ester;

[6-[[(2-Acetyl-6-hydroxyphenyl)amino]carbonyl]-2-benzothiazolyl]carbamic acid, 1,1-dimethylethyl ester;

[6-[[[4-[[(1,1-Dimethylethoxy)carbonyl]amino]-2,3,5,6-tetramethylphenyl]amino]carbonyl]-2-benzothiazolyl]carbamic acid, 1,1-dimethylethyl ester;

[6-[[(4-Bromo-2,6-dimethylphenyl)amino]carbonyl]-2-benzothiazolyl]carbamic acid, 1,1-dimethylethyl ester;

[6-[[[3-Acetylamino]-4,6-dimethylphenyl]amino]carbonyl]-2-benzothiazolyl]carbamic acid, 1,1-dimethylethyl ester;

[6-[[(2,6-Dimethoxyphenyl)amino]carbonyl]-2-benzothiazolyl]carbamic acid, 1,1-dimethylethyl ester;

[6-[[(2-Methyl-1-naphthalenyl)amino]carbonyl]-2-benzothiazolyl]carbamic acid, 1,1-dimethylethyl ester;

3-[[[2-[[(1,1-Dimethylethoxy)carbonyl]amino]-6-benzothiazolyl]carbonyl]amino]-4-methyl-2-thiophenecarboxylic acid, methyl ester;

[6-[[(2,4,6-Trimethylphenyl)amino]carbonyl]-2-benzothiazolyl]carbamic acid, methyl ester;

2-[[(Acetylamino)acetyl]amino]-N-(2,4,6-trimethylphenyl)-6-benzothiazolecarboxamide;

N-(2-Chloro-6-methylphenyl)-2-[[[(1,1-dimethylethyl)amino]carbonyl]amino]-6-benzothiazolecarboxamide;

N-(2,6-Dichlorophenyl)-2-[[[(1,1-dimethylethyl)amino]carbonyl]amino]-6-benzothiazolecarboxamide;

N-(4-Bromo-2,6-dimethylphenyl)-2-[[[(1,1-dimethylethyl)amino]carbonyl]amino]-6-benzothiazolecarboxamide;

N-(4-Carbomethoxy-2,6-Dimethylphenyl)-2-[[[1,1-dimethylethoxy]carbonyl]amino]-6-benzothiazolecarboxamide;

N-(4-Hydroxymethyl-2,6-Dimethylphenyl)-2-[[[1,1-dimethylethoxy]carbonyl]amino]-6-benzothiazolecarboxamide;

[4-Methyl-6-[[(2,4,6-trimethylphenyl)amino]carbonyl]-2-benzothiazolyl]carbamic acid, 1,1-dimethylethyl ester;

2-Amino-4-methyl-N-(2,4,6-trimethylphenyl)-6-benzothiazolecarboxamide, trifluoroacetate (1:1);

4-Methoxy-[6-[[(2,4,6-trimethylphenyl)amino]carbonyl]-2-benzothiazolyl]carbamic acid, 1,1-dimethylethyl ester;

2-Amino-4-methoxy-N-(2,4,6-trimethylphenyl)-6-benzothiazolecarboxamide, trifluoroacetate (1:1);

2-[[(Methylamino)carbonyl]amino]-N-(2,4,6-trimethylphenyl)-6-benzothiazolecarboxamide;

2-[[[Methylamino]carbonyl]amino]-4-methoxy-N-(2,4,6-trimethylphenyl)-6-benzothiazolecarboxamide;

5-Methoxy-[6-[[(2,4,6-trimethylphenyl)amino]carbonyl]-2-benzothiazolyl]carbamic acid, 1,1-dimethylethyl ester;

2-Amino-N-(4-N,N-dimethylamino-2,3,5,6-tetramethylphenyl)-6-benzothiazolecarboxamide, trifluoroacetate (1:1);

5-Chloro-[6-[[(2,4,6-trimethylphenyl)amino]carbonyl]-2-benzothiazolyl]carbamic acid, 1,1-dimethylethyl ester;

7-Chloro-[6-[[(2,4,6-trimethylphenyl)amino]carbonyl]-2-benzothiazolyl]carbamic acid, 1,1-dimethylethyl ester;

2-Amino-5-hydroxy-N-[2,4,6-trimethylphenyl]-6-benzothiazolecarboxamide;

5-tert-Butoxycarbonyloxy-[6-[[(2,4,6-trimethylphenyl) amino]carbonyl]-2-benzothiazolyl]carbamic acid, 1,1-dimethylethyl ester;

2-[[[(1,1-Dimethylethyl)amino]carbonyl]amino]-N-(2,6-dimethylphenyl)-6-benzothiazolecarboxamide;

2-[[(Cyclopropylamino)carbonyl]amino]-N-(2,6-dimethylphenyl)-6-benzothiazolecarboxamide;

2-[[(Cyclopentylamino)carbonyl]amino]-N-(2,6-dimethylphenyl)-6-benzothiazolecarboxamide;

2-[[[[1-(ethynyl)cyclohexyl]amino]carbonyl]amino]-N-(2,6-dimethylphenyl)-6-benzothiazolecarboxamide;

2-[[[(4-Methyl-cyclohexyl)amino]carbonyl]amino]-N-(2,6-dimethylphenyl)-6-benzothiazolecarboxamide;

2-[[[(2,3-Dihydro-1H-inden-1-yl)amino]carbonyl]amino]-N-(2,6-dimethylphenyl)-6-benzothiazolecarboxamide;

2-[[[[2-(1H-Imidazol-4-yl)ethyl]amino]carbonyl]amino]-N-(2,6-dimethylphenyl)-6-benzothiazolecarboxamide;

2-[[[[(Tetrahydro-2-furanyl)methyl]amino]carbonyl]amino]-N-(2,6-dimethylphenyl)-6-benzothiazolecarboxamide;

2-[[[[2-(5-Methoxy-1H-indol-3-yl)ethyl]amino]carbonyl]amino]-N-(2,6-dimethylphenyl)-6-benzothiazolecarboxamide;

2-[[[(1,1-Dimethyl-2-hydroxyethyl)amino]carbonyl]amino]-N-(2,6-dimethylphenyl)-6-benzothiazolecarboxamide;

2-[[[(1,1-Dimethyl-propyl)amino]carbonyl]amino]-N-(2,6-dimethylphenyl)-6-benzothiazolecarboxamide;

2-[[[[(3-Methoxyphenyl)methyl]amino]carbonyl]amino]-N-(2,6-dimethylphenyl)-6-benzothiazolecarboxamide;

2-[[[[(4-Methoxyphenyl)methyl]amino]carbonyl]amino]-N-(2,6-dimethylphenyl)-6-benzothiazolecarboxamide;

2-[[(2-Propynylamino)carbonyl]amino]-N-(2,6-dimethylphenyl)-6-benzothiazolecarboxamide;

2-[[(2-Propenylamino)carbonyl]amino]-N-(2,6-dimethylphenyl)-6-benzothiazolecarboxamide;

2-[[[(3-Phenylpropyl)amino]carbonyl]amino]-N-(2,6-dimethylphenyl)-6-benzothiazolecarboxamide;

2-[[[[1-(Hydroxymethyl)cyclopentyl]amino]carbonyl]amino]-N-(2,6-dimethylphenyl)-6-benzothiazolecarboxamide;

2-[[[[1-(Methoxymethyl)propyl]amino]carbonyl]amino]-N-(2,6-dimethylphenyl)-6-benzothiazolecarboxamide;

(R)-2-[[[(1-Phenylethyl)amino]carbonyl]amino]-N-(2,6-dimethylphenyl)-6-benzothiazolecarboxamide;

2-[[[(3,4,5-Trimethoxyphenyl)amino]carbonyl]amino]-N-(2,6-dimethylphenyl)-6-benzothiazolecarboxamide;

2-[[(1,3-Benzodioxol-5-ylamino)carbonyl]amino]-N-(2,6-dimethylphenyl)-6-benzothiazolecarboxamide;

2-[[[(4-Fluorophenyl)amino]carbonyl]amino]-N-(2,6-dimethylphenyl)-6-benzothiazolecarboxamide;

2-[[(Cyclopropylamino)carbonyl]amino]-N-(2-chloro-6-methylphenyl)-6-benzothiazolecarboxamide;

2-[[(Cyclopentylamino)carbonyl]amino]-N-(2-chloro-6-methylphenyl)-6-benzothiazolecarboxamide;

2-[[[[1-(ethynyl)cyclohexyl]amino]carbonyl]amino]-N-(2-chloro-6-methylphenyl)-6-benzothiazolecarboxamide;

2-[[[(4-Methyl-cyclohexyl)amino]carbonyl]amino]-N-(2-chloro-6-methylphenyl)-6-benzothiazolecarboxamide;

2-[[[(2,3-Dihydro-1H-inden-1-yl)amino]carbonyl]amino]-N-(2-chloro-6-methylphenyl)-6-benzothiazolecarboxamide;

2-[[[[2-(1H-Imidazol-4-yl)ethyl]amino]carbonyl]amino]-N-(2-chloro-6-methylphenyl)-6-benzothiazolecarboxamide;

2-[[[[(Tetrahydro-2-furanyl)methyl]amino]carbonyl]amino]-N-(2-chloro-6-methylphenyl)-6-benzothiazolecarboxamide;

2-[[[[2-(5-Methoxy-1H-indol-3-yl)ethyl]amino]carbonyl]amino]-N-(2-chloro-6-methylphenyl)-6-benzothiazolecarboxamide;

2-[[[(1,1-Dimethyl-2-hydroxyethyl)amino]carbonyl]amino]-N-(2-chloro-6-methylphenyl)-6-benzothiazolecarboxamide;

2-[[[(1,1-Dimethyl-propyl)amino]carbonyl]amino]-N-(2-chloro-6-methylphenyl)-6-benzothiazolecarboxamide;

2-[[[[(3-Methoxyphenyl)methyl]amino]carbonyl]amino]-N-(2-chloro-6-methylphenyl)-6-benzothiazolecarboxamide;

2-[[[[(4-Methoxyphenyl)methyl]amino]carbonyl]amino]-N-(2-chloro-6-methylphenyl)-6-benzothiazolecarboxamide;

2-[[(2-Propynylamino)carbonyl]amino]-N-(2-chloro-6-methylphenyl)-6-benzothiazolecarboxamide;

2-[[(2-Propenylamino)carbonyl]amino]-N-(2-chloro-6-methylphenyl)-6-benzothiazolecarboxamide;

2-[[[(3-Phenylpropyl)amino]carbonyl]amino]-N-(2-chloro-6-methylphenyl)-6-benzothiazolecarboxamide;

2-[[[[1-(Hydroxymethyl)cyclopentyl]amino]carbonyl]amino]-N-(2-chloro-6-methylphenyl)-6-benzothiazolecarboxamide;

2-[[[[1-(Methoxymethyl)propyl]amino]carbonyl]amino]-N-(2-chloro-6-methylphenyl)-6-benzothiazolecarboxamide;

(R)-2-[[[(1-Phenylethyl)amino]carbonyl]amino]-N-(2-chloro-6-methylphenyl)-6-benzothiazolecarboxamide;

2-[[[(2,3-Dimethyl-1H-indol-5-yl)amino]carbonyl]amino]-N-(2-chloro-6-methylphenyl)-6-benzothiazolecarboxamide;

2-[[[(3,4,5-Trimethoxyphenyl)amino]carbonyl]amino]-N-(2-chloro-6-methylphenyl)-6-benzothiazolecarboxamide;

2-[[(1,3-Benzodioxol-5-ylamino)carbonyl]amino]-N-(2-chloro-6-methylphenyl)-6-benzothiazolecarboxamide;

2-[[[(4-Fluorophenyl)amino]carbonyl]amino]-N-(2-chloro-6-methylphenyl)-6-benzothiazolecarboxamide;

2-[[[[(1-methoxycarbonyl)cyclopropyl]amino]carbonyl]amino-N-(2,4,6-trimethylphenyl)-6-benzothiazolecarboxamide;

[6-[[[(2,6-Dimethyl-4-phenyl)phenyl]amino]carbonyl]-2-benzothiazolyl]carbamic acid, 1,1-dimethylethyl ester;

[6-[[[(2,6-Dimethyl-4-(2-N,N-dimethylethoxy)phenyl]amino]carbonyl]-2-benzothiazolyl]carbamic acid, 1,1-dimethylethyl ester;

[6-[[[(2,6-Dimethyl-4-(2-morpholinoethoxy)phenyl]amino]carbonyl]-2-benzothiazolyl]carbamic acid, 1,1-dimethylethyl ester;

2-[(Cyclopropylcarbonyl)amino]-N-(2-chloro-6-methylphenyl)-6-benzothiazolecarboxamide;

2-[(2-Methyl-cyclopropylcarbonyl)amino]-N-(2-chloro-6-methylphenyl)-6-benzothiazolecarboxamide;

2-[(2,2-Dichloro-1-methyl-cyclopropylcarbonyl)amino]-N-(2-chloro-6-methylphenyl)-6-benzothiazolecarboxamide;

2-[(1-Hydroxy-cyclopropylcarbonyl)amino]-N-(2-chloro-6-methylphenyl)-6-benzothiazolecarboxamide;

N-(2-Chloro-6-methylphenyl)-2-[(cyclobutylcarbonyl) amino]-6-benzothiazolecarboxamide;

N-(2-Chloro-6-methylphenyl)-2-[(cyclopentylcarbonyl) amino]-6-benzothiazolecarboxamide;

N-(2-Chloro-6-methylphenyl)-2-[(cyclohexylacetyl) amino]-6-benzothiazolecarboxamide;

N-(2-Chloro-6-methylphenyl)-2-[(methoxyacetyl) amino]-6-benzothiazolecarboxamide;

N-(2-Chloro-6-methylphenyl)-2-[(1-oxo-2-phenylpropyl) amino]-6-benzothiazolecarboxamide;

N-(2-Chloro-6-methylphenyl)-2-[(1-oxo-2-methylpropyl)amino]-6-benzothiazolecarboxamide;

N-(2-Chloro-6-methylphenyl)-2-[(1-oxo-3-phenylpropyl) amino]-6-benzothiazolecarboxamide;

N-(2-Chloro-6-methylphenyl)-2-[[3-(2-methoxyphenyl)-1-oxopropyl]amino]-6-benzothiazolecarboxamide;

N-(2-Chloro-6-methylphenyl)-2-[[1-oxo-3-(2,3,4-trimethoxyphenyl)propyl]amino]-6-benzothiazolecarboxamide;

N-(2-Chloro-6-methylphenyl)-2-[(1,4-dioxopentyl) amino]-6-benzothiazolecarboxamide;

N-(2-Chloro-6-methylphenyl)-2-[(2,2-dimethyl-1-oxobutyl)amino]-6-benzothiazolecarboxamide;

2-[[(2-Chloro-6-fluorophenyl)acetyl]amino]-N-(2-chloro-6-methylphenyl)-6-benzothiazolecarboxamide;

N-(2-Chloro-6-methylphenyl)-2-[[(2-methylphenyl) acetyl]amino]-6-benzothiazolecarboxamide;

N-(2-Chloro-6-methylphenyl)-2-[[(3-methoxyphenyl) acetyl]amino]-6-benzothiazolecarboxamide;

N-(2-Chloro-6-methylphenyl)-2-[[(4-chlorophenyl) acetyl]amino]-6-benzothiazolecarboxamide;

N-(2-Chloro-6-methylphenyl)-2-[(1-oxo-4-pentynyl) amino]-6-benzothiazolecarboxamide;

5-[[6-[[(2-Chloro-6-methylphenyl)amino]carbonyl]-2-benzothiazolyl]amino]-5-oxopentanoic acid methyl ester;

N-(2-Chloro-6-methylphenyl)-2-[(1-oxohexyl)amino]-6-benzothiazolecarboxamide;

N-(2-Chloro-6-methylphenyl)-2-[[3-(3-methoxyphenyl)-1-oxopropyl]amino]-6-benzothiazolecarboxamide;

2-[[(1,3-Benzodioxol-5-yl)acetyl]amino]-N-(2-chloro-6-methylphenyl)-6-benzothiazolecarboxamide; 2-[[3-(1,3-Benzodioxol-5-yl)-1-oxopropyl;]amino]-N-(2-chloro-6-methylphenyl)-6-benzothiazolecarboxamide;

N-(2-Chloro-6-methylphenyl)-2-[[(3,5-dimethoxyphenyl)acetyl]amino]-6-benzothiazolecarboxamide;

N-(2-Chloro-6-methylphenyl)-2-[(cyclopropylacetyl) amino]-6-benzothiazolecarboxamide;

N-(2-Chloro-6-methylphenyl)-2-[[(1-methylcyclopropyl) carbonyl]amino]-6-benzothiazolecarboxamide;

N-(2-Chloro-6-methylphenyl)-2-[[[2-(trimethylsilyl) cyclopropyl]carbonyl]amino]-6-benzothiazolecarboxamide;

N-(2-Chloro-6-methylphenyl)-2-[[[1-(4-methoxyphenyl) cyclopropyl]carbonyl]amino]-6-benzothiazolecarboxamide;

trans-N-(2-Chloro-6-methylphenyl)-2-[[(2-phenylcyclopropyl)carbonyl]amino]-6-benzothiazolecarboxamide;

N-(2-Chloro-6-methylphenyl)-2-[[[1-(4-methylphenyl) cyclopropyl]carbonyl]amino]-6-benzothiazolecarboxamide;

N-(2-Chloro-6-methylphenyl)-2-[[[1-(4-chlorophenyl) cyclopropyl]carbonyl]amino]-6-benzothiazolecarboxamide;

[1-[[[6-[[(2-Chloro-6-methylphenyl)amino]carbonyl]-2-benzothiazolyl]amino]carbonyl]cyclopropyl]carbamic acid 1,1-dimethylethyl ester;

(1S-trans)-N-(2-Chloro-6-methylphenyl)-2-[[[2,2-dimethyl-3-(2-methyl-1-propenyl)cyclopropyl] carbonyl]amino]-6-benzothiazolecarboxamide;

(1S-cis)-N-(2-Chloro-6-methylphenyl)-2-[[[2,2-dimethyl-3-(2-methyl-1-propenyl)cyclopropyl] carbonyl]amino]-6-benzothiazolecarboxamide;

N-(2-Chloro-6-methylphenyl)-2-[[(1-phenylcyclopropyl) carbonyl]amino]-6-benzothiazolecarboxamide;

N-(2-Chloro-6-methylphenyl)-2-[[(2-formylcyclopropyl) carbonyl]amino]-6-benzothiazolecarboxamide;

2-[[[6-[[(2-Chloro-6-methylphenyl)amino]carbonyl]-2-benzothiazolyl]amino]carbonyl]cyclopropanecarboxylic acid ethyl ester;

2-[[[6-[[(2-Chloro-6-methylphenyl)amino]carbonyl]-2-benzothiazolyl]amino]carbonyl]-1-methylcyclopropanecarboxylic acid methyl ester;

N-(2-Chloro-6-methylphenyl)-2-[[[2-(phenylmethyl) cyclopropyl]carbonyl]amino]-6-benzothiazolecarboxamide;

N-[6-[[(2-Chloro-6-methylphenyl)amino]carbonyl]-2-benzothiazolyl]-2-quinolinecarboxamide;

N-(2-Chloro-6-methylphenyl)-2-[(2-pyridinylcarbonyl) amino]-6-benzothiazolecarboxamide;

N-(2-Chloro-6-methylphenyl)-2-[(2-pyridinylcarbonyl) amino]-6-benzothiazolecarboxamide, 1-oxide;

trans-N-(2-Chloro-6-methylphenyl)-2-[[[2-[(dimethylamino)methyl]cyclopropyl]carbonyl] amino]-6-benzothiazolecarboxamide;

N-(2-Chloro-6-methylphenyl)-2-[[(1-methyl-1H-pyrrol-2-yl)acetyl]amino]-6-benzothiazolecarboxamide;

N-(2-Chloro-6-methylphenyl)-2-[[5-(dimethylamino)-1-oxopentyl]amino]-6-benzothiazolecarboxamide;

N-(2-Chloro-6-methylphenyl)-2-[[4-(dimethylamino)-1-oxobutyl]amino]-6-benzothiazolecarboxamide;

trans-N-(2-Chloro-6-methylphenyl)-2-[[[2-(1-pyrrolidinylmethyl)cyclopropyl]carbonyl]amino]-6-benzothiazolecarboxamide;

trans-N-(2-Chloro-6-methylphenyl)-2-[[[2-(1-piperidinylmethyl)cyclopropyl]carbonyl]amino]-6-benzothiazolecarboxamide;

N-(2-Chloro-6-methylphenyl)-2-[[(dimethylamino) acetyl]amino]-6-benzothiazolecarboxamide;

N-(2-Chloro-6-methylphenyl)-2-[[3-(2-methyl-4-nitro-1H-imidazol-1-yl)-1-oxopropyl]amino]-6-benzothiazolecarboxamide;

2-[(Cyclobutylcarbonyl)amino]-N-(2,6-dimethylphenyl)-6-benzothiazolecarboxamide;

2-[(Cyclopentylcarbonyl)amino]-N-(2,6-dimethylphenyl)-6-benzothiazolecarboxamide;

2-[(Cyclohexylacetyl)amino]-N-(2,6-dimethylphenyl)-6-benzothiazolecarboxamide;

N-(2,6-Dimethylphenyl)-2-[(1-oxo-2-phenylpropyl) amino]-6-benzothiazolecarboxamide;

N-(2,6-Dimethylphenyl)-2-[(2-methyl-1-oxopropyl) amino]-6-benzothiazolecarboxamide;

N-(2,6-Dimethylphenyl)-2-[(1-oxo-3-phenylpropyl) amino]-6-benzothiazolecarboxamide;

N-(2,6-Dimethylphenyl)-2-[[3-(2-methoxyphenyl)-1-oxopropyl]amino]-6-benzothiazolecarboxamide;
N-(2,6-Dimethylphenyl)-2-[[3-(2,3,4-trimethoxyphenyl)-1-oxopropyl]amino]-6-benzothiazolecarboxamide;
N-(2,6-Dimethylphenyl)-2-[(1,4-dioxopentyl)amino]-6-benzothiazolecarboxamide;
2-[(2,2-Dimethyl-1-oxobutyl)amino]-N-(2,6-dimethylphenyl)-6-benzothiazolecarboxamide;
N-(2,6-Dimethylphenyl)-2-[(methoxyacetyl)amino]-6-benzothiazolecarboxamide;
N,N-Dimethyl-N'-[6-[[(2,6-dimethylphenyl)amino]carbonyl]-2-benzothiazolyl]butanediamide;
N-(2,6-Dimethylphenyl)-2-[[(1-methylcyclopropyl)carbonyl]amino]-6-benzothiazolecarboxamide;
2-[[(2-Chloro-6-fluorophenyl)acetyl]amino]-N-(2,6-dimethylphenyl)-6-benzothiazolecarboxamide;
N-(2,6-Dimethylphenyl)-2-[[(2-methylphenyl)acetyl]amino]-6-benzothiazolecarboxamide;
N-(2,6-Dimethylphenyl)-2-[[(3-methoxyphenyl)acetyl]amino]-6-benzothiazolecarboxamide;
2-[[(4-Chlorophenyl)acetyl]amino]-N-(2,6-dimethylphenyl)-6-benzothiazolecarboxamide;
N-(2,6-Dimethylphenyl)-2-[(1-oxo-4-pentynyl)amino]-6-benzothiazolecarboxamide;
N-(2,6-Dimethylphenyl)-2-[(1-oxohexyl)amino]-6-benzothiazolecarboxamide;
N-(2,6-Dimethylphenyl)-2-[[3-(3-methoxyphenyl)-1-oxopropyl]amino]-6-benzothiazolecarboxamide;
2-[[3-(1,3-Benzodioxol-5-yl)-1-oxopropyl]amino]-N-(2,6-dimethylphenyl)-6-benzothiazolecarboxamide;
2-[[(1,3-Benzodioxol-5-yl)acetyl]amino]-N-(2,6-dimethylphenyl)-6-benzothiazolecarboxamide;
2-[[(3,5-Dimethoxyphenyl)acetyl]amino]-N-(2,6-dimethylphenyl)-6-benzothiazolecarboxamide;
2-[(Cyclopropylacetyl)amino]-N-(2,6-dimethylphenyl)-6-benzothiazolecarboxamide;
N-(2,6-Dimethylphenyl)-2-[[[2-(phenylmethyl)cyclopropyl]carbonyl]amino]-6-benzothiazolecarboxamide;
N-(2,6-Dimethylphenyl)-2-[[[2-(trimethylsilyl)cyclopropyl]carbonyl]amino]-6-benzothiazolecarboxamide;
2-[(Cyclopropylcarbonyl)amino]-N-(2,6-dimethylphenyl)-6-benzothiazolecarboxamide;
N-(2,6-Dimethylphenyl)-2-[[(2-methylcyclopropyl)carbonyl]amino]-6-benzothiazolecarboxamide;
trans-N-(2,6-Dimethylphenyl)-2-[[(2-phenylcyclopropyl)carbonyl]amino]-6-benzothiazolecarboxamide;
N-(2,6-Dimethylphenyl)-2-[[[1-(4-methylphenyl)cyclopropyl]carbonyl]amino]-6-benzothiazolecarboxamide;
2-[[[1-(4-Chlorophenyl)cyclopropyl]carbonyl]amino]-N-(2,6-dimethylphenyl)-6-benzothiazolecarboxamide;
[1-[[[6-[[(2,6-Dimethylphenyl)amino]carbonyl]-2-benzothiazolyl]amino]carbonyl]cyclopropyl]carbamic acid 1,1-dimethylethyl ester;
(1S-cis)-2-[[[2,2-Dimethyl-3-(2-methyl-1-propenyl)cyclopropyl]carbonyl]amino]-N-(2,6-dimethylphenyl)-6-benzothiazolecarboxamide;
N-(2,6-Dimethylphenyl)-2-[[[1-(4-methoxyphenyl)cyclopropyl]carbonyl]amino]-6-benzothiazolecarboxamide;
N-(2,6-Dimethylphenyl)-2-[[(1-phenylcyclopropyl)carbonyl]amino]-6-benzothiazolecarboxamide;
N-(2,6-Dimethylphenyl)-2-[[(2-formylcyclopropyl)carbonyl]amino]-6-benzothiazolecarboxamide;
2-[[[6-[[(2,6-Dimethylphenyl)amino]carbonyl]-2-benzothiazolyl]amino]carbonyl]cyclopropanecarboxylic acid ethyl ester;
2-[[(2-Cyanocyclopropyl)carbonyl]amino]-N-(2,6-dimethylphenyl)-6-benzothiazolecarboxamide;
2-[[[6-[[(2,6-Dimethylphenyl)amino]carbonyl]-2-benzothiazolyl]amino]carbonyl]-1-methylcyclopropanecarboxylic acid methyl ester;
(1S-trans)-2-[[[2,2-Dimethyl-3-(2-methyl-1-propenyl)cyclopropyl]carbonyl]amino]-N-(2,6-dimethylphenyl)-6-benzothiazolecarboxamide;
N-(2,4,6-Trimethylphenyl)-2-[[[2-(trimethylsilyl)cyclopropyl]carbonyl]amino]-6-benzothiazolecarboxamide;
2-[[(2-Methylcyclopropyl)carbonyl]amino]-N-(2,4,6-trimethylphenyl)-6-benzothiazolecarboxamide;
trans-2-[[(2-Phenylcyclopropyl)carbonyl]amino]-N-(2,4,6-trimethylphenyl)-6-benzothiazolecarboxamide;
2-[[[6-[[(2,4,6-Trimethylphenyl)amino]carbonyl]-2-benzothiazolyl]amino]carbonyl]cyclopropanecarboxylic acid ethyl ester;
[1-[[[6-[[(2,4,6-Trimethylphenyl)amino]carbonyl]-2-benzothiazolyl]amino]carbonyl]cyclopropyl]carbamic acid 1,1-dimethylethyl ester;
(1S-trans)-2-[[[2,2-Dimethyl-3-(2-methyl-1-propenyl)cyclopropyl]carbonyl]amino]-N-(2,4,6-trimethylphenyl)-6-benzothiazolecarboxamide;
(1S-cis)-2-[[[2,2-Dimethyl-3-(2-methyl-1-propenyl)cyclopropyl]carbonyl]amino]-N-(2,4,6-trimethylphenyl)-6-benzothiazolecarboxamide;
2-[[(1-Phenylcyclopropyl)carbonyl]amino]-N-(2,4,6-trimethylphenyl)-6-benzothiazolecarboxamide;
2-[[(2-Formylcyclopropyl)carbonyl]amino]-N-(2,4,6-trimethylphenyl)-6-benzothiazolecarboxamide;
2-[[(2-Cyanocyclopropyl)carbonyl]amino]-N-(2,4,6-trimethylphenyl)-6-benzothiazolecarboxamide;
2-[[[6-[[(2,4,6-Trimethylphenyl)amino]carbonyl]-2-benzothiazolyl]amino]carbonyl]-1-methylcyclopropanecarboxylic acid methyl ester;
2-[[[2-(Phenylmethyl)cyclopropyl]carbonyl]amino]-N-(2,4,6-trimethylphenyl)-6-benzothiazolecarboxamide;
2-[[[1-(4-Methylphenyl)cyclopropyl]carbonyl]amino]-N-(2,4,6-trimethylphenyl)-6-benzothiazolecarboxamide;
2-[[[1-(4-Chlorophenyl)cyclopropyl]carbonyl]amino]-N-(2,4,6-trimethylphenyl)-6-benzothiazolecarboxamide;
2-[[[1-(4-Methoxyphenyl)cyclopropyl]carbonyl]amino]-N-(2,4,6-trimethylphenyl)-6-benzothiazolecarboxamide;
N-(2-Chloro-6-methylphenyl)-2-[[[[2-(1-piperidinyl)ethyl]amino]carbonyl]amino]-6-benzothiazolecarboxamide;
N-(2-Chloro-6-methylphenyl)-2-[[[[(2-chlorophenyl)methyl]amino]carbonyl]amino]-6-benzothiazolecarboxamide;
N-(2-Chloro-6-methylphenyl)-2-[[[[(2-fluorophenyl)methyl]amino]carbonyl]amino]-6-benzothiazolecarboxamide;
N-(2-Chloro-6-methylphenyl)-2-[[((2-phenoxyethyl)amino]carbonyl]amino]-6-benzothiazolecarboxamide;

2-[[[(Benzo[b]thiophen-3-ylmethyl)amino]carbonyl]amino]-N-(2-chloro-6-methylphenyl)-6-benzothiazolecarboxamide;

(R)-N-(2-Chloro-6-methylphenyl)-2-[[[(2-hydroxy-1-phenylethyl)amino]carbonyl]amino]-6-benzothiazolecarboxamide;

N-(2-Chloro-6-methylphenyl)-2-[[[[[4-(dimethylamino)phenyl]methyl]amino]carbonyl]amino]-6-benzothiazolecarboxamide;

(S)-N-(2-Chloro-6-methylphenyl)-2-[[[(2-hydroxy-1-phenylethyl)amino]carbonyl]amino]-6-benzothiazolecarboxamide;

N-(2-Chloro-6-methylphenyl)-2-[[[[(4-nitrophenyl)methyl]amino]carbonyl]amino]-6-benzothiazolecarboxamide;

N-(2-Chloro-6-methylphenyl)-2-[[[[2-(1-pyrrolidinyl)ethyl]amino]carbonyl]amino]-6-benzothiazolecarboxamide;

N-(2-Chloro-6-methylphenyl)-2-[[[[[4-(trifluoromethoxy)phenyl]methyl]amino]carbonyl]amino]-6-benzothiazolecarboxamide;

N-(2-Chloro-6-methylphenyl)-2-[[[[2-(2-pyridinyl)ethyl]amino]carbonyl]amino]-6-benzothiazolecarboxamide;

N-(2-Chloro-6-methylphenyl)-2-[[[(2-N-(2-Chloro-6-methylphenyl)-2-[[[(3-pyridinylmethyl)amino]carbonyl]amino]-6-benzothiazolecarboxamide;

N-(2-Chloro-6-methylphenyl)-2-[[[(4-pyridinylmethyl)amino]carbonyl]amino]-6-benzothiazolecarboxamide;

N-(2-Chloro-6-methylphenyl)-2-[[[[(3-chlorophenyl)methyl]amino]carbonyl]amino]-6-benzothiazolecarboxamide;

N-(2-Chloro-6-methylphenyl)-2-[[[[(2,3-dichlorophenyl)methyl]amino]carbonyl]amino]-6-benzothiazolecarboxamide;

N-(2-Chloro-6-methylphenyl)-2-[[[[(3,4-difluorophenyl)methyl]amino]carbonyl]amino]-6-benzothiazolecarboxamide;

N-(2-Chloro-6-methylphenyl)-2-[[[[(2,6-dimethoxyphenyl)methyl]amino]carbonyl]amino]-6-benzothiazolecarboxamide;

N-(2-Chloro-6-methylphenyl)-2-[[[[(2-ethoxyphenyl)methyl]amino]carbonyl]amino]-6-benzothiazolecarboxamide;

N-(2-Chloro-6-methylphenyl)-2-[[[[(2,3-dihydro-1,4-benzodioxin-2-yl)methyl]amino]carbonyl]amino]-6-benzothiazolecarboxamide;

N-(2-Chloro-6-methylphenyl)-2-[[[[2-(3-methoxyphenyl)ethyl]amino]carbonyl]amino]-6-benzothiazolecarboxamide;

N-(2-Chloro-6-methylphenyl)-2-[[[[2-(4-methoxyphenyl)ethyl]amino]carbonyl]amino]-6-benzothiazolecarboxamide;

N-(2-Chloro-6-methylphenyl)-2-[[[[(2-methylphenyl)methyl]amino]carbonyl]amino]-6-benzothiazolecarboxamide;

N-(2-Chloro-6-methylphenyl)-2-[[[[(3-methylphenyl)methyl]amino]carbonyl]amino]-6-benzothiazolecarboxamide;

N-(2-Chloro-6-methylphenyl)-2-[[[[(5-methyl-2-furanyl)methyl]amino]carbonyl]amino]-6-benzothiazolecarboxamide;

(S)-N-(2-Chloro-6-methylphenyl)-2-[[[[1-(hydroxymethyl)-2-phenylethyl]amino]carbonyl]amino]-6-benzothiazolecarboxamide;

N-(2-Chloro-6-methylphenyl)-2-[[[[2-(phenylamino)ethyl]amino]carbonyl]amino]-6-benzothiazolecarboxamide;

N-(2-Chloro-6-methylphenyl)-2-[[[(2-thienylmethyl)amino]carbonyl]amino]-6-benzothiazolecarboxamide;

N-(2-Chloro-6-methylphenyl)-2-[[[[2-(1H-indol-3-yl)ethyl]amino]carbonyl]amino]-6-benzothiazolecarboxamide;

2-[[[[(4-Aminophenyl)methyl]amino]carbonyl]amino]-N-(2-chloro-6-methylphenyl)-6-benzothiazolecarboxamide;

N-(2-Chloro-6-methylphenyl)-2-[[[(diphenylmethyl)amino]carbonyl]amino]-6-benzothiazolecarboxamide;

(1R-exo)-2-[[(Bicyclo[2.2.1]heptan-2-ylamino)carbonyl]amino]-N-(2-chloro-6-methylphenyl)-6-benzothiazolecarboxamide;

N-(2-Chloro-6-methylphenyl)-2-[[[[(4-chlorophenyl)methyl]amino]carbonyl]amino]-6-benzothiazolecarboxamide;

N-(2-Chloro-6-methylphenyl)-2-[[[[1-(4-chlorophenyl)ethyl]amino]carbonyl]amino]-6-benzothiazolecarboxamide;

(R)-N-(2-Chloro-6-methylphenyl)-2-[[[[1-(4-methylphenyl)ethyl]amino]carbonyl]amino]-6-benzothiazolecarboxamide;

(S)-N-(2-Chloro-6-methylphenyl)-2-[[[[1-(4-methylphenyl)ethyl]amino]carbonyl]amino]-6-benzothiazolecarboxamide;

N-(2-Chloro-6-methylphenyl)-2-[[[[(4-fluorophenyl)methyl]amino]carbonyl]amino]-6-benzothiazolecarboxamide;

N-(2-Chloro-6-methylphenyl)-2-[[[[1-(4-fluorophenyl)ethyl]amino]carbonyl]amino]-6-benzothiazolecarboxamide;

N-(2-Chloro-6-methylphenyl)-2-[[[(2-furanylmethyl)amino]carbonyl]amino]-6-benzothiazolecarboxamide;

N-(2-Chloro-6-methylphenyl)-2-[[[[1-(4-methoxyphenyl)ethyl]amino]carbonyl]amino]-6-benzothiazolecarboxamide;

(S)-N-(2-Chloro-6-methylphenyl)-2-[[[(1-phenylethyl)amino]carbonyl]amino]-6-benzothiazolecarboxamide;

□-[[[[6-[[(2-Chloro-6-methylphenyl)amino]carbonyl]-2-benzothiazolyl]amino]carbonyl]amino]benzeneacetic acid ethyl ester;

N-(2-Chloro-6-methylphenyl)-2-[[[[2-(4-methylphenyl)-1-phenylethyl]amino]carbonyl]amino]-6-benzothiazolecarboxamide;

(R)-N-(2-Chloro-6-methylphenyl)-2-[[[(1-phenylpropyl)amino]carbonyl]amino]-6-benzothiazolecarboxamide;

N-(2-Chloro-6-methylphenyl)-2-[[[[(4-methylphenyl)methyl]amino]carbonyl]amino]-6-benzothiazolecarboxamide;

(R)-N-(2-Chloro-6-methylphenyl)-2-[[[[1-(4-nitrophenyl)ethyl]amino]carbonyl]amino]-6-benzothiazolecarboxamide;

N-(2-Chloro-6-methylphenyl)-2-[[[[(4-chlorophenyl)phenylmethyl]amino]carbonyl]amino]-6-benzothiazolecarboxamide;

N-(2-Chloro-6-methylphenyl)-2-[[[[2-(phenylthio)ethyl]amino]carbonyl]amino]-6-benzothiazolecarboxamide;

2-[[[[(2-Bromophenyl)methyl]amino]carbonyl]amino]-N-(2-chloro-6-methylphenyl)-6-benzothiazolecarboxamide;

N-(2-Chloro-6-methylphenyl)-2-[[[[2-(3-fluorophenyl)ethyl]amino]carbonyl]amino]-6-benzothiazolecarboxamide;

N-(2-Chloro-6-methylphenyl)-2-[[[[4-(trifluoromethyl)phenyl]methyl]amino]carbonyl]amino]-6-benzothiazolecarboxamide;

2-[[[[(3-Bromophenyl)methyl]amino]carbonyl]amino]-N-(2-chloro-6-methylphenyl)-6-benzothiazolecarboxamide;

2-[[[[(4-Chloro-2-fluorophenyl)methyl]amino]carbonyl]amino]-N-(2-chloro-6-methylphenyl)-6-benzothiazolecarboxamide;

2-[[[(2-Amino-2-oxo-1-phenylethyl)amino]carbonyl]amino]-N-(2-chloro-6-methylphenyl)-6-benzothiazolecarboxamide;

N-(2-Chloro-6-methylphenyl)-2-[[[[3-(1H-imidazol-1-yl)propyl]amino]carbonyl]amino]-6-benzothiazolecarboxamide;

N-(2-Chloro-6-methylphenyl)-2-[[[[(2,4-dimethoxyphenyl)methyl]amino]carbonyl]amino]-6-benzothiazolecarboxamide;

N-(2-Chloro-6-methylphenyl)-2-[[[[(3-chloro-4-methylphenyl)methyl]amino]carbonyl]amino]-6-benzothiazolecarboxamide;

2-[[[[(3-Chloro-4-fluorophenyl)methyl]amino]carbonyl]amino]-N-(2-chloro-6-methylphenyl)-6-benzothiazolecarboxamide;

2-[[[[(2-Chloro-6-fluorophenyl)methyl]amino]carbonyl]amino]-N-(2-chloro-6-methylphenyl)-6-benzothiazolecarboxamide;

2-[[[[(2-Chloro-4-fluorophenyl)methyl]amino]carbonyl]amino]-N-(2-chloro-6-methylphenyl)-6-benzothiazolecarboxamide;

N-(2-Chloro-6-methylphenyl)-2-[[[[(3,5-difluorophenyl)methyl]amino]carbonyl]amino]-6-benzothiazolecarboxamide;

N-(2-Chloro-6-methylphenyl)-2-[[[[(2,5-dimethoxyphenyl)methyl]amino]carbonyl]amino]-6-benzothiazolecarboxamide;

N-(2-Chloro-6-methylphenyl)-2-[[[[(3,5-dimethylphenyl)methyl]amino]carbonyl]amino]-6-benzothiazolecarboxamide;

N-(2-Chloro-6-methylphenyl)-2-[[[[(3,4-dimethoxyphenyl)methyl]amino]carbonyl]amino]-6-benzothiazolecarboxamide;

N-(2-Chloro-6-methylphenyl)-2-[[[[(3,5-dimethoxyphenyl)methyl]amino]carbonyl]amino]-6-benzothiazolecarboxamide;

N-(2-Chloro-6-methylphenyl)-2-[[[[[4-(1-methylethyl)phenyl]methyl]amino]carbonyl]amino]-6-benzothiazolecarboxamide;

N-(2-Chloro-6-methylphenyl)-2-[[[[[4-(1,2,3-thiadiazol-4-yl)phenyl]methyl]amino]carbonyl]amino]-6-benzothiazolecarboxamide;

N-(2-Chloro-6-methylphenyl)-2-[[[[2-(2-chlorophenyl)ethyl]amino]carbonyl]amino]-6-benzothiazolecarboxamide;

N-(2-Chloro-6-methylphenyl)-2-[[[(1-methyl-1-phenylethyl)amino]carbonyl]amino]-6-benzothiazolecarboxamide;

N-(2-Chloro-6-methylphenyl)-2-[[[[(2,5-dichlorophenyl)methyl]amino]carbonyl]amino]-6-benzothiazolecarboxamide;

N-(2-Chloro-6-methylphenyl)-2-[[[[(2,4-dimethylphenyl)methyl]amino]carbonyl]amino]-6-benzothiazolecarboxamide;

N-(2-Chloro-6-methylphenyl)-2-[[[[1-(1-naphthalenyl)ethyl]amino]carbonyl]amino]-6-benzothiazolecarboxamide;

N-(2-Chloro-6-methylphenyl)-2-[[[[(3,4,5-trimethoxyphenyl)methyl]amino]carbonyl]amino]-6-benzothiazolecarboxamide;

N-(2-Chloro-6-methylphenyl)-2-[[[[(2,4,6-trimethoxyphenyl)methyl]amino]carbonyl]amino]-6-benzothiazolecarboxamide;

2-[[[[(4-Bromophenyl)methyl]amino]carbonyl]amino]-N-(2-chloro-6-methylphenyl)-6-benzothiazolecarboxamide;

[1R-(endo,endo)]-3-[[[[6-[[(2-Chloro-6-methylphenyl)amino]carbonyl]-2-benzothiazolyl]amino]carbonyl]amino]bicyclo[2.2.1]hept-5-ene-2-carboxylic acid ethyl ester;

[1S-(exo,exo)]-3-[[[[6-[[(2-Chloro-6-methylphenyl)amino]carbonyl]-2-benzothiazolyl]amino]carbonyl]amino]bicyclo[2.2.1]heptane-2-carboxylic acid ethyl ester;

[1R-(exo,exo)]-3-[[[[6-[[(2-Chloro-6-methylphenyl)amino]carbonyl]-2-benzothiazolyl]amino]carbonyl]amino]bicyclo[2.2.1]hept-5-ene-2-carboxylic acid ethyl ester;

[1R-(endo,endo)]-N-(2-Chloro-6-methylphenyl)-2-[[[[3-(hydroxymethyl)bicyclo[2.2.1]hept-5-en-2-yl]amino]carbonyl]amino]-6-benzothiazolecarboxamide;

[1S-(endo,endo)]-N-(2-Chloro-6-methylphenyl)-2-[[[[3-(hydroxymethyl)bicyclo[2.2.1]heptan-2-yl]amino]carbonyl]amino]-6-benzothiazolecarboxamide;

[1R-(exo,exo)]-N-(2-Chloro-6-methylphenyl)-2-[[[[3-(hydroxymethyl)bicyclo[2.2.1 ]heptan-2-yl]amino]carbonyl]amino]-6-benzothiazolecarboxamide;

N-(2-Chloro-6-methylphenyl)-2-[[[[(3-fluorophenyl)methyl]amino]carbonyl]amino]-6-benzothiazolecarboxamide;

N-(2-Chloro-6-methylphenyl)-2-[[[[(2-methoxyphenyl)methyl]amino]carbonyl]amino]-6-benzothiazolecarboxamide;

(exo,exo)-2-[[[3-(Aminocarbonyl)bicyclo[2.2.1]hept-5-en-2-yl]amino]carbonyl]amino]-N-(2-(chloro-6-methylphenyl)-6-benzothiazolecarboxamide;

(S)-N-(2-Chloro-6-methylphenyl)-2-[[[[1-(1-naphthalenyl)ethyl]amino]carbonyl]amino]-6-benzothiazolecarboxamide;

N-(2-Chloro-6-methylphenyl)-2-[[[[[3-(trifluoromethyl)phenyl]methyl]amino]carbonyl]amino]-6-benzothiazolecarboxamide;

N-(2-Chloro-6-methylphenyl)-2-[[[(phenylmethyl)amino]carbonyl]amino]-6-benzothiazolecarboxamide;

(endo,endo)-2-[[[3-(Aminocarbonyl)bicyclo[2.2.1]hept-5-en-2-yl]amino]carbonyl]amino]-N-(2-chloro-6-methylphenyl)-6-benzothiazolecarboxamide;

N-(2-Chloro-6-methylphenyl)-2-[[[[1-(4-hydroxyphenyl)ethyl]amino]carbonyl]amino]-6-benzothiazolecarboxamide;

N-(2-Chloro-6-methylphenyl)-2-[[[[(2,6-difluorophenyl)methyl]amino]carbonyl]amino]-6-benzothiazolecarboxamide;

N-(2-Chloro-6-methylphenyl)-2-[[[[(2,3-dimethylphenyl)methyl]amino]carbonyl]amino]-6-benzothiazolecarboxamide;

(R)-N-(2-Chloro-6-methylphenyl)-2-[[[[1-(1-naphthalenyl)ethyl]amino]carbonyl]amino]-6-benzothiazolecarboxamide;

N-(2-Chloro-6-methylphenyl)-2-[[[[2-(dimethylamino)ethyl]amino]carbonyl]amino]-6-benzothiazolecarboxamide;

N-(2-Chloro-6-methylphenyl)-2-[[[1,1-dimethyl-2-(dimethylamino)ethyl]amino]carbonyl]amino]-6-benzothiazolecarboxamide;

N-(2-Chloro-6-methylphenyl)-2-[[[[1-(phenylmethyl)-4-piperidinyl]amino]carbonyl]amino]-6-benzothiazolecarboxamide;

N-(2-Chloro-6-methylphenyl)-2-[[[[3-(2-methyl-1-piperidinyl)propyl]amino]carbonyl]amino]-6-benzothiazolecarboxamide;

N-(2-Chloro-6-methylphenyl)-2-[[[[2-(1-methyl-2-pyrrolidinyl)ethyl]amino]carbonyl]amino]-6-benzothiazolecarboxamide;

N-(2-Chloro-6-methylphenyl)-2-[[[[3-(4-morpholinyl)propyl]amino]carbonyl]amino]-6-benzothiazolecarboxamide;

N-(2-Chloro-6-methylphenyl)-2-[[[[1-(phenylmethyl)-3-pyrrolidinyl]amino]carbonyl]amino]-6-benzothiazolecarboxamide;

N-(2-Chloro-6-methylphenyl)-2-[[[[3-(diethylamino)propyl]amino]carbonyl]amino]-6-benzothiazolecarboxamide;

N-(2-Chloro-6-methylphenyl)-2-[[[[3-(4-methyl-1-piperazinyl)propyl]amino]carbonyl]amino]-6-benzothiazolecarboxamide;

N-(2-Chloro-6-methylphenyl)-2-[[[[2-(1-piperazinyl)ethyl]amino]carbonyl]amino]-6-benzothiazolecarboxamide;

N-(2-Chloro-6-methylphenyl)-2-[[[[2-(4-morpholinyl)ethyl]amino]carbonyl]amino]-6-benzothiazolecarboxamide;

N-(2-Chloro-6-methylphenyl)-2-[[[(2,2,6,6-tetramethyl-4-piperidinyl)amino]carbonyl]amino]-6-benzothiazolecarboxamide;

(R)-N-(2-Chloro-6-methylphenyl)-2-[[[[1-(phenylmethyl)-3-pyrrolidinyl]amino]carbonyl]amino]-6-benzothiazolecarboxamide;

(S)-N-(2-Chloro-6-methylphenyl)-2-[[[[1-(phenylmethyl)-3-pyrrolidinyl]amino]carbonyl]amino]-6-benzothiazolecarboxamide;

N-(2-Chloro-6-methylphenyl)-2-[[[[3-(1-piperidinyl)propyl]amino]carbonyl]amino]-6-benzothiazolecarboxamide;

N-(2-Chloro-6-methylphenyl)-2-[[[[3-(1-pyrrolidinyl)propyl]amino]carbonyl]amino]-6-benzothiazolecarboxamide;

N-(2-Chloro-6-methylphenyl)-2-[[[[1-(2-pyridinyl)ethyl]amino]carbonyl]amino]-6-benzothiazolecarboxamide;

N-(2-Chloro-6-methylphenyl)-2-[[[[1-(3-pyridinyl)ethyl]amino]carbonyl]amino]-6-benzothiazolecarboxamide;

N-(2-Chloro-6-methylphenyl)-2-[[[[3-(2-oxo-1-pyrrolidinyl)propyl]amino]carbonyl]amino]-6-benzothiazolecarboxamide;

4-[[[[6-[[(2-Chloro-6-methylphenyl)amino]carbonyl]-2-benzothiazolyl]amino]carbonyl]amino]-1-piperidinecarboxylic acid ethyl ester;

(S)-2-[[[[1-(4-Bromophenyl)ethyl]amino]carbonyl]amino]-N-(2-chloro-6-methylphenyl)-6-benzothiazolecarboxamide;

(1S-cis)-2-[[[[2-(Aminocarbonyl)cyclohexyl]amino]carbonyl]amino]-N-(2-chloro-6-methylphenyl)-6-benzothiazolecarboxamide;

2-[[[[3-(1H-Azepin-1-yl)propyl]amino]carbonyl]amino]-N-(2-chloro-6-methylphenyl)-6-benzothiazolecarboxamide;

N-(2-Chloro-6-methylphenyl)-2-[[[[2,2-dimethyl-3-(dimethylamino)propyl]amino]carbonyl]amino]-6-benzothiazolecarboxamide;

N-(2-Chloro-6-methylphenyl)-2-[[(3-pyrrolidinylamino)carbonyl]amino]-6-benzothiazolecarboxamide;

4-[[[[6-[[(2-Chloro-6-methylphenyl)amino]carbonyl]-2-benzothiazolyl]amino]carbonyl]amino]methyl]benzoic acid;

N-(2-Chloro-6-methylphenyl)-2-[[(3-pyridinylamino)carbonyl]amino]-6-benzothiazolecarboxamide;

N-(2-Chloro-6-methylphenyl)-2-[[(4-pyridinylamino)carbonyl]amino]-6-benzothiazolecarboxamide;

N-(2-Chloro-6-methylphenyl)-2-[[[[2-(1H-pyrrol-3-yl)ethyl]amino]carbonyl]amino]-6-benzothiazolecarboxamide;

N-(2-Chloro-6-methylphenyl)-2-[[(2-pyridinylamino)carbonyl]amino]-6-benzothiazolecarboxamide;

N-(2-Chloro-6-methylphenyl)-2-[[(2-pyrimidinylamino)carbonyl]amino]-6-benzothiazolecarboxamide;

4-[[[[6-[[(2-Chloro-6-methylphenyl)amino]carbonyl]-2-benzothiazolyl]amino]carbonyl]amino]methyl]benzoic acid methyl ester;

N-(2-Chloro-6-methylphenyl)-2-[[[[(1-ethyl-2-pyrrolidinyl)methyl]amino]carbonyl]amino]-6-benzothiazolecarboxamide;

N-(2-Chloro-6-methylphenyl)-2-[[[[2-[(5-nitro-2-pyridinyl)amino]ethyl]amino]carbonyl]amino]-6-benzothiazolecarboxamide;

N-(2-Chloro-6-methylphenyl)-2-[[[(1-ethyl-3-piperidinyl)amino]carbonyl]amino]-6-benzothiazolecarboxamide;

N-(2-Chloro-6-methylphenyl)-2-[[[[2-(6-fluoro-1H-indol-2-yl)ethyl]amino]carbonyl]amino]-6-benzothiazolecarboxamide;

trans-N-(2-Chloro-6-methylphenyl)-2-[[[2-[4-(1,1-dimethylethyl)phenyl]cyclopropyl]carbonyl]amino]-6-benzothiazolecarboxamide;

trans-N-(2-Chloro-6-methylphenyl)-2-[[[2-(4-ethoxyphenyl)cyclopropyl]carbonyl]amino]-6-benzothiazolecarboxamide;

trans-N-(2-Chloro-6-methylphenyl)-2-[[[2-(4-fluorophenyl)cyclopropyl]carbonyl]amino]-6-benzothiazolecarboxamide;

trans-N-(2-Chloro-6-methylphenyl)-2-[[[2-[4-(1-methylethyl)phenyl]cyclopropyl]carbonyl]amino]-6-benzothiazolecarboxamide;

trans-N-(2-Chloro-6-methylphenyl)-2-[[[2-[4-(trifluoromethyl)phenyl]cyclopropyl]carbonyl]amino]-6-benzothiazolecarboxamide;

trans-N-(2-Chloro-6-methylphenyl)-2-[[[2-(4-nitrophenyl)cyclopropyl]carbonyl]amino]-6-benzothiazolecarboxamide;

trans-N-(2-Chloro-6-methylphenyl)-2-[[[2-(4-cyanophenyl)cyclopropyl]carbonyl]amino]-6-benzothiazolecarboxamide;

trans-2-[[(2-[1,1'-Biphenyl]-4-ylcyclopropyl)carbonyl]amino]-N-(2-chloro-6-methylphenyl)-6-benzothiazolecarboxamide;

trans-2-[[[2-(1,3-Benzodioxol-4-yl)cyclopropyl]carbonyl]amino]-N-(2-chloro-6-methylphenyl)-6-benzothiazolecarboxamide;

trans-N-(2-Chloro-6-methylphenyl)-2-([[2-(3-chlorophenyl)cyclopropyl]carbonyl]amino]-6-benzothiazolecarboxamide;

trans-N-(2-Chloro-6-methylphenyl)-2-[[[2-(3-cyanophenyl)cyclopropyl]carbonyl]amino]-6-benzothiazolecarboxamide; and trans-N-(2-Chloro-6-methylphenyl)-2-[[[2-(3-nitrophenyl)cyclopropyl]carbonyl]amino]-6-benzothiazolecarboxamide.

2. A compound or salt thereof selected from the group consisting of:

[6-[[(2,4,6-Trimethylphenyl)amino]carbonyl]-2-benzothiazolyl]carbamic acid, 1,1-dimethylethyl ester;

2-Amino-N-(2,4,6-trimethylphenyl)-6-benzothiazolecarboxamide, trifluoroacetate (1:1);

2-(Acetylamino)-N-(2,4,6-trimethylphenyl)-6-benzothiazolecarboxamide;

2-(Benzoylamino)-N-(2,4,6-trimethylphenyl)-6-benzothiazolecarboxamide;

2-[(1-Oxopropyl)amino]-N-(2,4,6-trimethylphenyl)-6-benzothiazolecarboxamide;

2-[(1-Oxobutyl)amino]-N-(2,4,6-trimethylphenyl)-6-benzothiazolecarboxamide;

2-[[[(1,1-Dimethylethyl)amino]carbonyl]amino]-N-(2,4,6-trimethylphenyl)-6-benzothiazolecarboxamide;

2-[[[Bis(1-methylethyl)amino]carbonyl]amino]-N-(2,4,6-trimethylphenyl)-6-benzothiazolecarboxamide;

[6-Bromo-4-[[(2,4,6-Trimethylphenyl)amino]carbonyl]-2-benzothiazolyl]carbamic acid, 1,1-dimethylethyl ester;

[4-[[(2,4,6-Trimethylphenyl)amino]carbonyl]-2-benzothiazolyl]carbamic acid, 1,1-dimethylethyl ester;

[6-Bromo-7-[[(2,4,6-Trimethylphenyl)amino]carbonyl]-2-benzothiazolyl]carbamic acid, 1,1-dimethylethyl ester;

[7-[[(2,4,6-Trimethylphenyl)amino]carbonyl]-2-benzothiazolyl]carbamic acid, 1,1-dimethylethyl ester;

[6-Bromo-5-[[(2,4,6-Trimethylphenyl)amino]carbonyl]-2-benzothiazolyl]carbamic acid, 1,1-dimethylethyl ester;

[5-[[(2,4,6-Trimethylphenyl)amino]carbonyl]-2-benzothiazolyl]carbamic acid, 1,1-dimethylethyl ester;

2-[[[Phenylamino]carbonyl]amino]-N-(2,4,6-trimethylphenyl)-6-benzothiazolecarboxamide;

2-[[[(Phenylmethyl)amino]carbonyl]amino]-N-(2,4,6-trimethylphenyl)-6-benzothiazolecarboxamide;

2-[[[Ethylamino]carbonyl]amino]-N-(2,4,6-trimethylphenyl)-6-benzothiazolecarboxamide;

2-[[(Butylamino)carbonyl]amino]-N-(2,4,6-trimethylphenyl)-6-benzothiazolecarboxamide;

2-[[(Cyclopropylamino)carbonyl]amino]-N-(2,4,6-trimethylphenyl)-6-benzothiazolecarboxamide;

(R)-2-[[[[(3,3-Dimethylcyclohexyl)methyl]amino]carbonyl]amino]-N-(2,4,6-trimethylphenyl)-6-benzothiazolecarboxamide;

2-[[[(4-Methylcyclohexyl)amino]carbonyl]amino]-N-(2,4,6-trimethylphenyl)-6-benzothiazolecarboxamide;

2-[[[(Cyclohexylmethyl)amino]carbonyl]amino]-N-(2,4,6-trimethylphenyl)-6-benzothiazolecarboxamide;

2-[[[(2,3-Dihydro-1H-inden-1-yl)amino]carbonyl]amino]-N-(2,4,6-trimethylphenyl)-6-benzothiazolecarboxamide;

2-[[[(1-Naphthalenylmethyl)amino]carbonyl]amino]-N-(2,4,6-trimethylphenyl)-6-benzothiazolecarboxamide;

2-[[[[2-(1H-Imidazol-4-yl)ethyl]amino]carbonyl]amino]-N-(2,4,6-trimethylphenyl)-6-benzothiazolecarboxamide;

2-[[[[(Tetrahydro-2-furanyl)methyl]amino]carbonyl]amino]-N-(2,4,6-trimethylphenyl)-6-benzothiazolecarboxamide;

2-[[[[2-(5-Methoxy-1H-indol-3-yl)ethyl]amino]carbonyl]amino]-N-(2,4,6-trimethylphenyl)-6-benzothiazolecarboxamide;

2-[[[[2-(4-Morpholinyl)ethyl]amino]carbonyl]amino]-N-(2,4,6-trimethylphenyl)-6-benzothiazolecarboxamide;

2-[[[[2-(2-Pyridinyl)ethyl]amino]carbonyl]amino]-N-(2,4,6-trimethylphenyl)-6-benzothiazolecarboxamide;

2-[[[(1,1,3,3-Tetramethylbutyl)amino]carbonyl]amino]-N-(2,4,6-trimethylphenyl)-6-benzothiazolecarboxamide;

2-[[[(1,1-Dimethyl-propyl)amino]carbonyl]amino]-N-(2,4,6-trimethylphenyl)-6-benzothiazolecarboxamide;

2-[[[(1,5-Dimethylhexyl)amino]carbonyl]amino]-N-(2,4,6-trimethylphenyl)-6-benzothiazolecarboxamide;

2-[[(Cyclopentylamino)carbonyl]amino]-N-(2,4,6-trimethylphenyl)-6-benzothiazolecarboxamide;

2-[[[(1,1-Dimethyl-2-hydroxyethyl)amino]carbonyl]amino]-N-(2,4,6-trimethylphenyl)-6-benzothiazolecarboxamide;

2-[[[[(3-Methoxyphenyl)methyl]amino]carbonyl]amino]-N-(2,4,6-trimethylphenyl)-6-benzothiazolecarboxamide;

2-[[[[(3-Methylphenyl)methyl]amino]carbonyl]amino]-N-(2,4,6-trimethylphenyl)-6-benzothiazolecarboxamide;

2-[[[[(4-Chlorophenyl)methyl]amino]carbonyl]amino]-N-(2,4,6-trimethylphenyl)-6-benzothiazolecarboxamide;

2-[[[[2-(4-Methoxyphenyl)ethyl]amino]carbonyl]amino]-N-(2,4,6-trimethylphenyl)-6-benzothiazolecarboxamide;

2-[[(2-Propynylamino)carbonyl]amino]-N-(2,4,6-trimethylphenyl)-6-benzothiazolecarboxamide;

2-[[(2-Propenylamino)carbonyl]amino]-N-(2,4,6-trimethylphenyl)-6-benzothiazolecarboxamide;

2-[[[(3-Phenylpropyl)amino]carbonyl]amino]-N-(2,4,6-trimethylphenyl)-6-benzothiazolecarboxamide;

2-[[[[1-(Hydroxymethyl)cyclopentyl]amino]carbonyl]amino]-N-(2,4,6-trimethylphenyl)-6-benzothiazolecarboxamide;

2-[[[[4-(1,1-Dimethylethyl)cyclohexyl]amino]carbonyl]amino]-N-(2,4,6-trimethylphenyl)-6-benzothiazolecarboxamide;

2-[[[(1-Propylbutyl)amino]carbonyl]amino]-N-(2,4,6-trimethylphenyl)-6-benzothiazolecarboxamide;

2-[[[(1,3-Dimethylpentyl)amino]carbonyl]amino]-N-(2,4,6-trimethylphenyl)-6-benzothiazolecarboxamide;

2-[[[[3-(Methylthio)propyl]amino]carbonyl]amino]-N-(2,4,6-trimethylphenyl)-6-benzothiazolecarboxamide;

2-[[[[1-(Methoxymethyl)propyl]amino]carbonyl]amino]-N-(2,4,6-trimethylphenyl)-6-benzothiazolecarboxamide;

2-[[[[2-(2-Thienyl)ethyl]amino]carbonyl]amino]-N-(2,4,6-trimethylphenyl)-6-benzothiazolecarboxamide;
2-[[[[(2,6-Dimethoxyphenyl)methyl]amino]carbonyl]amino]-N-(2,4,6-trimethylphenyl)-6-benzothiazolecarboxamide;
(R)-2-[[[[1-(Hydroxymethyl)-2-phenylethyl]amino]carbonyl]amino]-N-(2,4,6-trimethylphenyl)-6-benzothiazolecarboxamide;
(R)-2-[[[(1-Phenylethyl)amino]carbonyl]amino]-N-(2,4,6-trimethylphenyl)-6-benzothiazolecarboxamide;
2-[[(1-Adamantylamino)carbonyl]amino]-N-(2,4,6-trimethylphenyl)-6-benzothiazolecarboxamide;
2-[[[[2-(4-Fluorophenyl)-1,1-dimethylethyl]amino]carbonyl]amino]-N-(2,4,6-trimethylphenyl)-6-benzothiazolecarboxamide;
2-[[[[2-(2-Pyridinyloxy)ethyl]amino]carbonyl]amino]-N-(2,4,6-trimethylphenyl)-6-benzothiazolecarboxamide;
2-[[[(1-Methyl-1-phenylethyl)amino]carbonyl]amino]-N-(2,4,6-trimethylphenyl)-6-benzothiazolecarboxamide;
(R)-2-[[[[1-(4-Methylphenyl)ethyl]amino]carbonyl]amino]-N-(2,4,6-trimethylphenyl)-6-benzothiazolecarboxamide;
2-[[[(1-Methylheptyl)amino]carbonyl]amino]-N-(2,4,6-trimethylphenyl)-6-benzothiazolecarboxamide;
2-[[[[(4-Methoxyphenyl)methyl]amino]carbonyl]amino]-N-(2,4,6-trimethylphenyl)-6-benzothiazolecarboxamide;
2-[[[(4-Cyclohexylphenyl)amino]carbonyl]amino]-N-(2,4,6-trimethylphenyl)-6-benzothiazolecarboxamide;
2-[[[(5,6,7,8-Tetrahydro-1-naphthalenyl)amino]carbonyl]amino]-N-(2,4,6-trimethylphenyl)-6-benzothiazolecarboxamide;
2-[[[(2,3-Dihydro-1H-inden-5-yl)amino]carbonyl]amino]-N-(2,4,6-trimethylphenyl)-6-benzothiazolecarboxamide;
2-[[(1,3-Benzodioxol-5-ylamino)carbonyl]amino]-N-(2,4,6-trimethylphenyl)-6-benzothiazolecarboxamide;
2-[[(2-Pyridinylamino)carbonyl]amino]-N-(2,4,6-trimethylphenyl)-6-benzothiazolecarboxamide;
2-[[[(3-Methyl-2-pyridinyl)amino]carbonyl]amino]-N-(2,4,6-trimethylphenyl)-6-benzothiazolecarboxamide;
2-[[[(4-Methyl-2-pyridinyl)amino]carbonyl]amino]-N-(2,4,6-trimethylphenyl)-6-benzothiazolecarboxamide;
2-[[[(2-Chloro-5-methylphenyl)amino]carbonyl]amino]-N-(2,4,6-trimethylphenyl)-6-benzothiazolecarboxamide;
2-[[[(2,6-Dichlorophenyl)amino]carbonyl]amino]-N-(2,4,6-trimethylphenyl)-6-benzothiazolecarboxamide;
2-[[[(2-Methoxyphenyl)amino]carbonyl]amino]-N-(2,4,6-trimethylphenyl)-6-benzothiazolecarboxamide;
2-[[[([1,1'-Biphenyl]-2-ylamino)carbonyl]amino]-N-(2,4,6-trimethylphenyl)-6-benzothiazolecarboxamide;
2-[[[(2-Benzoylphenyl)amino]carbonyl]amino]-N-(2,4,6-trimethylphenyl)-6-benzothiazolecarboxamide;
2-[[[(2-Methylphenyl)amino]carbonyl]amino]-N-(2,4,6-trimethylphenyl)-6-benzothiazolecarboxamide;
N-(2,4,6-Trimethylphenyl)-2-[[[(2,4,6-trimethylphenyl)amino]carbonyl]amino]-6-benzothiazolecarboxamide;
2-[[[[2-Methyl-6-(1-methylethyl)phenyl]amino]carbonyl]amino]-N-(2,4,6-trimethylphenyl)-6-benzothiazolecarboxamide;
2-[[[(3,5-Difluorophenyl)amino]carbonyl]amino]-N-(2,4,6-trimethylphenyl)-6-benzothiazolecarboxamide;
2-[[[(3-Methoxyphenyl)amino]carbonyl]amino]-N-(2,4,6-trimethylphenyl)-6-benzothiazolecarboxamide;
2-[[[(3-Methylphenyl)amino]carbonyl]amino]-N-(2,4,6-trimethylphenyl)-6-benzothiazolecarboxamide;
2-[[[(4-Cyanophenyl)amino]carbonyl]amino]-N-(2,4,6-trimethylphenyl)-6-benzothiazolecarboxamide;
2-[[[(4-Fluorophenyl)amino]carbonyl]amino]-N-(2,4,6-trimethylphenyl)-6-benzothiazolecarboxamide;
2-[[[(4-Chlorophenyl)amino]carbonyl]amino]-N-(2,4,6-trimethylphenyl)-6-benzothiazolecarboxamide;
4-[[[[6-[[(2,4,6-Trimethylphenyl)amino]carbonyl]-2-benzothiazolyl]amino]carbonyl]amino]benzoic acid, ethyl ester;
2-[[[(3,4,5-Trimethoxyphenyl)amino]carbonyl]amino]-N-(2,4,6-trimethylphenyl)-6-benzothiazolecarboxamide;
2-[[[(3,4-Dimethoxyphenyl)amino]carbonyl]amino]-N-(2,4,6-trimethylphenyl)-6-benzothiazolecarboxamide;
2-[[[[2,6-Bis(1-Methylethyl)phenyl]amino]carbonyl]amino]-N-(2,4,6-trimethylphenyl)-6-benzothiazolecarboxamide;
2-[[[(2-Propylphenyl)amino]carbonyl]amino]-N-(2,4,6-trimethylphenyl)-6-benzothiazolecarboxamide;
2-[[[(3-Bromo-2,4,6-trimethylphenyl)amino]carbonyl]amino]-N-(2,4,6-trimethylphenyl)-6-benzothiazolecarboxamide;
2-[[[[2-(4-Morpholinyl)phenyl]amino]carbonyl]amino]-N-(2,4,6-trimethylphenyl)-6-benzothiazolecarboxamide;
2-[[[(3-Bromo-2-methylphenyl)amino]carbonyl]amino]-N-(2,4,6-trimethylphenyl)-6-benzothiazolecarboxamide;
2-[[[(2,6-Dimethoxyphenyl)amino]carbonyl]amino]-N-(2,4,6-trimethylphenyl)-6-benzothiazolecarboxamide;
2-[[[(2-Bromo-5-methoxyphenyl)amino]carbonyl]amino]-N-(2,4,6-trimethylphenyl)-6-benzothiazolecarboxamide;
2-[[[(2-Methoxy-6-methylphenyl)amino]carbonyl]amino]-N-(2,4,6-trimethylphenyl)-6-benzothiazolecarboxamide;
2-[[[(2,3-Dimethyl-1H-indol-5-yl)amino]carbonyl]amino]-N-(2,4,6-trimethylphenyl)-6-benzothiazolecarboxamide;
2-[[[[3-(1,3,4-Oxadiazol-2-yl)phenyl]amino]carbonyl]amino]-N-(2,4,6-trimethylphenyl)-6-benzothiazolecarboxamide;
2-[[[(2-Chloro-6-methylphenyl)amino]carbonyl]amino]-N-(2,4,6-trimethylphenyl)-6-benzothiazolecarboxamide;
2-[[[[3-(Methylthio)phenyl]amino]carbonyl]amino]-N-(2,4,6-trimethylphenyl)-6-benzothiazolecarboxamide;
2-[[[(4-Methoxy-2-methylphenyl)amino]carbonyl]amino]-N-(2,4,6-trimethylphenyl)-6-benzothiazolecarboxamide;
2-[[[(4-Methoxycyclohexyl)carbonyl]amino]-N-(2,4,6-trimethylphenyl)-6-benzothiazolecarboxamide;
2-[(2,2-Dimethyl-1-oxopropyl)amino]-N-(2,4,6-trimethylphenyl)-6-benzothiazolecarboxamide;
2-[(2-Thienylacetyl)amino]-N-(2,4,6-trimethylphenyl)-6-benzothiazolecarboxamide;
2-[(Cyclopropylcarbonyl)amino]-N-(2,4,6-trimethylphenyl)-6-benzothiazolecarboxamide;
2-[(Cyclobutylcarbonyl)amino]-N-(2,4,6-trimethylphenyl)-6-benzothiazolecarboxamide;

2-[(Cyclopentylcarbonyl)amino]-N-(2,4,6-trimethylphenyl)-6-benzothiazolecarboxamide;

2-[(3-Cyclopentyl-1-oxopropyl)amino]-N-(2,4,6-trimethylphenyl)-6-benzothiazolecarboxamide;

2-[(1-Cyclopenten-1-ylcarbonyl)amino]-N-(2,4,6-trimethylphenyl)-6-benzothiazolecarboxamide;

2-[(Cyclohexylacetyl)amino]-N-(2,4,6-trimethylphenyl)-6-benzothiazolecarboxamide;

2-[(1-Oxo-2-phenylpropyl)amino]-N-(2,4,6-trimethylphenyl)-6-benzothiazolecarboxamide;

2-[(2-Methyl-1-oxopropyl)amino]-N-(2,4,6-trimethylphenyl)-6-benzothiazolecarboxamide;

2-[(1-Oxo-3-phenoxypropyl)amino]-N-(2,4,6-trimethylphenyl)-6-benzothiazolecarboxamide;

2-[(1-Oxo-3-phenylpropyl)amino]-N-(2,4,6-trimethylphenyl)-6-benzothiazolecarboxamide;

2-[[3-(2-Methoxyphenyl)-1-oxopropyl]amino]-N-(2,4,6-trimethylphenyl)-6-benzothiazolecarboxamide;

2-[[3-(2,3,4-Trimethoxyphenyl)-1-oxopropyl]amino]-N-(2,4,6-trimethylphenyl)-6-benzothiazolecarboxamide;

2-[(1,4-Dioxopentyl)amino]-N-(2,4,6-trimethylphenyl)-6-benzothiazolecarboxamide;

2-[(2-Naphthalenylacetyl)amino]-N-(2,4,6-trimethylphenyl)-6-benzothiazolecarboxamide;

2-[[(2-Chloro-6-fluorophenyl)acetyl]amino]-N-(2,4,6-trimethylphenyl)-6-benzothiazolecarboxamide;

2-[[(2-Methylphenyl)acetyl]amino]-N-(2,4,6-trimethylphenyl)-6-benzothiazolecarboxamide;

2-[[(3-Methoxyphenyl)acetyl]amino]-N-(2,4,6-trimethylphenyl)-6-benzothiazolecarboxamide;

2-[[(4-Chlorophenyl)acetyl]amino]-N-(2,4,6-trimethylphenyl)-6-benzothiazolecarboxamide;

2-[(1-Oxo-4-pentynyl)amino]-N-(2,4,6-trimethylphenyl)-6-benzothiazolecarboxamide;

5-Oxo-5-[[6-[[(2,4,6-trimethylphenyl)amino]carbonyl]-2-benzothiazolyl]amino]pentanoic acid, methyl ester;

2-[(1-Oxohexyl)amino]-N-(2,4,6-trimethylphenyl)-6-benzothiazolecarboxamide;

2-[(1-Oxoheptyl)amino]-N-(2,4,6-trimethylphenyl)-6-benzothiazolecarboxamide 2-[[1-Oxo-4-(2-thienyl)butyl]amino]-N-(2,4,6-trimethylphenyl)-6-benzothiazolecarboxamide;

2-[(3-Thienylcarbonyl)amino]-N-(2,4,6-trimethylphenyl)-6-benzothiazolecarboxamide;

2-[[(4-Nitrophenyl)acetyl]amino]-N-(2,4,6-trimethylphenyl)-6-benzothiazolecarboxamide;

2-[[3,5-Bis(trifluoromethyl)phenyl]acetyl]amino]-N-(2,4,6-trimethylphenyl)-6-benzothiazolecarboxamide;

2-[[2-[4-(2-Methypropyl)phenyl]-1-oxopropyl]amino]-N-(2,4,6-trimethylphenyl)-6-benzothiazolecarboxamide;

2-[[(3-Cyclohexen-1-yl)carbonyl]amino]-N-(2,4,6-trimethylphenyl)-6-benzothiazolecarboxamide;

2-[[3-(3-Methoxyphenyl)-1-oxopropyl]amino]-N-(2,4,6-trimethylphenyl)-6-benzothiazolecarboxamide;

2-[[(2,3,6-Trichlorophenyl)acetyl]amino]-N-(2,4,6-trimethylphenyl)-6-benzothiazolecarboxamide;

2-[[(1,3-Benzodioxol-5-yl)acetyl]amino]-N-(2,4,6-trimethylphenyl)-6-benzothiazolecarboxamide;

2-[[[2-(Phenylmethoxy)phenyl]acetyl]amino]-N-(2,4,6-trimethylphenyl)-6-benzothiazolecarboxamide;

2-[[(3,5-Dimethoxyphenyl)acetyl]amino]-N-(2,4,6-trimethylphenyl)-6-benzothiazolecarboxamide;

2-[[3-(1,3-Benzodioxol-5-yl)-1-oxopropyl]amino]-N-(2,4,6-trimethylphenyl)-6-benzothiazolecarboxamide;

2-[[(Tetrahydro-2-furanyl)carbonyl]amino]-N-(2,4,6-trimethylphenyl)-6-benzothiazolecarboxamide;

2-[[2-(Acetylamino)-1-oxopropyl]amino]-N-(2,4,6-trimethylphenyl)-6-benzothiazolecarboxamide;

2-[[2-(Acetylamino)-1-oxohexyl]amino]-N-(2,4,6-trimethylphenyl)-6-benzothiazolecarboxamide;

2-[(Cyclopropylacetyl)amino]-N-(2,4,6-trimethylphenyl)-6-benzothiazolecarboxamide;

N,N-Dimethyl-N'-[6-[[(2,4,6-trimethylphenyl)amino]carbonyl]-2-benzothiazolyl]butanediamide;

2-[(1-Adamantylcarbonyl)amino]-N-(2,4,6-trimethylphenyl)-6-benzothiazolecarboxamide;

2-[[(4-Methylcyclohexyl)carbonyl]amino]-N-(2,4,6-trimethylphenyl)-6-benzothiazolecarboxamide;

2-[(3-Methoxy-1-oxopropyl)amino]-N-(2,4,6-trimethylphenyl)-6-benzothiazolecarboxamide;

[6-[[(2,3-Dihydro-1H-inden-5-yl)amino]carbonyl]-2-benzothiazolyl]carbamic acid, 1,1-dimethylethyl ester;

[6-[(2-Naphthylenylamino)carbonyl]-2-benzothiazolyl]carbamic acid, 1,1-dimethylethyl ester;

[6-[[(3-Hydroxy-2-naphthalenyl)amino]carbonyl]-2-benzothiazolyl]carbamic acid, 1,1-dimethylethyl ester;

[6-[[(2-Fluoro-5-methylphenyl)amino]carbonyl]-2-benzothiazolyl]carbamic acid, 1,1-dimethylethyl ester;

[6-[[(2-Chloro-6-methylphenyl)amino]carbonyl]-2-benzothiazolyl]carbamic acid, 1,1-dimethylethyl ester;

[6-[[(2,6-Dimethylphenyl)amino]carbonyl]-2-benzothiazolyl]carbamic acid, 1,1-dimethylethyl ester;

[6-[[(4-Bromo-2-methylphenyl)amino]carbonyl]-2-benzothiazolyl]carbamic acid, 1,1-dimethylethyl ester;

[6-[[(3-Bromo-2,4,6-trimethylphenyl)amino]carbonyl]-2-benzothiazolyl]carbamic acid, 1,1-dimethylethyl ester;

[6-[[[2,6-Dimethyl-3-(1-methylethyl)phenyl]amino]carbonyl]-2-benzothiazolyl]carbamic acid, 1,1-dimethylethyl ester;

[6-[[(2-Bromo-4,6-dimethylphenyl)amino]carbonyl]-2-benzothiazolyl]carbamic acid, 1,1-dimethylethyl ester;

[6-[[(2-Methyl-6-quinolinyl)amino]carbonyl]-2-benzothiazolyl]carbamic acid, 1,1-dimethylethyl ester;

[6-[[(4-Methoxy-2-naphthalenyl)amino]carbonyl]-2-benzothiazolyl]carbamic acid, 1,1-dimethylethyl ester;

[6-[[(6-Methyl-5-quinolinyl)amino]carbonyl]-2-benzothiazolyl]carbamic acid, 1,1-dimethylethyl ester;

[6-[[[2-(2-Hydroxyethyl)-6-methylphenyl]amino]carbonyl]-2-benzothiazolyl]carbamic acid, 1,1-dimethylethyl ester;

[6-[[(2,6-Dimethyl-3-nitrophenyl)amino]carbonyl]-2-benzothiazolyl]carbamic acid, 1,1-dimethylethyl ester;

[6-[[(2-Bromo-3,4,6-trimethylphenyl)amino]carbonyl]-2-benzothiazolyl]carbamic acid, 1,1-dimethylethyl ester;

[6-[[(2-Actyl-6-hydroxyphenyl)amino]carbonyl]-2-benzothiazolyl]carbamic acid, 1,1-dimethylethyl ester;

[6-[[[4-[[(1,1-Dimethylethoxy)carbonyl]amino]-2,3,5,6-tetramethylphenyl]amino]carbonyl]-2-benzothiazolyl]carbamic acid, 1,1-dimethylethyl ester;

[6-[[(4-Bromo-2,6-dimethylphenyl)amino]carbonyl]-2-benzothiazolyl]carbamic acid, 1,1-dimethylethyl ester;

[6-[[[3-Acetylamino]-4,6-dimethylphenyl]amino]carbonyl]-2-benzothiazolyl]carbamic acid, 1,1-dimethylethyl ester;

[6-[[(2,6-Dimethoxyphenyl)amino]carbonyl]-2-benzothiazolyl]carbamic acid, 1,1-dimethylethyl ester;

[6-[[(2-Methyl-1-naphthalenyl)amino]carbonyl]-2-benzothiazolyl]carbamic acid, 1,1-dimethylethyl ester;

3-[[[2-[[(1,1-Dimethylethoxy)carbonyl]amino]-6-benzothiazolyl]carbonyl]amino]-4-methyl-2-thiophenecarboxylic acid, methyl ester;

[6-[[(2,4,6-Trimethylphenyl)amino]carbonyl]-2-benzothiazolyl]carbamic acid, methyl ester;

2-[[(Acetylamino)acetyl]amino]-N-(2,4,6-trimethylphenyl)-6-benzothiazolecarboxamide;

N-(2-Chloro-6-methylphenyl)-2-[[[(1,1-dimethylethyl)amino]carbonyl]amino]-6-benzothiazolecarboxamide;

N-(2,6-Dichlorophenyl)-2-[[[(1,1-dimethylethyl)amino]carbonyl]amino]-6-benzothiazolecarboxamide;

N-(4-Bromo-2,6-dimethylphenyl)-2-[[[(1,1-dimethylethyl)amino]carbonyl]amino]-6-benzothiazolecarboxamide;

N-(4-Carbomethoxy-2,6-Dimethylphenyl)-2-[[[1,1-dimethylethoxy]carbonyl]amino]-6-benzothiazolecarboxamide;

N-(4-Hydroxymethyl-2,6-Dimethylphenyl)-2-[[[1,1-dimethylethoxy]carbonyl]amino]-6-benzothiazolecarboxamide;

[4-Methyl-6-[[(2,4,6-trimethylphenyl)amino]carbonyl]-2-benzothiazolyl]carbamic acid, 1,1-dimethylethyl ester;

2-Amino-4-methyl-N-(2,4,6-trimethylphenyl)-6-benzothiazolecarboxamide, trifluoroacetate (1:1);

4-Methoxy-[6-[[(2,4,6-trimethylphenyl)amino]carbonyl]-2-benzothiazolyl]carbamic acid, 1,1-dimethylethyl ester;

2-Amino-4-methoxy-N-(2,4,6-trimethylphenyl)-6-benzothiazolecarboxamide, trifluoroacetate (1:1);

2-[[(Methylamino)carbonyl]amino]-N-(2,4,6-trimethylphenyl)-6-benzothiazolecarboxamide;

2-[[[Methylamino]carbonyl]amino]-4-methoxy-N-(2,4,6-trimethylphenyl)-6-benzothiazolecarboxamide;

5-Methoxy-[6-[[(2,4,6-trimethylphenyl)amino]carbonyl]-2-benzothiazolyl]carbamic acid, 1,1-dimethylethyl ester;

2-Amino-N-(4-N,N-dimethylamino-2,3,5,6-tetramethylphenyl)-6-benzothiazolecarboxamide, trifluoroacetate (1:1);

5-Chloro-[6-[[(2,4,6-trimethylphenyl)amino]carbonyl]-2-benzothiazolyl]carbamic acid, 1,1-dimethylethyl ester;

7-Chloro-[6-[[(2,4,6-trimethylphenyl)amino]carbonyl]-2-benzothiazolyl]carbamic acid, 1,1-dimethylethyl ester;

2-Amino-5-hydroxy-N-[2,4,6-trimethylphenyl]-6-benzothiazolecarboxamide;

5-tert-Butoxycarbonyloxy-[6-[[(2,4,6-trimethylphenyl)amino]carbonyl]-2-benzothiazolyl]carbamic acid, 1,1-dimethylethyl ester;

2-[[[(1,1-Dimethylethyl)amino]carbonyl]amino]-N-(2,6-dimethylphenyl)-6-benzothiazolecarboxamide;

2-[[(Cyclopropylamino)carbonyl]amino]-N-(2,6-dimethylphenyl)-6-benzothiazolecarboxamide;

2-[[(Cyclopentylamino)carbonyl]amino]-N-(2,6-dimethylphenyl)-6-benzothiazolecarboxamide;

2-[[[[1-(ethynyl)cyclohexyl]amino]carbonyl]amino]-N-(2,6-dimethylphenyl)-6-benzothiazolecarboxamide;

2-[[[(4-Methyl-cyclohexyl)amino]carbonyl]amino]-N-(2,6-dimethylphenyl)-6-benzothiazolecarboxamide;

2-[[[(2,3-Dihydro-1H-inden-1-yl)amino]carbonyl]amino]-N-(2,6-dimethylphenyl)-6-benzothiazolecarboxamide;

2-[[[[2-(1H-imidazol-4-yl)ethyl]amino]carbonyl]amino]-N-(2,6-dimethylphenyl)-6-benzothiazolecarboxamide;

2-[[[[(Tetrahydro-2-furanyl)methyl]amino]carbonyl]amino]-N-(2,6-dimethylphenyl)-6-benzothiazolecarboxamide;

2-[[[[2-(5-Methoxy-1H-indol-3-yl)ethyl]amino]carbonyl]amino]-N-(2,6-dimethylphenyl)-6-benzothiazolecarboxamide;

2-[[[(1,1-Dimethyl-2-hydroxyethyl)amino]carbonyl]amino]-N-(2,6-dimethylphenyl)-6-benzothiazolecarboxamide;

2-[[[(1,1-Dimethyl-propyl)amino]carbonyl]amino]-N-(2,6-dimethylphenyl)-6-benzothiazolecarboxamide;

2-[[[[(3-Methoxyphenyl)methyl]amino]carbonyl]amino]-N-(2,6-dimethylphenyl)-6-benzothiazolecarboxamide;

2-[[[[(4-Methoxyphenyl)methyl]amino]carbonyl]amino]-N-(2,6-dimethylphenyl)-6-benzothiazolecarboxamide;

2-[[(2-Propynylamino)carbonyl]amino]-N-(2,6-dimethylphenyl)-6-benzothiazolecarboxamide;

2-[[(2-Propenylamino)carbonyl]amino]-N-(2,6-dimethylphenyl)-6-benzothiazolecarboxamide;

2-[[[(3-Phenylpropyl)amino]carbonyl]amino]-N-(2,6-dimethylphenyl)-6-benzothiazolecarboxamide;

2-[[[[1-(Hydroxymethyl)cyclopentyl]amino]carbonyl]amino]-N-(2,6-dimethylphenyl)-6-benzothiazolecarboxamide;

2-[[[[1-(Methoxymethyl)propyl]amino]carbonyl]amino]-N-(2,6-dimethylphenyl)-6-benzothiazolecarboxamide;

(R)-2-[[[(1-Phenylethyl)amino]carbonyl]amino]-N-(2,6-dimethylphenyl)-6-benzothiazolecarboxamide;

2-[[[(3,4,5-Trimethoxyphenyl)amino]carbonyl]amino]-N-(2,6-dimethylphenyl)-6-benzothiazolecarboxamide;

2-[[(1,3-Benzodioxol-5-ylamino)carbonyl]amino]-N-(2,6-dimethylphenyl)-6-benzothiazolecarboxamide;

2-[[[(4-Fluorophenyl)amino]carbonyl]amino]-N-(2,6-dimethylphenyl)-6-benzothiazolecarboxamide;

2-[[(Cyclopropylamino)carbonyl]amino]-N-(2-chloro-6-methylphenyl)-6-benzothiazolecarboxamide;

2-[[(Cyclopentylamino)carbonyl]amino]-N-(2-chloro-6-methylphenyl)-6-benzothiazolecarboxamide;

2-[[[[1-(ethynyl)cyclohexyl]amino]carbonyl]amino]-N-(2-chloro-6-methylphenyl)-6-benzothiazolecarboxamide;

2-[[[(4-Methyl-cyclohexyl)amino]carbonyl]amino]-N-(2-chloro-6-methylphenyl)-6-benzothiazolecarboxamide;

2-[[[(2,3-Dihydro-1H-inden-1-yl)amino]carbonyl]amino]-N-(2-chloro-6-methylphenyl)-6-benzothiazolecarboxamide;

2-[[[[2-(1H-Imidazol-4-yl)ethyl]amino]carbonyl]amino]-N-(2-chloro-6-methylphenyl)-6-benzothiazolecarboxamide;

2-[[[[(Tetrahydro-2-furanyl)methyl]amino]carbonyl]amino]-N-(2-chloro-6-methylphenyl)-6-benzothiazolecarboxamide;

2-[[[[2-(5-Methoxy-1H-indol-3-yl)ethyl]amino]carbonyl]amino]-N-(2-chloro-6-methylphenyl)-6-benzothiazolecarboxamide;

2-[[[(1,1-Dimethyl-2-hydroxyethyl)amino]carbonyl]amino]-N-(2-chloro-6-methylphenyl)-6-benzothiazolecarboxamide;

2-[[[(1,1-Dimethyl-propyl)amino]carbonyl]amino]-N-(2-chloro-6-methylphenyl)-6-benzothiazolecarboxamide;

2-[[[[(3-Methoxyphenyl)methyl]amino]carbonyl]amino]-N-(2-chloro-6-methylphenyl)-6-benzothiazolecarboxamide;

2-[[[[(4-Methoxyphenyl)methyl]amino]carbonyl]amino]-N-(2-chloro-6-methylphenyl)-6-benzothiazolecarboxamide;

2-[[[(2-Propynylamino)carbonyl]amino]-N-(2-chloro-6-methylphenyl)-6-benzothiazolecarboxamide;

2-[[[(2-Propenylamino)carbonyl]amino]-N-(2-chloro-6-methylphenyl)-6-benzothiazolecarboxamide;

2-[[[(3-Phenylpropyl)amino]carbonyl]amino]-N-(2-chloro-6-methylphenyl)-6-benzothiazolecarboxamide;

2-[[[[1-(Hydroxymethyl)cyclopentyl]amino]carbonyl]amino]-N-(2-chloro-6-methylphenyl)-6-benzothiazolecarboxamide;

2-[[[[1-(Methoxymethyl)propyl]amino]carbonyl]amino]-N-(2-chloro-6-methylphenyl)-6-benzothiazolecarboxamide;

(R)-2-[[[(1-Phenylethyl)amino]carbonyl]amino]-N-(2-chloro-6-methylphenyl)-6-benzothiazolecarboxamide;

2-[[[(2,3-Dimethyl-1H-indol-5-yl)amino]carbonyl]amino]-N-(2-chloro-6-methylphenyl)-6-benzothiazolecarboxamide;

2-[[[(3,4,5-Trimethoxyphenyl)amino]carbonyl]amino]-N-(2-chloro-6-methylphenyl)-6-benzothiazolecarboxamide;

2-[[(1,3-Benzodioxol-5-ylamino)carbonyl]amino]-N-(2-chloro-6-methylphenyl)-6-benzothiazolecarboxamide;

2-[[[(4-Fluorophenyl)amino]carbonyl]amino]-N-(2-chloro-6-methylphenyl)-6-benzothiazolecarboxamide;

2-[[[[(1-methoxycarbonyl)cyclopropyl]amino]carbonyl]amino]-N-(2,4,6-trimethylphenyl)-6-benzothiazolecarboxamide;

[6-[[[(2,6-Dimethyl-4-phenyl)phenyl]amino]carbonyl]-2-benzothiazolyl]carbamic acid, 1,1-dimethylethyl ester;

[6-[[[(2,6-Dimethyl-4-(2-N,N-dimethylethoxy)phenyl]amino]carbonyl]-2-benzothiazolyl]carbamic acid, 1,1-dimethylethyl ester;

[6-[[[(2,6-Dimethyl-4-(2-morpholinoethoxy)phenyl]amino]carbonyl]-2-benzothiazolyl]carbamic acid, 1,1-dimethylethyl ester;

2-[(Cyclopropylcarbonyl)amino]-N-(2-chloro-6-methylphenyl)-6-benzothiazolecarboxamide;

2-[(2-Methyl-cyclopropylcarbonyl)amino]-N-(2-chloro-6-methylphenyl)-6-benzothiazolecarboxamide;

2-[(2,2-Dichloro-1-methyl-cyclopropylcarbonyl)amino]-N-(2-chloro-6-methylphenyl)-6-benzothiazolecarboxamide; and 2-[(1-Hydroxy-cyclopropylcarbonyl)amino]-N-(2-chloro-6-methylphenyl)-6-benzothiazolecarboxamide.

\* \* \* \* \*

UNITED STATES PATENT AND TRADEMARK OFFICE
CERTIFICATE OF CORRECTION

PATENT NO. : 6,825,355 B2  Page 1 of 1
APPLICATION NO. : 10/032609
DATED : November 30, 2004
INVENTOR(S) : Das et al.

It is certified that error appears in the above-identified patent and that said Letters Patent is hereby corrected as shown below:

<u>Title page, item (54) and Col. 1, line 1,</u>
Should read : -- BENZOTHIAZOLE PROTEIN TYROSINE KINASE INHIBITORS --

Signed and Sealed this

Seventeenth Day of October, 2006

JON W. DUDAS
*Director of the United States Patent and Trademark Office*